(12) United States Patent
Larsen et al.

(10) Patent No.: US 7,737,113 B2
(45) Date of Patent: Jun. 15, 2010

(54) ANTIARRHYTHMIC PEPTIDES

(75) Inventors: Bjarne Due Larsen, Roskilde (DK);
Jørgen Søberg Petersen, Gentofte (DK); Eddi Meier, Vaerlose (DK); Anne Louise Kjolbye, Copenhagen (DK); Niklas Rye Jorgensen, Frederiksberg (DK); Morten Schak Nielsen, Copenhagen (DK); James B. Martins, Iowa City, IA (US); Niels-Henrik Holstein-Rathlou, Herlev (DK)

(73) Assignee: Zealand Pharma A/S, Glostrup (DK)

( * ) Notice: Subject to any disclaimer, the term of this patent is extended or adjusted under 35 U.S.C. 154(b) by 461 days.

(21) Appl. No.: 10/772,774

(22) Filed: Feb. 4, 2004

(65) Prior Publication Data

US 2005/0075280 A1    Apr. 7, 2005

Related U.S. Application Data

(63) Continuation of application No. 09/792,286, filed on Feb. 22, 2001, now Pat. No. 7,250,397.

(60) Provisional application No. 60/251,659, filed on Dec. 6, 2000.

(30) Foreign Application Priority Data

Feb. 23, 2000  (DK) ............................... 2000 00288
May 4, 2000    (DK) ............................... 2000 00738

(51) Int. Cl.
*A61K 38/12* (2006.01)
(52) U.S. Cl. .............................. 514/9; 514/16; 514/17; 514/18
(58) Field of Classification Search ........................ None
See application file for complete search history.

(56) References Cited

U.S. PATENT DOCUMENTS 4,775,743 A    10/1988  Mimura et al.
5,817,316 A *  10/1998  Sodroski et al. .......... 424/188.1

FOREIGN PATENT DOCUMENTS

| DE | 19707854 A 1 | 9/1998 |
| EP | 0 214 659 A | 3/1987 |
| WO | WO 96/21674 | 7/1996 |
| WO | WO 01/62775 | 8/2001 |
| WO | WO 02/077017 | 10/2002 |

OTHER PUBLICATIONS

Lazar et al., Molecular and Cellular Biology, 1988, vol. 8, pp. 1247-1252.*
Y. Kohama, et al. "Effect of N-3-(4-Hydroxyphenyl) propionyl Pro-Pro-Gly-Ala-Gly on Calcium-Induced Arrhythmias", Chemical & Pharmaceutical Bulletin, vol. 36, No. 11, 1988, pp. 4597-4599.
S. Dhein, et al. "Therapeutic Potential of Antiarrhythmic Peptides", Drugs, vol. 49, No. 6, 1995, pp. 851-855.
B. Kundu "Synthesis, conformational features and biological activity of Pro-3 antiarrhythmic peptide", Collection of Czechoslovak Chemical Communications, vol. 54, No. 3, 1989, pp. 760-771.
B. Weinstein "Chemistry and Biochemistry of Amino Acids, Peptides and Proteins" 1982, Marcel Dekker Inc., New York and Basel, p. 357.
Chorev et al., "Recent developments in retro peptides and proteins—an ongoing topochemical exploration" *TIBTECH* 13:438-445, (1995).
Dhein et al,, "A new synthetic antiarrhythmic peptide reduces dispersion of epicardical activation recovery interval and diminishes alterations of epicardial activation patterns induced by regional ischemia" *Naunyn-Schmiedeberg's Arch Pharmacol* 350:174-184, (1994).
Grover et al., "Spatial structure determination of antiarrhythmic peptide using nuclear magnetic resonance spectrospcopy" *Peptides* 19:1725-1729, (1998).
Office Action in Japanese Application No. 2001-562556 mailed Sep. 16, 2008 and English language translation.

* cited by examiner

*Primary Examiner*—Christopher R. Tate
*Assistant Examiner*—Roy Teller
(74) *Attorney, Agent, or Firm*—Clark & Elbing LLP; Kristina Bieker-Brady

(57) ABSTRACT

Disclosed are novel peptides including antiarrhythmic peptides that have improved stability. Further disclosed are compositions that include such peptides and methods of using the compositions particularly as medicaments.

15 Claims, 15 Drawing Sheets

PI-turnover in neonatal rat cardiomyocytes

ANTIARRHYTHMIC PEPTIDES

CROSS-REFERENCES TO RELATED APPLICATIONS

The present application is a continuation of co-pending application U.S. Ser. No. 09/792,286 filed on Feb. 22, 2001, which application claims the benefit of U.S. Provisional Application No. 60/251,659 filed on 6 Dec. 2000, Danish Application No. PA 2000 00288 filed on 23 Feb. 2000, and Danish Application No. PA 2000 00738 filed 4 May 2000. The disclosures of said U.S. application Ser. No. 09/792,286, Provisional Application No. 60/251,659, Danish Application No. PA 2000 00288, and Danish Application No. PA 2000 00738 are each incorporated herein by reference.

CROSS-REFERENCES TO RELATED APPLICATIONS

The present invention relates to novel peptides including novel antiarrhythmic peptides of linear or cyclic structure having improved stability in vitro and/or in vivo, to compositions comprising said peptides, and to uses of said peptides for the preparation of medicaments.

BACKGROUND OF THE INVENTION

Sudden death due to cardiac arrhythmias is one of the leading causes of death in the Western world. The most common disease responsible for sudden death is ischemic heart disease but in younger subjects inherited diseases such as hypertrophic cardiomyopathy and long QT syndrome are also important.

Cardiac arrhythmias may arise from abnormalities in impulse formation, impulse conduction, or a combination of both. The regulation of impulse formation and conduction involves a complex interaction between the autonomic nervous system, cardiac ion channels, and cardiac gap junctions.

The results of pharmacological prevention of especially ischemia-induced arrhythmias have been disappointing. Thus, clinical trials have documented that several class I and class III antiarrhythmic drugs increase mortality in patients with ischemic heart disease[1]. A common feature of all antiarrhythmic drugs presently in use is that they interfere with either cardiac ion channels (sodium, potassium, and calcium channels) or the autonomic nervous system, thereby interfering with the generation of the action potential. This is probably why they not only act antiarrhythmically, but also has a proarrhythmic action with the potential for inducing lethal arrhythmias particularly in patients with reduced left ventricular function, congestive heart failure or a history of sustained ventricular tachyarrhythmia. Examples of antiarrhythmic drugs are flecainide, encainide, moricizine, and quinidine. Antiarrhythmic drugs that lengthen cardiac repolarization such as amiodarone and sotalol are associated with potential development of a specific and striking arrhythmia, torsades de pointes. Torsades, a very fast ventricular arrhythmia, probably occurs when a set of associated features hypokalemia, bradycardia, and possibly delayed conduction alters membrane stability, promoting oscillations. Amiodarone, like sotalol, is approved only for life-threatening arrhythmias. The drug blocks the sodium channels and to some extent the calcium channels, and it also has beta-blocking effects. In early trials, side effects (which are dose-related) resulted in drug discontinuation in up to 20% of patients at one year. Cardiac toxicities include sinus bradycardia, atrioventricular block, congestive heart failure, and ventricular arrhythmias.

In summary, the currently available antiarrhythmic drugs have failed to prevent sudden death caused by cardiac arrhythmias. Therefore, there is a great unmet need for new, safe, and effective antiarrhythmic drugs in the treatment of life threatening arrhythmias. Due to the serious side effects that limit the use of the present antiarrhythmic drugs a new class of antiarrhythmic drugs with a completely different mode of action is desirable. As mentioned above the regulation of impulse formation and conduction is a complex interaction between the autonomic nervous system, the cardiac ion channels, and the cardiac gap junctions. Hitherto the development of antiarrhythmic drugs has focused on the autonomic nervous system and the cardiac ion channels and no currently available drugs function as cardiac gap junction openers. However, recently several lines of evidence have proven the important role for gap junctions in the development of arrhythmias and the modulation of gap junctions is therefore a very interesting new target in the treatment of arrhythmias.

Gap junctions are specialized regions of the cell membrane with clusters of hundreds to thousands of densely packed gap junction channels that directly connect the cytoplasmic compartment of two neighboring cells. The gap junction channels are composed of two hemichannels (connexons) provided by each of two neighboring cells. Each connexon consists of six proteins called connexins. The connexins are a large family of proteins all sharing the basic structure of four transmembrane domains, two extracellular loops, and a cytoplasmic loop. There is a high degree of conservation of the extracellular loops and transmembrane domains among species and connexin isoforms. The length of the C-terminus, however, varies considerably giving rise to the classification of the connexins on the basis of the molecular weight. The distribution of the different types of connexins (Cx) varies throughout the heart. The Cx43 isoform is the predominant type in the ventricles whereas Cx40 is the must abundant isoform in the atrias and the conduction system. The gap junction channel can switch between an open and a closed state by a twisting motion. In the open state ions and small molecules smaller than about 1000 D can pass through the pore. The conduction of the electrical impulse takes place through the gap junctions and normally functioning gap junctions are therefore a prerequisite for normal conduction and thereby normal rhythm of the heart.

An increased understanding of the important role of gap junctions in abnormal conduction has been provided by the development of knockout mice lacking different types of connexins. From these studies it has been shown that mice homozygous for a targeted deletion of the Cx43 gene die shortly after birth from cardiac and pulmonary malformations, whereas heterozygous mice survive. However, the heterozygous genotype has a significantly slowed conduction compared to wild-type mice[2]. In adult mice (6-9 month old) ventricular epicardial conduction of paced beats is slowed by 44% and QRS complexes of ECG recordings are significantly prolonged compared to those of wild-type mice. The reduced expression of Cx43 is directly linked to an increased incidence of ventricular arrhythmias during ischemia in mice heterozygous for the Cx43 gene deletion[3]. Thus, the incidence of spontaneous ventricular tachycardia after the induction of regional ischemia in isolated perfused hearts from heterozygous mice is twice the incidence in wild-type hearts. In addition, mice with cardiac specific loss of Cx43 develop spontaneous ventricular arrhythmias and sudden cardiac death, with 100% mortality by two months of age. Knockout of the Cx40 gene is not fatal, however, atrial, atrioventricular, and His-Purkinje conduction are significantly slower in Cx40−/− mice relative to Cx40+/+ mice, and Cx40−/− mice are at increased risk of arrhythmias and bundle branch block[4-6].

The link between abnormalities in connexins and heart disease has also been established in humans. One example is Chagas' disease caused by the protozoan parasite *Trypanosoma cruzi*. This disease is a major cause of cardiac dysfunction in Latin America. An altered Cx43 distribution has been observed in cells infected by *Trypanosoma cruzi* and this alteration may be involved in the genesis of the conduction disturbances characterizing the disease[7]. Several studies of the expression and distribution of Cx43 in chronically ischemic, hibernating, or hypertrophied hearts also describe a reduced degree of Cx43 expression and a changed pattern of distribution[8-10]. In fact the expression and/or distribution of connexins have been altered in all chronic disease states of the heart investigated so far.

In summary, there is plenty of evidence linking malfunction or absence of gap junctions to an increased risk of arrhythmias and plenty of evidence showing an altered connexin expression/distribution in chronic heart disease. As mentioned above no currently available antiarrhythmic drugs act by increasing gap junction function. However a group of peptides (the antiarrhythmic peptides) capable of increasing gap junction conductance has been described in the past.

The Antiarrhythmic Peptides

In 1980, a hexapeptide with a molecular weight of 470D was isolated from bovine atria by Aonuma and colleagues[11]. In neonatal rat cardiomyocytes, it was demonstrated that 0.1 µg/ml of this peptide could convert fibrillation induced by either ouabain, high calcium (3 mM) or low potassium (0.7 mM) to normal rhythm. In addition, 2.5-5.0 µg/ml of this peptide could convert arrhythmic movement of isolated rat atria induced by the combination of low potassium (0.3 mM) and acetylcholine to normal rhythm. Thus, this peptide was named antiarrhytmic peptide (AAP) (Comparative Example 1 below (CE1)). When added to cell culture medium, AAP increased the number of beating centers, the relative content of spreading cells and protein synthesis[12]. In 1982, the amino acid sequence of AAP was determined to be (SEQ ID NO: 1) H-Gly-Pro-4Hyp-Gly-Ala-Gly-OH[13]. In later in vivo studies, the antiarrhythmic effect of AAP observed in vitro was confirmed. It was shown that AAP, 10 mg/kg, was effective against $CaCl_2$—, oubain and acotinine-induced arrhythmia in mice[14]. Several synthetic derivatives of AAP have been tested and found to be more potent than the endogenous AAP against experimentally induced arrhythmias in mice and rats[15-17]. The synthetic derivative that has been most thoroughly investigated is AAP10 (SEQ ID NO: 2) (H-Gly-Ala-Gly-4Hyp-Pro-Tyr-$NH_2$) (Comparative Example 2 below (CE2)). In the isolated perfused rabbit heart 0.1 nmol/l to 10 nmol/l of this peptide reduced the dispersion of activation-recovery intervals measured at 256 ventricular epicardial electrodes during normal conditions[18]. AAP10 had no effect on mean action potential duration, left ventricular end-diastolic pressure, coronary flow, QRS duration, or on the PQ interval. If hearts were subjected to regional ischemia by occlusion of the descending branch of the left coronary artery for 30 min, pretreatment with 10 nmol/l AAP10 led to a significant reduction in ischemia-induced alterations of activation patterns and reduced dispersion of activation-recovery intervals[18]. Additional studies showed that AAP10 did not affect the action potential in isolated papillary muscles from guinea pig hearts in concentrations up to 1 µmol/l[18]. These findings are in accordance with the findings of Argentieri and colleagues[19] who investigated the mechanism of the antiarrhythmic properties of AAP by examining the effect on the action potential in isolated canine purkinje fibers. In this model, AAP did not affect inotropy or any of the eletrophysiological parameters measured (maximum diastolic potential, action potential amplitude, maximum rate of depolarization, and action potential duration at 50% and 95% repolarization). Therefore, it was concluded that AAP's does not affect transmembrane ion currents. In guinea pig papillary muscle the effect on coupling time, i.e. the time interval between electrostimulation and onset of the action potential, was examined[20]. It was found that high concentrations of AAP10 (1 µM) could decrease the stimulus-response-interval by about 10% under normoxic conditions. Furthermore, during hypoxia and glucose-free perfusion the increase in stimulus-response-interval indicating uncoupling was prevented by 10 nmol/l of AAP10. Since the effect of AAP10 on coupling time was most pronounced on poorly coupled cells, the authors suggested that AAP10 preferentially acts on poorly coupled cells. The effect on coupling time suggested that AAP10 exerts its actions via an effect on gap junction conductance. To test this theory, the authors examined the effect of AAP10 on gap junction conductance in adult guinea pig ventricular cardiomyocytes using the double-cell voltage clamp technique. These studies demonstrated that 10 nmol/l AAP10 produced a rapid and reversible increase in gap junction conductance. Thus, the antiarrhythmic properties of AAP10 were explained by an improvement of gap junction coupling thereby reducing action potential dispersion and preventing slowing of conduction.

In summary, the antiarrhythmic peptides are a group of peptides that exert their effect selectively on gap junctions and thus decrease cellular uncoupling and reduce dispersion of action potential duration and refractoriness without affecting the action potential duration or shape. Therefore, the antiarrhythmic peptides are expected to lack the proarrhythmic effects limiting the use of many currently available antiarrhythmic drugs. This makes the antiarrhythmic peptides extremely interesting as a potentially new and safer class of antiarrhythmic compounds. However, the native AAP as well as the synthetic AAP10 possess several undesired features, such as, low stability, high effective concentration etc. that has hitherto prevented their utilisation as drugs. Grover and Dhein[21] have characterised two semi cyclic conformations of AAP10 using nuclear magnetic resonance spectroscopy. Therefore, one approach to obtaining a stable antiarrhytmic peptide could be the provision of cyclic derivatives of antiarrhythmic peptides. DE19707854 discloses apparently cyclic (SEQ ID NO: 3) $CF_3C(OH)$-Gly-Ala-Gly-4Hyp-Pro-Tyr-CONH and cyclic (SEQ ID NO: 4) CO-Gly-Ala-Gly-4Hyp-Pro-Tyr-CONH having the same antiarrhythmic properties as AAP and AAP10, but stated to have improved stability in aqueous solution and after repeated cycles of freezing and thawing. However, the experimental conditions described in DE19707854 are insufficient for the preparation of said cyclic compounds, and the chemical identification data given therein using HPLC is not sufficient for identification of said cyclic compounds. U.S. Pat. No. 4,775,743 discloses HP5, a peptide derivative having the sequence (SEQ ID NO: 5) N-3-(4-hydroxyphenyl)propionyl-Pro-4Hyp-Gly-Ala-Gly-OH and being active against platelet agglutination. Dhein and Tudyka[22] have reviewed the literature on peptides including peptide derivatives belonging to the group of antiarrhythmic peptides for activity and concentration, cf. table 1 therein, and found only 7 compounds to be active and further 4 compounds to be weakly active. However, none of these peptides or peptide derivatives have been shown to be sufficiently stable to be effective in a therapy regimen.

Furthermore, cyclic depsipeptides having antiarrhythmic action but having an ester bond being labile towards endogenous esterases are disclosed in JP patent application No. 08281636 and in JP patent application No. 09308589. Moreover, WO96/21674 discloses AAP10 derivatives where a hydrogen at the phenyl ring of the tyrosine residue has been substituted with halogen. Said AAP10 derivatives have antiarrhythmic properties and a reduced proarrhythmic risk compared to lidocain and flecainid.

The following AAP peptides and AAP-like compounds are described in the literature:

| | |
|---|---|
| (AAP) H-Gly-Pro-4Hyp-Gly-Ala-Gly-OH, | (SEQ ID NO: 6) |
| H-Gly-Pro-4Hyp-OH, | |
| H-Gly-Pro-OH, | |
| H-Gly-Pro-Leu-OH, | |
| H-Gly-Pro-4Hyp-Gly-OH, | |
| H-Gly-Pro-Leu-Gly-Pro-OH, | (SEQ ID NO: 7) |
| H-4Hyp-Gly-OH, | |
| H-Gly-Ala-Gly-OH, | |
| H-Gly-Gly-Gly-OH, | |
| H-Pro-Pro-Gly-OH, | |
| H-Pro-4Hyp-Gly-Ala-Gly-OH, | (SEQ ID NO: 8) |
| H-Pro-4Hyp-OH, | |
| H-Pro-4Hyp-Gly-OH, | |
| H-Pro-4Hyp-Gly-Ala-OH, | |
| (HP5) N-3-(4-hydroxyphenyl)propionyl-Pro-4Hyp-Gly-Ala-Gly-OH, | (SEQ ID NO: 9) |
| N-3-phenylpropionyl-Pro-4Hyp-Gly-Ala-Gly-OH, | (SEQ ID NO: 10) |
| N-3-phenylpropyl-Pro-4Hyp-Gly-Ala-Gly-OH, | (SEQ ID NO: 11) |
| N-3-(4-hydroxyphenyl)propionyl-Pro-4Hyp-Gly-Ala-OH, | |
| N-3-(4-hydroxyphenyl)propionyl-Pro-4Hyp-Gly-OH, | |
| N-3-(4-hydroxyphenyl)propionyl-Pro-4Hyp-OH, | |
| N-3-(4-hydroxyphenyl)propionyl-Pro-Pro-Gly-Ala-Gly-OH, | (SEQ ID NO: 12) |
| (AAP10) H-Gly-Ala-Gly-4Hyp-Pro-Tyr-NH₂, | (SEQ ID NO: 13) |
| H-Gly-Ala-Gly-4Hyp-Pro-Tyr-OH, | (SEQ ID NO: 14) |
| H-Ala-Gly-4Hyp-Pro-Tyr-NH₂, | (SEQ ID NO: 15) |
| H-Gly-Sar-Pro-Gly-Ala-Gly-OH, | (SEQ ID NO: 16) |
| H-Gly-Pro-Sar-Gly-Ala-Gly-OH, | (SEQ ID NO: 17) |
| H-Gly-Sar-Sar-Gly-Ala-Gly-OH, | (SEQ ID NO: 18) |
| H-Gly-Ala-Gly-Hyp-Pro-Tyr(3-I)-NH₂ | (SEQ ID NO: 19) |
| H-Gly-Ala-Gly-Hyp-Pro-Tyr(3-F)-NH₂ | (SEQ ID NO: 20) |
| H-Gly-Ala-Gly-Hyp-Pro-Tyr(3-Cl)-NH₂ | (SEQ ID NO: 21) |
| H-Gly-Ala-Gly-Hyp-Pro-Tyr(3-Br)-NH₂ | (SEQ ID NO: 22) |
| H-Arg-Ala-Gly-Hyp-Pro-Tyr-NH₂ | (SEQ ID NO: 23) |
| H-Val-Ala-Gly-Hyp-Pro-Tyr-NH₂ | (SEQ ID NO: 24) |
| H-Ala-Ala-Gly-Hyp-Pro-Tyr-NH₂ | (SEQ ID NO: 25) |
| H-Gly-Ala-Gly-Hyp-His-Tyr-NH₂ | (SEQ ID NO: 26) |
| H-Gly-Ala-Gly-Hyp-Pro-Phe-NH₂ | (SEQ ID NO: 27) |
| Cyclo(CF₃C(OH)-Gly-Ala-Gly-4Hyp-Pro-Tyr-CONH), and | (SEQ ID NO: 28) |
| Cyclo(CO-Gly-Ala-Gly-4Hyp-Pro-Tyr-CONH). | (SEQ ID NO: 29) |

The following compounds

| | |
|---|---|
| H-Gly-Pro-4Hyp-Gly-Ala-Gly-OH (AAP), | (SEQ ID NO: 30) |
| H-Gly-Pro-4Hyp-Gly-Ala-Gly-OH, | (SEQ ID NO: 31) |
| H-Gly-Ala-Gly-4Hyp-Pro-Tyr-NH₂ (AAP10), | (SEQ ID NO: 32) |
| H-Gly-Ala-Gly-4Hyp-Pro-Tyr-OH, | (SEQ ID NO: 33) |
| H-Gly-Ala-Gly-Hyp-Pro-Tyr(3-I)-NH₂, | (SEQ ID NO: 34) |
| H-Gly-Pro-Sar-Gly-Ala-Gly-OH, | (SEQ ID NO: 35) |
| N-3-(4-hydroxyphenyl)propionyl-Pro-4Hyp-Gly-Ala-Gly-OH (HP5), | (SEQ ID NO: 36) |
| N-3-phenylpropionyl-Pro-4Hyp-Gly-Ala-Gly-OH, | (SEQ ID NO: 37) |
| N-3-(4-hydroxyphenyl)propionyl-Pro-Pro-Gly-Ala-Gly-OH, | (SEQ ID NO: 38) |
| Cyclo(CF₃C(OH)-Gly-Ala-Gly-4Hyp-Pro-Tyr-CONH), and | (SEQ ID NO: 39) |
| Cyclo(CO-Gly-Ala-Gly-4Hyp-Pro-Tyr-CONH) | (SEQ ID NO: 40) | have shown activity or weak activity in test models, cf., e.g., Dhein and Tyduka (1995).

Although active antiarrhythmic peptides have been provided none of these have lead to the development of a much sought for antiarrhythmic medicament. The purpose of the present invention is to provide further antiarrhythmic peptides and functional analogues thereof useful in the treatment of various coronary heart diseases and useful for the preparation of medicaments. Furthermore, the novel peptides herein increase gap junction intercellular communication (GJIC) in vertebrate tissue, and specifically in mammalian tissue, and are useful in the treatment of a wide spectrum of diseases and ailments in vertebrates, such as mammals, relating to or caused by a decreased function of intercellular gap junction communication as is described below.

SUMMARY OF THE INVENTION

The purpose of the present invention is achieved with the present peptides including antiarrhythmic peptide compounds that are characterised in having the following general formula I

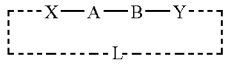

where the dashed line indicates that formula I is optionally cyclic, and the bonds shown represent covalent bonds;

and wherein A represents a chemical moiety having an amino group (radical) and a carboxy group (radical) that forms part of the peptide bond connecting A to X and B;

B represents a chemical moiety having an amino group (radical) and a carboxy group (radical) that forms part of the peptide bond connecting B to A and Y;

X represents a peptide sequence of from 1 to 3 amino acid residues which independently may be an L or D form when Y represents a C-terminal peptide sequence of from 2 to 5 amino acid residues which may independently be L- or D-forms;

or X represents an N-terminal modification of the group A-B when Y represents a C-terminal peptide sequence of from 2 to 5 amino acid residues which may independently be L- or D-forms; or X represents a peptide sequence of from 2 to 5 amino acid residues which may independently be L- or D-forms when Y represents a C-terminal peptide sequence of from 1 to 3 amino acid residues which independently may be an L or D form;

and when formula I represents a linear peptide X is optionally chemically modified at its N-terminal, and L is an optional linking group comprising from 0 to 8 backbone atoms;

and a mirror image or a retro analogue of formula I, or a derivative of formula I which is a pharmaceutically acceptable salt, an alkyl, aryl or aralkyl ester, an amide, a mono or disubstituted amide where the substituent is an alkyl, an aryl or an aralkyl, a hydrazide, or an alcohol;

with the proviso that the compounds

H-Gly-Pro-Leu-Gly-Pro-OH, (SEQ ID NO: 41)

H-Pro-4Hyp-Gly-Ala-Gly-OH, (SEQ ID NO: 42)

-continued

N-3-(4-hydroxyphenyl)propionyl-Pro-4Hyp-Gly-Ala-Gly-OH, (SEQ ID NO: 43)

N-3-phenylpropionyl-Pro-4Hyp-Gly-Ala-Gly-OH, (SEQ ID NO: 44)

N-3-phenylpropyl-Pro-4Hyp-Gly-Ala-Gly-OH, (SEQ ID NO: 45)

N-3-(4-hydroxyphenyl)propionyl-Pro-4Hyp-Gly-Ala-OH,

N-3-(4-hydroxyphenyl)propionyl-Pro-4Hyp-Gly-OH,

N-3-(4-hydroxyphenyl)propionyl-Pro-4Hyp-OH,

N-3-(4-hydroxyphenyl)propionyl-Pro-Pro-Gly-Ala-Gly-OH, (SEQ ID NO: 46)

H-Gly-Ala-Gly-4Hyp-Pro-Tyr-$NH_2$, (SEQ ID NO: 47)

H-Gly-Ala-Gly-4Hyp-Pro-Tyr-OH, (SEQ ID NO: 48)

H-Ala-Gly-4Hyp-Pro-Tyr-$NH_2$, (SEQ ID NO: 49)

H-Gly-Sar-Pro-Gly-Ala-Gly-OH, (SEQ ID NO: 50)

H-Gly-Pro-Sar-Gly-Ala-GlyOH, (SEQ ID NO: 51)

H-Gly-Sar-Sar-Gly-Ala-Gly-OH, (SEQ ID NO: 52)

H-Gly-Ala-Gly-Hyp-Pro-Tyr(3-I)-$NH_2$, (SEQ ID NO: 53)

H-Gly-Ala-Gly-Hyp-Pro-Tyr(3-F)-$NH_2$ (SEQ ID NO: 54)

H-Gly-Ala-Gly-Hyp-Pro-Tyr(3-Cl)-$NH_2$ (SEQ ID NO: 55)

H-Gly-Ala-Gly-Hyp-Pro-Tyr(3-Br)-$NH_2$ (SEQ ID NO: 56)

H-Arg-Ala-Gly-Hyp-Pro-Tyr-$NH_2$ (SEQ ID NO: 57)

H-Val-Ala-Gly-Hyp-Pro-Tyr-$NH_2$ (SEQ ID NO: 58)

H-Ala-Ala-Gly-Hyp-Pro-Tyr-$NH_2$ (SEQ ID NO: 59)

H-Gly-Ala-Gly-Hyp-His-Tyr-$NH_2$ (SEQ ID NO: 60)

H-Gly-Ala-Gly-Hyp-Pro-Phe-$NH_2$ (SEQ ID NO: 61)

Cyclo($CF_3$C(OH)-Gly-Ala-Gly-4Hyp-Pro-Tyr-CONH), (SEQ ID NO: 62)

Cyclo(CO-Gly-Ala-Gly-4Hyp-Pro-Tyr-CONH). (SEQ ID NO: 63)

are not covered by the general formula I.

DETAILED DESCRIPTION OF THE INVENTION

Figure 1:
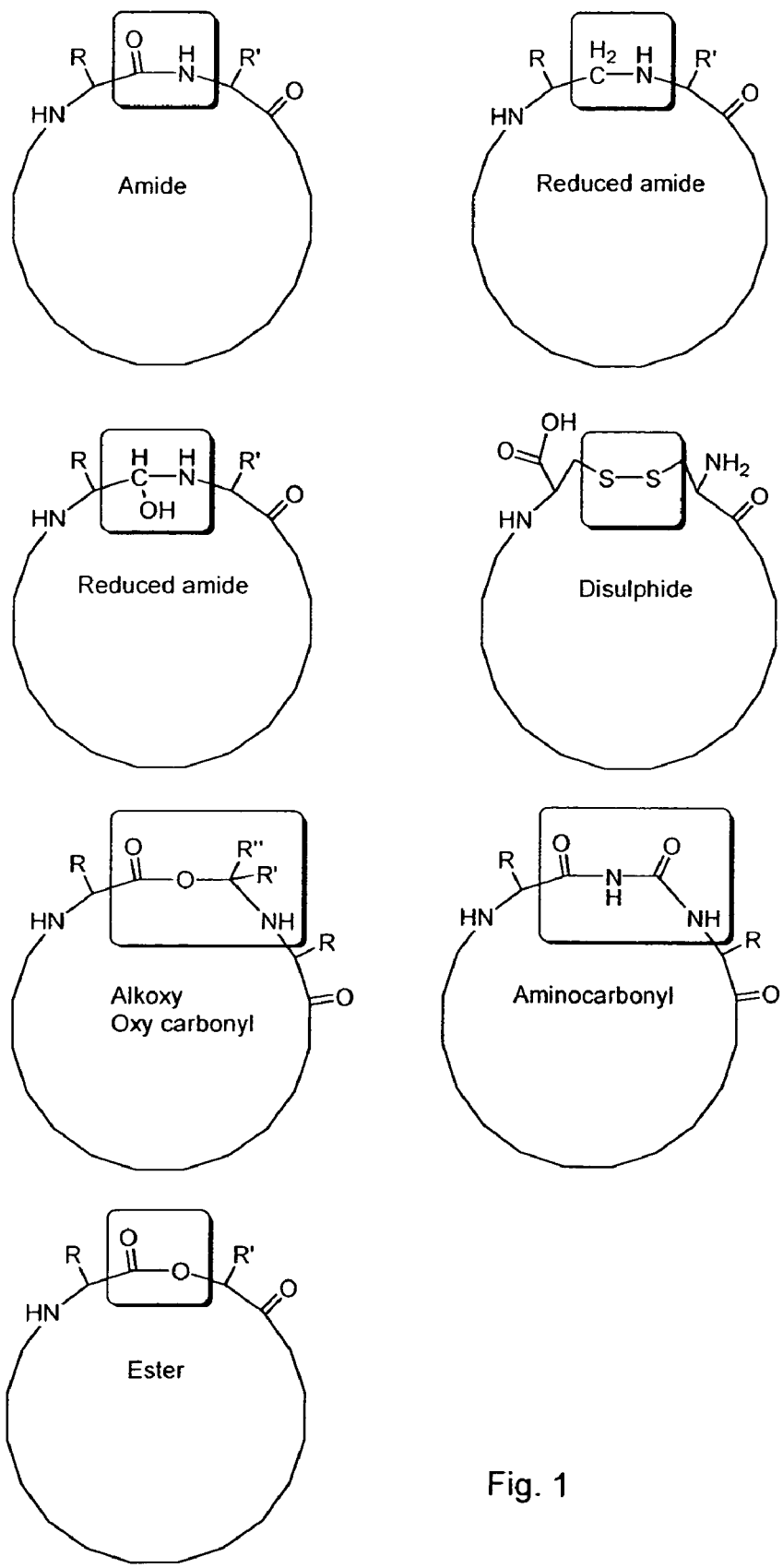
FIG. 1 is an illustration of different principles useful in the cyclisation of peptide sequences.

In preferred embodiments of the invention the covalent bonds are selected from peptide bonds, disulphide bonds, ester bonds, reduced amide bonds, alkoxy bonds, oxycarbonyl bonds, and acyloxyalkoxy bonds.

Examples of A and B include the formula II

(II)

wherein n is an integer having the value 3, 4, or 5, and R represents an optional substituent, preferably selected from the group consisting of halogen, phenyl, hydroxy, $NH_2$, and C(1-6)alkyl. In a preferred embodiment of the invention A and B each represents an amino acid or an amino acid derivative having functional amino and carboxylic acid groups. Further examples of A and B are represented by the formula IIa

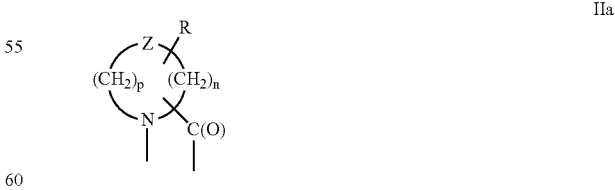

IIa

Wherein n is an integer having the value 0, 1, 2, and 3, p is an integer having the value 0, 1, 2, and 3, Z represents O or S, and R represents an optional substituent, preferably selected from the group consisting of halogen, phenyl, hydroxy, $NH_2$, and C(1-6)alkyl. Exemplary compounds of the invention wherein A or B is represented by the formula IIa are

```
Compound 11
H-Gly-Ala-Gly-NCG-Pro-Tyr-NH₂      (SEQ ID NO: 64)

Compound 12
H-Gly-Ala-Gly-T4C-Pro-Tyr-NH₂      (SEQ ID NO: 65)

Compound 13
H-Gly-Ala-Gly-A2C-Pro-Tyr-NH₂      (SEQ ID NO: 66)

Compound 14
H-Gly-Ala-Gly-PC-Pro-Tyr-NH₂       (SEQ ID NO: 67)
``` and salts thereof.

Examples of A and B include but are not limited to N— and C(O)— radicals of the following compounds:
D/L-azetidin-3-carboxylic acid,
D/L-azetidin-2-carboxylic acid,
D/L-Indolin-2-carboxylic acid,
D/L-1,3-dihydro-isoindol-1-carboxylic acid,
D/L-thiazolidin-4-carboxylic acid,
D/L-pipecolinic acid,
D/L-Nipecotinic acid,
Isonipecotinic acid,
L/D-2-carboxymorpholin,
L/D-1,2,3,4-tetrahydroquinolin-3-carboxylic acid,
L/D-1,2,3,4-tetrahydroquinolin-3-carboxylic acid, and
4-carboxy-4-phenyl-piperidin.

Preferably, the chemical moiety of A and B each represents an amino acid residue having a saturated carbocyclic structure of 4, 5 or 6 members comprising one or more heteroatoms, such as N and S. Said amino acids include L and D forms, natural and unnatural amino acids and derivatives thereof, such as a Prolin residue having one or more substituents in the 3, 4 or 5 position, said substituents being preferably selected from hydroxy, amino or phenyl; and N-substituted amino acids, such as Sarcosin, N-cyclohexylglycine, and N-phenylglycine.

Preferably the sequence A-B represents a dipeptide selected from the group consisting of Sar-Sar, Sar-Hyp, Hyp-Sar, Pro-Sar, Sar-Pro, Pro-Hyp, Pro-Pro, Hyp-Pro, and Hyp-Hyp, where Pro and Hyp independently may be an L or D form, where the ring structure of Pro and Hyp is optionally substituted with halogen, nitro, methyl, amino, or phenyl, and Hyp represents 3-hydroxyproline or 4-hydroxyproline, or one or both of the amino acid residues of A-B is a Sar, or N-cyclohexylglycine residue;

In one preferred embodiment of the invention, formula I represents a linear peptide wherein said chemical modification of the N-terminal of X is
- an acylation with an optionally substituted C(1-22)alkyl carboxylic acid, such as acetic acid, propionic acid, butyric acid and other fatty acids, or an optionally substituted C(2-22)alkenyl carboxylic acid, or an aryl carboxylic acid, such as benzoic acid, where the substitutent is selected from hydroxy, halogen, C(1-6)alkyl, nitro or cyano and may be situated on the carbon chain or the aromatic moiety; or
- an alkylation with an optionally substituted C(1-22)alkyl, C(2-22)alkenyl, or aryl C(1-22)alkyl, such as methyl, ethyl, propyl, butyl, phenylpropyl, 2-hydroxyphenylpropyl, and 4-hydroxyphenylpropyl, where the substitutent is selected from hydroxy, halogen, C(1-6)alkyl, nitro or cyano and may be situated on the carbon chain or the aromatic moiety.

More preferably, X is selected from the group consisting of L-Tyr and D-Tyr optionally acylated with a C(1-4)carboxylic acid, preferably acetic acid, when Y represents a C-terminal peptide sequence of from 2 to 5 amino acid residues as defined above.

It is also preferred that X represents an N-terminal modification of the group A-B, said modifications being preferably selected from phenylpropionic acid and derivatives thereof, such as 4HPP and 2HPP; phenylacetic acid and derivatives thereof, such as 4HPA, 3HPA and 2HPA; phenoxyacetic acid and derivatives thereof, such as 4HPPA, 2HPPA and 4HMPA; benzoylglycine and derivatives thereof, such as 4HBG, 3HBG and 2HBG; and phenylglycine and derivatives thereof bound via an amide bond to A.

A-B is more preferably selected from the group consisting of Pro-Hyp, Pro-Pro, Hyp-Pro, and Hyp-Hyp where Pro and Hyp independently may be an L or D form and Hyp preferably represents 4Hyp.

Preferably, Y represents a peptide of from 3 to 5 amino acid residues, or preferably 3 or 4 amino acid residues, being independently L- or D-forms, and preferably having Sar or Gly at its C-terminal, and more preferably Y represents a peptide sequence selected from the group consisting of
Gly-L-Ala-Gly-OH,
Gly-L-Ala-Gly-NH₂,
Gly-D-Ala-Gly-OH,
Gly-D-Ala-Gly-NH₂, and
Sar-Aib-Sar-OH/NH₂, when X represents a single amino acid.

Examples of linear compounds of formula I are

| | |
|---|---|
| H-Gly-Ala-Gly-Gly-Pro-Tyr-OH/NH₂, | (SEQ ID NO: 68) |
| Ac-L-Tyr-L-Pro-L-4Hyp-Gly-L-Ala- | (SEQ ID NO: 69) |
| Gly-OH/NH₂, | |
| Ac-D-Tyr-D-Pro-D-4Hyp-Gly-D-Ala- | |
| Gly-OH, | |
| Ac-D-Tyr-D-Pro-D-4Hyp-Gly-D-Ala- | |
| Gly-NH₂ (Compound 2) | |
| Ac-Tyr-Pro-4Hyp-Gly-Ala-Gly-OH | (SEQ ID NO: 70) |
| (Compound 1) | |
| Ac-Tyr-Pro-4Hyp-Gly-Ala-Gly-NH₂ | (SEQ ID NO: 71) |
| Ac-Tyr-Pro-Pro-Gly-Ala-Gly-OH/NH₂ | (SEQ ID NO: 72) |
| Ac-D-Tyr-D-Pro-D-Pro-Gly-D-Ala- | |
| Gly-OH/NH₂ | |
| Ac-Tyr-4Hyp-Pro-Gly-Ala-Gly-OH/NH₂ | (SEQ ID NO: 73) |
| Ac-D-Tyr-D-4Hyp-D-Pro-Gly-D-Ala- | |
| Gly-OH/NH₂ | |
| Ac-Tyr-4Hyp-4Hyp-Gly-Ala-Gly- | (SEQ ID NO: 74) |
| OH/NH₂ | |
| Ac-D-Tyr-D-4Hyp-D-4Hyp-Gly-D-Ala- | |
| Gly-OH/NH₂ | |
| Ac-Tyr-Sar-4Hyp-Gly-Ala-Gly-OH/NH₂ | (SEQ ID NO: 75) |
| Ac-D-Tyr-Sar-D-4Hyp-Gly-D-Ala-Gly- | |
| OH/NH₂ | |

-continued

| | |
|---|---|
| Ac-Tyr-4Hyp-Sar-Gly-Ala-Gly-OH/NH$_2$ | (SEQ ID NO: 76) |
| Ac-D-Tyr-D-4Hyp-Sar-Gly-D-Ala-Gly-OH/NH$_2$ | |
| Ac-Tyr-Pro-Sar-Gly-Ala-Gly-OH/NH$_2$ | (SEQ ID NO: 77) |
| Ac-D-Tyr-D-Pro-Sar-Gly- D-Ala-Gly-OH/NH$_2$ | |
| Ac-Tyr-Sar-Pro-Gly-Ala-Gly-OH/NH$_2$ | (SEQ ID NO: 78) |
| Ac-D-Tyr-Sar- D-Pro-Gly- D-Ala-Gly-OH/NH$_2$ | |
| Ac-Tyr-Sar-Sar-Gly-Ala-Gly-OH/NH$_2$ | (SEQ ID NO: 79) |
| Ac-D-Tyr-Sar- Sar-Gly- D-Ala-Gly-OH/NH$_2$ | |
| Tfa-L-Tyr-L-Pro-L-4Hyp-Gly-L-Ala-Gly-OH, | (SEQ ID NO: 80) |
| Tfa-D-Tyr-D-Pro-D-4Hyp-Gly-D-Ala-Gly-OH, | |
| Tfa-Tyr-Pro-4Hyp-Gly-Ala-Gly-OH | (SEQ ID NO: 81) |
| Tfa -Tyr-Pro-4Hyp-Gly-Ala-Gly-NH$_2$ | (SEQ ID NO: 82) |
| Tfa -D-Tyr-D-Pro-D-4Hyp-Gly-D-Ala-Gly-NH$_2$ | |
| Tfa -Tyr-Pro-Pro-Gly-Ala-Gly-OH/NH$_2$ | (SEQ ID NO: 83) |
| Tfa -D-Tyr-D-Pro-D-Pro-Gly-D-Ala-Gly-OH/NH$_2$ | |
| Tfa -Tyr-4Hyp-Pro-Gly-Ala-Gly-OH/NH$_2$ | (SEQ ID NO: 84) |
| Tfa -D-Tyr-D-4Hyp-D-Pro-Gly-D-Ala-Gly-OH/NH$_2$ | |
| Tfa -Tyr-4Hyp-4Hyp-Gly-Ala-Gly-OH/NH$_2$ | (SEQ ID NO: 85) |
| Tfa -D-Tyr-D-4Hyp-D-4Hyp-Gly-D-Ala-Gly-OH/NH$_2$ | |
| Tfa -Tyr-Sar-4Hyp-Gly-Ala-Gly-OH/NH$_2$ | (SEQ ID NO: 86) |
| Tfa -D-Tyr-Sar-D-4Hyp-Gly-D-Ala-Gly-OH/NH$_2$ | |
| Tfa -Tyr-4Hyp-Sar-Gly-Ala-Gly-OH/NH$_2$ | (SEQ ID NO: 87) |
| Tfa -D-Tyr-D-4Hyp-Sar-Gly-D-Ala-Gly-OH/NH$_2$ | |
| Tfa -Tyr-Pro-Sar-Gly-Ala-Gly-OH/NH$_2$ | (SEQ ID NO: 88) |
| Tfa -D-Tyr-D-Pro-Sar-Gly -D-Ala-Gly-OH/NH$_2$ | |
| Tfa -Tyr-Sar-Pro-Gly-Ala-Gly-OH/NH$_2$ | (SEQ ID NO: 89) |
| Tfa -D-Tyr-Sar- D-Pro-Gly- D-Ala-Gly-OH/NH$_2$ | |
| Tfa -Tyr-Sar-Sar-Gly-Ala-Gly-OH/NH$_2$ | (SEQ ID NO: 90) |
| Tfa -D-Tyr-Sar- Sar-Gly- D-Ala-Gly-OH/NH$_2$ | |
| 4HPP-D-Pro- D-4Hyp-Gly-D-Ala-Gly-OH/NH$_2$ | |
| 4HPPA-Pro-4Hyp-Gly-Ala-Gly-OH/NH$_2$ | (SEQ ID NO: 91) |
| 4HPPA-D-Pro- D-4Hyp-Gly-D-Ala-Gly-OH/NH$_2$ | |
| 4HMPA-Pro-4Hyp-Gly-Ala-Gly-OH/NH$_2$ | (SEQ ID NO: 92) |
| 4HMPA-D-Pro- D-4Hyp-Gly-D-Ala-Gly-OH/NH$_2$ | |
| 4HPA-Pro-4Hyp-Gly-Ala-Gly-OH/NH$_2$ | (SEQ ID NO: 93) |
| 4HPA-D-Pro- D-4Hyp-Gly-D-Ala-Gly-OH/NH$_2$ | |
| 4HBG-Pro-4Hyp-Gly-Ala-Gly-OH/NH$_2$ | (SEQ ID NO: 94) |
| 4HBG-D-Pro- D-4Hyp-Gly-D-Ala-Gly-OH/NH$_2$ | |
| 4HPP-Pro-Pro-Gly-Ala-Gly-OH/NH$_2$ | (SEQ ID NO: 95) |
| 4HPP-D-Pro- D-Pro-Gly-D-Ala-Gly-OH/NH$_2$ | |
| 4HPPA-Pro-Pro-Gly-Ala-Gly-OH/NH$_2$ | (SEQ ID NO: 96) |
| 4HPPA-D-Pro- D-Pro-Gly-D-Ala-Gly-OH/NH$_2$ | |
| 4HMPA-Pro-Pro-Gly-Ala-Gly-OH/NH$_2$ | (SEQ ID NO: 97) |
| 4HMPA-D-Pro- D-Pro-Gly-D-Ala-Gly-OH/NH$_2$ | |
| 4HPA-Pro-Pro-Gly-Ala-Gly-OH/NH$_2$ | (SEQ ID NO: 98) |
| 4HPA-D-Pro- D-Pro-Gly-D-Ala-Gly-OH/NH$_2$ | |

-continued

| | |
|---|---|
| 4HBG-Pro-Pro-Gly-Ala-Gly-OH/NH$_2$ | (SEQ ID NO: 99) |
| 4HBG-D-Pro- D-Pro-Gly-D-Ala-Gly-OH/NH$_2$ | |
| 4HPP-4Hyp-4Hyp-Gly-Ala-Gly-OH/NH$_2$ | |
| 4HPP-D-4Hyp- D-4Hyp-Gly-D-Ala-Gly-OH/NH$_2$ | |
| 4HPPA-4Hyp-4Hyp-Gly-Ala-Gly-OH/NH$_2$ | |
| 4HPPA-D-4Hyp- D-4Hyp-Gly-D-Ala-Gly-OH/NH$_2$ | |
| 4HMPA-4Hyp-4Hyp-Gly-Ala-Gly-OH/NH$_2$ | |
| 4HMPA-D-4Hyp- D-4Hyp-Gly-D-Ala-Gly-OH/NH$_2$ | |
| 4HPA-4Hyp-4Hyp-Gly-Ala-Gly-OH/NH$_2$ | |
| 4HPA-D-4Hyp- D-4Hyp-Gly-D-Ala-Gly-OH/NH$_2$ | |
| 4HBG-4Hyp-4Hyp-Gly-Ala-Gly-OH/NH$_2$ | |
| 4HBG-D-4Hyp- D-4Hyp-Gly-D-Ala-Gly-OH/NH$_2$ | |
| 4HPP-4Hyp-Pro-Gly-Ala-Gly-OH/NH$_2$ | (SEQ ID NO: 100) |
| 4HPP-D-4Hyp- D-Pro-Gly-D-Ala-Gly-OH/NH$_2$ | |
| 4HPPA-4Hyp-Pro-Gly-Ala-Gly-OH/NH$_2$ | (SEQ ID NO: 101) |
| 4HPPA-D-4Hyp- D-Pro-Gly-D-Ala-Gly-OH/NH$_2$ | |
| 4HMPA-4Hyp-Pro-Gly-Ala-Gly-OH/NH$_2$ | (SEQ ID NO: 102) |
| 4HMPA-D-4Hyp- D-Pro-Gly-D-Ala-Gly-OH/NH$_2$ | |
| 4HPA-4Hyp-Pro-Gly-Ala-Gly-OH/NH$_2$ | (SEQ ID NO: 103) |
| 4HPA-D-4Hyp- D-Pro-Gly-D-Ala-Gly-OH/NH$_2$ | |
| 4HBG-4Hyp-Pro-Gly-Ala-Gly-OH/NH$_2$ | (SEQ ID NO: 104) |
| 4HBG-D-4Hyp- D-Pro-Gly-D-Ala-Gly-OH/NH$_2$ | |
| 4HPP-Sar-Pro-Gly-Ala-Gly-OH/NH$_2$ | (SEQ ID NO: 105) |
| 4HPP-Sar- D-Pro-Gly-D-Ala-Gly-OH/NH$_2$ | |
| 4HPPA-Sar-Pro-Gly-Ala-Gly-OH/NH$_2$ | (SEQ ID NO: 106) |
| 4HPPA-Sar- D-Pro-Gly-D-Ala-Gly-OH/NH$_2$ | |
| 4HMPA-Sar-Pro-Gly-Ala-Gly-OH/NH$_2$ | (SEQ ID NO: 107) |
| 4HMPA-Sar- D-Pro-Gly-D-Ala-Gly-OH/NH$_2$ | |
| 4HPA-Sar-Pro-Gly-Ala-Gly-OH/NH$_2$ | (SEQ ID NO: 108) |
| 4HPA-Sar- D-Pro-Gly-D-Ala-Gly-OH/NH$_2$ | |
| 4HBG-Sar-Pro-Gly-Ala-Gly-OH/NH$_2$ | (SEQ ID NO: 109) |
| 4HBG-Sar- D-Pro-Gly-D-Ala-Gly-OH/NH$_2$ | |
| 4HPP-Pro-Sar-Gly-Ala-Gly-OH/NH$_2$ | (SEQ ID NO: 110) |
| 4HPP-D-Pro- Sar-Gly-D-Ala-Gly-OH/NH$_2$ | |
| 4HPPA-Pro-Sar-Gly-Ala-Gly-OH/NH$_2$ | (SEQ ID NO: 111) |
| 4HPPA-D-Pro- Sar-Gly-D-Ala-Gly-OH/NH$_2$ | |
| 4HMPA-Pro-Sar-Gly-Ala-Gly-OH/NH$_2$ | (SEQ ID NO: 112) |
| 4HMPA-D-Pro- Sar-Gly-D-Ala-Gly-OH/NH$_2$ | |
| 4HPA-Pro-Sar-Gly-Ala-Gly-OH/NH$_2$ | (SEQ ID NO: 113) |
| 4HPA-D-Pro- Sar-Gly-D-Ala-Gly-OH/NH$_2$ | |
| 4HBG-Pro-Sar-Gly-Ala-Gly-OH/NH$_2$ | (SEQ ID NO: 114) |
| 4HBG-D-Pro- Sar-Gly-D-Ala-Gly-OH/NH$_2$ | |
| 4HPP-Sar-4Hyp-Gly-Ala-Gly-OH/NH$_2$ | |
| 4HPP-Sar- D-4Hyp-Gly-D-Ala-Gly-OH/NH$_2$ | |
| 4HPPA-Sar-4Hyp-Gly-Ala-Gly-OH/NH$_2$ | |
| 4HPPA-Sar- D-4Hyp-Gly-D-Ala-Gly-OH/NH$_2$ | |
| 4HMPA-Sar-4Hyp-Gly-Ala-Gly-OH/NH$_2$ | |
| 4HMPA-Sar- D-4Hyp-Gly-D-Ala-Gly-OH/NH$_2$ | |
| 4HPA-Sar-4Hyp-Gly-Ala-Gly-OH/NH$_2$ | |
| 4HPA-Sar- D-4Hyp-Gly-D-Ala-Gly-OH/NH$_2$ | |
| 4HBG-Sar-4Hyp-Gly-Ala-Gly-OH/NH$_2$ | |
| 4HBG-Sar- D-4Hyp-Gly-D-Ala-Gly-OH/NH$_2$ | |

-continued

4HPP-4Hyp-Sar-Gly-Ala-Gly-OH/NH$_2$
4HPP-D-4Hyp- Sar-Gly-D-Ala-Gly-OH/NH$_2$
4HPPA-4Hyp-Sar-Gly-Ala-Gly-OH/NH$_2$
4HPPA-D-4Hyp- Sar-Gly-D-Ala-Gly-OH/NH$_2$
4HMPA-4Hyp-Sar-Gly-Ala-Gly-OH/NH$_2$
4HMPA-D-4Hyp- Sar-Gly-D-Ala-Gly-OH/NH$_2$
4HPA-4Hyp-Sar-Gly-Ala-Gly-OH/NH$_2$
4HPA-D-4Hyp- Sar-Gly-D-Ala-Gly-OH/NH$_2$
4HBG-4Hyp-Sar-Gly-Ala-Gly-OH/NH$_2$
4HBG-D-4Hyp- Sar-Gly-D-Ala-Gly-OH/NH$_2$
4HPP-Sar-Sar-Gly-Ala-Gly-OH/NH$_2$
4HPP-Sar- Sar-Gly-D-Ala-Gly-OH/NH$_2$
4HPPA-Sar-Sar-Gly-Ala-Gly-OH/NH$_2$
4HPPA-Sar- Sar-Gly-D-Ala-Gly-OH/NH$_2$
4HMPA-Sar-Sar-Gly-Ala-Gly-OH/NH$_2$
4HMPA-Sar- Sar-Gly-D-Ala-Gly-OH/NH$_2$
4HPA-Sar-Sar-Gly-Ala-Gly-OH/NH$_2$
4HPA-Sar- Sar-Gly-D-Ala-Gly-OH/NH$_2$
4HBG-Sar-Sar-Gly-Ala-Gly-OH/NH$_2$
4HBG-Sar- Sar-Gly-D-Ala-Gly-OH/NH$_2$
Ac-Tyr-Pro-4Hyp-Sar-Ala-Sar-OH/NH$_2$
Ac-D-Tyr- D-Pro- D-4Hyp-Sar- D-Ala-Sar-OH/NH$_2$
Ac-Tyr-Pro-Pro-Sar-Ala-Sar-OH/NH$_2$ (SEQ ID NO: 115)
Ac-D-Tyr- D-Pro- D-Pro-Sar- D-Ala-Sar-OH/NH$_2$
Ac-Tyr-4Hyp-Pro-Sar-Ala-Sar-OH/NH$_2$
Ac-D-Tyr- D-4Hyp- D-Pro-Sar- D-Ala-Sar-OH/NH$_2$
Ac-Tyr-4Hyp-4Hyp-Sar-Ala-Sar-OH/NH$_2$
Ac-D-Tyr- D-4Hyp- D-4Hyp-Sar- D-Ala-Sar-OH/NH$_2$
Ac-Tyr-Sar-4Hyp-Sar-Ala-Sar-OH/NH$_2$
Ac-D-Tyr-Sar- D-4Hyp-Sar- D-Ala-Sar-OH/NH$_2$
Ac-Tyr-4Hyp-Sar-Sar-Ata-Sar-OH/NH$_2$
Ac-D-Tyr- D-4Hyp-Sar-Sar- D-Ala-Sar-OH/NH$_2$
Ac-Tyr-Pro-Sar-Sar-Ala-Sar-OH/NH$_2$
Ac-D-Tyr- D-Pro-Sar-Sar- D-Ala-Sar-OH/NH$_2$
Ac-Tyr-Sar-Pro-Sar-Ala-Sar-OH/NH$_2$
Ac-D-Tyr- Sar- D-Pro-Sar- D-Ala-Sar-OH/NH$_2$
Tfa-Tyr-Pro-4Hyp-Sar-Ala-Sar-OH/NH$_2$
Tfa -D-Tyr- D-Pro- D-4Hyp-Sar- D-Ala-Sar-OH/NH$_2$
Tfa -Tyr-Pro-Pro-Sar-Ala-Sar-OH/NH$_2$ (SEQ ID NO: 116)
Tfa -D-Tyr- D-Pro- D-Pro-Sar- D-Ala-Sar-OH/NH$_2$
Tfa -Tyr-4Hyp-Pro-Sar-Ala-Sar-OH/NH$_2$
Tfa -D-Tyr- D-4Hyp- D-Pro-Sar- D-Ala-Sar-OH/NH$_2$
Tfa -Tyr-4Hyp-4Hyp-Sar-Ala-Sar-OH/NH$_2$
Tfa -D-Tyr- D-4Hyp- D-4Hyp-Sar- D-Ala-Sar-OH/NH$_2$
Tfa -Tyr-Sar-4Hyp-Sar-Ala-Sar-OH/NH$_2$
Tfa -D-Tyr-Sar- D-4Hyp-Sar- D-Ala-Sar-OH/NH$_2$
Tfa -Tyr-4Hyp-Sar-Sar-Ala-Sar-OH/NH$_2$
Tfa -D-Tyr- D-4Hyp-Sar-Sar- D-Ala-Sar-OH/NH$_2$
Tfa -Tyr-Pro-Sar-Sar-Ala-Sar-OH/NH$_2$

Tfa-D-Tyr-D-Pro-Sar-Sar-D-Ala-Sar-OH/NH$_2$
Tfa-Tyr-Sar-Pro-Sar-Ala-Sar-OH/NH$_2$
Tfa-D-Tyr-Sar-D-Pro-Sar-D-Ala-Sar-OH/NH$_2$
4HPP-Pro-4Hyp-Sar-Ala-Sar-OH/NH$_2$
4HPP-D-Pro-D-4Hyp-Sar-D-Ala-Sar-OH/NH$_2$
4HPPA-Pro-4Hyp-Sar-Ala-Sar-OH/NH$_2$
4HPPA-D-Pro-D-4Hyp-Sar-D-Ala-Sar-OH/NH$_2$
4HMPA-Pro-4Hyp-Sar-Ala-Sar-OH/NH$_2$
4HMPA-D-Pro-D-4Hyp-Sar-D-Ala-Sar-OH/NH$_2$
4HPA-Pro-4Hyp-Sar-Ala-Sar-OH/NH$_2$
4HPA-D-Pro-D-4Hyp-Sar-D-Ala-Sar-OH/NH$_2$
4HBG-Pro-4Hyp-Sar-Ala-Sar-OH/NH$_2$
4HBG-D-Pro-D-4Hyp-Sar-D-Ala-Sar-OH/NH$_2$
4HPP-Pro-Pro-Sar-Ala-Sar-OH/NH$_2$
4HPP-D-Pro-D-Pro-Sar-D-Ala-Sar-OH/NH$_2$
4HPPA-Pro-Pro-Sar-Ala-Sar-OH/NH$_2$
4HPPA-D-Pro-D-Pro-Sar-D-Ala-Sar-OH/NH$_2$
4HMPA-Pro-Pro-Sar-Ala-Sar-OH/NH$_2$
4HMPA-D-Pro-D-Pro-Sar-D-Ala-Sar-OH/NH$_2$
4HPA-Pro-Pro-Sar-Ala-Sar-OH/NH$_2$
4HPA-D-Pro-D-Pro-Sar-D-Ala-Sar-OH/NH$_2$
4HBG-Pro-Pro-Sar-Ala-Sar-OH/NH$_2$
4HBG-D-Pro-D-Pro-Sar-D-Ala-Sar-OH/NH$_2$
4HPP-4Hyp-4Hyp-Sar-Ala-Sar-OH/NH$_2$
4HPP-D-4Hyp-D-4Hyp-Sar-D-Ala-Sar-OH/NH$_2$
4HPPA-4Hyp-4Hyp-Sar-Ala-Sar-OH/NH$_2$
4HPPA-D-4Hyp-D-4Hyp-Sar-D-Ala-Sar-OH/NH$_2$
4HMPA-4Hyp-4Hyp-Sar-Ala-Sar-OH/NH$_2$
4HMPA-D-4Hyp-D-4Hyp-Sar-D-Ala-Sar-OH/NH$_2$
4HPA-4Hyp-4Hyp-Sar-Ala-Sar-OH/NH$_2$
4HPA-D-4Hyp-D-4Hyp-Sar-D-Ala-Sar-OH/NH$_2$
4HBG-4Hyp-4Hyp-Sar-Ala-Sar-OH/NH$_2$
4HBG-D-4Hyp-D-4Hyp-Sar-D-Ala-Sar-OH/NH$_2$
4HPP-4Hyp-Pro-Sar-Ala-Sar-OH/NH$_2$
4HPP-D-4Hyp-D-Pro-Sar-D-Ala-Sar-OH/NH$_2$
4HPPA-4Hyp-Pro-Sar-Ala-Sar-OH/NH$_2$
4HPPA-D-4Hyp-D-Pro-Sar-D-Ala-Sar-OH/NH$_2$
4HMPA-4Hyp-Pro-Sar-Ala-Sar-OH/NH$_2$
4HMPA-D-4Hyp-D-Pro-Sar-D-Ala-Sar-OH/NH$_2$
4HPA-4Hyp-Pro-Sar-Ala-Sar-OH/NH$_2$
4HPA-D-4Hyp-D-Pro-Sar-D-Ala-Sar-OH/NH$_2$
4HBG-4Hyp-Pro-Sar-Ala-Sar-OH/NH$_2$
4HBG-D-4Hyp-D-Pro-Sar-D-Ala-Sar-OH/NH$_2$
4HPP-Sar-Pro-Sar-Ala-Sar-OH/NH$_2$
4HPP-Sar-D-Pro-Sar-D-Ala-Sar-OH/NH$_2$
4HPPA-Sar-Pro-Sar-Ala-Sar-OH/NH$_2$
4HPPA-Sar-D-Pro-Sar-D-Ala-Sar-OH/NH$_2$
4HMPA-Sar-Pro-Sar-Ala-Sar-OH/NH$_2$
4HMPA-Sar-D-Pro-Sar-D-Ala-Sar-OH/NH$_2$
4HPA-Sar-Pro-Sar-Ala-Sar-OH/NH$_2$
4HPA-Sar-D-Pro-Sar-D-Ala-Sar-OH/NH$_2$

4HBG-Sar-Pro-Sar-Ala-Sar-OH/NH₂

4HBG- Sar- D-Pro-Sar-D-Ala-Sar-OH/NH₂

4HPP-Pro-Sar-Sar-Ala-Sar-OH/NH₂

4HPP- D-Pro- Sar-Sar-D-Ala-Sar-OH/NH₂

4HPPA-Pro-Sar-Sar-Ala-Sar-OH/NH₂

4HPPA- D-Pro- Sar-Sar-D-Ala-Sar-OH/NH₂

4HMPA-Pro-Sar-Sar-Ala-Sar-OH/NH₂

4HMPA- D-Pro- Sar-Sar-D-Ala-Sar-OH/NH₂

4HPA-Pro-Sar-Sar-Ala-Sar-OH/NH₂

4HPA- D-Pro- Sar-Sar-D-Ala-Sar-OH/NH₂

4HBG-Pro-Sar-Sar-Ala-Sar-OH/NH₂

4HBG- D-Pro- Sar-Sar-D-Ala-Sar-OH/NH₂

4HPP-Sar-4Hyp-Sar-Ala-Sar-OH/NH₂

4HPP- Sar- D-4Hyp-Sar-D-Ala-Sar-OH/NH₂

4HPPA-Sar-4Hyp-Sar-Ala-Sar-OH/NH₂

4HPPA- Sar- D-4Hyp-Sar-D-Ala-Sar-OH/NH₂

4HMPA-Sar-4Hyp-Sar-Ala-Sar-OH/NH₂

4HMPA- Sar- D-4Hyp-Sar-D-Ala-Sar-OH/NH₂

4HPA-Sar-4Hyp-Sar-Ala-Sar-OH/NH₂

4HPA- Sar- D-4Hyp-Sar-D-Ala-Sar-OH/NH₂

4HBG-Sar-4Hyp-Sar-Ala-Sar-OH/NH₂

4HBG- Sar- D-4Hyp-Sar-D-Ala-Sar-OH/NH₂

4HPP-4Hyp-Sar-Sar-Ala-Sar-OH/NH₂

4HPP- D-4Hyp- Sar-Sar-D-Ala-Sar-OH/NH₂

4HPPA-4Hyp-Sar-Sar-Ala-Sar-OH/NH₂

4HPPA- D-4Hyp- Sar-Sar-D-Ala-Sar-OH/NH₂

4HMPA-4Hyp-Sar-Sar-Ala-Sar-OH/NH₂

4HMPA- D-4Hyp- Sar-Sar-D-Ala-Sar-OH/NH₂

4HPA-4Hyp-Sar-Sar-Ala-Sar-OH/NH₂

4HPA- D-4Hyp- Sar-Sar-D-Ala-Sar-OH/NH₂

4HBG-4Hyp-Sar-Sar-Ala-Sar-OH/NH₂

4HBG- D-4Hyp- Sar-Sar-D-Ala-Sar-OH/NH₂

4HPP-Sar-Sar-Sar-Ala-Sar-OH/NH₂

4HPP- Sar- Sar-Sar-D-Ala-Sar-OH/NH₂

4HPPA-Sar-Sar-Sar-Ala-Sar-OH/NH₂

4HPPA- Sar- Sar-Sar-D-Ala-Sar-OH/NH₂

4HMPA-Sar-Sar-Sar-Ala-Sar-OH/NH₂

4HMPA- Sar- Sar-Sar-D-Ala-Sar-OH/NH₂

4HPA-Sar-Sar-Sar-Ala-Sar-OH/NH₂

4HPA- Sar- Sar-Sar-D-Ala-Sar-OH/NH₂

4HBG-Sar-Sar-Sar-Ala-Sar-OH/NH₂

4HBG- Sar- Sar-Sar-D-Ala-Sar-OH/NH₂

Ac-Tyr-Pro-4Hyp-Sar-Ala-Gly-OH/NH₂ (SEQ ID NO: 117)

Ac-D-Tyr- D-Pro- D-4Hyp-Sar- D-Ala-Gly-OH/NH₂

Ac-Tyr-Pro-Pro-Sar-Ala-Gly-OH/NH₂ (SEQ ID NO: 118)

Ac-D-Tyr- D-Pro- D-Pro-Sar- D-Ala-Gly-OH/NH₂

Ac-Tyr-4Hyp-Pro-Sar-Ala-Gly-OH/NH₂ (SEQ ID NO: 119)

Ac-D-Tyr- D-4Hyp- D-Pro-Sar- D-Ala-Gly-OH/NH₂

Ac-Tyr-4Hyp-4Hyp-Sar-Ala-Gly-OH/NH₂

Ac-D-Tyr- D-4Hyp- D-4Hyp-Sar- D-Ala-Gly-OH/NH₂

Ac-Tyr-Sar-4Hyp-Sar-Ala-Gly-OH/NH₂

Ac-D-Tyr-Sar- D-4Hyp-Sar- D-Ala-Gly-OH/NH₂

Ac-Tyr-4Hyp-Sar-Sar-Ala-Gly-OH/NH$_2$
Ac-D-Tyr- D-4Hyp-Sar-Sar- D-Ala-Gly-OH/NH$_2$
Ac-Tyr-Pro-Sar-Sar-Ala-Gly-OH/NH$_2$ (SEQ ID NO: 120)
Ac-D-Tyr- D-Pro-Sar-Sar- D-Ala-Gly-OH/NH$_2$
Ac-Tyr-Sar-Pro-Sar-Ala-Gly-OH/NH$_2$ (SEQ ID NO: 121)
Ac-D-Tyr- Sar- D-Pro-Sar- D-Ala-Gly-OH/NH$_2$
Tfa-Tyr-Pro-4Hyp-Sar-Ala-Gly-OH/NH$_2$ (SEQ ID NO: 122)
Tfa -D-Tyr- D-Pro- D-4Hyp-Sar- D-Ala-Gly-OH/NH$_2$
Tfa -Tyr-Pro-Pro-Sar-Ala-Gly-OH/NH$_2$ (SEQ ID NO: 123)
Tfa -D-Tyr- D-Pro- D-Pro-Sar- D-Ala-Gly-OH/NH$_2$
Tfa -Tyr-4Hyp-Pro-Sar-Ala-Gly-OH/NH$_2$ (SEQ ID NO: 124)
Tfa -D-Tyr- D-4Hyp- D-Pro-Sar- D-Ala-Gly-OH/NH$_2$
Tfa -Tyr-4Hyp-4Hyp-Sar-Ala-Gly-OH/NH$_2$
Tfa -D-Tyr- D-4Hyp- D-4Hyp-Sar- D-Ala-Gly-OH/NH$_2$
Tfa -Tyr-Sar-4Hyp-Sar-Ala-Gly-OH/NH$_2$
Tfa -D-Tyr-Sar- D-4Hyp-Sar- D-Ala-Gly-OH/NH$_2$
Tfa -Tyr-4Hyp-Sar-Sar-Ala-Gly-OH/NH$_2$
Tfa -D-Tyr- D-4Hyp-Sar-Sar- D-Ala-Gly-OH/NH$_2$
Tfa -Tyr-Pro-Sar-Sar-Ala-Gly-OH/NH$_2$ (SEQ ID NO: 125)
Tfa -D-Tyr- D-Pro-Sar-Sar- D-Ala-Gly-OH/NH$_2$
Tfa -Tyr-Sar-Pro-Sar-Ala-Gly-OH/NH$_2$ (SEQ ID NO: 126)
Tfa -D-Tyr- Sar- D-Pro-Sar- D-Ala-Gly-OH/NH$_2$
4HPP-Pro-4Hyp-Sar-Ala-Gly-OH/NH$_2$
4HPP- D-Pro- D-4Hyp-Sar-D-Ala-Gly-OH/NH$_2$
4HPPA-Pro-4Hyp-Sar-Ala-Gly-OH/NH$_2$
4HPPA- D-Pro- D-4Hyp-Sar-D-Ala-Gly-OH/NH$_2$
4HMPA-Pro-4Hyp-Sar-Ala-Gly-OH/NH$_2$
4HMPA- D-Pro- D-4Hyp-Sar-D-Ala-Gly-OH/NH$_2$
4HPA-Pro-4Hyp-Sar-Ala-Gly-OH/NH$_2$
4HPA- D-Pro- D-4Hyp-Sar-D-Ala-Gly-OH/NH$_2$
4HBG-Pro-4Hyp-Sar-Ala-Gly-OH/NH$_2$
4HBG- D-Pro- D-4Hyp-Sar-D-Ala-Gly-OH/NH$_2$
4HPP-Pro-Pro-Sar-Ala-Gly-OH/NH$_2$ (SEQ ID NO: 127)
4HPP- D-Pro- D-Pro-Sar-D-Ala-Gly-OH/NH$_2$
4HPPA-Pro-Pro-Sar-Ala-Gly-OH/NH$_2$ (SEQ ID NO: 128)
4HPPA- D-Pro- D-Pro-Sar-D-Ala-Gly-OH/NH$_2$
4HMPA-Pro-Pro-Sar-Ala-Gly-OH/NH$_2$ (SEQ ID NO: 129)
4HMPA- D-Pro- D-Pro-Sar-D-Ala-Gly-OH/NH$_2$
4HPA-Pro-Pro-Sar-Ala-Gly-OH/NH$_2$ (SEQ ID NO: 130)
4HPA- D-Pro- D-Pro-Sar-D-Ala-Gly-OH/NH$_2$
4HBG-Pro-Pro-Sar-Ala-Gly-OH/NH$_2$ (SEQ ID NO: 131)
4HBG- D-Pro- D-Pro-Sar-D-Ala-Gly-OH/NH$_2$
4HPP-4Hyp-4Hyp-Sar-Ala-Gly-OH/NH$_2$
4HPP- D-4Hyp- D-4Hyp-Sar-D-Ala-Gly-OH/NH$_2$
4HPPA-4Hyp-4Hyp-Sar-Ala-Gly-OH/NH$_2$
4HPPA- D-4Hyp- D-4Hyp-Sar-D-Ala-Gly-OH/NH$_2$
4HMPA-4Hyp-4Hyp-Sar-Ala-Gly-OH/NH$_2$
4HMPA- D-4Hyp- D-4Hyp-Sar-D-Ala-Gly-OH/NH$_2$

4HPA-4Hyp-4Hyp-Sar-Ala-Gly-OH/NH$_2$

4HPA- D-4Hyp- D-4Hyp-Sar-D-Ala-Gly-OH/NH$_2$

4HBG-4Hyp-4Hyp-Sar-Ala-Gly-OH/NH$_2$

4HBG- D-4Hyp- D-4Hyp-Sar-D-Ala-Gly-OH/NH$_2$

4HPP-4Hyp-Pro-Sar-Ala-Gly-OH/NH$_2$

4HPP- D-4Hyp- D-Pro-Sar-D-Ala-Gly-OH/NH$_2$

4HPPA-4Hyp-Pro-Sar-Ala-Gly-OH/NH$_2$

4HPPA- D-4Hyp- D-Pro-Sar-D-Ala-Gly-OH/NH$_2$

4HMPA-4Hyp-Pro-Sar-Ala-Gly-OH/NH$_2$

4HMPA- D-4Hyp- D-Pro-Sar-D-Ala-Gly-OH/NH$_2$

4HPA-4Hyp-Pro-Sar-Ala-Gly-OH/NH$_2$

4HPA- D-4Hyp- D-Pro-Sar-D-Ala-Gly-OH/NH$_2$

4HBG-4Hyp-Pro-Sar-Ala-Gly-OH/NH$_2$

4HBG- D-4Hyp- D-Pro-Sar-D-Ala-Gly-OH/NH$_2$

4HPP-Sar-Pro-Sar-Ala-Gly-OH/NH$_2$

4HPP- Sar- D-Pro-Sar-D-Ala-Gly-OH/NH$_2$

4HPPA-Sar-Pro-Sar-Ala-Gly-OH/NH$_2$

4HPPA- Sar- D-Pro-Sar-D-Ala-Gly-OH/NH$_2$

4HMPA-Sar-Pro-Sar-Ala-Gly-OH/NH$_2$

4HMPA- Sar- D-Pro-Sar-D-Ala-Gly-OH/NH$_2$

4HPA-Sar-Pro-Sar-Ala-Gly-OH/NH$_2$

4HPA- Sar- D-Pro-Sar-D-Ala-Gly-OH/NH$_2$

4HBG-Sar-Pro-Sar-Ala-Gly-OH/NH$_2$

4HBG- Sar- D-Pro-Sar-D-Ala-Gly-OH/NH$_2$

4HPP-Pro-Sar-Sar-Ala-Gly-OH/NH$_2$

4HPP- D-Pro- Sar-Sar-D-Ala-Gly-OH/NH$_2$

4HPPA-Pro-Sar-Sar-Ala-Gly-OH/NH$_2$

4HPPA- D-Pro- Sar-Sar-D-Ala-Gly-OH/NH$_2$

4HMPA-Pro-Sar-Sar-Ala-Gly-OH/NH$_2$

4HMPA- D-Pro- Sar-Sar-D-Ala-Gly-OH/NH$_2$

4HPA-Pro-Sar-Sar-Ala-Gly-OH/NH$_2$

4HPA- D-Pro- Sar-Sar-D-Ala-Gly-OH/NH$_2$

4HBG-Pro-Sar-Sar-Ala-Gly-OH/NH$_2$

4HBG- D-Pro- Sar-Sar-D-Ala-Gly-OH/NH$_2$

4HPP-Sar-4Hyp-Sar-Ala-Gly-OH/NH$_2$

4HPP- Sar- D-4Hyp-Sar-D-Ala-Gly-OH/NH$_2$

4HPPA-Sar-4Hyp-Sar-Ala-Gly-OH/NH$_2$

4HPPA- Sar- D-4Hyp-Sar-D-Ala-Gly-OH/NH$_2$

4HMPA-Sar-4Hyp-Sar-Ala-Gly-OH/NH$_2$

4HMPA- Sar- D-4Hyp-Sar-D-Ala-Gly-OH/NH$_2$

4HPA-Sar-4Hyp-Sar-Ala-Gly-OH/NH$_2$

4HPA- Sar- D-4Hyp-Sar-D-Ala-Gly-OH/NH$_2$

4HBG-Sar-4Hyp-Sar-Ala-Gly-OH/NH$_2$

4HBG- Sar- D-4Hyp-Sar-D-Ala-Gly-OH/NH$_2$

4HPP-4Hyp-Sar-Sar-Ala-Gly-OH/NH$_2$

4HPP- D-4Hyp- Sar-Sar-D-Ala-Gly-OH/NH$_2$

4HPPA-4Hyp-Sar-Sar-Ala-Gly-OH/NH$_2$

4HPPA- D-4Hyp- Sar-Sar-D-Ala-Gly-OH/NH$_2$

4HMPA-4Hyp-Sar-Sar-Ala-Gly-OH/NH$_2$

4HMPA- D-4Hyp- Sar-Sar-D-Ala-Gly-OH/NH$_2$

4HPA-4Hyp-Sar-Sar-Ala-Gly-OH/NH$_2$

4HPA- D-4Hyp- Sar-Sar-D-Ala-Gly-OH/NH$_2$

4HBG-4Hyp-Sar-Sar-Ala-Gly-OH/NH$_2$
4HBG- D-4Hyp- Sar-Sar-D-Ala-Gly-OH/NH$_2$
Ac-Tyr-Pro-4Hyp-Gly-Ala-Sar-OH/NH$_2$ (SEQ ID NO: 132)
Ac-D-Tyr- D-Pro- D-4Hyp-Gly- D-Ala-Sar-OH/NH$_2$
Ac-Tyr-Pro-Pro-Gly-Ala-Sar-OH/NH$_2$ (SEQ ID NO: 133)
Ac-D-Tyr- D-Pro- D-Pro-Gly- D-Ala-Sar-OH/NH$_2$
Ac-Tyr-4Hyp-Pro-Gly-Ala-Sar-OH/NH$_2$ (SEQ ID NO: 134)
Ac-D-Tyr- D-4Hyp- D-Pro-Gly- D-Ala-Sar-OH/NH$_2$
Ac-Tyr-4Hyp-4Hyp-Gly-Ala-Sar-OH/NH$_2$
Ac-D-Tyr- D-4Hyp- D-4Hyp-Gly- D-Ala-Sar-OH/NH$_2$
Ac-Tyr-Sar-4Hyp-Gly-Ala-Sar-OH/NH$_2$
Ac-D-Tyr-Sar- D-4Hyp-Gly- D-Ala-Sar-OH/NH$_2$
Ac-Tyr-4Hyp-Sar-Gly-Ala-Sar-OH/NH$_2$
Ac-D-Tyr- D-4Hyp-Sar-Gly- D-Ala-Sar-OH/NH$_2$
Ac-Tyr-Pro-Sar-Gly-Ala-Sar-OH/NH$_2$ (SEQ ID NO: 135)
Ac-D-Tyr- D-Pro-Sar-Gly- D-Ala-Sar-OH/NH$_2$
Ac-Tyr-Sar-Pro-Gly-Ala-Sar-OH/NH$_2$ (SEQ ID NO: 136)
Ac-D-Tyr- Sar- D-Pro-Gly- D-Ala-Sar-OH/NH$_2$
Ac-Tyr-Sar-Sar-Gly-Ala-Sar-OH/NH$_2$
Ac-D-Tyr- Sar- Sar-Gly- D-Ala-Sar-OH/NH$_2$
Tfa -Tyr-Pro-4Hyp-Gly-Ala-Sar-OH/NH$_2$ (SEQ ID NO: 137)
Tfa -D-Tyr- D-Pro- D-4Hyp-Gly- D-Ala-Sar-OH/NH$_2$
Tfa -Tyr-Pro-Pro-Gly-Ala-Sar-OH/NH$_2$ (SEQ ID NO: 138)
Tfa -D-Tyr- D-Pro- D-Pro-Gly- D-Ala-Sar-OH/NH$_2$
Tfa -Tyr-4Hyp-Pro-Gly-Ala-Sar-OH/NH$_2$ (SEQ ID NO: 139)
Tfa -D-Tyr- D-4Hyp- D-Pro-Gly- D-Ala-Sar-OH/NH$_2$
Tfa -Tyr-4Hyp-4Hyp-Gly-Ala-Sar-OH/NH$_2$
Tfa -D-Tyr- D-4Hyp- D-4Hyp-Gly- D-Ala-Sar-OH/NH$_2$
Tfa -Tyr-Sar-4Hyp-Gly-Ala-Sar-OH/NH$_2$
Tfa -D-Tyr-Sar- D-4Hyp-Gly- D-Ala-Sar-OH/NH$_2$
Tfa -Tyr-4Hyp-Sar-Gly-Ala-Sar-OH/NH$_2$
Tfa -D-Tyr- D-4Hyp-Sar-Gly- D-Ala-Sar-OH/NH$_2$
Tfa -Tyr-Pro-Sar-Gly-Ala-Sar-OH/NH$_2$ (SEQ ID NO: 140)
Tfa -D-Tyr- D-Pro-Sar-Gly- D-Ala-Sar-OH/NH$_2$
Tfa -Tyr-Sar-Pro-Gly-Ala-Sar-OH/NH$_2$ (SEQ ID NO: 141)
Tfa -D-Tyr- Sar- D-Pro-Gly- D-Ala-Sar-OH/NH$_2$
Tfa -Tyr-Sar-Sar-Gly-Ala-Sar-OH/NH$_2$
Tfa-D-Tyr- Sar- Sar-Gly- D-Ala-Sar-OH/NH$_2$
4HPP-Pro-4Hyp-Gly-Ala-Sar-OH/NH$_2$
4HPP- D-Pro- D-4Hyp-Gly-D-Ala-Sar-OH/NH$_2$
4HPPA-Pro-4Hyp-Gly-Ala-Sar-OH/NH$_2$
4HPPA- D-Pro- D-4Hyp-Gly-D-Ala-Sar-OH/NH$_2$
4HMPA-Pro-4Hyp-Gly-Ala-Sar-OH/NH$_2$
4HMPA- D-Pro- D-4Hyp-Gly-D-Ala-Sar-OH/NH$_2$
4HPA-Pro-4Hyp-Gly-Ala-Sar-OH/NH$_2$
4HPA- D-Pro- D-4Hyp-Gly-D-Ala-Sar-OH/NH$_2$

4HBG-Pro-4Hyp-Gly-Ala-Sar-OH/NH₂
4HBG- D-Pro- D-4Hyp-Gly-D-Ala-Sar-OH/NH₂
4HPP-Pro-Pro-Gly-Ala-Sar-OH/NH₂ (SEQ ID NO: 142)
4HPP- D-Pro- D-Pro-Gly-D-Ala-Sar-OH/NH₂
4HPPA-Pro-Pro-Gly-Ala-Sar-OH/NH₂ (SEQ ID NO: 143)
4HPPA- D-Pro- D-Pro-Gly-D-Ala-Sar-OH/NH₂
4HMPA-Pro-Pro-Gly-Ala-Sar-OH/NH₂ (SEQ ID NO: 144)
4HMPA- D-Pro- D-Pro-Gly-D-Ala-Sar-OH/NH₂
4HPA-Pro-Pro-Gly-Ala-Sar-OH/NH₂ (SEQ ID NO: 145)
4HPA- D-Pro- D-Pro-Gly-D-Ala-Sar-OH/NH₂
4HBG-Pro-Pro-Gly-Ala-Sar-OH/NH₂ (SEQ ID NO: 146)
4HBG- D-Pro- D-Pro-Gly-D-Ala-Sar-OH/NH₂
4HPP-4Hyp-4Hyp-Gly-Ala-Sar-OH/NH₂
4HPP- D-4Hyp- D-4Hyp-Gly-D-Ala-Sar-OH/NH₂
4HPPA-4Hyp-4Hyp-Gly-Ala-Sar-OH/NH₂
4HPPA- D-4Hyp- D-4Hyp-Gly-D-Ala-Sar-OH/NH₂
4HMPA-4Hyp-4Hyp-Gly-Ala-Sar-OH/NH₂
4HMPA- D-4Hyp- D-4Hyp-Gly-D-Ala-Sar-OH/NH₂
4HPA-4Hyp-4Hyp-Gly-Ala-Sar-OH/NH₂
4HPA- D-4Hyp- D-4Hyp-Gly-D-Ala-Sar-OH/NH₂
4HBG-4Hyp-4Hyp-Gly-Ala-Sar-OH/NH₂
4HBG- D-4Hyp- D-4Hyp-Gly-D-Ala-Sar-OH/NH₂
4HPP-4Hyp-Pro-Gly-Ala-Sar-OH/NH₂
4HPP- D-4Hyp- D-Pro-Gly-D-Ala-Sar-OH/NH₂
4HPPA-4Hyp-Pro-Gly-Ala-Sar-OH/NH₂
4HPPA- D-4Hyp- D-Pro-Gly-D-Ala-Sar-OH/NH₂
4HMPA-4Hyp-Pro-Gly-Ala-Sar-OH/NH₂
4HMPA- D-4Hyp- D-Pro-Gly-D-Ala-Sar-OH/NH₂
4HPA-4Hyp-Pro-Gly-Ala-Sar-OH/NH₂
4HPA- D-4Hyp- D-Pro-Gly-D-Ala-Sar-OH/NH₂
4HBG-4Hyp-Pro-Gly-Ala-Sar-OH/NH₂
4HBG- D-4Hyp- D-Pro-Gly-D-Ala-Sar-OH/NH₂
4HPP-Sar-Pro-Gly-Ala-Sar-OH/NH₂
4HPP- Sar- D-Pro-Gly-D-Ala-Sar-OH/NH₂
4HPPA-Sar-Pro-Gly-Ala-Sar-OH/NH₂
4HPPA- Sar- D-Pro-Gly-D-Ala-Sar-OH/NH₂
4HMPA-Sar-Pro-Gly-Ala-Sar-OH/NH₂
4HMPA- Sar- D-Pro-Gly-D-Ala-Sar-OH/NH₂
4HPA-Sar-Pro-Gly-Ala-Sar-OH/NH₂
4HPA- Sar- D-Pro-Gly-D-Ala-Sar-OH/NH₂
4HBG-Sar-Pro-Gly-Ala-Sar-OH/NH₂
4HBG- Sar- D-Pro-Gly-D-Ala-Sar-OH/NH₂
4HPP-Pro-Sar-Gly-Ala-Sar-OH/NH₂
4HPP- D-Pro- Sar-Gly-D-Ala-Sar-OH/NH₂
4HPPA-Pro-Sar-Gly-Ala-Sar-OH/NH₂
4HPPA- D-Pro- Sar-Gly-D-Ala-Sar-OH/NH₂
4HMPA-Pro-Sar-Gly-Ala-Sar-OH/NH₂
4HMPA- D-Pro- Sar-Gly-D-Ala-Sar-OH/NH₂
4HPA-Pro-Sar-Gly-Ala-Sar-OH/NH₂
4HPA- D-Pro- Sar-Gly-D-Ala-Sar-OH/NH₂
4HBG-Pro-Sar-Gly-Ala-Sar-OH/NH₂
4HBG- D-Pro- Sar-Gly-D-Ala-Sar-OH/NH₂

4HPP-Sar-4Hyp-Gly-Ala-Sar-OH/NH₂
4HPP- Sar- D-4Hyp-Gly-D-Ala-Sar-OH/NH₂
4HPPA-Sar-4Hyp-Gly-Ala-Sar-OH/NH₂
4HPPA- Sar- D-4Hyp-Gly-D-Ala-Sar-OH/NH₂
4HMPA-Sar-4Hyp-Gly-Ala-Sar-OH/NH₂
4HMPA- Sar- D-4Hyp-Gly-D-Ala-Sar-OH/NH₂
4HPA-Sar-4Hyp-Gly-Ala-Sar-OH/NH₂
4HPA- Sar- D-4Hyp-Gly-D-Ala-Sar-OH/NH₂
4HBG-Sar-4Hyp-Gly-Ala-Sar-OH/NH₂
4HBG- Sar- D-4Hyp-Gly-D-Ala-Sar-OH/NH₂
4HPP-4Hyp-Sar-Gly-Ala-Sar-OH/NH₂
4HPP- D-4Hyp- Sar-Gly-D-Ala-Sar-OH/NH₂
4HPPA-4Hyp-Sar-Gly-Ala-Sar-OH/NH₂
4HPPA- D-4Hyp- Sar-Gly-D-Ala-Sar-OH/NH₂
4HMPA-4Hyp-Sar-Gly-Ala-Sar-OH/NH₂
4HMPA- D-4Hyp- Sar-Gly-D-Ala-Sar-OH/NH₂
4HPA-4Hyp-Sar-Gly-Ala-Sar-OH/NH₂
4HPA- D-4Hyp- Sar-Gly-D-Ala-Sar-OH/NH₂
4HBG-4Hyp-Sar-Gly-Ala-Sar-OH/NH₂
4HBG- D-4Hyp- Sar-Gly-D-Ala-Sar-OH/NH₂
4HPP-Sar-Sar-Gly-Ala-Sar-OH/NH₂
4HPP- Sar- Sar-Gly-D-Ala-Sar-OH/NH₂
4HPPA-Sar-Sar-Gly-Ala-Sar-OH/NH₂
4HPPA- Sar- Sar-Gly-D-Ala-Sar-OH/NH₂
4HMPA-Sar-Sar-Gly-Ala-Sar-OH/NH₂
4HMPA- Sar- Sar-Gly-D-Ala-Sar-OH/NH₂
4HPA-Sar-Sar-Gly-Ala-Sar-OH/NH₂
4HPA- Sar- Sar-Gly-D-Ala-Sar-OH/NH₂
4HBG-Sar-Sar-Gly-Ala-Sar-OH/NH₂
4HBG- Sar- Sar-Gly-D-Ala-Sar-OH/NH₂
Ac-Tyr-Pro-4Hyp-Gly-Aib-Gly-OH/NH₂ (SEQ ID NO: 147)
Ac-D-Tyr- D-Pro- D-4Hyp-Gly- Aib-Gly-OH/NH₂
Ac-Tyr-Pro-Pro-Gly-Aib-Gly-OH/NH₂ (SEQ ID NO: 148)
Ac-D-Tyr- D-Pro- D-Pro-Gly- Aib-Gly-OH/NH₂
Ac-Tyr-4Hyp-Pro-Gly-Aib-Gly-OH/NH₂ (SEQ ID NO: 149)
Ac-D-Tyr- D-4Hyp- D-Pro-Gly- Aib-Gly-OH/NH₂
Ac-Tyr-4Hyp-4Hyp-Gly-Aib-Gly-OH/NH₂
Ac-D-Tyr- D-4Hyp- D-4Hyp-Gly- Aib-Gly-OH/NH₂
Ac-Tyr-Sar-4Hyp-Gly-Aib-Gly-OH/NH₂
Ac-D-Tyr-Sar- D-4Hyp-Gly- Aib-Gly-OH/NH₂
Ac-Tyr-4Hyp-Sar-Gly-Aib-Gly-OH/NH₂
Ac-D-Tyr- D-4Hyp-Sar-Gly- Aib-Gly-OH/NH₂
Ac-Tyr-Pro-Sar-Gly-Aib-Gly-OH/NH₂ (SEQ ID NO: 150)
Ac-D-Tyr- D-Pro-Sar-Gly- Aib-Gly-OH/NH₂
Ac-Tyr-Sar-Pro-Gly-Aib-Gly-OH/NH₂ (SEQ ID NO: 151)
Ac-D-Tyr- Sar- D-Pro-Gly- Aib-Gly-OH/NH₂
Ac-Tyr-Sar-Sar-Gly-Aib-Gly-OH/NH₂
Ac-D-Tyr- Sar- Sar-Gly- Aib-Gly-OH/NH₂
4HPP-Pro-4Hyp-Gly-Aib-Gly-OH/NH₂
Tfa -Tyr-Pro-4Hyp-Gly-Aib-Gly-OH/NH₂ (SEQ ID NO: 152)
Tfa -D-Tyr- D-Pro- D-4Hyp-Gly-Aib-Gly-OH/NH₂

-continued

Tfa-Tyr-Pro-Pro-Gly-Aib-Gly-OH/NH₂ (SEQ ID NO: 153)

Tfa-D-Tyr-D-Pro-D-Pro-Gly-Aib-Gly-OH/NH₂

Tfa-Tyr-4Hyp-Pro-Gly-Aib-Gly-OH/NH₂ (SEQ ID NO: 154)

Tfa-D-Tyr-D-4Hyp-D-Pro-Gly-Aib-Gly-OH/NH₂

Tfa-Tyr-4Hyp-4Hyp-Gly-Aib-Gly-OH/NH₂

Tfa-D-Tyr-D-4Hyp-D-4Hyp-Gly-Aib-Gly-OH/NH₂

Tfa-Tyr-Sar-4Hyp-Gly-Aib-Gly-OH/NH₂

Tfa-D-Tyr-Sar-D-4Hyp-Gly-Aib-Gly-OH/NH₂

Tfa-Tyr-4Hyp-Sar-Gly-Aib-Gly-OH/NH₂

Tfa-D-Tyr-D-4Hyp-Sar-Gly-Aib-Gly-OH/NH₂

Tfa-Tyr-Pro-Sar-Gly-Aib-Gly-OH/NH₂ (SEQ ID NO: 155)

Tfa-D-Tyr-D-Pro-Sar-Gly-Aib-Gly-OH/NH₂

Tfa-Tyr-Sar-Pro-Gly-Aib-Gly-OH/NH₂ (SEQ ID NO: 156)

Tfa-D-Tyr-Sar-D-Pro-Gly-Aib-Gly-OH/NH₂

Tfa-Tyr-Sar-Sar-Gly-Aib-Gly-OH/NH₂

Tfa-D-Tyr-Sar-Sar-Gly-Aib-Gly-OH/NH₂

4HPP-D-Pro-D-4Hyp-Gly-Aib-Gly-OH/NH₂

4HPPA-Pro-4Hyp-Gly-Aib-Gly-OH/NH₂

4HPPA-D-Pro-D-4Hyp-Gly-Aib-Gly-OH/NH₂

4HMPA-Pro-4Hyp-Gly-Aib-Gly-OH/NH₂

4HMPA-D-Pro-D-4Hyp-Gly-Aib-Gly-OH/NH₂

4HPA-Pro-4Hyp-Gly-Aib-Gly-OH/NH₂

4HPA-D-Pro-D-4Hyp-Gly-Aib-Gly-OH/NH₂

4HBG-Pro-4Hyp-Gly-Aib-Gly-OH/NH₂

4HBG-D-Pro-D-4Hyp-Gly-Aib-Gly-OH/NH₂

4HPP-Pro-Pro-Gly-Aib-Gly-OH/NH₂ (SEQ ID NO: 157)

4HPP-D-Pro-D-Pro-Gly-Aib-Gly-OH/NH₂

4HPPA-Pro-Pro-Gly-Aib-Gly-OH/NH₂ (SEQ ID NO: 158)

4HPPA-D-Pro-D-Pro-Gly-Aib-Gly-OH/NH₂

4HMPA-Pro-Pro-Gly-Aib-Gly-OH/NH₂ (SEQ ID NO: 159)

4HMPA-D-Pro-D-Pro-Gly-Aib-Gly-OH/NH₂

4HPA-Pro-Pro-Gly-Aib-Gly-OH/NH₂ (SEQ ID NO: 160)

4HPA-D-Pro-D-Pro-Gly-Aib-Gly-OH/NH₂

4HBG-Pro-Pro-Gly-Aib-Gly-OH/NH₂ (SEQ ID NO: 161)

4HBG-D-Pro-D-Pro-Gly-Aib-Gly-OH/NH₂

4HPP-4Hyp-4Hyp-Gly-Aib-Gly-OH/NH₂

4HPP-D-4Hyp-D-4Hyp-Gly-Aib-Gly-OH/NH₂

4HPPA-4Hyp-4Hyp-Gly-Aib-Gly-OH/NH₂

4HPPA-D-4Hyp-D-4Hyp-Gly-Aib-Gly-OH/NH₂

4HMPA-4Hyp-4Hyp-Gly-Aib-Gly-OH/NH₂

4HMPA-D-4Hyp-D-4Hyp-Gly-Aib-Gly-OH/NH₂

4HPA-4Hyp-4Hyp-Gly-Aib-Gly-OH/NH₂

4HPA-D-4Hyp-D-4Hyp-Gly-Aib-Gly-OH/NH₂

4HBG-4Hyp-4Hyp-Gly-Aib-Gly-OH/NH₂

4HBG-D-4Hyp-D-4Hyp-Gly-Aib-Gly-OH/NH₂

4HPP-4Hyp-Pro-Gly-Aib-Gly-OH/NH₂

4HPP-D-4Hyp-D-Pro-Gly-Aib-Gly-OH/NH₂

4HPPA-4Hyp-Pro-Gly-Aib-Gly-OH/NH₂
4HPPA- D-4Hyp- D-Pro-Gly-Aib-Gly-OH/NH₂
4HMPA-4Hyp-Pro-Gly-Aib-Gly-OH/NH₂
4HMPA- D-4Hyp- D-Pro-Gly-Aib-Gly-OH/NH₂
4HPA-4Hyp-Pro-Gly-Aib-Gly-OH/NH₂
4HPA- D-4Hyp- D-Pro-Gly-Aib-Gly-OH/NH₂
4HBG-4Hyp-Pro-Gly-Aib-Gly-OH/NH₂
4HBG- D-4Hyp- D-Pro-Gly-Aib-Gly-OH/NH₂
4HPP-Sar-Pro-Gly-Aib-Gly-OH/NH₂
4HPP- Sar- D-Pro-Gly-Aib-Gly-OH/NH₂
4HPPA-Sar-Pro-Gly-Aib-Gly-OH/NH₂
4HPPA- Sar- D-Pro-Gly-Aib-Gly-OH/NH₂
4HMPA-Sar-Pro-Gly-Aib-Gly-OH/NH₂
4HMPA- Sar- D-Pro-Gly-Aib-Gly-OH/NH₂
4HPA-Sar-Pro-Gly-Aib-Gly-OH/NH₂
4HPA- Sar- D-Pro-Gly-Aib-Gly-OH/NH₂
4HBG-Sar-Pro-Gly-Aib-Gly-OH/NH₂
4HBG- Sar- D-Pro-Gly-Aib-Gly-OH/NH₂
4HPP-Pro-Sar-Gly-Aib-Gly-OH/NH₂
4HPP- D-Pro- Sar-Gly-Aib-Gly-OH/NH₂
4HPPA-Pro-Sar-Gly-Aib-Gly-OH/NH₂
4HPPA- D-Pro- Sar-Gly-Aib-Gly-OH/NH₂
4HMPA-Pro-Sar-Gly-Aib-Gly-OH/NH₂
4HMPA- D-Pro- Sar-Gly-Aib-Gly-OH/NH₂
4HPA-Pro-Sar-Gly-Aib-Gly-OH/NH₂
4HPA- D-Pro- Sar-Gly-Aib-Gly-OH/NH₂
4HBG-Pro-Sar-Gly-Aib-Gly-OH/NH₂
4HBG- D-Pro- Sar-Gly-Aib-Gly-OH/NH₂
4HPP-Sar-4Hyp-Gly-Aib-Gly-OH/NH₂
4HPP- Sar- D-4Hyp-Gly-Aib-Gly-OH/NH₂
4HPPA-Sar-4Hyp-Gly-Aib-Gly-OH/NH₂
4HPPA- Sar- D-4Hyp-Gly-Aib-Gly-OH/NH₂
4HMPA-Sar-4Hyp-Gly-Aib-Gly-OH/NH₂
4HMPA- Sar- D-4Hyp-Gly-Aib-Gly-OH/NH₂
4HPA-Sar-4Hyp-Gly-Aib-Gly-OH/NH₂
4HPA- Sar- D-4Hyp-Gly-Aib-Gly-OH/NH₂
4HBG-Sar-4Hyp-Gly-Aib-Gly-OH/NH₂
4HBG- Sar- D-4Hyp-Gly-Aib-Gly-OH/NH₂
4HPP-4Hyp-Sar-Gly-Aib-Gly-OH/NH₂
4HPP- D-4Hyp- Sar-Gly-Aib-Gly-OH/NH₂
4HPPA-4Hyp-Sar-Gly-Aib-Gly-OH/NH₂
4HPPA- D-4Hyp- Sar-Gly-Aib-Gly-OH/NH₂
4HMPA-4Hyp-Sar-Gly-Aib-Gly-OH/NH₂
4HMPA- D-4Hyp- Sar-Gly-Aib-Gly-OH/NH₂
4HPA-4Hyp-Sar-Gly-Aib-Gly-OH/NH₂
4HPA- D-4Hyp- Sar-Gly-Aib-Gly-OH/NH₂
4HBG-4Hyp-Sar-Gly-Aib-Gly-OH/NH₂
4HBG- D-4Hyp- Sar-Gly-Aib-Gly-OH/NH₂
4HPP-Sar-Sar-Gly-Aib-Gly-OH/NH₂
4HPPA-Sar-Sar-Gly-Aib-Gly-OH/NH₂
4HMPA-Sar-Sar-Gly-Aib-Gly-OH/NH₂
4HPA-Sar-Sar-Gly-Aib-Gly-OH/NH₂
4HBG-Sar-Sar-Gly-Aib-Gly-OH/NH₂

-continued

Ac-Tyr-Pro-4Hyp-Sar-Aib-Sar-OH/NH$_2$
Ac-D-Tyr-D-Pro-D-4Hyp-Sar-Aib-Sar-OH/NH$_2$
Ac-Tyr-Pro-Pro-Sar-Aib-Sar-OH/NH$_2$
Ac-D-Tyr-D-Pro-D-Pro-Sar-Aib-Sar-OH/NH$_2$
Ac-Tyr-4Hyp-Pro-Sar-Aib-Sar-OH/NH$_2$
Ac-D-Tyr-D-4Hyp-D-Pro-Sar-Aib-Sar-OH/NH$_2$
Ac-Tyr-4Hyp-4Hyp-Sar-Aib-Sar-OH/NH$_2$
Ac-D-Tyr-D-4Hyp-D-4Hyp-Sar-Aib-Sar-OH/NH$_2$
Ac-Tyr-Sar-4Hyp-Sar-Aib-Sar-OH/NH$_2$
Ac-D-Tyr-Sar-D-4Hyp-Sar-Aib-Sar-OH/NH$_2$
Ac-Tyr-4Hyp-Sar-Sar-Aib-Sar-OH/NH$_2$
Ac-D-Tyr-D-4Hyp-Sar-Sar-Aib-Sar-OH/NH$_2$
Ac-Tyr-Pro-Sar-Sar-Aib-Sar-OH/NH$_2$
Ac-D-Tyr-D-Pro-Sar-Sar-Aib-Sar-OH/NH$_2$
Ac-Tyr-Sar-Pro-Sar-Aib-Sar-OH/NH$_2$
Ac-D-Tyr-Sar-D-Pro-Sar-Aib-Sar-OH/NH$_2$
Ac-Tyr-Sar-Sar-Sar-Aib-Sar-OH/NH$_2$
Ac-D-Tyr-Sar-Sar-Sar-Aib-Sar-OH/NH$_2$
Tfa-Tyr-Pro-4Hyp-Sar-Aib-Sar-OH/NH$_2$
Tfa-D-Tyr-D-Pro-D-4Hyp-Sar-Aib-Sar-OH/NH$_2$
Tfa-Tyr-Pro-Pro-Sar-Aib-Sar-OH/NH$_2$
Tfa-D-Tyr-D-Pro-D-Pro-Sar-Aib-Sar-OH/NH$_2$
Tfa-Tyr-4Hyp-Pro-Sar-Aib-Sar-OH/NH$_2$
Tfa-D-Tyr-D-4Hyp-D-Pro-Sar-Aib-Sar-OH/NH$_2$
Tfa-Tyr-4Hyp-4Hyp-Sar-Aib-Sar-OH/NH$_2$
Tfa-D-Tyr-D-4Hyp-D-4Hyp-Sar-Aib-Sar-OH/NH$_2$
Tfa-Tyr-Sar-4Hyp-Sar-Aib-Sar-OH/NH$_2$
Tfa-D-Tyr-Sar-D-4Hyp-Sar-Aib-Sar-OH/NH$_2$
Tfa-Tyr-4Hyp-Sar-Sar-Aib-Sar-OH/NH$_2$
Tfa-D-Tyr-D-4Hyp-Sar-Sar-Aib-Sar-OH/NH$_2$
Tfa-Tyr-Pro-Sar-Sar-Aib-Sar-OH/NH$_2$
Tfa-D-Tyr-D-Pro-Sar-Sar-Aib-Sar-OH/NH$_2$
Tfa-Tyr-Sar-Pro-Sar-Aib-Sar-OH/NH$_2$
Tfa-D-Tyr-Sar-D-Pro-Sar-Aib-Sar-OH/NH$_2$
Tfa-Tyr-Sar-Sar-Sar-Aib-Sar-OH/NH$_2$
Tfa-D-Tyr-Sar-Sar-Sar-Aib-Sar-OH/NH$_2$
4HPP-Pro-4Hyp-Sar-Aib-Sar-OH/NH$_2$
4HPP-D-Pro-D-4Hyp-Sar-Aib-Sar-OH/NH$_2$
4HPPA-Pro-4Hyp-Sar-Aib-Sar-OH/NH$_2$
4HPPA-D-Pro-D-4Hyp-Sar-Aib-Sar-OH/NH$_2$
4HMPA-Pro-4Hyp-Sar-Aib-Sar-OH/NH$_2$
4HMPA-D-Pro-D-4Hyp-Sar-Aib-Sar-OH/NH$_2$
4HPA-Pro-4Hyp-Sar-Aib-Sar-OH/NH$_2$
4HPA-D-Pro-D-4Hyp-Sar-Aib-Sar-OH/NH$_2$
4HBG-Pro-4Hyp-Sar-Aib-Sar-OH/NH$_2$
4HBG-D-Pro-D-4Hyp-Sar-Aib-Sar-OH/NH$_2$
4HPP-Pro-Pro-Sar-Aib-Sar-OH/NH$_2$
4HPP-D-Pro-D-Pro-Sar-Aib-Sar-OH/NH$_2$

4HPPA-Pro-Pro-Sar-Aib-Sar-OH/NH$_2$
4HPPA- D-Pro- D-Pro-Sar-Aib-Sar-OH/NH$_2$
4HMPA-Pro-Pro-Sar-Aib-Sar-OH/NH$_2$
4HMPA- D-Pro- D-Pro-Sar-Aib-Sar-OH/NH$_2$
4HPA-Pro-Pro-Sar-Aib-Sar-OH/NH$_2$
4HPA- D-Pro- D-Pro-Sar-Aib-Sar-OH/NH$_2$
4HBG-Pro-Pro-Sar-Aib-Sar-OH/NH$_2$
4HBG- D-Pro- D-Pro-Sar-Aib-Sar-OH/NH$_2$
4HPP-4Hyp-4Hyp-Sar-Aib-Sar-OH/NH$_2$
4HPP- D-4Hyp- D-4Hyp-Sar-Aib-Sar-OH/NH$_2$
4HPPA-4Hyp-4Hyp-Sar-Aib-Sar-OH/NH$_2$
4HPPA- D-4Hyp- D-4Hyp-Sar-Aib-Sar-OH/NH$_2$
4HMPA-4Hyp-4Hyp-Sar-Aib-Sar-OH/NH$_2$
4HMPA- D-4Hyp- D-4Hyp-Sar-Aib-Sar-OH/NH$_2$
4HPA-4Hyp-4Hyp-Sar-Aib-Sar-OH/NH$_2$
4HPA- D-4Hyp- D-4Hyp-Sar-Aib-Sar-OH/NH$_2$
4HBG-4Hyp-4Hyp-Sar-Aib-Sar-OH/NH$_2$
4HBG- D-4Hyp- D-4Hyp-Sar-Aib-Sar-OH/NH$_2$
4HPP-4Hyp-Pro-Sar-Aib-Sar-OH/NH$_2$
4HPP- D-4Hyp- D-Pro-Sar-Aib-Sar-OH/NH$_2$
4HPPA-4Hyp-Pro-Sar-Aib-Sar-OH/NH$_2$
4HPPA- D-4Hyp- D-Pro-Sar-Aib-Sar-OH/NH$_2$
4HMPA-4Hyp-Pro-Sar-Aib-Sar-OH/NH$_2$
4HMPA- D-4Hyp- D-Pro-Sar-Aib-Sar-OH/NH$_2$
4HPA-4Hyp-Pro-Sar-Aib-Sar-OH/NH$_2$
4HPA- D-4Hyp- D-Pro-Sar-Aib-Sar-OH/NH$_2$
4HBG-4Hyp-Pro-Sar-Aib-Sar-OH/NH$_2$
4HBG- D-4Hyp- D-Pro-Sar-Aib-Sar-OH/NH$_2$
4HPP-Sar-Pro-Sar-Aib-Sar-OH/NH$_2$
4HPP- Sar- D-Pro-Sar-Aib-Sar-OH/NH$_2$
4HPPA-Sar-Pro-Sar-Aib-Sar-OH/NH$_2$
4HPPA- Sar- D-Pro-Sar-Aib-Sar-OH/NH$_2$
4HMPA-Sar-Pro-Sar-Aib-Sar-OH/NH$_2$
4HMPA- Sar- D-Pro-Sar-Aib-Sar-OH/NH$_2$
4HPA-Sar-Pro-Sar-Aib-Sar-OH/NH$_2$
4HPA- Sar- D-Pro-Sar-Aib-Sar-OH/NH$_2$
4HBG-Sar-Pro-Sar-Aib-Sar-OH/NH$_2$
4HBG- Sar- D-Pro-Sar-Aib-Sar-OH/NH$_2$
4HPP-Pro-Sar-Sar-Aib-Sar-OH/NH$_2$
4HPP- D-Pro- Sar-Sar-Aib-Sar-OH/NH$_2$
4HPPA-Pro-Sar-Sar-Aib-Sar-OH/NH$_2$
4HPPA- D-Pro- Sar-Sar-Aib-Sar-OH/NH$_2$
4HMPA-Pro-Sar-Sar-Aib-Sar-OH/NH$_2$
4HMPA- D-Pro- Sar-Sar-Aib-Sar-OH/NH$_2$
4HPA-Pro-Sar-Sar-Aib-Sar-OH/NH$_2$
4HPA- D-Pro- Sar-Sar-Aib-Sar-OH/NH$_2$
4HBG-Pro-Sar-Sar-Aib-Sar-OH/NH$_2$
4HBG- D-Pro- Sar-Sar-Aib-Sar-OH/NH$_2$
4HPP-Sar-4Hyp-Sar-Aib-Sar-OH/NH$_2$
4HPP- Sar- D-4Hyp-Sar-Aib-Sar-OH/NH$_2$
4HPPA-Sar-4Hyp-Sar-Aib-Sar-OH/NH$_2$
4HPPA- Sar- D-4Hyp-Sar-Aib-Sar-OH/NH$_2$

-continued

4HMPA-Sar-4Hyp-Sar-Aib-Sar-OH/NH$_2$
4HMPA-Sar-D-4Hyp-Sar-Aib-Sar-OH/NH$_2$
4HPA-Sar-4Hyp-Sar-Aib-Sar-OH/NH$_2$
4HPA-Sar-D-4Hyp-Sar-Aib-Sar-OH/NH$_2$
4HBG-Sar-4Hyp-Sar-Aib-Sar-OH/NH$_2$
4HBG-Sar-D-4Hyp-Sar-Aib-Sar-OH/NH$_2$
4HPP-4Hyp-Sar-Sar-Aib-Sar-OH/NH$_2$
4HPP-D-4Hyp-Sar-Sar-Aib-Sar-OH/NH$_2$
4HPPA-4Hyp-Sar-Sar-Aib-Sar-OH/NH$_2$
4HPPA-D-4Hyp-Sar-Sar-Aib-Sar-OH/NH$_2$
4HMPA-4Hyp-Sar-Sar-Aib-Sar-OH/NH$_2$
4HMPA-D-4Hyp-Sar-Sar-Aib-Sar-OH/NH$_2$
4HPA-4Hyp-Sar-Sar-Aib-Sar-OH/NH$_2$
4HPA-D-4Hyp-Sar-Sar-Aib-Sar-OH/NH$_2$
4HBG-4Hyp-Sar-Sar-Aib-Sar-OH/NH$_2$
4HBG-D-4Hyp-Sar-Sar-Aib-Sar-OH/NH$_2$
4HPP-Sar-Sar-Sar-Aib-Sar-OH/NH$_2$
4HPPA-Sar-Sar-Sar-Aib-Sar-OH/NH$_2$
4HMPA-Sar-Sar-Sar-Aib-Sar-OH/NH$_2$
4HPA-Sar-Sar-Sar-Aib-Sar-OH/NH$_2$
4HBG-Sar-Sar-Sar-Aib-Sar-OH/NH$_2$
Ac-Tyr-Pro-4Hyp-Sar-Aib-Gly-OH/NH$_2$
Ac-D-Tyr-D-Pro-D-4Hyp-Sar-Aib-Gly-OH/NH$_2$
Ac-Tyr-Pro-Pro-Sar-Aib-Gly-OH/NH$_2$ (SEQ ID NO: 162)
Ac-D-Tyr-D-Pro-D-Pro-Sar-Aib-Gly-OH/NH$_2$
Ac-Tyr-4Hyp-Pro-Sar-Aib-Gly-OH/NH$_2$
Ac-D-Tyr-D-4Hyp-D-Pro-Sar-Aib-Gly-OH/NH$_2$
Ac-Tyr-4Hyp-4Hyp-Sar-Aib-Gly-OH/NH$_2$
Ac-D-Tyr-D-4Hyp-D-4Hyp-Sar-Aib-Gly-OH/NH$_2$
Ac-Tyr-Sar-4Hyp-Sar-Aib-Gly-OH/NH$_2$
Ac-D-Tyr-Sar-D-4Hyp-Sar-Aib-Gly-OH/NH$_2$
Ac-Tyr-4Hyp-Sar-Sar-Aib-Gly-OH/NH$_2$
Ac-D-Tyr-D-4Hyp-Sar-Sar-Aib-Gly-OH/NH$_2$
Ac-Tyr-Pro-Sar-Sar-Aib-Gly-OH/NH$_2$
Ac-D-Tyr-D-Pro-Sar-Sar-Aib-Gly-OH/NH$_2$
Ac-Tyr-Sar-Pro-Sar-Aib-Gly-OH/NH$_2$
Ac-D-Tyr-Sar-D-Pro-Sar-Aib-Gly-OH/NH$_2$
Ac-Tyr-Sar-Sar-Sar-Aib-Gly-OH/NH$_2$
Ac-D-Tyr-Sar-Sar-Sar-Aib-Gly-OH/NH$_2$
4HPP-Pro-4Hyp-Sar-Aib-Gly-OH/NH$_2$
Tfa-Tyr-Pro-4Hyp-Sar-Aib-Gly-OH/NH$_2$
Tfa-D-Tyr-D-Pro-D-4Hyp-Sar-Aib-Gly-OH/NH$_2$
Tfa-Tyr-Pro-Pro-Sar-Aib-Gly-OH/NH$_2$ (SEQ ID NO: 163)
Tfa-D-Tyr-D-Pro-D-Pro-Sar-Aib-Gly-OH/NH$_2$
Tfa-Tyr-4Hyp-Pro-Sar-Aib-Gly-OH/NH$_2$
Tfa-D-Tyr-D-4Hyp-D-Pro-Sar-Aib-Gly-OH/NH$_2$
Tfa-Tyr-4Hyp-4Hyp-Sar-Aib-Gly-OH/NH$_2$
Tfa-D-Tyr-D-4Hyp-D-4Hyp-Sar-Aib-Gly-OH/NH$_2$
Tfa-Tyr-Sar-4Hyp-Sar-Aib-Gly-OH/NH$_2$
Tfa-D-Tyr-Sar-D-4Hyp-Sar-Aib-Gly-OH/NH$_2$
Tfa-Tyr-4Hyp-Sar-Sar-Aib-Gly-OH/NH$_2$

Tfa-D-Tyr-D-Hyp-Sar-Sar-Aib-Gly-OH/NH$_2$
Tfa-Tyr-Pro-Sar-Sar-Aib-Gly-OH/NH$_2$
Tfa-D-Tyr-D-Pro-Sar-Sar-Aib-Gly-OH/NH$_2$
Tfa-Tyr-Sar-Pro-Sar-Aib-Gly-OH/NH$_2$
Tfa-D-Tyr-Sar-D-Pro-Sar-Aib-Gly-OH/NH$_2$
Tfa-Tyr-Sar-Sar-Sar-Aib-Gly-OH/NH$_2$
Tfa-D-Tyr-Sar-Sar-Sar-Aib-Gly-OH/NH$_2$
4HPP-D-Pro-D-4Hyp-Sar-Aib-Gly-OH/NH$_2$
4HPPA-Pro-4Hyp-Sar-Aib-Gly-OH/NH$_2$
4HPPA- D-Pro- D-4Hyp-Sar-Aib-Gly-OH/NH$_2$
4HMPA-Pro-4Hyp-Sar-Aib-Gly-OH/NH$_2$
4HMPA- D-Pro- D-4Hyp-Sar-Aib-Gly-OH/NH$_2$
4HPA-Pro-4Hyp-Sar-Aib-Gly-OH/NH$_2$
4HPA- D-Pro- D-4Hyp-Sar-Aib-Gly-OH/NH$_2$
4HBG-Pro-4Hyp-Sar-Aib-Gly-OH/NH$_2$
4HBG- D-Pro- D-4Hyp-Sar-Aib-Gly-OH/NH$_2$
4HPP-Pro-Pro-Sar-Aib-Gly-OH/NH$_2$
4HPP- D-Pro- D-Pro-Sar-Aib-Gly-OH/NH$_2$
4HPPA-Pro-Pro-Sar-Aib-Gly-OH/NH$_2$
4HPPA- D-Pro- D-Pro-Sar-Aib-Gly-OH/NH$_2$
4HMPA-Pro-Pro-Sar-Aib-Gly-OH/NH$_2$
4HMPA- D-Pro- D-Pro-Sar-Aib-Gly-OH/NH$_2$
4HPA-Pro-Pro-Sar-Aib-Gly-OH/NH$_2$
4HPA- D-Pro- D-Pro-Sar-Aib-Gly-OH/NH$_2$
4HBG-Pro-Pro-Sar-Aib-Gly-OH/NH$_2$
4HBG- D-Pro- D-Pro-Sar-Aib-Gly-OH/NH$_2$
4HPP-4Hyp-4Hyp-Sar-Aib-Gly-OH/NH$_2$
4HPP- D-4Hyp- D-4Hyp-Sar-Aib-Gly-OH/NH$_2$
4HPPA-4Hyp-4Hyp-Sar-Aib-Gly-OH/NH$_2$
4HPPA- D-4Hyp- D-4Hyp-Sar-Aib-Gly-OH/NH$_2$
4HMPA-4Hyp-4Hyp-Sar-Aib-Gly-OH/NH$_2$
4HMPA- D-4Hyp- D-4Hyp-Sar-Aib-Gly-OH/NH$_2$
4HPA-4Hyp-4Hyp-Sar-Aib-Gly-OH/NH$_2$
4HPA- D-4Hyp- D-4Hyp-Sar-Aib-Gly-OH/NH$_2$
4HBG-4Hyp-4Hyp-Sar-Aib-Gly-OH/NH$_2$
4HBG- D-4Hyp- D-4Hyp-Sar-Aib-Gly-OH/NH$_2$
4HPP-4Hyp-Pro-Sar-Aib-Gly-OH/NH$_2$
4HPP- D-4Hyp- D-Pro-Sar-Aib-Gly-OH/NH$_2$
4HPPA-4Hyp-Pro-Sar-Aib-Gly-OH/NH$_2$
4HPPA- D-4Hyp- D-Pro-Sar-Aib-Gly-OH/NH$_2$
4HMPA-4Hyp-Pro-Sar-Aib-Gly-OH/NH$_2$
4HMPA- D-4Hyp- D-Pro-Sar-Aib-Gly-OH/NH$_2$
4HPA-4Hyp-Pro-Sar-Aib-Gly-OH/NH$_2$
4HPA- D-4Hyp- D-Pro-Sar-Aib-Gly-OH/NH$_2$
4HBG-4Hyp-Pro-Sar-Aib-Gly-OH/NH$_2$
4HBG- D-4Hyp- D-Pro-Sar-Aib-Gly-OH/NH$_2$
4HPP-Sar-Pro-Sar-Aib-Gly-OH/NH$_2$
4HPP- Sar- D-Pro-Sar-Aib-Gly-OH/NH$_2$
4HPPA-Sar-Pro-Sar-Aib-Gly-OH/NH$_2$
4HPPA- Sar- D-Pro-Sar-Aib-Gly-OH/NH$_2$
4HMPA-Sar-Pro-Sar-Aib-Gly-OH/NH$_2$
4HMPA- Sar- D-Pro-Sar-Aib-Gly-OH/NH$_2$

4HPA-Sar-Pro-Sar-Aib-Gly-OH/NH₂
4HPA- Sar- D-Pro-Sar-Aib-Gly-OH/NH₂
4HBG-Sar-Pro-Sar-Aib-Gly-OH/NH₂
4HBG- Sar- D-Pro-Sar-Aib-Gly-OH/NH₂
4HPP-Pro-Sar-Sar-Aib-Gly-OH/NH₂
4HPP- D-Pro- Sar-Sar-Aib-Gly-OH/NH₂
4HPPA-Pro-Sar-Sar-Aib-Gly-OH/NH₂
4HPPA- D-Pro- Sar-Sar-Aib-Gly-OH/NH₂
4HMPA-Pro-Sar-Sar-Aib-Gly-OH/NH₂
4HMPA- D-Pro- Sar-Sar-Aib-Gly-OH/NH₂
4HPA-Pro-Sar-Sar-Aib-Gly-OH/NH₂
4HPA- D-Pro- Sar-Sar-Aib-Gly-OH/NH₂
4HBG-Pro-Sar-Sar-Aib-Gly-OH/NH₂
4HBG- D-Pro- Sar-Sar-Aib-Gly-OH/NH₂
4HPP-Sar-4Hyp-Sar-Aib-Gly-OH/NH₂
4HPP- Sar- D-4Hyp-Sar-Aib-Gly-OH/NH₂
4HPPA-Sar-4Hyp-Sar-Aib-Gly-OH/NH₂
4HPPA- Sar- D-4Hyp-Sar-Aib-Gly-OH/NH₂
4HMPA-Sar-4Hyp-Sar-Aib-Gly-OH/NH₂
4HMPA- Sar- D-4Hyp-Sar-Aib-Gly-OH/NH₂
4HPA-Sar-4Hyp-Sar-Aib-Gly-OH/NH₂
4HPA- Sar- D-4Hyp-Sar-Aib-Gly-OH/NH₂
4HBG-Sar-4Hyp-Sar-Aib-Gly-OH/NH₂
4HBG- Sar- D-4Hyp-Sar-Aib-Gly-OH/NH₂
4HPP-4Hyp-Sar-Sar-Aib-Gly-OH/NH₂
4HPP- D-4Hyp- Sar-Sar-Aib-Gly-OH/NH₂
4HPPA-4Hyp-Sar-Sar-Aib-Gly-OH/NH₂
4HPPA- D-4Hyp- Sar-Sar-Aib-Gly-OH/NH₂
4HMPA-4Hyp-Sar-Sar-Aib-Gly-OH/NH₂
4HMPA- D-4Hyp- Sar-Sar-Aib-Gly-OH/NH₂
4HPA-4Hyp-Sar-Sar-Aib-Gly-OH/NH₂
4HPA- D-4Hyp- Sar-Sar-Aib-Gly-OH/NH₂
4HBG-4Hyp-Sar-Sar-Aib-Gly-OH/NH₂
4HBG- D-4Hyp- Sar-Sar-Aib-Gly-OH/NH₂
4HPP- Sar- Sar-Sar-Aib-Gly-OH/NH₂
4HPPA- Sar- Sar-Sar-Aib-Gly-OH/NH₂
4HMPA- Sar- Sar-Sar-Aib-Gly-OH/NH₂
4HPA-Sar-Sar-Sar-Aib-Gly-OH/NH₂
4HBG-Sar-Sar-Sar-Aib-Gly-OH/NH₂
Ac-Tyr-Pro-4Hyp-Gly-Aib-Sar-OH/NH₂
Ac-D-Tyr-D-Pro-D-4Hyp-Gly-Aib-Sar-OH/NH₂
Ac-Tyr-Pro-Pro-Gly-Aib-Sar-OH/NH₂ (SEQ ID NO: 164)
Ac-D-Tyr-D-Pro-D-Pro-Gly-Aib-Sar-OH/NH₂
Ac-Tyr-4Hyp-Pro-Gly-Aib-Sar-OH/NH₂
Ac-D-Tyr-D-4Hyp-D-Pro-Gly-Aib-Sar-OH/NH₂
Ac-Tyr-4Hyp-4Hyp-Gly-Aib-Sar-OH/NH₂
Ac-D-Tyr-D-4Hyp-D-4Hyp-Gly-Aib-Sar-OH/NH₂
Ac-Tyr-Sar-4Hyp-Gly-Aib-Sar-OH/NH₂
Ac-D-Tyr-Sar-D-4Hyp-Gly-Aib-Sar-OH/NH₂
Ac-Tyr-4Hyp-Sar-Gly-Aib-Sar-OH/NH₂
Ac-D-Tyr-D-4Hyp-Sar-Gly-Aib-Sar-OH/NH₂
Ac-Tyr-Pro-Sar-Gly-Aib-Sar-OH/NH₂
Ac-D-Tyr-D-Pro-Sar-Gly-Aib-Sar-OH/NH₂

-continued

Ac-Tyr-Sar-Pro-Gly-Aib-Sar-OH/NH₂
Ac-D-Tyr-Sar-D-Pro-Gly-Aib-Sar-OH/NH₂
Ac-Tyr-Sar-Sar-Gly-Aib-Sar-OH/NH₂
Ac-D-Tyr-Sar-Sar-Gly-Aib-Sar-OH/NH₂
4HPP-Pro-4Hyp-Gly-Aib-Sar-OH/NH₂
Tfa-Tyr-Pro-4Hyp-Gly-Aib-Sar-OH/NH₂
Tfa-D-Tyr-D-Pro-D-4Hyp-Gly-Aib-Sar-OH/NH₂
Tfa-Tyr-Pro-Pro-Gly-Aib-Sar-OH/NH₂ (SEQ ID NO: 165)
Tfa-D-Tyr-D-Pro-D-Pro-Gly-Aib-Sar-OH/NH₂
Tfa-Tyr-4Hyp-Pro-Gly-Aib-Sar-OH/NH₂
Tfa-D-Tyr-D-4Hyp-D-Pro-Gly-Aib-Sar-OH/NH₂
Tfa-Tyr-4Hyp-4Hyp-Gly-Aib-Sar-OH/NH₂
Tfa-D-Tyr-D-4Hyp-D-4Hyp-Gly-Aib-Sar-OH/NH₂
Tfa-Tyr-Sar-4Hyp-Gly-Aib-Sar-OH/NH₂
Tfa-D-Tyr-Sar-D-4Hyp-Gly-Aib-Sar-OH/NH₂
Tfa-Tyr-4Hyp-Sar-Gly-Aib-Sar-OH/NH₂
Tfa-D-Tyr-D-4Hyp-Sar-Gly-Aib-Sar-OH/NH₂
Tfa-Tyr-Pro-Sar-Gly-Aib-Sar-OH/NH₂
Tfa-D-Tyr-D-Pro-Sar-Gly-Aib-Sar-OH/NH₂
Tfa-Tyr-Sar-Pro-Gly-Aib-Sar-OH/NH₂
Tfa-D-Tyr-Sar-D-Pro-Gly-Aib-Sar-OH/NH₂
Tfa-Tyr-Sar-Sar-Gly-Aib-Sar-OH/NH₂
Tfa-D-Tyr-Sar-Sar-Gly-Aib-Sar-OH/NH₂
4HPP-D-Pro-D-4Hyp-Gly-Aib-Sar-OH/NH₂
4HPPA-Pro-4Hyp-Gly-Aib-Sar-OH/NH₂
4HPPA-D-Pro-D-4Hyp-Gly-Aib-Sar-OH/NH₂
4HMPA-Pro-4Hyp-Gly-Aib-Sar-OH/NH₂
4HMPA-D-Pro-D-4Hyp-Gly-Aib-Sar-OH/NH₂
4HPA-Pro-4Hyp-Gly-Aib-Sar-OH/NH₂
4HPA-D-Pro-D-4Hyp-Gly-Aib-Sar-OH/NH₂
4HBG-Pro-4Hyp-Gly-Aib-Sar-OH/NH₂
4HBG-D-Pro-D-4Hyp-Gly-Aib-Sar-OH/NH₂
4HPP-Pro-Pro-Gly-Aib-Sar-OH/NH₂
4HPP-D-Pro-D-Pro-Gly-Aib-Sar-OH/NH₂
4HPPA-Pro-Pro-Gly-Aib-Sar-OH/NH₂
4HPPA-D-Pro-D-Pro-Gly-Aib-Sar-OH/NH₂
4HMPA-Pro-Pro-Gly-Aib-Sar-OH/NH₂
4HMPA-D-Pro-D-Pro-Gly-Aib-Sar-OH/NH₂
4HPA-Pro-Pro-Gly-Aib-Sar-OH/NH₂
4HPA-D-Pro-D-Pro-Gly-Aib-Sar-OH/NH₂
4HBG-Pro-Pro-Gly-Aib-Sar-OH/NH₂
4HBG-D-Pro-D-Pro-Gly-Aib-Sar-OH/NH₂
4HPP-4Hyp-4Hyp-Gly-Aib-Sar-OH/NH₂
4HPP-D-4Hyp-D-4Hyp-Gly-Aib-Sar-OH/NH₂
4HPPA-4Hyp-4Hyp-Gly-Aib-Sar-OH/NH₂
4HPPA-D-4Hyp-D-4Hyp-Gly-Aib-Sar-OH/NH₂
4HMPA-4Hyp-4Hyp-Gly-Aib-Sar-OH/NH₂
4HMPA-D-4Hyp-D-4Hyp-Gly-Aib-Sar-OH/NH₂

-continued

4HPA-4Hyp-4Hyp-Gly-Aib-Sar-OH/NH$_2$

4HPA-D-4Hyp-D-4Hyp-Gly-Aib-Sar-OH/NH$_2$

4HBG-4Hyp-4Hyp-Gly-Aib-Sar-OH/NH$_2$

4HBG-D-4Hyp-D-4Hyp-Gly-Aib-Sar-OH/NH$_2$

4HPP-4Hyp-Pro-Gly-Aib-Sar-OH/NH$_2$

4HPP-D-4Hyp-D-Pro-Gly-Aib-Sar-OH/NH$_2$

4HPPA-4Hyp-Pro-Gly-Aib-Sar-OH/NH$_2$

4HPPA-D-4Hyp-D-Pro-Gly-Aib-Sar-OH/NH$_2$

4HMPA-4Hyp-Pro-Gly-Aib-Sar-OH/NH$_2$

4HMPA-D-4Hyp-D-Pro-Gly-Aib-Sar-OH/NH$_2$

4HPA-4 Hyp-Pro-Gly-Aib-Sar-OH/NH$_2$

4HPA-D-4Hyp-D-Pro-Gly-Aib-Sar-OH/NH$_2$

4HBG-4Hyp-Pro-Gly-Aib-Sar-OH/NH$_2$

4HBG-D-4Hyp-D-Pro-Gly-Aib-Sar-OH/NH$_2$

4HPP-Sar-Pro-Gly-Aib-Sar-OH/NH$_2$

4HPP-Sar-D-Pro-Gly-Aib-Sar-OH/NH$_2$

4HPPA-Sar-Pro-Gly-Aib-Sar-OH/NH$_2$

4HPPA-Sar-D-Pro-Gly-Aib-Sar-OH/NH$_2$

4HMPA-Sar-Pro-Gly-Aib-Sar-OH/NH$_2$

4HMPA-Sar-D-Pro-Gly-Aib-Sar-OH/NH$_2$

4HPA-Sar-Pro-Gly-Aib-Sar-OH/NH$_2$

4HPA-Sar-D-Pro-Gly-Aib-Sar-OH/NH$_2$

4HBG-Sar-Pro-Gly-Aib-Sar-OH/NH$_2$

4HBG-Sar-D-Pro-Gly-Aib-Sar-OH/NH$_2$

4HPP-Pro-Sar-Gly-Aib-Sar-OH/NH$_2$

4HPP-D-Pro-Sar-Gly-Aib-Sar-OH/NH$_2$

4HPPA-Pro-Sar-Gly-Aib-Sar-OH/NH$_2$

4HPPA-D-Pro-Sar-Gly-Aib-Sar-OH/NH$_2$

4HMPA-Pro-Sar-Gly-Aib-Sar-OH/NH$_2$

4HMPA-D-Pro-Sar-Gly-Aib-Sar-OH/NH$_2$

4HPA-Pro-Sar-Gly-Aib-Sar-OH/NH$_2$

4HPA-D-Pro-Sar-Gly-Aib-Sar-OH/NH$_2$

4HBG-Pro-Sar-Gly-Aib-Sar-OH/NH$_2$

4HBG-D-Pro-Sar-Gly-Aib-Sar-OH/NH$_2$

4HPP-Sar-4Hyp-Gly-Aib-Sar-OH/NH$_2$

4HPP-Sar-D-4Hyp-Gly-Aib-Sar-OH/NH$_2$

4HPPA-Sar-4Hyp-Gly-Aib-Sar-OH/NH$_2$

4HPPA-Sar-D-4Hyp-Gly-Aib-Sar-OH/NH$_2$

4HMPA-Sar-4Hyp-Gly-Aib-Sar-OH/NH$_2$

4HMPA-Sar-D-4Hyp-Gly-Aib-Sar-OH/NH$_2$

4HPA-Sar-4Hyp-Gly-Aib-Sar-OH/NH$_2$

4HPA-Sar-D-4Hyp-Gly-Aib-Sar-OH/NH$_2$

4HBG-Sar-4Hyp-Gly-Aib-Sar-OH/NH$_2$

4HBG-Sar-D-4Hyp-Gly-Aib-Sar-OH/NH$_2$

4HPP-4Hyp-Sar-Gly-Aib-Sar-OH/NH$_2$

4HPP-D-4Hyp-Sar-Gly-Aib-Sar-OH/NH$_2$

4HPPA-4Hyp-Sar-Gly-Aib-Sar-OH/NH$_2$

4HPPA-D-4Hyp-Sar-Gly-Aib-Sar-OH/NH$_2$

4HMPA-4Hyp-Sar-Gly-Aib-Sar-OH/NH$_2$

4HMPA-D-4Hyp-Sar-Gly-Aib-Sar-OH/NH$_2$

4HPA-4Hyp-Sar-Gly-Aib-Sar-OH/NH$_2$

4HPA-D-4Hyp-Sar-Gly-Aib-Sar-OH/NH$_2$

4HBG-4Hyp-Sar-Gly-Aib-Sar-OH/NH$_2$

4HBG-D-4Hyp-Sar-Gly-Aib-Sar-OH/NH$_2$

4HPP-Sar-Sar-Gly-Aib-Sar-OH/NH$_2$

4HPPA-Sar-Sar-Gly-Aib-Sar-OH/NH$_2$

4HMPA-Sar-Sar-Gly-Aib-Sar-OH/NH$_2$

4HPA-Sar-Sar-Gly-Aib-Sar-OH/NH$_2$

4HBG-Sar-Sar-Gly-Aib-Sar-OH/NH$_2$ and the mirror images thereof, the retro analogues thereof, and derivatives thereof which are selected from the group consisting of pharmaceutically acceptable salts; alkyl, aryl and aralkyl esters; mono and disubstituted amides where the substituent is selected from the group consisting of alkyl, aryl, and aralkyl; hydrazides; and alcohols.

In another preferred embodiment of the invention, formula I represents a cyclic peptide wherein A-B is selected from the group consisting of Sar-Sar, Sar-Hyp, Hyp-Sar, Pro-Sar, Sar-Pro, Pro-Hyp, Pro-Pro, Hyp-Pro, and Hyp-Hyp where Pro and Hyp independently may be an L or D form and Hyp preferably represents 4-hydroxyproline. More preferably, A-B represents unsubstituted L-Pro-L-4Hyp, L-4Hyp-L-Pro, D-Pro-D-4Hyp, or D-4Hyp-D-Pro.

X represents a single amino acid residue, preferably L-Tyr or D-Tyr optionally further substituted with halogen, phenyl, hydroxy, NH$_2$, and C(1-6)alkyl optionally substituted with halogen, at its aromatic ring when Y represents a peptide of 3 or 4 amino acid residues being independently L- or D-forms, preferably having Asp or Glu at its C-terminal, and more preferably when Y represents a peptide sequence selected from the group consisting of

```
Gly-L-Ala-L-Asn,
Gly-D-Ala-L-Asn,
Gly-L-Ala-Gly-L-Asn,     (SEQ ID NO: 166)
Gly-L-Ala-Gly-D-Asn,
Gly-L-Ala-L-Gln,
Gly-L-Ala-Gly-L-Gln,     (SEQ ID NO: 167)
Gly-L-Ala-Gly-D-Gln,
Gly-D-Ala-D-Asn,
Gly-D-Ala-Gly-D-Asn,
Gly-D-Ala-Gly-L-Asn,
Gly-D-Ala-D-Gln,
Gly-D-Ala-Gly-D-Gln,
Gly-D-Ala-L-Gln,
Gly-D-Ala-Gly-D-Gln,
Gly-L-Ala-L-Asp,
Gly-D-Ala-L-Asp,
Gly-L-Ala-Gly-L-Asp,     (SEQ ID NO: 168)
Gly-L-Ala-Gly-D-Asp,
Gly-L-Ala-L-Glu,
Gly-L-Ala-Gly-L-Glu,     (SEQ ID NO: 169)
Gly-L-Ala-Gly-D-Glu,
Gly-D-Ala-D-Asp,
Gly-D-Ala-Gly-D-Asp,
Gly-D-Ala-Gly-L-Asp,
Gly-D-Ala-D-Glu,
Gly-D-Ala-Gly-D-Glu,
Gly-D-Ala-L-Glu,
Gly-D-Ala-Gly-D-Glu,
```

Or X represents a peptide sequence preferably selected from the group consisting of

```
Gly-L-Ala-L-Asp,
Gly-L-Ala-Gly-L-Asp,     (SEQ ID NO: 170)
Gly-L-Ala-L-Glu,
Gly-L-Ala-Gly-L-Glu,     (SEQ ID NO: 171)
Gly-D-Ala-D-Asp,
Gly-D-Ala-Gly-D-Asp,
Gly-D-Ala-D-Glu,
Gly-D-Ala-Gly-D-Glu,
``` when Y represents a single amino acid residue, preferably L-Tyr or D-Tyr optionally further substituted with halogen, such as Cl, at its aromatic ring.

Formula I may represent a cyclic peptide sequence comprising all L-forms, all D-forms, or a sequence of mixed L- and D-forms of the amino acid residues.

Examples of cyclic compounds of formula I are

```
(SEQ ID NO: 172) Cyclo(L-Tyr-L-Pro-L-4Hyp-Gly-L-Ala-L-Asn) (Compound 4),
Cyclo(L-Tyr-L-Pro-L-4Hyp-Gly-D-Ala-L-Asn),
(SEQ ID NO: 173) Cyclo(L-Tyr-L-Pro-L-4Hyp-Gly-L-Ala-L-Asp),
(SEQ ID NO: 174) Cyclo(L-Tyr-L-Pro-L-4Hyp-Gly-L-Ala-Gly-L-Asn) (Compound 3),
(SEQ ID NO: 175) Cyclo(L-Tyr-L-Pro-L-4Hyp-Gly-L-Ala-Gly-L-Asp),
Cyclo(D-Tyr-L-Pro-L-4Hyp-Gly-L-Ala-Gly-L-Asp),
Cyclo(D-Tyr-D-Pro-D-4Hyp-Gly-D-Ala-D-Asn),
Cyclo(D-Tyr-D-Pro-D-4Hyp-Gly-D-Ala-D-Asp),
Cyclo(D-Tyr-L-Pro-L-4Hyp-Gly-D-Ala-D-Asp),
Cyclo(D-Tyr-D-Pro-D-4Hyp-Gly-D-Ala-Gly-D-Asn),
Cyclo(D-Tyr-L-Pro-L-4Hyp-Gly-D-Ala-Gly-L-Asn),
Cyclo(D-Tyr-D-Pro-D-4Hyp-Gly-D-Ala-Gly-D-Asp),
(SEQ ID NO: 176) Cyclo(L-Tyr-L-Pro-L-4Hyp-Gly-L-Ala-L-Gln),
Cyclo(L-Tyr-L-Pro-L-4Hyp-Gly-D-Ala-L-Gln),
```

```
(SEQ ID NO: 177) Cyclo(L-Tyr-L-Pro-L-4Hyp-Gly-L-Ala-L-Glu), (SEQ ID NO: 178) Cyclo(L-Tyr-L-Pro-L-4Hyp-Gly-L-Ala-Gly-L-Gln), (SEQ ID NO: 179) Cyclo(L-Tyr-L-Pro-L-4Hyp-Gly-L-Ala-Gly-L-Glu), Cyclo(D-Tyr-L-Pro-L-4Hyp-Gly-L-Ala-Gly-L-Glu), Cyclo(D-Tyr-D-Pro-D-4Hyp-Gly-D-Ala-D-Gln), Cyclo(D-Tyr-D-Pro-D-4Hyp-Gly-D-Ala-D-Glu), Cyclo(D-Tyr-L-Pro-L-4Hyp-Gly-D-Ala-D-Glu), Cyclo(D-Tyr-D-Pro-D-4Hyp-Gly-D-Ala-Gly-D-Gln), Cyclo(D-Tyr-L-Pro-L-4Hyp-Gly-D-Ala-Gly-L-Gln), Cyclo(D-Tyr-D-Pro-D-4Hyp-Gly-D-Ala-Gly-D-Glu), (SEQ ID NO: 180) Cyclo(-Tyr-Ala-Ser-Ala-Gly-Asn-) Compound 44

(SEQ ID NO: 181) Cyclo(-Tyr-Gly-Asn-Tyr-Gly-Asn-) Compound 45

(SEQ ID NO: 182) Cyclo(-Tyr-Gly-Asn-Tyr-Ala-Gly-Asn-) Compound 46

(SEQ ID NO: 183) Cyclo(-Tyr-Val-Ser-Gly-Ala-Gly-Asn-) Compound 47
``` and the mirror images thereof, the retro analogues thereof, and derivatives thereof, such as pharmaceutically acceptable salts and amides.

In another preferred embodiment of the invention formula I represents a cyclic compound where the groups X and Y are connected via an amino carbonyl bond, an alkoxy bond, an ester bond, a reduced amide bond, or a disulphide bond.

Examples of compounds where X and Y are connected via an alkoxy bond having the linker L of formula III:

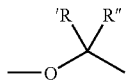

(III)

wherein R' and R" each represents hydrogen or lower alkyl and/or lower aryl, preferably methyl and phenyl are listed below and the mirror images thereof, the retro analogues thereof, and derivatives thereof, such as pharmaceutically acceptable salts and amides.

Examples of compounds where X and Y are connected via an amino carbonyl bond having the linker L of formula IV

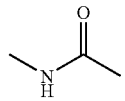

(IV)

are listed below:

```
                                                        (SEQ ID NO: 193)

Cyclo(O-C(R',R")-Tyr-Pro-4Hyp-Gly-Ala-Gly)              (SEQ ID NO: 184)

Cyclo(O-C(R',R")-Tyr-4-Hyp-Pro-Gly-Ala-Gly)             (SEQ ID NO: 185)

Cyclo(O-C(R',R")-Tyr-4-Hyp-4-Hyp-Gly-Ala-Gly)           (SEQ ID NO: 186)

Cyclo(O-C(R',R")-Tyr-Pro-Pro-Gly-Ala-Gly)               (SEQ ID NO: 187)

Cyclo(O-C(R',R")-Tyr-Sar-Sar-Gly-Ala-Gly)               (SEQ ID NO: 188)

Cyclo(O-C(R',R")-Tyr-Sar-Pro-Gly-Ala-Gly)               (SEQ ID NO: 189)

Cyclo(O-C(R',R")-Tyr-4-Hyp-Sar-Gly-Ala-Gly)             (SEQ ID NO: 190)

Cyclo(O-CH2-Tyr-Pro-Sar-Gly-Ala-Gly)                    (SEQ ID NO: 191)

Cyclo(O-C(methyl,phenyl)-Tyr-Sar-4-Hyp-Gly-Ala-Gly)     (SEQ ID NO: 192)
```

```
Cyclo(HNC(O)-Tyr-Pro-4Hyp-Gly-Ala-Gly)
                                              (SEQ ID NO: 194)
Cyclo(HNC(O)-Tyr-4-Hyp-Pro-Gly-Ala-Gly)
                                              (SEQ ID NO: 195)
Cyclo(HNC(O)-Tyr-4-Hyp-4-Hyp-Gly-Ala-Gly)
                                              (SEQ ID NO: 196)
Cyclo(HNC(O)-Tyr-Pro-Pro-Gly-Ala-Gly)
                                              (SEQ ID NO: 197)
Cyclo(HNC(O)-Tyr-Sar-Sar-Gly-Ala-Gly)
                                              (SEQ ID NO: 198)
Cyclo(HNC(O)-Tyr-Sar-Pro-Gly-Ala-Gly)
                                              (SEQ ID NO: 199)
Cyclo(HNC(O)-Tyr-4-Hyp-Sar-Gly-Ala-Gly)
                                              (SEQ ID NO: 200)
Cyclo(HNC(O)-Tyr-Pro-Sar-Gly-Ala-Gly)
                                              (SEQ ID NO: 201)
Cyclo(HNC(O)-Tyr-Sar-4-Hyp-Gly-Ala-Gly)
``` and the mirror images thereof, the retro analogues thereof, and derivatives thereof, such as pharmaceutically acceptable salts and amides.

Examples of compounds where X and Y are connected via an ester bond having the linker L of formula V:

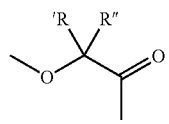

(V)

wherein R' and R" each represents hydrogen or lower alkyl and/or lower aryl, preferably methyl and phenyl, preferably R'≠R", are listed below:

```
Cyclo(O-C(R',R")C(O)-Tyr-Pro-4Hyp-Gly-Ala-Gly)          (SEQ ID NO: 202)

Cyclo(O-C(R',R")C(O)-Tyr-4-Hyp-Pro-Gly-Ala-Gly)         (SEQ ID NO: 203)

Cyclo(O-C(R',R")C(O)-Tyr-4-Hyp-4-Hyp-Gly-Ala-Gly)       (SEQ ID NO: 204)

Cyclo(O-C(R',R")C(O)-Tyr-Pro-Pro-Gly-Ala-Gly)           (SEQ ID NO: 205)

Cyclo(O-C(R',R")C(O)-Tyr-Sar-Sar-Gly-Ala-Gly)           (SEQ ID NO: 206)

Cyclo(O-C(R',R")C(O)-Tyr-Sar-Pro-Gly-Ala-Gly)           (SEQ ID NO: 207)

Cyclo(O-C(R',R")C(O)-Tyr-4-Hyp-Sar-Gly-Ala-Gly)         (SEQ ID NO: 208)

Cyclo(O-C(R',R")C(O)-Tyr-Pro-Sar-Gly-Ala-Gly)           (SEQ ID NO: 209)

Cyclo(O-C(phenyl,methyl)C(O)-Tyr-Sar-4-Hyp-Gly-Ala-Gly) (SEQ ID NO: 210)
``` and the mirror images thereof, the retro analogues thereof, and derivatives thereof, such as pharmaceutically acceptable salts and amides.

When an ester bond is part of the backbone in the cyclic compounds of the invention, L may be derived from a hydroxy-carboxylic acid, such as a hydroxy C(3-6)alkyl carbocylic acid. In one embodiment L is derived from an α-hydroxy-carboxylic acid preferably of the general formula HO—C(R1)(R2)-COOH wherein R1 and R2 independently is H, C(1-6)-alkyl, C(2-6)-alkenyl, aryl, aryl-C(1-4)-alkyl, heteroaryl or heteroaryl-C(1-4)-alkyl; or R1 and R2 together with the carbon atom to which they are bound form a cyclopentyl, cyclohexyl, or cycloheptyl ring; where an alkyl or alkenyl group may be substituted with from one to three substituents selected from amino, cyano, halogen, isocyano, isothiocyano, thiocyano, sulfamyl, C(1-4)-alkylthio, mono- or di-C(1-4)-alkyl-amino, hydroxy, C(1-4)-alkoxy, aryl, heteroaryl, aryloxy, carboxy, C(1-4)-alkoxycarbonyl, C(1-4)-alkylcarbonyloxy, aminocarbonyl, mono- or di-C(1-4)-alkyl-aminocarbonyl, mono- or di-C(1-4)-alkyl-amino, mono- or di-C(1-4)-alkyl-amino-C(1-4)-alkyl, C(1-4)-alkylcarbonylamino, sulfono, and sulfino; and where a aryl or a heteroaryl group may be substituted with from one to three substituents selected from C(1-4)-alkyl, C(2-4)-alkenyl, nitro, amino, cyano, halogen, isocyano, isothiocyano, thiocyano, sulfamyl, C(1-4)-alkylthio, mono- or di-C(1-4)-alkyl-amino, hydroxy, C(1-4)-alkoxy, aryloxy, carboxy, C(1-4)-alkoxycarbonyl, C(1-4)-alkylcarbonyloxy, aminocarbonyl, mono- or di-C(1-4)-alkyl-aminocarbonyl, mono- or di-C(1-4)-alkyl-amino, mono- or di-C(1-4)-alkyl-amino-C(1-4)-alkyl, C(1-4)-alkylcarbonylamino, sulfono, and sulfino. In another embodiment L is derived from a hydroxy aryl-C(3-6)-alkyl-carboxylic acid, or L is derived from a hydroxy C(2-6)alkenyl-carboxylic acid, or L is derived from a hydroxy C(3-6)alkyl carboxylic acid. It is preferred that R1 and R2 represent different groups.

In cyclic compounds of the invention where the cyclisation is formed as an ester bond and the number of amino acid residues is 5, the group A-B is selected from the group consisting of Sar-Hyp, Hyp-Sar, Pro-Hyp, Pro-Pro, Hyp-Pro, and Hyp-Hyp where Pro and Hyp independently may be an L or D form and Hyp preferably represents 4-hydroxyproline. More preferably, A-B represents unsubstituted L-Pro-L-4Hyp, L-4Hyp-L-Pro, D-Pro-D-4Hyp, or D-4Hyp-D-Pro.

Examples of compounds of the invention are
(SEQ ID NO: 211) Cyclo(O—(CH$_2$)$_5$C(O)-Tyr-Pro-4-Hyp-Gly-Ala-Gly) and (SEQ ID NO: 212) Cyclo(O—(CH$_2$)$_5$C(O)-Tyr-4-Hyp-Pro-Gly-Ala-Gly) when L is a hydroxy C(3-6)alkyl carbocylic acid, and (SEQ ID NO: 213) Cyclo(O—(4-hydroxymethylbenzoyl)C(O)-Tyr-Pro-4-Hyp-Gly-Ala-Gly) and (SEQ ID NO: 214) Cyclo(O—(4-hydroxymethylbenzoyl)C(O)-Tyr-4-Hyp-Pro-Gly-Ala-Gly) when L is a hydroxy aryl-C(1-4)alkyl carboxylic acid, and the mirror images thereof, the retro analogues thereof, and derivatives thereof, such as pharmaceutically acceptable salts and amides.

Cyclic compounds of the invention where the cyclisation is formed with Serine:

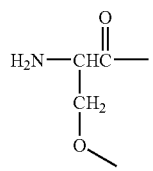

VI (SEQ ID NO: 215)

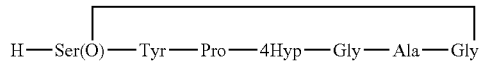
H—Ser(O)—Tyr—Pro—4Hyp—Gly—Ala—Gly (SEQ ID NO: 216)

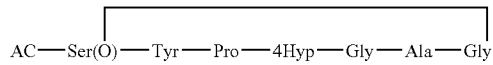
AC—Ser(O)—Tyr—Pro—4Hyp—Gly—Ala—Gly and with Threonine:

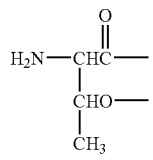

VII (SEQ ID NO: 217)

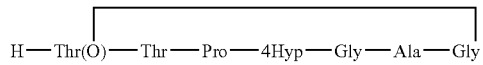
H—Thr(O)—Thr—Pro—4Hyp—Gly—Ala—Gly (SEQ ID NO: 218)

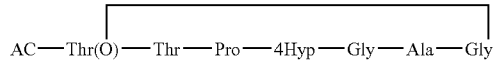
AC—Thr(O)—Thr—Pro—4Hyp—Gly—Ala—Gly

Examples of cyclic compounds of the invention having a disulphide bond are

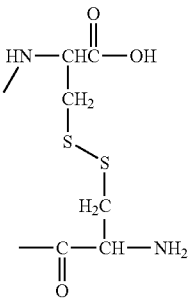

VIII (SEQ ID NO: 219)

H—Cys–Gly–Hyp–Pro–Tyr–Cys–NH$_2$/OH, cf. Compound 21 os ex. 21
SEQ ID NO: 220)

H—Cys–Tyr–Pro–4Hyp-Gly–Ala–Gly–Cys–OH/NH$_2$
(SEQ ID NO: 221)

H—Cys—Tyr—Pro—4Hyp—Gly—Ala—Cys—OH/NH$_2$
(SEQ ID NO: 222)

H—Cys–Tyr–Pro–4Hyp-Gly–Cys–OH/NH$_2$, cf. Compound 20 of Ex. 20
(SEQ ID NO: 223)

H—Cys—Tyr—Pro—4Hyp—Cys—OH/NH$_2$

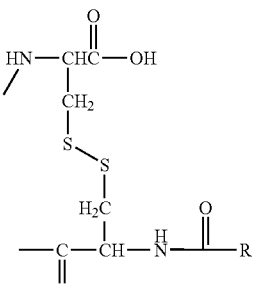

IX (SEQ ID NO: 224)

R—C(O)-Cys–Tyr–Pro–4Hyp-Gly–Ala–Gly–Cys–OH/NH$_2$
(SEQ ID NO: 225)

R—C(O)—Cys–Tyr–Pro–4Hyp–Gly–Ala–Cys–OH/NH$_2$
(SEQ ID NO: 226)

R—C(O)—Cys—Tyr—Pro—4Hyp—Gly—Cys—OH/NH$_2$
(SEQ ID NO: 227)

R—C(O)—Cys—Tyr—Pro—4Hyp—Cys—OH/NH$_2$ including compounds having combinations of L and D amino acids, amino acid substituted with Sar and other N-substituted natural amino acids, and the mirror image of each of them, their retro analogues as well as derivatives, such as pharmaceutically acceptable salts and amides.

Examples of compounds where X and Y are connected via a reduced amide bond having the linker L of formula X:

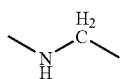 (X)

are listed below:

```
Cyclo(ψCH₂NH)-Tyr-Pro-4Hyp-Gly-Ala-Gly)      (SEQ ID NO: 228)

Cyclo(ψCH₂NH)-Tyr-4-Hyp-Pro-Gly-Ala-Gly)     (SEQ ID NO: 229)

Cyclo(ψCH₂NH)-Tyr-4-Hyp-4-Hyp-Gly-Ala-Gly)   (SEQ ID NO: 230)

Cyclo(ψCH₂NH)-Tyr-Pro-Pro-Gly-Ala-Gly)       (SEQ ID NO: 231)

Cyclo(ψCH₂NH)-Tyr-Sar-Sar-Gly-Ala-Gly)       (SEQ ID NO: 232)

Cyclo(ψCH₂NH)-Tyr-Sar-Pro-Gly-Ala-Gly)       (SEQ ID NO: 233)

Cyclo(ψCH₂NH)-Tyr-4-Hyp-Sar-Gly-Ala-Gly)     (SEQ ID NO: 234)

Cyclo(ψCH₂NH)-Tyr-Pro-Sar-Gly-Ala-Gly)       (SEQ ID NO: 235)

Cyclo(ψCH₂NH)-Tyr-Sar-4-Hyp-Gly-Ala-Gly)     (SEQ ID NO: 236)
``` and the mirror images thereof, the retro analogues thereof, and derivatives thereof, such as pharmaceutically acceptable salts and amides.

Examples of compounds where X and Y are connected via a reduced amide bond having the linker L of formula XI:

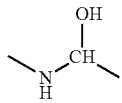

are listed below

```
Cyclo(ψCH(OH)NH)-Tyr-Pro-4Hyp-Gly-Ala-Gly)      (SEQ ID NO: 237)

Cyclo(ψCH(OH)NH)-Tyr-4-Hyp-Pro-Gly-Ala-Gly)     (SEQ ID NO: 238)

Cyclo(ψCH(OH)NH)-Tyr-4-Hyp-4-Hyp-Gly-Ala-Gly)   (SEQ ID NO: 239)

Cyclo(ψCH(OH)NH)-Tyr-Pro-Pro-Gly-Ala-Gly)       (SEQ ID NO: 240)

Cyclo(ψCH(OH)NH)-Tyr-Sar-Sar-Gly-Ala-Gly)       (SEQ ID NO: 241)

Cyclo(ψCH(OH)NH)-Tyr-Sar-Pro-Gly-Ala-Gly)       (SEQ ID NO: 242)

Cyclo(ψCH(OH)NH)-Tyr-4-Hyp-Sar-Gly-Ala-Gly)     (SEQ ID NO: 243)

Cyclo(ψCH(OH)NH)-Tyr-Pro-Sar-Gly-Ala-Gly)       (SEQ ID NO: 244)

Cyclo(ψCH(OH)NH)-Tyr-Sar-4-Hyp-Gly-Ala-Gly)     (SEQ ID NO: 245)
``` and the mirror images thereof, the retro analogues thereof, and derivatives thereof, such as pharmaceutically acceptable salts and amides.

More preferably, the invention relates to peptides and peptide derivatives of the general formula XII

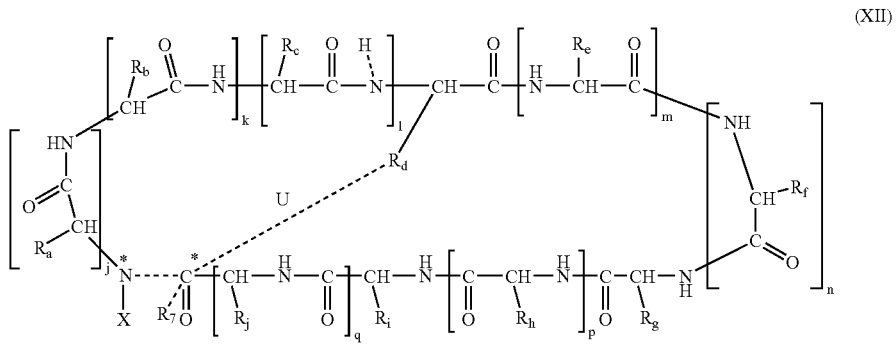

representing a peptide sequence wherein the amino acid residues may be D- and/or L-forms, having the N-terminal at N* and the C-terminal at C* and being optionally cyclic via a covalent bond between N* and C* as shown by a broken line or between $R_d$ and C* as shown by the broken line U; and wherein X represents an N-terminal moiety such as a photoprobe capable of being bond to the amino terminal N*, or an acyl group derived from a C(2-22)alkyl carboxylic acid, such as acetic acid, propionic acid, butyric acid and other fatty acids, such as behenic acid, optionally substituted with one or more substituents selected from the group consisting of hydroxy, halogen, C(1-6)alkyl, nitro and cyano; or X represents hydrogen;

$R_7$ represents OH, $NH_2$, $NHNH_2$ or $OR_8$ when the bond between N* and C* is missing, or $R_7$ is absent when there is a bond between N* and C*; $R_8$ represents H or a straight or branched C(1-6)alkyl group, an aryl or an aralkyl group.

$R_a$ represents the amino acid side chain of Hyp or Pro;

$R_b$ represents the amino acid side chain of Hyp or Pro;

$R_c$ represents the amino acid side chain of Gly, Sar, an aromatic amino acid side chain optionally substituted with one or more hydroxy, halogen or lower alkoxy group in the aromatic ring or $R_c$;

$R_d$ represents the amino acid side chain of Ala, Gly, Glu, Asp, Dab, Dapa, Lys, Asn, Gin, Orn, or Cys;

$R_e$ represents the amino acid side chain of Ala;

$R_f$ represents the amino acid side chain of Ala, Sar or Gly;

$R_g$ represents any amino acid side chain except the side chain of L-4Hyp or a moiety of formula II or IIa;

$R_h$ represents the amino acid side chain of Ala, or $R_h$ represents a moiety of formula II or IIa, preferably Pro;

$R_i$ represents the amino acid side chain of Gly or $R_i$ represents an aromatic amino acid optionally substituted with one or more halogen groups in the aromatic ring, preferably Tyr, Phe, Trp or Nal;

$R_j$ represents Asn, Gln, Asp, Glu, Cys, or Tyr;

and each of j, k, l, m, n, p and q is independently 0 or 1;

and the retro form, all D form, or retro all-D form of the peptide sequence of formula XII, and salts and amides thereof.

In preferred embodiments of formula XII X is preferably selected from the group consisting of photoprobes such as ASAL optionally iodinated in position 5, such as 2-hydroxy-4-azido-5-iodo benzoyl, and AB, and an acyl group such as Ac. $R_7$ is preferably $NH_2$. $R_a$ is preferably the amino acid side chain of Pro. $R_b$ is preferably the amino acid side chain of Hyp. $R_c$ is preferably the amino acid side chain of Gly or Tyr. $R_d$ is preferably the amino acid side chain of Gly, Asp, Glu, Dapa, or Dab. $R_e$ is preferably Ala. $R_f$ is preferably the amino acid side chain of Gly or Ala. $R_g$ is preferably the amino acid side chain of Asn, Gly, D-4Hyp or L-/D-Pro when formula XII represents a linear peptide, or when formula XII represents a peptide cyclised between N* and C* then $R_g$ represents the amino acid side chain of L-/D-4Hyp or L-/D-Pro. $R_h$ is preferably the amino acid side chain of Ala when U is missing, or $R_h$ is Pro or Hyp when U is present. $R_i$ is preferably Tyr, Phe, Trp, Nal optionally substituted with one or more hydroxy or halogen group, preferably F or Cl, in the aromatic ring. $R_j$ is preferably the amino acid side chain of Asp or Glu. $R_8$ represents H, benzyl, tert-butyl or $CH_3$.

j and k are preferably 0 when U is present, and j and k are preferably 1 when U is missing and formula XII represents a cyclic peptide, m is preferably 0 when U is missing, p is preferably 1 when U is present, and q is preferably 0 when U is present. Non-cyclic or linear peptides of formula XII are preferably of the retro all-D form. When formula XII represents a cyclic peptide, then the peptide preferably consists of between 3 and 9 amino acid residues, more preferably between 3 and 7 amino acid residues.

It will be apparent to a person skilled in the art that peptide-like compounds having a formula comparable to formula XII, but wherein one or more of the peptide bonds have been changed into a covalent bond selected from, i.a., a disulphide bond, an ester bond, a reduced amide bond, an alkoxy bond, an oxycarbonyl bond, and an acyloxyalkoxy bond would be useful for the treatment of the same conditions and ailments as the compounds of the present invention.

In a preferred embodiment the invention relates to compounds of the general formula XIII

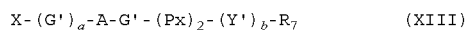

specifying a peptide sequence wherein the amino acid residues may be L and/or D forms, and wherein X represents H or Ac; when all amino acid residues are L-forms then X represents Ac;

G' represents a glycine residue or a glycine analogue such as Sar, G' is preferably glycine;

A represents alanine;
Px represents an amino acid residue of formula II or IIa such as Hyp or Pro, preferably proline;
Y' represents tyrosine or phenylalanine optionally substituted in the phenyl ring with halogen or hydroxy; Y' is preferably tyrosine;
a and b are independently 0 or 1,
$R_7$ represents OH, $NH_2$, $NHNH_2$, Asn-$NH_2$, or Gln-$NH_2$;
and retro forms thereof having the formula XIIIa: X-(Y')$_b$-(Px)$_2$-G'-A-(G')$_a$-$R_7$ wherein all amino acid residues preferably are D-forms and wherein all symbols have the same meaning as defined above for formula XIII;
and peptide compounds of formula XIII wherein at least one Px residue is a D-amino acid and the rest are L-amino acids;
and cyclic sequences of formula XIII wherein X represents H, $R_7$ represents Asn or Gln having a covalent bond to Y', b is 1, and a is 1;
and salts thereof.

Preferred cyclic peptide compounds of formula XII are characterised in having one of the general formulae XIV or XV:

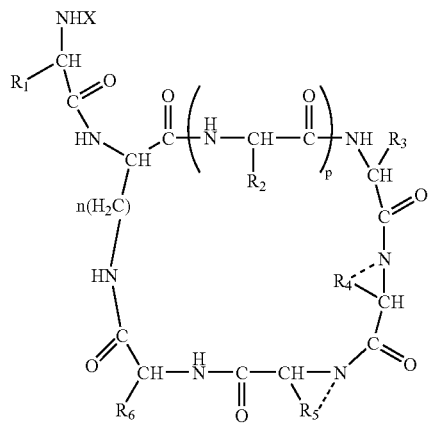

XIV wherein
X represents H or an N-terminal moiety such as a photoprobe capable of binding to the N terminal or an acylation with a C(2-22)alkyl carboxylic acid, such as acetic acid, propionic acid, butyric acid and other fatty acids such as behenic acid, being optionally substituted with one or more substituents selected from the group consisting of hydroxy, halogen, C(1-6)alkyl, nitro and cyano;
$R_1$ represents H or $CH_3$, preferably H;
$R_2$ and $R_3$ are different or the same and represent any possible amino acid side chain, preferably H or $CH_3$;
⋯ represents an optional bond;
$R_5$ and $R_4$ represent any possible amino acid side chain or when the optional bond is present $R_5$ and $R_4$ represent together with the attached C and N atoms a proline ring which is optionally substituted with OH, preferably in the 4-position, or $R_5$ and $R_4$ represent together with the attached C and N atoms a moiety of formula II or IIa above, preferably Pro or Hyp;
$R_6$ represents an aromatic amino acid side chain, preferably benzyl optionally substituted in the phenyl ring with one or more substituents selected from halogen, nitro and hydroxy, preferably $R_6$ represents Tyr;

p is 0 or 1;
n is 1, 2, 3 or 4; preferably n is 1;
and salts thereof.

Exemplary compounds of formula XIV are (SEQ ID NO: 246)

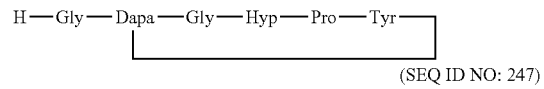

(SEQ ID NO: 247)

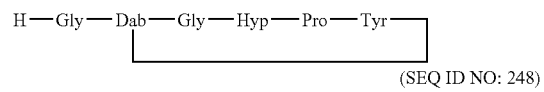

(SEQ ID NO: 248)

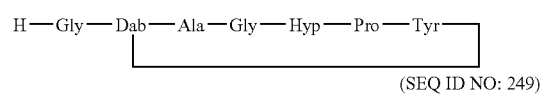

(SEQ ID NO: 249)

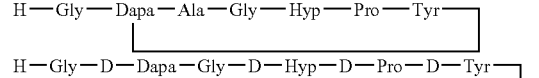

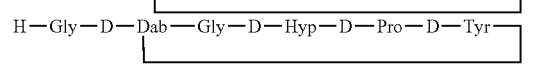

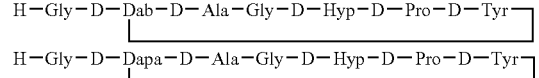

and their salts.

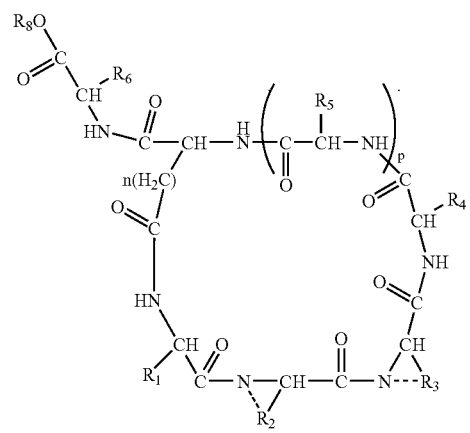

XV

Wherein $R_8$ is the same as defined above, preferably H;
$R_6$ represents H or $CH_3$, preferably H;
$R_4$ and $R_5$ are different or the same and represent any possible amino acid side chain, preferably Gly or Ala;
⋯ represents an optional bond;
$R_2$ and $R_3$ represent any possible amino acid side chain, or when the optional bond is present $R_2$ and $R_3$ represent together with the attached C and N atoms a proline ring which is optionally substituted with OH preferably in the 4-position or $R_2$ and $R_3$ represent a moiety of formula II or IIa;
$R_1$ represents an aromatic amino acid side chain, preferably a Tyr side chain;

p is 0 or 1;

n is 1, 2, 3 or 4; preferably n is 1;

and salts thereof.

Exemplary compounds of formula XV are

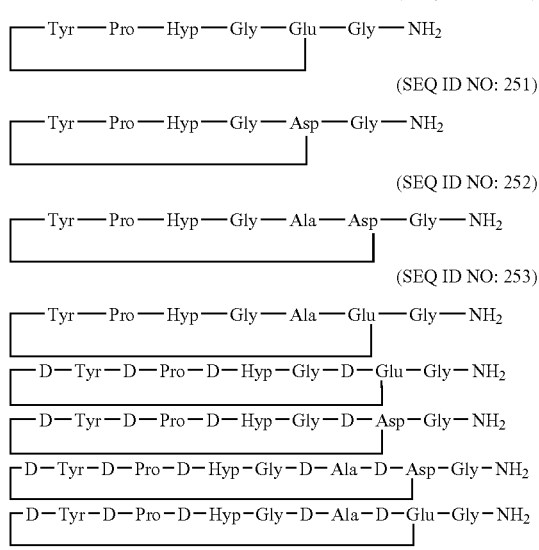

(SEQ ID NO: 250)
Tyr—Pro—Hyp—Gly—Glu—Gly—NH$_2$ (SEQ ID NO: 251)
Tyr—Pro—Hyp—Gly—Asp—Gly—NH$_2$ (SEQ ID NO: 252)
Tyr—Pro—Hyp—Gly—Ala—Asp—Gly—NH$_2$ (SEQ ID NO: 253)
Tyr—Pro—Hyp—Gly—Ala—Glu—Gly—NH$_2$

D—Tyr—D—Pro—D—Hyp—Gly—D—Glu—Gly—NH$_2$

D—Tyr—D—Pro—D—Hyp—Gly—D—Asp—Gly—NH$_2$

D—Tyr—D—Pro—D—Hyp—Gly—D—Ala—D—Asp—Gly—NH$_2$

D—Tyr—D—Pro—D—Hyp—Gly—D—Ala—D—Glu—Gly—NH$_2$

Furthermore, it has surprisingly been found that substituting an asparagine or a glutamine residue for the Hyp-Pro sequence in AAP10 results in a novel antiarrhythmic peptide, Compound 21 of Example 21 below. Thus, a preferred embodiment of the invention relates to peptide compounds wherein the amino acid residues may be D- and/or L-forms, and having the general formula XVI

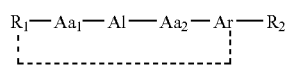

$R_1$—Aa$_1$—Al—Aa$_2$—Ar—$R_2$  XVI

Wherein $R_1$ represents an optional amide bond between the N and the C terminal of the peptide, H or Ac;

Aa$_1$ represents a peptide sequence, preferably of between 0 and 4 amino acid residues, when Aa$_1$ represents a peptide sequence of from 1 to 4 amino acid residues Aa$_1$ is preferably selected from the group consisting of Ala, Gly-Ala, Gly-Asn-Tyr, and Gly-Asn-Tyr-Ala;

Al represents an amino acid residue selected from the group consisting of Gly, beta Alanine and Sar;

Aa$_2$ represents an amino acid residue selected from the group consisting of Asn, Gln, Gly, Tyr, or a chemical unit, such as a hydroxy acid, an amino sulphonic acid, a phosphate group or a hydrocarbon chain connecting G and Ar via 4 covalent bonds; Ar represents an aromatic amino acid residue, such as a Tyr, Trp, Phe, His, or Nal, optionally substituted with one or more halogen, such as F, Cl, Br, I, OH, NO$_2$, NH$_2$, COOH, CONH;

$R_2$ represents OH, NH$_2$ or is missing;

and retro analogues, retro all-D analogues (retro-inverse analogues) and salts thereof.

Exemplary compounds of formula XVI are

| | | |
|---|---|---|
| Compound 39 | H-Gly-Ala-Gly-Asn-Tyr-NH$_2$ | (SEQ ID NO: 254) |
| Compound 44 | cyclo(-Tyr-Ala-Ser-Ala-Gly-Asn-) | (SEQ ID NO: 255) |
| Compound 45 | cyclo(-Tyr-Ala-Ser-Ala-Gly-Asn-) | (SEQ ID NO: 256) |
| Compound 46 | cyclo(-Tyr-Gly-Asn-Tyr-Ala-Gly-Asn-) | (SEQ ID NO: 257) |
| Compound 47 | cyclo(-Tyr-Val-Ser-Gly-Ala-Gly-Asn-) | (SEQ ID NO: 258) |
| Compound 40 | Ac-Gly-Asn-Tyr-NH$_2$ | |
| Compound 41 | H-Gly-Asn-Tyr-NH$_2$ | |
| Compound 42 | Ac-Ala-Gly-Asn-Tyr-NH$_2$ | (SEQ ID NO: 259) |
| Compound 43 | H-Ala-Gly-Asn-Tyr-NH$_2$ | (SEQ ID NO: 260) | and their salts as defined herein.

Photo/Thermo Labile Peptide Derivatives

Affinity labeling is a frequently used technique for studying the interactions of biologically active molecules. A photo or a thermo labile analogue of the compound is used for the investigation.

A photolabile analogue of the compound under investigation, which is stable in the dark, is converted by illumination into a reactive intermediate that can participate in insertion reactions. This, by forming a covalent bond, stabilizes the interaction based on biological affinity. As photo probes aromatic azides and stabilized diazo compounds produce on photolysis very reactive and nonspecific intermediates, nitrenes and carbenes, respectively capable of participating in insertion reactions. Thus, photo affinity labeling using aryl azides and stabilized diazo compounds as photo probes can be done on any binding site which contains carbon-hydrogen bonds and do not require the presence of a particular reactive functional group at the binding site. Specificity of labeling therefore depends solely on the specific binding of the ligand to the receptor, which is then followed by a nonspecific covalent bond forming reaction that guarantees labeling of the binding site. Photoaffinity probes is particularly useful for labeling hormone receptor sites where reactive functional groups may not be present, but which surely contains carbon-hydrogen bonds. As photo active functionality the azido, diazirino, α-diazo ketones, thia- and selenodiazoles, benzophenone, nitrophenyl are especially useful. The labeling process using aryl azides includes photolysis at $\lambda_{ex}$=300-320 nm for approx. 0.5-2 h at room temperature of an aqueous solution containing the photo labile peptide analogue and the receptor.

A thermo labile compound contains a reactive group which can form a covalent bond in a thermal controlled reaction with specificity towards amino or mercapto groups. As thermo probes aliphatic halides especially iodine and bromine, active esters such as N-hydroxysuccinimid, acid chlorides, pyridyidisulphides, isocyanates, isothiocyanates, carbodiimides, and maleimido can be used.

Labels for in vitro applications are most often chosen as radioactive isotopes such as Iodine-125 and 131, C-14 and tritium or fluorescence probes or biotin or haptens. The influence of the label on the binding activity of the ligand needs to be investigated, in order to secure that the receptor affinity is maintained. As radioactive label Iodine-125 is often used for in-vitro applications, due to its 60 days half-life and low energy photon emissions. The long half-life permits the preparation and storage of labeled photoactive analogues and the resulting labeled protein products for extended periods prior to usage or analysis. The incorporation of Iodine (I-125) into peptide ligands can easily be done if e.g. tyrosine og histidine are present in the peptide sequence. The influence of the labeling of the peptide on the biological activity of the ligand needs to be investigated, in order to secure that the biological activity is maintained. Dhein et al. (WO96/21674) have shown that a derivative of AAP10 where the phenyl ring of the Tyr residues carries an Iodine-125 substituent has biological activity. However, the use of said AAP10 variant as an affinity probe is not possible due to the reversible binding to a possible ligand or receptor. Photoaffinity labeling using aryl azides results generally in 50-60% peptide ligand non-reversibly attached to the target protein (receptor). Thus, it is a purpose of the present invention to further provide an antiarrhythmic peptide suitably modified with a photo or a thermo probe and optionally a radioactive label to be used in assays for the identification of possible ligands or receptors for the antiarrhythmic peptide. Said purpose is achieved with a compound of formulae I, XII, XIII or 9 herein, derivatised with one of the above mentioned photo probes, preferably 4-azidosalicyloyl (ASAL) and AB (4-azidobenzoyl). Preferably, said derivatised compound is further substituted with a radioactive label, such as Iodine-125.

Exemplary photo probe modified and radioactively labeled compounds of Formula I, XII or 9 are

```
(SEQ ID NO: 261)

Compound 31    ASAL-Pro-Hyp-Gly-Ala-Gly-NH2

(SEQ ID NO: 262)

Compound 32    ASAL(3-I)-Pro-Hyp-Gly-Ala-Gly-NH2

(SEQ ID NO: 263)

Compound 32a   ASAL(6-I)-Pro-Hyp-Gly-Ala-Gly-NH2

(SEQ ID NO: 264)

Compound 33    AB-Tyr-Pro-Hyp-Gly-Ala-Gly-NH2

(SEQ ID NO: 265)
```

Compound 34 AB-Tyr(3,5-di-I)-Pro-Hyp-Gly-Ala-Gly-NH$_2$ and salts thereof, cf. Synthesis Examples 31-34 below.

Furthermore, the invention relates to peptide compounds selected from the group consisting of the general formulae 2: H-GAG-(Pa)$_2$—NH$_2$ wherein Pa is any amino acid residue or a moiety of formula II or IIa; at least one of Pa is a D amino acid; preferably Pa is Hyp, P, G or A;

3: H-GAG-(Px)$_2$—Y—NH$_2$ wherein Px is a moiety of formula II or IIa, where one Px is a moiety of formula II, IIa and the other Px is P or Hyp;

4: Ac-Y'-(Px)$_2$-GAG-OH wherein Y' is Y or F, and Px is P or Hyp;

5: Cys(Acm)-AAP10*-Cys(Acm) or Cys(Acm)-retroAAP10*-Cys(Acm) wherein Acm is acetamidomethyl radical and AAP10* is the AAP10 sequence or a truncated form thereof;

6: X-G-D-A-G-(D-Px)$_2$-D-Y—NH$_2$ wherein X is H or Ac, and Px is a moiety of formula II or IIa, preferably Hyp or P; optionally having one or more C or N isotopes;

7: H-(Px)$_n$-Y(N/Q)G-AG-(Px)$_m$-NH$_2$ wherein Px is P or Hyp, n is 1 or 2, and m is 0 or 1, preferably m=0 when n=2, and m=1 when n=1;

8: H-G'-A-G'-(Px)$_2$-Y—NH$_2$ wherein G' is Sar or Gly and at least one G' is Sar, and Px is P or Hyp;

9: X—(Y)$_p$-(Px)$_2$-GAG-NH$_2$ wherein X is ASAL or AB, p is 0 or 1, and the phenyl ring of Y has optionally one or more halogen substitutent, preferably I, and Px is P or Hyp;

10: Cyclo(-GAG-(Px)$_2$-Y—N/Q-) wherein Px is P or Hyp;

11: Cyclo(-Y-(Px)$_2$-GA-(G)$_q$-N/Q-) wherein q is 0 or 1, the phenyl ring of Y has optionally one or more halogen substitutents, preferably I, and Px is P or Hyp;

12: X-Zd-G(N/Q)Y—NH$_2$ wherein Zd is a sequence of 0, 1, or 2 amino acid residues selected from G or A, and X is H or Ac;

and the salts thereof.

Salts

It is preferred that compounds of the invention are used in the form of a pharmaceutically acceptable salt, an alkyl ester, an amide, an alkylamide, a dialkylamide or a hydrazide formed with the C-terminal carboxylic acid function of a linear compound or a free carboxylic acid function, if present, of a cyclic compound. Amides and lower alkyl amides of linear compounds are among the preferred compounds of the invention. Salts include pharmaceutically acceptable salts, such as acid addition salts and basic salts. Examples of acid addition salts are hydrochloride salts, sodium salts, calcium salts, potassium salts, etc. Examples of basic salts are salts where the cation is selected from alkali metals, such as sodium and potassium, alkaline earth metals, such as calcium, and ammonium ions $^+$N (R$^3$)$_3$(R$^4$), where R$^3$ and R$^4$ independently designates optionally substituted C$_{1-6}$-alkyl, optionally substituted C$_{2-6}$-alkenyl, optionally substituted aryl, or optionally substituted heteroaryl. Other examples of pharmaceutically acceptable salts are; e.g., those described in "Remington's Pharmaceutical Sciences" 17. Ed. Alfonso R. Gennaro (Ed.), Mark Publishing Company, Easton, Pa., U.S.A., 1985 and more recent editions, and in Encyclopedia of Pharmaceutical Technology.

DEFINITIONS

Throughout the description and claims the three letter code for natural amino acids is used as well as generally accepted three letter codes for other α-amino acids, such as Sarcosin (Sar), α-Amino-iso-butanoic acid (Aib), Naphthylalanine (Nal) including 1-naphthylalanine (1Nal) and 2-naphthylalanine (2Nal), Phenylglycine Phg, 2,4-Diaminobutanoic acid (Dab), 2,3-Diaminopropanoic acid (Dapa), and Hydroxyproline (Hyp). Where nothing is specified Hyp represents 4-hydroxyproline. The natural or essential amino acids are the amino acid constituents of proteins. The aromatic amino acids are Phe, Tyr, Trp, 1Nal, 2Nal and His. Where the L or D form has not been specified it is to be understood that the amino acid in question has the natural L form, cf. Pure & Appl. Chem. Vol. 56(5) pp 595-624 (1984). Where nothing is specified it is to be understood that the C-terminal amino acid of a compound of the invention exists as the free carboxylic acid, this may also be specified as "—OH". The C-terminal amino acid of a compound of the invention may be shown to have the terminal function "—OH/NH$_2$," which means that there are two preferred forms of the compound: the free carboxylic acid and the amidated derivative. Hexapeptide compounds of the invention comprising the sequence Ala-Gly-Hyp and having an —NH$_2$ group at the C-terminal do not contain a C-terminal Phe or Tyr or derivatives thereof having a halogen substitution in the phenyl ring.

By "functional analogues" of antiarrhythmic peptides is meant any chemical entity or compound which has a structural conformation and/or binding properties that are sufficiently similar to the endogeneous AAP to provide one or more of the beneficial antiarrhythmic or antithrombotic properties of the endogeneous AAP.

The term "heteroaryl" includes 5- or 6-membered aromatic monocyclic heterocyclic groups containing 1-4 heteroatoms selected from nitrogen, oxygen and sulfur, such as pyrrolyl, furyl, pyrazolyl, imidazolyl, oxazolyl, isoxazolyl, thiazolyl, isothiazolyl, oxadiazolyl, thiadiazolyl, triazolyl, pyridyl, and aromatic bicyclic heterocyclic groups containing 1-6 heteroatoms selected from nitrogen, oxygen and sulfur, such as quinolinyl.

The term "retro analogue" is intended to mean a peptide whose sequence is the reverse of the named peptide.

The term "halogen" refers to F, Cl, Br, and I, where F and I are preferred.

The term "alkyl" refers to univalent groups derived from alkanes by removal of a hydrogen atom from any carbon atom: $C_nH_{2n+1}$—. The groups derived by removal of a hydrogen atom from a terminal carbon atom of unbranched alkanes form a subclass of normal alkyl (n-alkyl) groups: H[CH$_2$]$_n$—. The groups RCH$_2$—, R$_2$CH— (R not equal to H), and R$_3$C— (R not equal to H) are primary, secondary and tertiary alkyl groups respectively. C(1-22)alkyl refers to any alkyl group having from 1 to 22 carbon atoms and includes C(1-6)alkyl, such as methyl, ethyl, propyl, iso-propyl, butyl, pentyl and hexyl and all possible isomers thereof. By "lower alkyl" is meant C(1-6)alkyl, preferably C(1-4)alkyl, more preferably, methyl and ethyl.

The term "alkenyl" refers to a straight or branched or cyclic hydrocarbon group containing one or more carbon-carbon double bonds. C(2-22)alkenyl refers to any alkenyl group having from 1 to 22 carbon atoms and includes C(2-6)alkenyl, vinyl, allyl, 1-butenyl, etc.

The term "aralkyl" refers to aryl C(1-22)alkyl, and the term "aryl" throughout this specification means phenyl or naphthyl.

HPP refers to hydroxyphenylpropionyl
4HPP refers to 3-(4-hydroxyphenyl)propionyl
2HPP refers to 3-(2-hydroxyphenyl)propionyl
4HPPA refers to 4-hydroxyphenoxyacetic acid
2HPPA refers to 2-hydroxyphenoxyacetic acid
4HMPA refers to 4-(hydroxymethyl)phenoxyacetic acid
4HPA refers to 4-hydroxyphenylacetic acid
3HPA refers to 3-hydroxyphenylacetic acid
2HPA refers to 2-hydroxyphenylacetic acid
4HBG refers to N-(4-hydroxybenzoyl)glycine
3HBG refers to N-(3-hydroxybenzoyl)glycine
2HBG refers to N-(2-hydroxybenzoyl)glycine
4HPG refers to N-(4-hydroxyphenyl)glycine
Ac refers to the acetyl radical
Tfa refers to trifluoroacetyl radical
ASAL refers to 4-azidosalicyloyl radical
AB refers to 4-azidobenzoyl radical
HOBt refers to 1-hydroxybenzotriazole
HOAt refers to 1-Hydroxy-7-azabenzotriazole
Acm refers to Acetamidomethyl radical
Pd(PPh$_3$)$_4$ is tetrakis(triphenylphosphine)palladium(0)

Stability of the Compounds of the Invention

Furthermore, the compounds of the present invention are characterised in being stable towards enzymatic degradation, and/or being stable towards degradation in plasma, and/or having an improved in vivo half life.

It is preferred that the compounds including the antiarrhythmic compounds of the present invention are stable towards enzymatic degradation and/or stable in plasma. The various derivatives and chemical modifications of the native peptide sequence of AAP as presented by the invention, e.g., the C-terminal amidation or esterification, the use of D-amino acids and derivatives of natural amino acids, the N-terminal modifications, and the cyclic analogues all represent modifications that are designed to enhance stability while retaining the essential antiarrhythmic and/or antithrombotic properties of native AAP.

Table 1 below shows the half life of degradation ($T_{1/2}$) of various compounds of the invention compared to AAP10, AAP and HP5. It appears from the table that the compounds 2, 3, 27, 48 and 49 of the invention having half lives of 3 hours or more are considerably more stable in plasma and serum than AAP10 which has a half life of less than 10 minutes, and HP5 which has a half life of less than 12 minutes.

TABLE 1

Results of in vitro stability test in plasma and serum, $T_{1/2}$ in min and hrs

| MEDIA AND COMPOUNDS | PLASMA, HEPARIN | | | SERUM | |
|---|---|---|---|---|---|
| | RAT | RABBIT | HUMAN | RABBIT | HUMAN |
| Compound CE1 AAP | | 4.4 min ± 12% | 7.6 min ± 6% | | |
| Compound CE2 AAP10 | 8.2 min ± 13% | 9.5 min ± 12% | — | 2.7 min ± 4% | — |
| Compound CE3 HP5 | | 3.7 min ± 1% | 11.9 min ± 11% | | |
| Compound 3 | — | *>5 hrs | — | — | *>5 hrs |
| Compound 2 | — | *>5 hrs | *>5 hrs | — | *>5 hrs |
| Compound 27 | — | 3.8 hrs ± 13% | — | — | 3.1 hrs ± 6% |

TABLE 1-continued

Results of in vitro stability test in plasma and serum, $T_{1/2}$ in min and hrs

| MEDIA AND | PLASMA, HEPARIN | | | SERUM | |
|---|---|---|---|---|---|
| COMPOUNDS | RAT | RABBIT | HUMAN | RABBIT | HUMAN |
| Compound 49 | — | 30.4 hrs ± 28% | 13.1 hrs ± 3% | — | — |
| Compound 48 | — | 13.6 hrs ± 17% | 14.8 hrs ± 3% | — | — |

*no reaction over 5 hrs

Method of Analysis of In Vitro Plasma Stability

The stability of peptides is analysed in different plasma and serum types. The peptides are incubated at 37° C. in plasma and samples taken at approx. 9 regular intervals between t=0 and t=156 min are analysed by HPLC.

Appropriate conditions (column, solvent, gradient, and temp.) for the HPLC analyses are estimated to ensure that the drug peak and the plasma peaks do not have the same retention time. This is done by subsequent injections of the drug, plasma, and a co-injection with the drug and the plasma, followed by optimisation of the LC method parameters until a satisfactory separation is obtained. Three parallel experiments are performed for each plasma type. 100 µl of peptide is mixed with 900 µl plasma at t=0 and incubated at 37° C. (drug-plasma mixture conc. 0.1 mg/ml). Samples of 100 µl of the drug-plasma mixture are removed at appropriate intervals and the degradation stopped by precipitation of the sample with 10 µl MeCN:TFA 50:50 v/v. A control plasma sample without the drug treated in the same manner is also taken. The plasma samples are centrifuged for 15 min. at 12,000 rpm (Eppendorf centrifuge) at ambient temperature. The resulting supernatant solution is transferred to 300 µl HP autosamler vials and analyzed by HPLC. HPLC analysis are performed as follows:

Compound CE1
Column: Vydac 218MS52, 250×2.1 mm, flow: 0.200 mL/min. Temp.: 40° C.
Solvent: MeCN/MQW/TFA (0.1%). Run time: 25 min.
Inj. vol.: 15 µL. Detection: DAD1 A, 214.5 nm Compound CE2
Column: Kromasil KR100-10C8, 250×4.6 mm, flow: 1 mL/min. Temp.: 40° C.
Solvent: MeCN/MQW/TFA (0.1%). Run time: 20 min.
Inj. vol.: 25 µL. Detection: VWD 1 A, 214.5 nm.
Except for rabbit serum: DAD1 A, 214.5 nm
Except for rat plasma: Solvent: MeOH/MQW/TFA (0.1%). Detection: VWD1 A, 210 nm Compound CE3
Column: Vydac 218MS52, 250×2.1 mm, flow: 0.200 mL/min. Temp.: 40° C.
Solvent: MeCN/MQW/TFA (0.1%). Run time: 35 min.
Inj. vol.: 15 µL. Detection: DAD1 A, 214.5 nm Compound 3
Column: Kromasil KR100-10C8, 250×4.6 mm, flow: 1 mL/min. Temp.: 40° C.
Solvent: MeCN/MQW/TFA (0.1%). Run time: 25 min.
Inj. vol.: 25 µL. Detection: DAD1 A, 214.5 nm Compound 2
Column: Luna 3u C18(2), 150×2 mm, flow: 0.250 mL/min. Temp.: 40° C.
Solvent: MeOH/MQW/HFBA (0.02%). Run time: 25 min.
Inj. vol.: 25 µL. Detection: DAD1 A, 214.5 nm.
Except for human plasma: Column: Luna 5u C18, 150×2 mm, Temp.: 10° C.
Except for human serum: Column: Kromasil KR100-10C8, 250×4.6 mm, flow: 1 mL/min. Solvent: MeCN/MQW/TFA (0.1%).

Compound 27
Column: Kromasil KR100-10C8, 250×4.6 mm, flow: 1 mL/min. Temp.: 40° C.
Solvent: MeCN/MQW/TFA (0.1%). Run time: 20 and 25 min.
Inj. vol.: 25 µL. Detection: VWD1 A, 214 nm Compound 49
Column: Kromasil KR100-10C8, 250×4.6 mm, flow: 1 mL/min. Temp.: 40° C.
Solvent: MeCN/MQW/TFA (0.1%). Run time: 25 min.
Inj. vol.: 25 µL. Detection: DAD1 A, 214.5 nm Compound 48180
Column: Kromasil KR100-10C8, 250×4.6 mm, flow: 1 mL/min. Temp.: 40° C.
Solvent: MeCN/MQW/TFA (0.1%). Run time: 25 min.
Inj. vol.: 25 µL. Detection: DAD1 A, 214.5 nm The samples are analyzed in the following order: blank, the peptide at 0.1 mg/mL, the plasma without the peptide, the three parallel samples for t=0, the three parallel samples for t=5 min. the three parallel samples for t=10 min. etc. And finally the three parallel samples for t=0 are repeated to make sure that there have been no degradation or other failure during the analyses. The sample concentrations (peak height in mAU) are plotted vs. time and fitted to a function describing a mono exponential decay (Excel). The half-life of the peptides in the different types of plasma are presented in Table 1 as mean (n=3)±standard deviation.

General Background on Gap Junctions

In a multicellular organism, co-ordination between cells is of paramount importance. Among the various means of cellular cross talk, gap junctions provide the most direct pathway. Gap junctions are one type of junctional complex formed between adjacent cells and consist of aggregated channels that directly link the interiors (cytoplasm) of neighbouring cells. In the adult mammal, gap junctions are found in most cell types with one known exception being circulating blood elements.

The structural unit of the gap junction channel is the connexon or hemi-channel. Each connexon is comprised of six connexin polypeptides (Cx) which oligomerise to form an aqueous pore that spans a single plasma membrane. To form a complete gap junction channel, two connexons from adjacent cells align and dock with each other to form a continuous channel, linking the cytoplasm of the two cells.

The gap junction channel-forming connexins comprise a multi-gene family with at least fourteen mammalian connexins discovered thus far. Connexin expression is tissue and cell specific, with some cells expressing multiple connexin isoforms. Experimental evidence suggests two different hybrid configurations are possible: heterotypic cell-to-cell channels in which each connexon or hemichannel consists of a specific connexin isoform; or heteromeric channels where each connexon is a mixture of the different connexin isoforms expressed in a particular cell type. Connexins are expressed in a cell-, tissue-, and development-specific manner.

Relatively little is known about the connexin gene structure. Results reported for mouse Cx43 revealed that Cx43 contains two exons and an intron located in the 5' untranslated region. Further analysis showed that the Cx43 transcription start point in both embryos and adult tissues. Several putative transcription factor binding sites have been identified in the 5' proximal promotor. In vitro studies have shown that permeable channels could be produced by hemichannels composed of different pairs of Cx. For example, Cx43 can produce functional channels with Cx32, Cx 37 and endogenous Cx of oocytes (Cx38) but not with Cx26 oocytes. However, very little is known about their properties as well as about the regulation of permeability of these heterochannels. Cx are expressed in the vast majority of tissues and single cell are able to express several different Cx. Permeable gap junctions can be formed between cells, which express different types of Cx. Thus the gap junction intracellular communication (GJIC) in tissues appears to be very important for maintenance of tissue integrity. It appears that several genes are making the equivalent products in order to prevent the loss of GJIC due to a mutation in one of the genes.

The pore diameter of the gap junction channel formed has been reported to be in the range of 0.8-1.4 nm. Gap junctions are relatively non-selective and allow the passage of molecules up to about 1000 Daltons. Such substances are, i.a., ions, water, sugars, nucleotides, amino acids, fatty acids, small peptides, drugs, and carcinogens. Channel passage does not require ATP and appears to result from passive diffusion. This flux of materials between cells via gap junction channels is known as gap junctional intercellular communication (GJIC), which plays an important role in the regulation of cell metabolism, proliferation, and cell-to-cell signalling. One of the most significant physiological implications for GJIC is that gap junction coupled cells within a tissue are not individual, discrete entities, but are highly integrated with their neighbors. This property facilitates homeostasis and also permits the rapid, direct transfer of second messengers between cells to co-ordinate cellular responses within the tissue.

The process of GJIC is regulated by a variety of mechanisms that can be broadly divided into two major categories. The first type of regulation controls the cellular quantity of gap junctions by influencing the expression, degradation, cellular trafficking of connexins to the plasma membrane, or assembly of connexins into functional gap junctions. Impaired GJIC caused by the down-regulation of connexin expression in tumour cells is an example of this mode of regulation. The second type of regulation does not generally involve any gross alteration of the cellular levels of gap junctions or connexins, but induces opening or closure or gating of existing gap junctions. Extracellular soluble factors, such as mitogens (e.g. DDT), hormones (e.g. catecholamines), anaesthetics (e.g. halothane), intracellular biomolecules (e.g. cAMP), and cell stress (e.g. mechanical or metabolic stress) can result in this type of regulation. Additionally, GJIC is regulated during the cell cycle and during cellular migration.

The mode of GJIC regulation or junctional gating has been widely studied for gap junctions especially gap junctions composed of connexin43 (Cx43) and thus used as a representative of all connexins. Some factors exert their inhibitory effects on GJIC indirectly, for example, by altering the lipid environment and cell membrane fluidity, whereas other GJIC inhibitors include oncogenes, growth factors, and tumour promoters, which induce various modifications of the Cx43. Disruption of junctional permeability may be necessary for mediating the specific biological functions of the latter group. These agents initiate complex signalling pathways consisting of the activation of kinases, phosphatases, and interacting proteins. Understanding the mechanisms of action of these GJIC modulators will not only define their respective signalling pathways responsible for junctional regulation, but will also provide experimental tools for characterising the biological functions of GJIC and connexins.

Changes in the phosphorylation of specific sites of the cytoplasmic carboxy terminal domain of Cx43 appear to be pivotal to the opening and closing of the gap junctional channel. Phosphorylation of the carboxy terminal domain may also be important to the process of bringing Cx43 gap junctional hemicomplex to the surface membrane, its internalisation and degradation. Connexins have half-lives (hours) that are much shorter than most plasma membrane proteins (days), e.g. the half-life of Cx43 in rat heart is less than 1½ hour. Thus, regulation of the turnover rate would be an important factor in regulating GJIC.

The carboxy terminal domain contains putative phosphorylation sites for multiple protein kinases (PKA, PKC, PKG, MAPK, CaMkII and tyrosine kinase). Phosphorylation of these sites of the carboxy terminal domain results in closure of gap junctional channels and various inhibitors of Cx43 gap junctional channels use different signalling pathways to induce phosphorylation of the carboxy terminal domain. The cell type and the particular inhibitor determine which signalling pathways to be used and the type of the involved protein kinase points to the intracellular messenger system utilised. Thus activation of PKA has been reported by to require involvement of the cAMP second messenger system while PKC requires involvement of the phosphoinositol intracellular signalling system.

Other mechanisms regulating channel gating include intracellular levels of hydrogen and calcium ions, transjunctional voltage, and free radicals. Decreased pH or pCa induce channel closure in a cell- and connexin-specific manner.

Many physiological roles besides growth control have been proposed for GJIC: Homeostasis. GJIC permits the rapid equilibration of nutrients, ions, and fluids between cells. This might be the most ancient, widespread, and important function for these channels.

Electrical coupling. Gap junctions serve as electrical synapses in electrically excitable cells such as cardiac myocytes, smooth muscle cells, and neurones. In these tissues, electrical coupling permits more rapid cell-to-cell transmission of action potentials than chemical synapses. In cardiomyocytes and smooth muscle cells, this enables their synchronous contraction.

Tissue response to hormones. GJIC may enhance the responsiveness of tissues to external stimuli. Second messengers such as cyclic nucleotides, calcium, and inositol phosphates are small enough to pass from hormonally activated cells to quiescent cells through junctional channels and activate the latter. Such an effect may increase the tissue response to an agonist.

Regulation of embryonic development. Gap junctions may serve as intercellular pathways for chemical and/or electrical developmental signals in embryos and for defining the boundaries of developmental compartments. GJIC occurs in specific patterns in embryonic cells and the impairment of GJIC has been related to developmental anomalies and the teratogenic effects of many chemicals.

The intercellular communication ensures that the activities of the individual cells happen in co-ordinated fashion and integrate these activities into the dynamics of a working tissue serving the organism in which it is set. It is therefore not very surprising that a wide variety of pathological conditions have been associated with decreased GJIC.

Pharmacology

Cardiac Indications

As outlined in the description of background of the invention, there is ample evidence supporting an important role of GJIC in cardiomyocytes under normal and pathological conditions. Specific cardiac conditions associated with impaired GJIC are discussed below and in vitro and in vivo evidence are presented to demonstrate that compounds that increase GJIC in the heart are useful for the prevention and/or treatment of a series of pathological conditions in the heart.

Reentry Arrhythmias

Cardiac arrhythmiac are caused by either abnormal impulse initiation or abnormal impulse conduction. Among arrhythmias with abnormal impulse conduction, arrhythmias caused by a reentrant mechanism are the most serious.

Ventricular Reentry:

Reentry is the major cause of sustained ventricular fibrillation and sudden cardiac death. Reentry occurs when the propagating impulse does not die out after complete activation of the heart, but persists to reexcite the heart after the end of the refractory period. The induction of reentry is facilitated by slow conduction, increased dispersion of repolarization, non-uniform anisotropy and unidirectional conduction block. The underlying disease responsible for the majority of cases of ventricular reentry is ischemic heart disease (e.g., acute myocardial infarction, chronic myocardial infarction, stable angina pectoris, and unstable angina pectoris). During acute ischemia the gap junction channels close leading to an uncoupling of neighboring cells. Heterogeneous changes in ion channel and gap junction function lead to increased dispersion of action potential duration and effective refractory period especially in the border zone separating the ischemic area from the normal myocardium. Increased dispersion of action potential duration has long been known to facilitate the induction of ventricular fibrillation[23]. Normally, in well-coupled cells, the difference in action potential duration is smoothened due to the electrical coupling. However, uncoupling will prevent this smoothening and contribute to an unmasking of dispersion of action potential duration and refractory period[24]. If ischemia is prolonged a reduced degree of Cx43 expression and a changed pattern of distribution can be observed. The closure of gap junction channels during acute ischemia as well as the changes in expression and distribution pattern in chronic ischemia may lead to slow conduction, increased dispersion, non-uniform anisotropy, and unidirectional conduction block, and thereby facilitate the induction of reentry arrhythmias. Thus, experimental studies have shown a correlation between the site of abnormal connexin expression and distribution and the location of reentrant ventricular tachycardia circuits[25].

The conditions that favor the development of reentry, i.e., slow conduction, increased dispersion of repolarization, non-uniform anisotropy and unidirectional conduction block are present to a various extent in a lot of other heart diseases.

Thus, in infectious or autonomic cardiomyopathy the inflammation that takes place may lead to deposition of fibrous tissue in the myocardium thereby creating foci of slow conduction increased dispersion and possibly unidirectional conduction block. Hypertrophic cardiomyopathy (e.g. due to hypertension, aortic stenosis, congenital) may result in reentry arrhythmias due to the mismatch between the large amount of myocardial tissue and the relative small amount of conductive tissue which may lead to slow conduction, increased dispersion and unidirectional conduction block. Congenital diseases (e.g., the long-QT syndrome) and drugs that prolong the QT interval (e.g., antiarrhythmic drugs, antipsycotic drugs, antihistamines, antibacterial drugs etc.) also increase the dispersion of action potential duration possibly due to the heterogeneity of distribution of ion channels throughout the different layers of the myocardium and is a major cause of reentry-induced sudden death in younger subjects[26].

Atrial Reentry:

Atrial fibrillation—the most common cardiac arrhythmia—is also caused by a reentrant mechanism. In this case multiple wavelets travel across the atria and re-excite the tissue that is no longer refractory. Atrial fibrillation can persist for years and will eventually lead to a remodelling of the atrias. An important part of the remodelling process is the changes in distribution of gap junctions. Thus, the Cx40 distribution pattern becomes increasingly heterogeneous. The time course of changes in the distribution and content of Cx40 gap junctions correlates with an increase in stability and complexity of AF and suggests that Cx40 gap junctional remodeling might be involved in the pathogenesis of sustained atrial fibrillation[27]. Moreover, several lines of evidence support the notion that during conditions with slowing of atrial conduction the susceptibility to atrial fibrillation is elevated.

Repolarization Alternans

The appearance of electrocardiographic T-wave alternans with elevated heart rate or metabolic insult has been observed for nearly a century. Macroscopic T-wave alternans is often noted as a harbinger of sudden arrhythmic death. Recent work suggest a common mechanism that may link the presence of discordant repolarization alternans to the initiation of diverse reentrant arrhythmias, depending on the anatomic nature of the substrate[28]. Under chronotropic or metabolic stress, the repolarization phase of the myocardial action potential develops an alternation in morphology and duration. With additional stress or in the presence of structural barriers, repolarization alternans becomes spatially discordant. Discordant alternans leads to sufficiently large repolarization gradients to produce unidirectional block and reentry. Without a structural barrier, the reentry is functional and manifests as ventricular fibrillation or polymorphic ventricular tachycardia. In the setting of a structural barrier, reentry can become anatomically fixed, resulting in monomorphic ventricular tachycardia[29].

In summary, it appears that a substance such as the compounds of the present invention, which increases gap junction conductance and make the anisotropy more uniform will prevent unidirectional block and reentry arrhythmias. Such a substance will be useful is patients with reentry circuits of both atrial and ventricular origin. Patients with T-wave alternans are prone to reentry arrhythmias, and a substance that increases gap junctional coupling and decreases anisotropy may be useful in the prevention of lethal ventricular arrhythmias in these patients.

Bradyarrhythmias

Bradyarrhythmias can be caused by slowed conduction or conduction block of the sinoatrial node, atrioventricular node, bundle of His or right or left bundle branch. The major connexin responsible for the conductance throughout the conductive system is Cx40. Mice homozygous for a knockout of the Cx40 gene have significantly slower atrial, atrioventricular, and His-Purkinje conduction and are at increased risk of arrhythmias and bundle branch block[4-6]. Thus, normal functioning Cx40 gap junctions are essential for the maintenance of normal rhythm.

A substance, such as the compounds of the present invention which increases gap junction conductance is useful in the prevention and/or treatment of slowed conduction in the heart.

Reduced Contractility

Reduced contractility is a common feature of many chronic heart diseases. During the worst case scenario, (i.e., end-stage heart failure), the contractility is reduced to a point where the ejection fraction is so low that the basal needs for organ perfusion can no longer be maintained. Experimental as well as clinical evidence has shown that the expression and distribution of connexins in hearts from patients with endstage heart failure is changed. Thus, Cx43 is significantly down-regulated with a highly irregular distribution in the abnormal tissue. Cx45 expression, which under normal conditions is very limited, is significantly increased in failing hearts; however, the conductive properties of Cx45 are inferior to the properties of Cx43 and therefore can not compensate for the reduction in Cx43. Recent evidence indicates that some regulatory ion channels and receptors are concentrated at sites of inter-cellular junction and it is therefore highly likely that the changes in expression and distribution of Cx43 can affect the excitation-contraction coupling and thus the contractility[30]. A strong evidence for a link between gap junction function and contractility is the fact that chimeric mice formed from Cx43-null embryonic stem cells and wild-type blastocysts, thus expressing a heterogeneous loss of Cx43, develop severe contractile defects[31].

We suggest that a substance, which increases gap junction conductance will improve the intercellular communication of the mediators involved in excitation-contraction coupling and thereby improve contractility.

Experimental Example 1

Effect of Compound 2 on GJIC in Cardiomyocytes

Cell preparation: Cells were isolated from guinea pig hearts by perfusion with collagenase according to the Langendorf method. In brief, guinea pigs were heparinised with an intraperitoneal injection of heparin (1000 IU/kg). After 30 minutes the animal was sacrificed by a blow to the neck followed by cutting the spine at the neck. The chest was opened and the aorta cannulated. Then the cannula was fixed to the aorta by a ligature, exised and perfused with Tyrodes solution for a couple of minutes. The Tyrodes solution had the following composition in mM: $Na^+$ 135.33, $K^+$ 4, $Cl^-$ 145, $PO_4^-$ 0.33, $Mg^{2+}$ 1, $Ca^{2+}$ 2, Hepes 10, Glucose 10, pH 7.4. All perfusion media were bubbled by 100% oxygen. After this the heart was perfused for two minutes with Tyrodes solution without $Ca^{2+}$, followed by perusion for two minutes with a high $K^+$ solution containing in mM: $Na^+$ 20, $K^+$ 120, $Cl^-$ 22, glutamate 120, $Mg^{2+}$ 1, $Ca^{2+}$ 25 µM, Hepes 10, Glucose 10, pH 7.4.

Then the heart was perfused with high $K^+$ solution with 0.6 mg/ml collagenase, this was done for 10-15 minutes judged from the apperance of the heart. The atria were cut off, the ventricles minced, whereafter the pieces were stirred in the collagenase solution by gently bubbling with 100% oxygen. The cells were then passed through a sieve to isolate the liberated cells, and the collagenase was removed by centrifugation. The cells were resuspended in $Ca^{2+}$ free Tyrodes solution and $Ca^{2+}$ was slowly increased to 0.65 mM. The cells were kept in this solution at room temperature until transferred to the experimental chamber.

Electrophysiology: Cover slips are mounted in an open chamber on the stage of an inverted microscope, where the cells are superfused with Dulbeccos phosphate buffered saline (PBS) at 1 ml/min, 37° C. The solution contain (in mM): $Na^+$ 152, $K^+$ 4.2, $Cl^-$ 141.5, $PO_4^{3-}$ 9.5, $Ca^{2+}$ 0.9, $Mg^{2+}$ 0.5, pH 7.2. Patch clamp pipettes are pulled from 1.5 mm glass capillaries (GC150F-15, Harvard Apparatus) on a Sutter Flaming-Brown P-87 microelectrode puller and fire polished to a resistance of 4-6 MΩ. Pipettes are filled with an intracellular like solution containing in mM: $K^+$ 145, $Na^+$ 15, $Cl^-$ 5, $Gluconate^-$ 153, Pyruvate 5, EGTA 1, HEPES 5, $Ca^{2+}$ 0.42 mM, $Mg^{2+}$ 1.6, pH 7.2. To this solution amphotericin B (240 µg/ml) is added from a 60 mg/ml stock solution (Solvent: DMSO).

The patch clamp set-up consists of two synchronised discontinuous amplifiers (SEC-05LX, NPI electronics) and data is digitised using an INT-10 interface (NPI electronics) and a PC1200 data acquisition board (National Instruments). Both current and voltage signals are low pass filtered at 1 kHz using the internal filters of the amplifiers and digitised at 10 kHz.

One cell of a pair is approached with an electrode using a PatchMan 5173 micromanipulator (Eppendorf). When contact with the cell is obtained (seen as a sudden increase in input resistance), suction is applied until the Giga seal configuration is established. This procedure is then repeated on the other cell. Then the membrane under the pipettes are broken by a brief application of suction and the potential of the cell interior is clamped to −70 mV, which is close to the spontaneous membrane potential of the cells. For every 10 second each of the cells are consecutively hyperpolarised by 10 mV for 1 second and resulting current change in the other cell can the be used to calculate the intercellular conductance ($G_j$) using the formula:

$$G_j = \frac{\Delta I_p}{\Delta U_j} = \frac{I_{p,pulse} - I_{p,rest}}{U_p - U_a} \quad \text{(Equation 1)}$$

Where $I_{p,pulse}$ and $I_{p,rest}$ represent the current in the passive cell during the pulse and before the pulse respectively, and $U_p$ and $U_a$ represent the voltage of the passive and active cell. This kind of experiments does not allow comparison on absolute $G_j$ values due to differences in cell-to-cell contact and therefore the amount of functional gap junction channels. However, the change in $G_j$ value to a standardized intervention like a drug can be analysed by comparing the relative changes in $G_j$.

Figure 2:
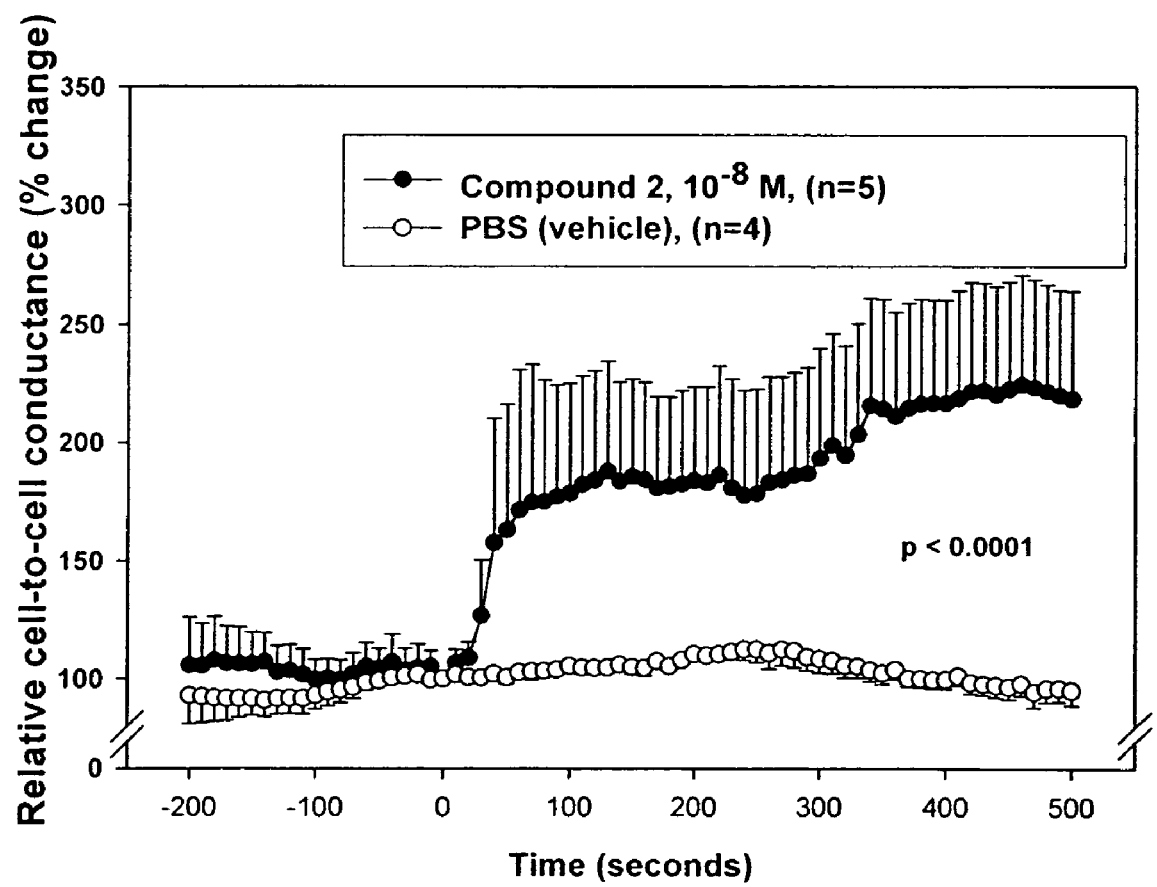
FIG. 2 shows the relative changes in intercellular conductance Gj as a function of time before and during stimulation with Compound 2 ($10^{-8}$ M), or vehicle in isolated guinea pig myocytes. The change in conductance is expressed as percent change relative to the conductance immediately prior to perfusion with Compound 2.

Results: The results from nine successful experiments are summarized in FIG. 2. This figure shows the relative $G_j$ as a function of time before and during stimulation with Compound 2 ($10^{-8}$ M). In all five experiments where the cells were treated with Compound 2, the compound produced a significant increase in $G_j$, which reached a steady-state level after about 400 seconds of stimulation ($\Delta G_j$=+120±46%). The conductance was unchanged throughout in all four vehicle treated preparations ($\Delta G_j$=−3±5%).

These findings are in good agreement with experiments reported in the literature using the synthetic AAP analogue AAP10, showing an increased electrical coupling between cardiomyocytes after stimulation[32]. However, in the study by Müller et al.[32], gap junction conductance was not stable during control conditions. Thus, in three out of six experiments application of AAP10 did not increase the conductance, but prevented run-down of gap junction conductance and in two out of six experiments gap junction conductance actually increased during the control period. In the experiments presented herein, Compound 2 increased gap junction conductance in preparations with stable control conditions.

Experimental Example 2

Binding of Compound 2 to Tissue Preparations of Murine Heart

Preparation

Hearts are excised from mice (Balb/cJ, 20 g), rinsed twice in ice-cold (0° C.) 0.32 M sucrose and homogenized on ice in 10 volumes of sucrose with an Ultra Turrax homogeniser (1000 rpm) for 2 minutes. The homogenate is centrifuged at 1000 $g_{mean}$ for 10 minutes at 4° C. and the supernatant collected and filtrated through 4 layers of gauze. The filtrate is then centrifuged at 50,000 $g_{mean}$ for 45 min at 4° C. and the pellet resuspended in 10 $vol_{org.\ wet\ weight}$ ice-cold distilled water and incubated for 60 min at 0° C. and re-centrifuged at 50,000 $g_{mean}$ at 45 min at 40° C. The resulting pellet is resuspended in 2 $vol_{org.\ wet\ weight}$ of PBS (Phosphate Buffered Saline) and stored at −80° C. until use.

Displacement Experiments with Compound 2

40-250 μg filtrate or membrane material are incubated in a total volume of 100 μl D-PBS (Dulbecco's Phosphate Buffered Saline containing 1 g/l $MgCl_2.6H_2O$ & $CaCl_2$) containing 0.8 nM [$^{125}$I]AAP10 and increasing concentration of the test compounds AAP and Compound 2. Non-specific binding is determined at 10 μM AAP10 (CE2).

Calculations

Data from the displacement experiments are fitted to the equation:

$f=(Total-ns)/(1+s/IC_{50})+ns$ where Total is the total bound radioactivity at concentration s of labelled ligand, ns is non-specific binding and $IC_{50}$ is the concentration of test compound reducing specific binding (Total−ns) to 50% of maximum specific binding.

Results

TABLE 2

Displacement of 0.8 nM [$^{125}$I]AAP10 from murine heart tissue preparations (n.t.: not tested).

| Test Compounds | Filtrate $IC_{50}$ (nM) | Membranes $IC_{50}$ (nM) |
| --- | --- | --- |
| AAP | 1.2 | n.t. |
| AAP10 (CE 2) | 1.2 | n.t. |
| Compound 2 | 3.6 | 1.2 |

The values given in Table 2 above are in the same order of magnitude (0.2 nM) as that given for AAP10 by Dhein et al.[33] using membranes from rabbit heart.

Method of In Situ Binding on Intact Cells

CHO Cell Cultures

CHO cells are seeded in 24-multi well dishes in a density of 7,900 cells/$cm^2$ (~15,000 cells/well) and grown for 3 Days In Vitro (DIV) in 1 ml/well of F-12K Nutrient Mixture supplemented with 10% Foetal Calf Serum (FCS) and 1000 units penicillin/1000 μg streptomycin (pen/strep) in an atmosphere of 5% $CO_2$ and 100% humidity at 37° C. The cell density has at that time increased to 295,000 cells/$cm^2$ (152 $\mu g_{prot}$/cell ~85 $\mu g_{prot}$/well).

Pre-Treatment

On the day of analysis cells are removed from the incubator and each well is washed twice with, depending on the experiment, either 2 ml pre-warmed (37° C.) or ice-cold (0° C.) D-PBS to remove serum. It is important to keep the period to a minimum during which cells are left without physiological solutions to avoid that they dry out during washing procedures. The cold washed cells are used directly for binding assays while the warm washed cells are used for experiments with glucose and oxygen deprivation.

Glucose and Oxygen Deprivation

Cells are incubated for 10 min in an $N_2$-atmosphere in glucose free D-PBS (pH 7.2) pre-equilibrated with $N_2$ for at least 10 min at 37° C. Control cells are incubated likewise for 10 min at 37° C., only, at normal atmospheric conditions and in D-PBS containing glucose (6 mM).

Binding Assay

The in situ binding is performed by a modified protocol based on the description by Koenig[34]. D-PBS is removed from the cell culture and 0.50 ml [$^{125}$I]AAP10 solution with or without unlabeled ligand or test compound is added. Cells incubate overnight at 4° C. to reach equilibrium. Each well, one at the time, is then rinsed rapidly with 2×1 ml D-PBS and left to dry.

0.25 ml of 0.5% Triton-X-100 (v/v) is added to each well and cells left for at least 1 h to solubilize. The extract is transferred to counting vials, the wells rinsed with 0.25 ml water and the rinse extract added to the corresponding vials. The vials are counted in a γ-counter.

TABLE 3

In situ binding, $IC_{50}$ (nM).

| Test compounds | $IC_{50}$ (nM) |
| --- | --- |
| AAP (CE1) | 0.8 |
| AAP10 (CE2) | 130 |
| Compound 2 | 0.5 |
| Compound 32 | 0.5 |
| Compound 24 | 65 |

These results demonstrate high affinity binding to CHO cells by several different substances of the present invention comparable to peptides of the prior art.

Experimental Example 3

Effect of Compound 2 on cAMP Formation in CHO Cells

CHO Cell Cultures

CHO cells are seeded in 96-well microtiter plates in a density of 6,000 cells/$cm^2$ (~2,000 cells/well) and grown for 4 days in vitro in 200 μl/well of growth media as described in the previous section.

Pre-Treatment

On the day of analysis cells are removed from the incubator and washed twice with 200 µl pre-warmed (37° C.) D-PBS (pH 7.2) to remove serum. Cells are incubated for 10 min in glucose free D-PBS and an $N_2$-atmosphere as described in the previous section.

cAMP Efficacy Assay

CHO cells are incubated at 37° C. in D-PBS (pH 7.2) containing 6 mM glucose, 2.0 mM IBMX (phospodiesterase blocker), 10 µM forskoline (stimulates CAMP formation) and increasing concentrations of test peptide. The reaction is stopped after 20 min by addition of 20 µl 0.5 M HCl and left for at least 20 min at room temperature.

The content of CAMP is analysed by mixing 20 µl of the acid cell extract into FlashPlate™ wells (NEN assay kit SMP001) containing 180 µl [$^{125}$I]cAMP tracer solution. FlashPlates™ are incubated overnight at 4° C. and plate bound radioactivity counted in TopCount (Packard Instrument). Data are calculated as described in the previous section.

Results

The inhibition of forskoline-stimulated cAMP formation of APP-like compounds in CHO cells indicates that AAP receptors are negatively coupled to the cAMP second messenger system. Moreover, it demonstrates the presence of functional AAP receptors in CHO cells.

TABLE 4

Inhibition of forskoline stimulated cAMP formation in CHO cells

| Test compounds | $EC_{50}$ (nM) |
|---|---|
| AAP | 53 |
| AAP10 (CE 2) | 11 |
| Compound 2 | 6.2 |

Experimental Example 4

Phosphoinositol-Analysis in Rat Primary Cardiomyocytes

Primary Cardiomyocyte Culture

Neonatal Wistar rats (1-2 days old) are used. Hank's calcium- and magnesium-free balanced salt solution, buffered with 10 mM HEPES is used for washing during cell separation procedures. The hearts are excised, the ventricles isolated and the tissue cut into small pieces. The myocardial cells are isolated by stepwise enzymatic degradation with collagenase 0.05%, as described by[35]. After repeated rounds of centrifugation and washing, the precipitated cells are resuspended in culture medium M199 with Earle's salt, 10% NCS, penicillin (75 U/mL), and streptomycin (75 U/mL) and pre-plated in a Petri dish for 90 minutes. The non-adherent cells are collected in the culture medium and plated in multidishes at $2.5*10^5$ cells/well. The cultures are kept in a water-saturated $CO_2$-incubator at 37° C. The cardiomyocyte cultures are used for analyses after 6-7 days.

Analysis of Phosphoinositol-Turnover

Cardiomyocyte cultures are incubated for 48 hours in culture medium containing 4 µCi/mL myo-[2-$^3$H]inositol to label the inositol phospholipids. On the day of analysis the medium is replaced by a buffer solution containing lithium and incubated at 37° C., as described by Meier et al.[36]. After at least five minutes this buffer is replaced by the same volume of buffer containing test compound and incubated for exactly 20 minutes. The reaction is stopped by rapid replacement of the buffer by ice cold 4% v/v perchloric acid (PCA) and incubation for at least 20 minutes at 0° C. The PCA-extract is neutralised and the [$^3$H]inositol phosphates are separated by anion-exchange chromatography using Amprep™ columns containing 100 mg SAX Quaternary amine. The [$^3$H]inositol mono-phosphates are eluted and radioactivity in the fraction measured by liquid scintillation counting.

Glucose and Oxygen Deprivation

Before adding test substances to the cultures, the cells are depleted of glucose and oxygen by incubating them in a $N_2$-atmosphere in glucose-free lithium-buffer for 10 minutes at 37° C. Control cells are incubated likewise only at normal atmospheric conditions and in a buffer containing glucose.

Figure 3:
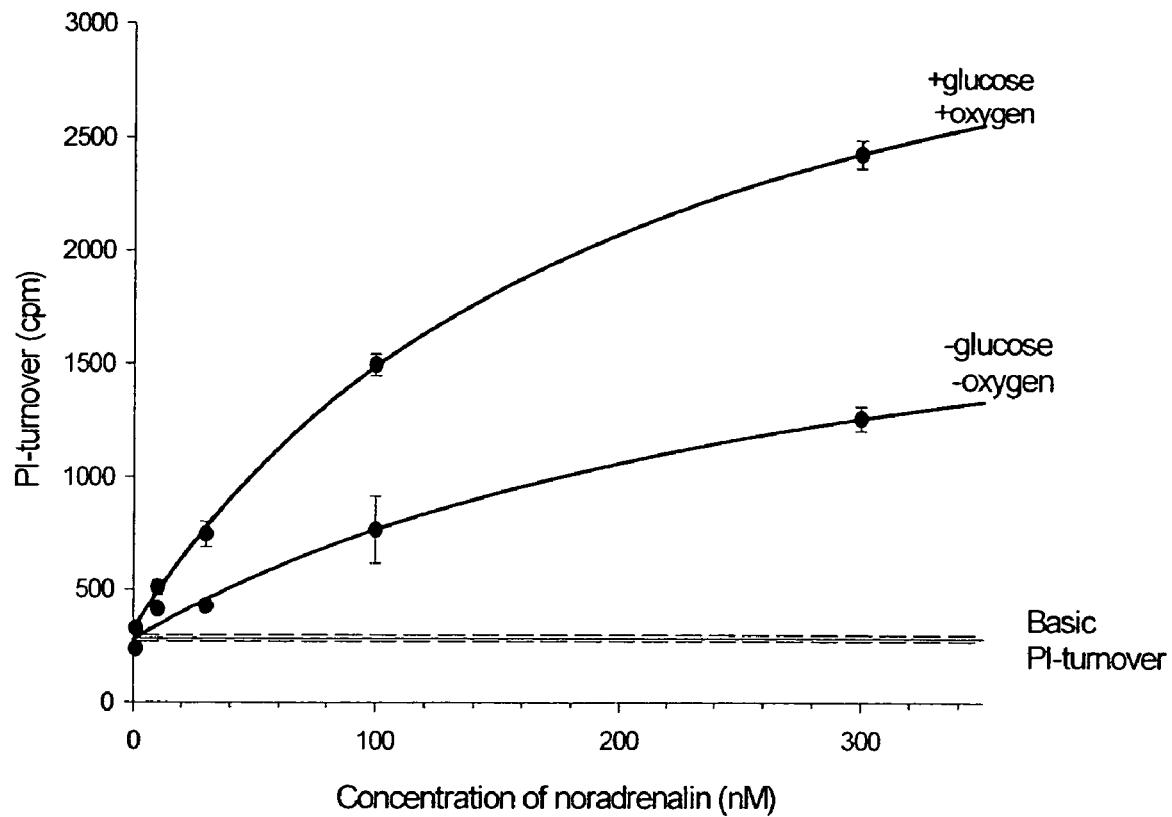
FIG. 3 shows phosphoinositol (PI) turnover as a function of noradrenalin concentration in cultures of cardiomyocytes isolated from neonatal Wistar rats, following 10 minutes of glucose and oxygen deprivation.

Noradrenaline (NA) stimulates phosphoinositol turnover in the cardiomyocyte cultures in a concentration-dependent manner. However, the ability of noradrenaline (300 nM NA) to stimulate phosphoinositol turnover is considerably reduced in cultures following 10 minutes of glucose and oxygen deprivation as shown in FIG. 3.

Under normal atmospheric and nutritional conditions we obtained an $E_{max}$ value of 3852±266 cpm and an $EC_{50}$ value of 203 nM ($SD_R$=1.2), whereas in cells subjected to an atmosphere of $N_2$ and depleted of glucose, an $E_{max}$ value of 2248±702 cpm and an $EC_{50}$ value of 303 nM ($SD_R$=1.7) were demonstrated.

To examine the effect of substances of this invention on the attenuated noradrenaline-induced increase in phospho-inositol turnover during cell stress induced by ischemia and glucose starvation, Compound 2 or AAP10 (CE 2) were added to the cardiomyocyte cultures. Both substances very potently enhanced phospho-inositol turnover, with Compound 2 being the most potent. As illustrated in Table 5 below, the $EC_{50}$ value for AAP10 (CE 2) was 200 fold higher during normoxia and 10-fold higher during metabolic stress induced by anoxia and glucose deprivation than the $EC_{50}$ value for Compound 2.

TABLE 5

Enhancement of phospho-inositol turnover during metabolic stress induced by anoxia and glucose starvation by Compound 2 and AAP10

|  | $EC_{50}$ (nM) AAP10 (CE2) | $EC_{50}$ (nM) Compound 2 |
|---|---|---|
| Normal conditions | 2000 | 10 |
| Glucose and oxygen deprivation | 100 | 10 |

Figure 4:
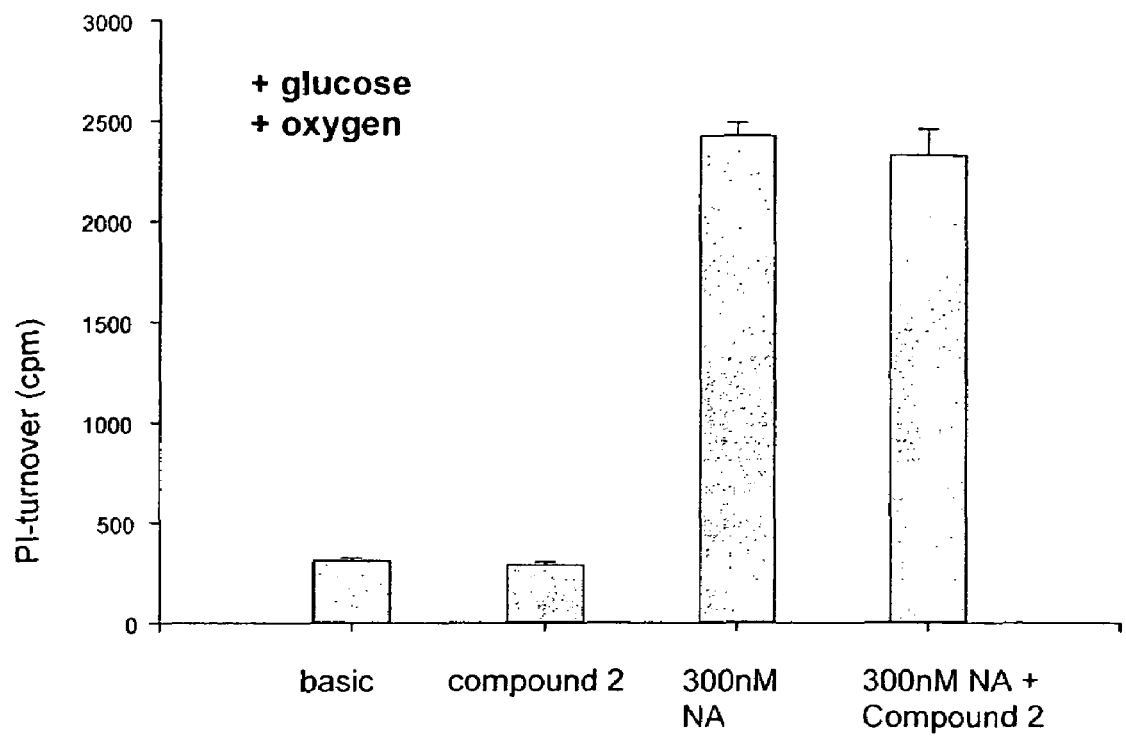
FIG. 4 shows the effect of Compound 2 on the attenuated noradrenaline-induced increase in phospho-inositol turnover during metabolic stress induced by ischemia and glucose starvation when added to the cardiomyocyte culture.
Figure 4:
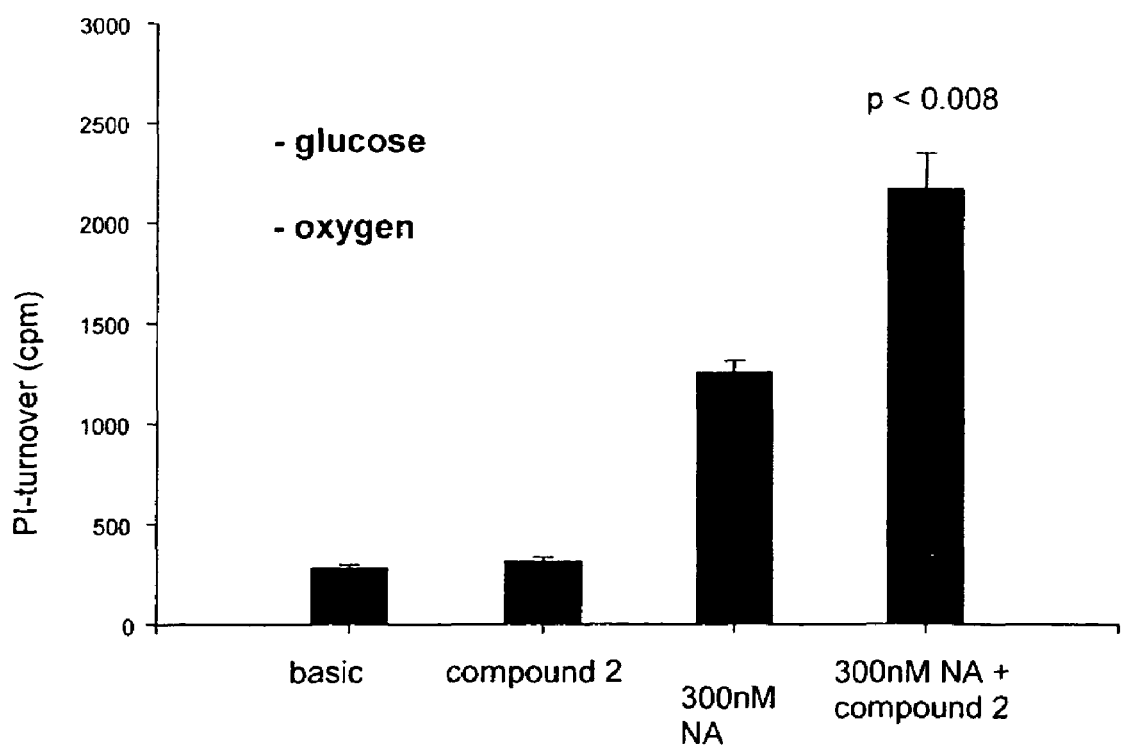

Addition of Compound 2 (100 nM) had no further effect on noradrenaline (300 nM) induced increase in phospho-inositol turnover in neonatal rat cardiomyocytes during control conditions, but in cells subjected to anoxia and glucose deprivation (metabolic stress), addition of Compound 2 (100 nM)+ noradrenaline (300 nM) normalized the impaired phosphoinositol turnover as shown in FIG. 4, an increase that was about 70% higher than the increase effected by noradrenaline alone.

Experimental Example 5

Calcium-Induced Arhythmia Model in Mice

The antiarrhythmic effects of compounds of this invention were tested in an in vivo model of calcium-induced arrythmias according to the model of Lynch et al.[37]. Mice (25-30 g) were anaesthetised with a neurolept anaesthetic combination (Hypnorm® (fentanyl citrate 0.315 mg/ml and fuanisone 10 mg/ml)+midazolam (5 mg/ml)). Commercial solutions of hypnorm and midazolam were diluted 1:1 in distilled water and one part diluted Hypnorm® is mixed with one part diluted midazolam.

The anaesthesia was induced by s.c. administration in a dose of 0.05-0.075 µl/10 gram mouse. An i.v. cannula was inserted into the tail vein. The lead II ECG signal was recorded continuously by positioning of a stainless steel ECG electrodes on the right forelimb and on the left hind limb. The ground electrode was placed on the right hind limb. The signal was amplified (×5.000-10.000) and filtered (0.1-150 Hz) via a Hugo Sachs Electronic model 689 ECG module. The analogue signal was digitised via a 12 bit data acquisition board (Data Translation model DT321) and sampled at 1000 Hz using the Notocord HEM 3.1 software for Windows NT. After a 10-min equilibration period, the test sample of drug was injected into the tail vein. Mice pre-treated with vehicle were tested as a measure of the control level in untreated animals. The injection volume was 100 µl in all experiments. Infusion of CaCl$_2$ (30 mg/ml, 0.1 ml/min≈100 mg/kg/min (calciumchlorid-2-hydrat, Riedel-de Haën, Germany)) was started 3 min after i.v. administration of drug or vehicle. The time lag to onset of 2nd degree AV-block was determined as the time from the start of CaCl$_2$ infusion until the first arrhythmic event occurred. An event of 2nd degree AV-block was defined as intermittent failure of the AV conduction characterised by a P-wave without the concomitant QRS complex.

Responses were expressed relative to the time until 2nd degree AV-block occurred in vehicle treated mice. The maximal effect of each of the tested substances is summarized in Table 6 below.

Table 6, In vivo antiarrhythmic activity of compounds of the invention. +++ refers to >60% increase in time until arrhythmia; ++ refers to 30-50% increase in time until arrhythmia; + refers to 15-29% increase in time until arrhythmia; (+) refers to ≦15% increase in time until arrhythmia, and nd to "not determined".

| Cpd No. | Compound name | In vivo activity |
|---|---|---|
| Group 1 | Comparative examples | |
| (SEQ ID NO: 266) | | |
| CE-1 | H-Gly-Pro-Hyp-Gly-Ala-Gly-OH (AAP) | ++ |
| (SEQ ID NO: 267) | | |
| CE-2 | H-Gly-Ala-Gly-Hyp-Pro-Tyr-NH$_2$ (AAP10) | +++ |
| (SEQ ID NO: 268) | | |
| CE-3 | 3-(4-hydroxyphenyl)propionyl-Pro-Hyp-Gly-Ala-Gly-OH (HP5) | ++ |
| 5 | H-Gly-Ala-Gly-D-Hyp-Pro-Tyr-NH$_2$ | ++ |
| 6 | H-Gly-Ala-Gly-D-Pro-Pro-Tyr-NH$_2$ | Nd |
| 7 | H-Gly-Ala-Gly-D-Pro-Ala-Tyr-NH$_2$ | Nd |
| 8 | H-Gly-Ala-Gly-Gly-D-Pro-Tyr-NH$_2$ | Nd |
| 9 | H-Gly-Ala-Gly-D-Hyp-Ala-Tyr-NH$_2$ | + |
| 10 | H-Gly-Ala-Gly-D-Hyp-D-Pro-Tyr-NH$_2$ | +++ |

H-GAG-(Pa)$_2$-NH$_2$: Pa is any amino acid residue or a

Group 2 moiety of formula II or IIa; at least one of Pa is a D amino

Formula 2 acid; preferably Pa is Hyp, P, G or A;

H-GAG-(Px)$_2$-Y—NH$_2$: Px is a moiety of formula II or IIa,

Group 3 where one Px is a moiety of formula II, IIa and the other
Formula 3 Px is P or Hyp

```
          (SEQ ID
          NO: 269)
          11        H-Gly-Ala-Gly-NCG-Pro-Tyr-NH2              Nd (SEQ ID
          NO: 270)
          12        H-Gly-Ala-Gly-T4C-Pro-Tyr-NH2              ++

(SEQ ID
          NO: 271)
          13        H-Gly-Ala-Gly-A2C-Pro-Tyr-NH2              Nd (SEQ ID
          NO: 272)
          14        H-Gly-Ala-Gly-PC-Pro-Tyr-NH2               +
```

Group 4

Formula 4 Ac-Y'-(Px)$_2$-GAG-OH: Y' is Y or F; Px is P or Hyp

```
          (SEQ ID
          NO: 273)
          1         Ac-Tyr-Pro-Hyp-Gly-Ala-Gly-OH              +

(SEQ ID
          NO: 274)
          15        Ac-Tyr-Pro-Hyp-Gly-Ala-Gly-NH2             Nd
```

Group 5

Formula 5 Cys(Acm)-AAP10*/retroAAP10*-Cys(Acm)

```
          (SEQ ID
          NO: 275)
          16        H-Cys(Acm)-Gly-Ala-Gly-Hyp-Pro-Tyr-Cys(Acm)-NH2    +

(SEQ ID
          NO: 276)
          17        H-Cys(Acm)-Gly-Hyp-Pro-Tyr-Cys(Acm)-NH2            Nd (SEQ ID
          NO: 277)
          18        H-Cys(Acm)-Tyr-Pro-Hyp-Gly-Ala-Gly-Cys(Acm)-NH2    Nd (SEQ ID
          NO: 278)
          19        H-Cys(Acm)-Tyr-Pro-Hyp-Gly-Cys(Acm)-NH2            Nd
```

X-G-D-A-G-(D-Px)$_2$-D-Y—NH$_2$: X is H, Ac; Px is a moiety of
Group 6 formula II, IIa, preferably Hyp or P; optionally having one
Formula 6 or more C or N isotopes

```
          22 H-Gly-D-Ala-Gly-D-Hyp-D-Pro-D-Tyr-NH2                 Nd
          23 H-Gly-D-Ala-Gly-D-Hyp-D-Pro-D-Tyr-D-Asp-OH            Nd
           2 Ac-D-Tyr-D-Pro-D-Hyp-Gly-D-Ala-Gly-NH2                +++
          24 Ac-D-Tyr(3,5-di-I)-D-Pro-D-Hyp-Gly-D-Ala-Gly-NH2      Nd
```

| | -continued | |
|---|---|---|
| 25 | Ac-D-Tyr(phenyl ring mono-iodo substituted)-D-Pro-D-Hyp-Gly-D-Ala-Gly-NH$_2$ | Nd |
| 26 | Ac-D-Tyr-D-Pro-D-Hyp-(1,2$^{13}$C, $^{15}$N-Gly)-D-Ala-(1,2$^{13}$C, $^{15}$N-Gly)-NH$_2$ | nd |

Group 7  H-(Px)$_n$-Y(N/Q)G-AG-(Px)$_m$-NH$_2$: Px is P or Hyp, n is 1 or 2; m is 0 or 1; preferably m=0 when n=2 and m=1 when
Formula 7  n=1

| | (SEQ ID NO: 279) | |
|---|---|---|
| 27 | H-Pro-Tyr-Asn-Gly-Ala-Gly-Hyp-NH$_2$ | nd |
| | (SEQ ID NO: 280) | |
| 28 | H-Hyp-Pro-Tyr-Asn-Gly-Ala-Gly-NH$_2$ | (+) |

Group 8  H-G'-A-G'-(Px)$_2$-Y—NH$_2$: G' is Sar or Gly and at least one
Formula 8  G' is Sar; Px is P or Hyp

| | (SEQ ID NO: 281) | |
|---|---|---|
| 29 | H-Sar-Ala-Sar-Hyp-Pro-Tyr-NH$_2$ | + |
| 30 | H-Gly-Ala-Sar-Hyp-Pro-Tyr-NH$_2$ | ++ |

Group 9  X-(Y)$_p$-(Px)$_2$-GAG-NH$_2$: X is ASAL or AB; p is 0 or 1;
Formula 9  phenyl ring of Y has optionally one or more halogen substitutent, preferably I; Px is P or Hyp

| | (SEQ ID NO: 282) | |
|---|---|---|
| 31 | ASAL-Pro-Hyp-Gly-Ala-Gly-NH$_2$ | nd |
| | (SEQ ID NO: 283) | |
| 32 | ASAL(mono-iodo substituted)-Pro-Hyp-Gly-Ala-Gly-NH$_2$ | +++ |
| | (SEQ ID NO: 284) | |
| 33 | AB-Tyr-Pro-Hyp-Gly-Ala-Gly-NH$_2$ | nd |
| | (SEQ ID NO: 285) | |

Group 10  Cyclo(-GAG-(Px)$_2$-Y—N/Q-): Px is P or Hyp
Formula 10

| | (SEQ ID NO: 286) | |
|---|---|---|
| 35 | cyclo(-Gly-Ala-Gly-Hyp-Pro-Tyr-Gln-) | ++ |
| | (SEQ ID NO: 287) | |
| 36 | cyclo(-Gly-Ala-Gly-Hyp-Pro-Tyr-Asn-) | +++ |
| | (SEQ ID NO: 288) | |
| 37 | cyclo(-Gly-Ala-Gly-Pro-Pro-Tyr-Asn-) | nd |

Group 11 Cyclo(-Y-(Px)$_2$-GA-(G)$_q$-N/Q-) q is 0 or 1, phenyl ring of Y
Formula has optionally one or more halogen substitutents,
11 preferably I; Px is P or Hyp
34 AB-Tyr(3,5-di-I)-Pro-Hyp-Gly-Ala-Gly-NH$_2$
nd (SEQ ID NO: 289)
3      cyclo(-Tyr-Pro-Hyp-Gly-Ala-Gly-Asn-)      +++

(SEQ ID NO: 290)
4      cyclo(-Tyr-Pro-Hyp-Gly-Ala-Asn-)      nd (SEQ ID NO: 291)
38     cyclo(-Tyr(3-I, 5-I)-Pro-4Hyp-Gly-Ala-Gly-Asn)     nd Group 12
Formula X-Zd-G(N/Q)Y-NH$_2$: Zd is a sequence of 0, 1, or 2 amino
12 acid residues selected from G or A; X is H, Ac (SEQ ID NO: 292)
39     H-Gly-Ala-Gly-Asn-Tyr-NH$_2$     +++

40     Ac-Gly-Asn-Tyr-NH$_2$     ++

41     H-Gly-Asn-Tyr-NH$_2$     ++

(SEQ ID NO: 293)
42     Ac-Ala-Gly-Asn-Tyr-NH$_2$     nd (SEQ ID NO: 294)
43     H-Ala-Gly-Asn-Tyr-NH$_2$     nd

As can be seen from the results shown in Table 6 a wide range of novel compounds of the present invention exhibit antiarrhythmic activity comparable to the compounds AAP, AAP10 and HP5 of the prior art.

Experimental Example 6

Effects of Compound 2 on Isolated Perfused Rabbit Hearts

The Principle of the Langendorff Technique

The Langendorff technique provides a method of maintaining adequate metabolic requirements to an isolated heart, thereby enabling in vitro experiments on the entire heart for several hours. In the Langendorff set-up the heart is perfused retrogradely through a cannula inserted into aorta. When the perfusion solution enters aorta the resulting pressure in aorta closes the aortic valves, thereby preventing fluid from entering the heart chambers. Instead the perfusion solution enters the coronary circulation supplying the heart. In the Langendorff technique total flow in aorta thus equals coronary flow. The Langendorff experiments are performed using the ISOLATED HEART SIZE 5, Type 833 apparatus manufactured by Hugo Sachs Elektronik, Germany. The central component of this apparatus is the aortic block to which the heart is attached by a cannula. The aortic block is directly connected to an artificial flow resistor operated by a rotary knob thereby enabling adjustments of the afterload and hence the perfusion pressure. Perfusion fluid is delivered from a thermostated reservoir to the aortic block by tubes connected to a roller pump. The volume delivered by the pump can be adjusted to accommodate different needs. Excessive fluid flows back from the aortic block into the reservoir. Beneath the aortic block is a thermostated heart chamber that can be elevated to cover the heart. This set-up allows for continuous recordings of coronary flow, left ventricular pressure (LVP), perfusion pressure, a 12-lead ECG, and 8 monophasic action potentials (MAP's). The output of these multiple recordings is analyzed using the NOTOCORD HEM 3.3 software. This software enables calculations of a wide range of cardiac electrophysiological and hemodynamic parameters.

Perfusion Technique and Perfusion Media

The experiments are conducted in the constant pressure perfusion mode. The flow pump is set to give 70 ml/min and the afterload is set at 50 mmHg, ensuring a perfusion pressure of approximately 60 mmHg. The hearts are, unless otherwise specified, perfused with a pre-warmed (38° C.) modified Krebs-Henseleit solution with the following composition (mmol/l): NaCl: 118, KCl: 4.7, CaCl$_2$,2H$_2$O: 2.52, KH$_2$PO$_4$: 1.18, Mg$_2$SO$_4$,7H$_2$O: 1.64, sodium pyruvate: 2.0, NaHCO$_3$: 24.88, glucose: 5.55. The solution is filtered through a 45 μm bottletop filter prior to use.

A pH of approximately 7.4 and adequate oxygen content of the solution is obtained by continuously bubbling with carbogen (95% O$_2$/5% CO$_2$). Volumes of 2 or more liters are allowed to equilibrate with carbogen for at least 20 min whereas volumes less than 1 liter are allowed to equilibrate for 10 min.

Anaesthesia, Surgery, and Experimental Procedures

Male Ssc:CPH rabbits (2.5-4.0 kg) obtained from Hvidesten, Allerød, Denmark are used. They are sedated with 1.2 ml Hypnorm® (fentanyl citrate 0.315 mg/ml and fluanisone 10 mg/ml) i.m. Ten min later anaesthesia is induced by slow i.v. administration of 0.55 ml Dormicum® (midazolam 5 mg/ml). In addition, they are given 500 IU of heparin i.v. to prevent coagulation.

The rabbits are placed on the back with the forelegs fixed to the sides and an incision is made to expose trachea. Tracheotomy is performed and the rabbits are ventilated with oxygen using a Ugo Basile rodent ventilator (tidal volume: 18 ml, frequency: 60 pr. min). The abdominal cavity is opened just caudally to the xiphoid process and the abdominal muscles are cut laterally in both sides. To gain access to the thoracic cavity the diaphragm is opened substernally and the cut is extended bilaterally along the costal curvature. Mediastinum is cut as close to sternum as possible and the ribs are cut in both sides on a line parallel to sternum to allow the thoracic wall to be lifted in the cranial direction. The lifted thorax wall is fixed over the rabbit's head to provide a full overview of the thoracic cavity. The pericardial sac is opened and aorta is exposed. A loose ligature is placed around aorta. The caudal vena cava is clamped just cranially to the liver to reduce back flow to the heart and the cranial vena cava and pulmonary artery are opened to reduce volume overload of the heart. Aorta is opened and the cannula, connected to the aortic block by an extension tube filled with perfusion fluid, is immediately inserted into aorta to allow for artificial perfusion. The ligature is tightened and the heart is excised and transferred to the perfusion apparatus. The time from clamping of the caudal vena cava to insertion of the cannula is approximately 30 sec.

When the heart has been transferred to the apparatus an incision is made in the left auricle to allow for the insertion of a fluid filled balloon (size 12) in the left ventricle for measurements of left ventricular pressure. The volume of the balloon is adjusted to give an end-diastolic pressure of approximately 10 mmHg. The electrode ring for measurements of a 12-lead ECG is placed around the heart at the level of the coronary sulcus, with the tip of the left auricle between the $5^{th}$ and $6^{th}$ precordial lead. The 8 MAP electrodes are placed on the heart in direct contact with the epicardium. MAP5 and MAP6 are placed on the right ventricle whereas the other MAP electrodes are evenly distributed over the left ventricle. This method is similar to the one used by Zabel et al.[38]. When all electrodes are in place the heart chamber is elevated to insure that the heart is immersed in 38° C. Krebs-Henseleit solution at all times.

Before the experiment is started, a ligature is placed around a major branch of the circumflex artery supplying a large part of the left ventricle. Both ends of the ligature are passed through a small plastic tube enabling induction of ischemia by pressing the plastic tube against the heart and clamping the ends of the ligature. All hearts are allowed to equilibrate for 15 min before the beginning of the experiment.

The time schedule for the experiment is as follows:
1. 15 min of perfusion with normal Krebs-Henseleit buffer (the equilibration period)
2. 15 min of perfusion with compound added to normal Krebs-Henseleit buffer (the normokalemic control period; t=0-15 min).
3. 15 min of perfusion with compound added to Krebs-Henseleit solution containing a reduced $K^+$ concentration (2.5 mM) (the hypokalemic control period: t=15-30 min).
4. Induction of regional ischemia followed by 30 min of perfusion with compound added to Krebs-Henseleit solution containing a reduced $K^+$ concentration (2.5 mM) (the hypokalemic ischemia period; t=30-60 min).

At the end of the experiment the hearts are perfused with Evans Blue dye to evaluate the area at risk of infarction. The atria's and the right ventricle are cut off and the remaining left ventricle is separated into the area stained by Evans Blue and the area that does not stain, i.e., the area at risk. The two areas are blotted dry using paper towel and weighed to determine the percentage area at risk of infarction.

Recordings

The following parameters are continuously recorded: coronary flow, left ventricular pressure, perfusion pressure, a 12-lead ECG, and 8 MAP recordings. The ECG and the MAP's are sampled at 2000 Hz, and the pressure and flow parameters at 500 Hz. Average action potential duration is calculated from the 8 MAP recordings as the average duration from the time of maximal depolarizatrion (time of dV/dt Max) to the time of 90% of repolarization. This duration is referred to as $APD_{90}$ and the $APD_{90}$ dispersion is measured as the standard deviation of the 8 measurements of $APD_{90}$.

Results

Figure 5:
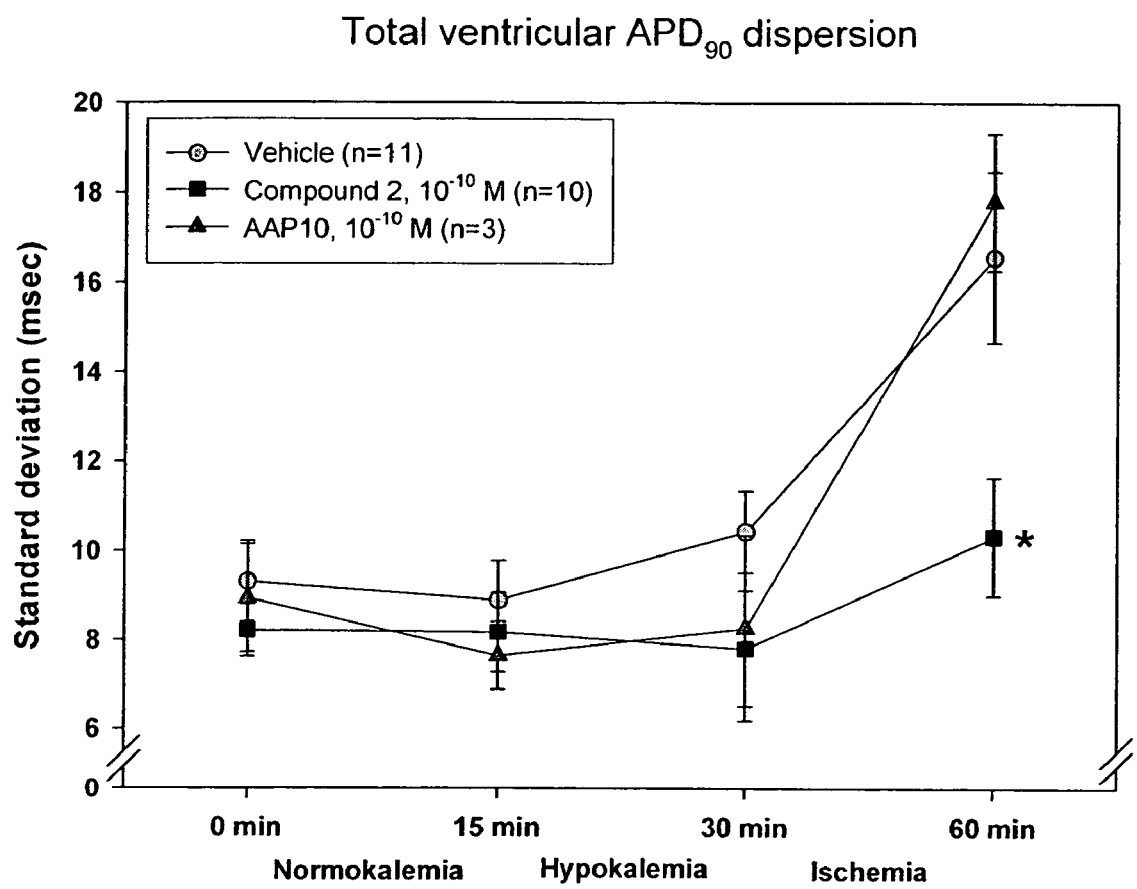
FIG. 5 shows measurements of the standard deviation of $APD_{90}$ as a measure of electrical dispersion ($APD_{90}$ dispersion) during four consecutive perfusion protocols. * indicates $p<0.05$ versus the vehicle treated group.

As illustrated in FIG. 5, three groups were studied. The rabbit hearts were either perfused with Krebs-Henseleit buffer alone (vehicle; n=11 experiments), $10^{-10}$ mol/l Compound 2, (n=10 experiments), or $10^{-10}$ mol/l of AAP10 (CE2; n=3 experiments). The increase in $APD_{90}$ dispersion observed during hypokalemic, acute myocardial ischemia in vehicle-treated rabbit hearts was prevented by $10^{-10}$ mol/l of Compound 2, but not by $10^{-10}$ mol/l of AAP10 (CE2). These findings demonstrate that Compound 2 prevents the increase in electrical dispersion during ischemia and it suggests that the antiarrhythmic properties of Compound 2 are related to this mechanism. It has previously been reported that AAP10 (CE2) is able to reduce the dispersion of the epicardial activation-recovery interval and diminish alterations of epicardial activation patterns induced by regional ischemia in the rabbit with maximal effect at a concentration of $10^{-8}$ mol/l [39]. In our experiments, Compound 2 effectively prevented the increase in electrical dispersion induced during ischemia at a concentration of $10^{-10}$ mol/l while AAP10 (CE2) was ineffective at this concentration. These differences were not due to differences in the size of the myocardial infarction because the decrease in coronary flow during ischemia and the area of risk were similar in all groups. These results indicate that Compound 2 is more potent that AAP10 (CE2).

Experimental Example 7

Effect of Compound 2 on Ventricular Reentry Arrhythmias in Dogs

The influence of gap junctions in arrhythmias has been clarified in studies on the influence of connexin 43 (Cx43) in conduction properties of the ventricle[33]. In a heterozygote knockout mouse deficient in Cx43, there is two times the frequency of spontaneous VT with coronary artery occlusion (CAO)[3]. Ischemia down regulates the effect of Cx43 after 6 hours in the dog showing 60% decrease in end-to-end CX43 and 49% decrease in side-to-side Cx43[40], probably secondary to dephosphorylation. In subacute ischemia in the dog, epicardial reentry is facilitated in areas where Cx43 is decreased[25]. Thus reentrant mechanisms may be critically dependent on ischemia mediated down regulation of CX43 and presumably resistance of gap junctions making heterogeneity of recovery and conduction properties predisposing to VT and VF.

In the studies described below, we examined the effect of Compound 2 on reentry arrhythmias during myocardial ischemia elicited by CAO of the anterior descending artery.

Animal Preparation

Three dogs were studied in the anesthetized, open chest state to facilitate electrode placement for mapping. α-chloralose was given as a bolus (200 mg/kg) and then a constant infusion at 8 mg/kg/hr (dissolved in polyethylene glycol, MW=200). The femoral vein and artery was cannulated for administration of fluid and drugs and for measurement of ascending aortic pressure, respectively.

Electrophysiological Methods

The sinus node was clamped and the atrial appendage was paced with a programmable stimulator with constant current outputs at two times diastolic threshold. Pacing rate was ≧200 b/min to control heart rates. Ventricular pacing one pole of a multipolar needle in the normal zone employed an anode (7 cm² stainless steel) in the abdominal muscle. Endocardial Effective Refractory Period (ERP) was measured by the standard extrastimulus technique. Late ventricular diastolic threshold was measured during each intervention; the pacing current was four times threshold.

Recording of Electrogram

Test sites were chosen along the shaft of 16 pole needles (J. Kassell, Fayetteville, N.C.); each pole completely surrounds the needle shaft to prevent directionality of needle orientation from recording of adjacent Purkinje strands. Six bipolar electrograms (1 mm spacing) were recorded sequentially down the shaft of the needle by amplifying up to 1000 times, filtering from 3-1300 Hz and recording via oscilloscope during atrial pacing. Four intramural electrograms are recorded on each multipolar needle. Epicardial electrograms are activated latest on each needle. An array of 23 multipolar electrodes was used with 17 in the infarcted risk zone of the anterior descending coronary artery and 6 in the surrounding normal zone as described in detail by Xing and Martins[41]. Interneedle distance measured on epicardium varies over 6-10 mm in dogs weighing 12-16 kg.

Arrhythmia Induction

The endocardium was paced at the base, apical septum and lateral free wall just outside the risk zone. After ERP was determined, the S1-S2 interval was prolonged by 4 msec>ERP and a S3 was added to the protocol initially with an S2-S3 interval equal to 50 msec>S1-S2. The intervals were shortened until failure to capture. If ventricular tachycardia was not induced at any pacing site, a third (S4) and fourth (S5) extrastimulus was added. We performed a full ventricular tachycardia induction protocol prior to CAO to exclude artifact ventricular tachycardia due to needle mass or ischemia due to needles compromising blood flow. After confirming physiological blood gases and adequate anesthesia the anterior descending CAO was ligated. After 60 minutes the infarct size is nearly 75% of the risk zone and further enlargement of the infarct zone is negligible. Then ventricular tachycardia was induced at least twice before interventions. Repeat testing was done every 20 minutes and continued up to 3 hours after CAO. Normal cardiac muscle ERP was recorded with each intervention.

Arrhythmia Mapping

Epicardial mapping was performed using a computer based system from BARD Electrophysiology Inc. The software takes 64 channels of data at 12-bit resolution with a sampling frequency of 1 kHz/channel. Filtering was from 30-300 Hz. Eight-second windows are triggered externally including up to 8 sec of data prior to the trigger signal. This system is used to record from the outer, epicardial 2-3 bipoles on each recording electrode.

Customized computer software system was used to resolve the Purkinje signals from the inner 3 bipoles on each endocardial multipolar electrode by sampling at 3 kHz per channel. The filters incorporate Purkinje frequency (3-1300 Hz). The sampling rate was 235 kHz. The PC was interfaced with an amplifier consisting of an analog signal multiplexor and 64 instrument amplifier circuits. Each had selectable gain (up to 1000), and bandwidth cutoffs. Acquisition, processing and visualization of the electrophysiological data was performed by software. High-speed acquisition, allowed us 14 sec of data including up to 8 sec before a trigger signal.

Mapping Analysis

Mapping analysis was done off line. The computer selects activation times using the first maximum dv/dt. Electrograms were considered uninterpretable and excluded from maps only if not reproducible with stimuli; there was no exclusion based on voltage of electrograms. Electrotonic or far field potentials are considered present when substantial voltage and dv/dt loss occurs in a complex with coupling intervals shorter than refractoriness. Isochrones are drawn by hand. Ventricular tachycardia mechanisms are defined as follows: Reentrant ventricular tachycardia occurs where the electrode recording the earliest activity, occurring after unidirectional block is located immediately adjacent to the site of the latest activation from the previous complex and diastolic activity is recorded between complexes. Epicardial reentry is most always recorded in acute ischemia, so retrograde activation (epicardial to endocardial) of the wall is observed.

Experimental Protocol

After instrumentation of the heart and one hour of CAO had taken place, pacing protocols to induce ventricular tachycardia were performed to confirm either reproducible inducibility (induction twice of ventricular tachycardias with similar surface morphologies) or failure of inducibility (pacing all three sites twice without ventricular tachycardia over one hour). In three dogs with reinducable ventricular tachycardia a reentry mechanism was identified. In these three dogs, Compound 2 was given as an i.v. bolus injection followed by 30 min constant infusion at three dose levels in two dogs, while the third dog was treated with saline. Extrastimulus testing was then repeated through the entire protocol at all sites to determine if the ventricular tachycardia was present, or not. Compound 2 was administered i.v. at three dose levels in order to produce plasma concentrations of $10^{-10}$ M (bolus: 0.1 µg/kg; infusion: 2 ng/kg/min), $10^{-9}$ M (bolus: 1.1 µg/kg; infusion: 21 ng/kg/min), and $10^{-8}$ M (bolus: 11 µg/kg; infusion: 210 ng/kg/min), respectively.

Results

Figure 6:
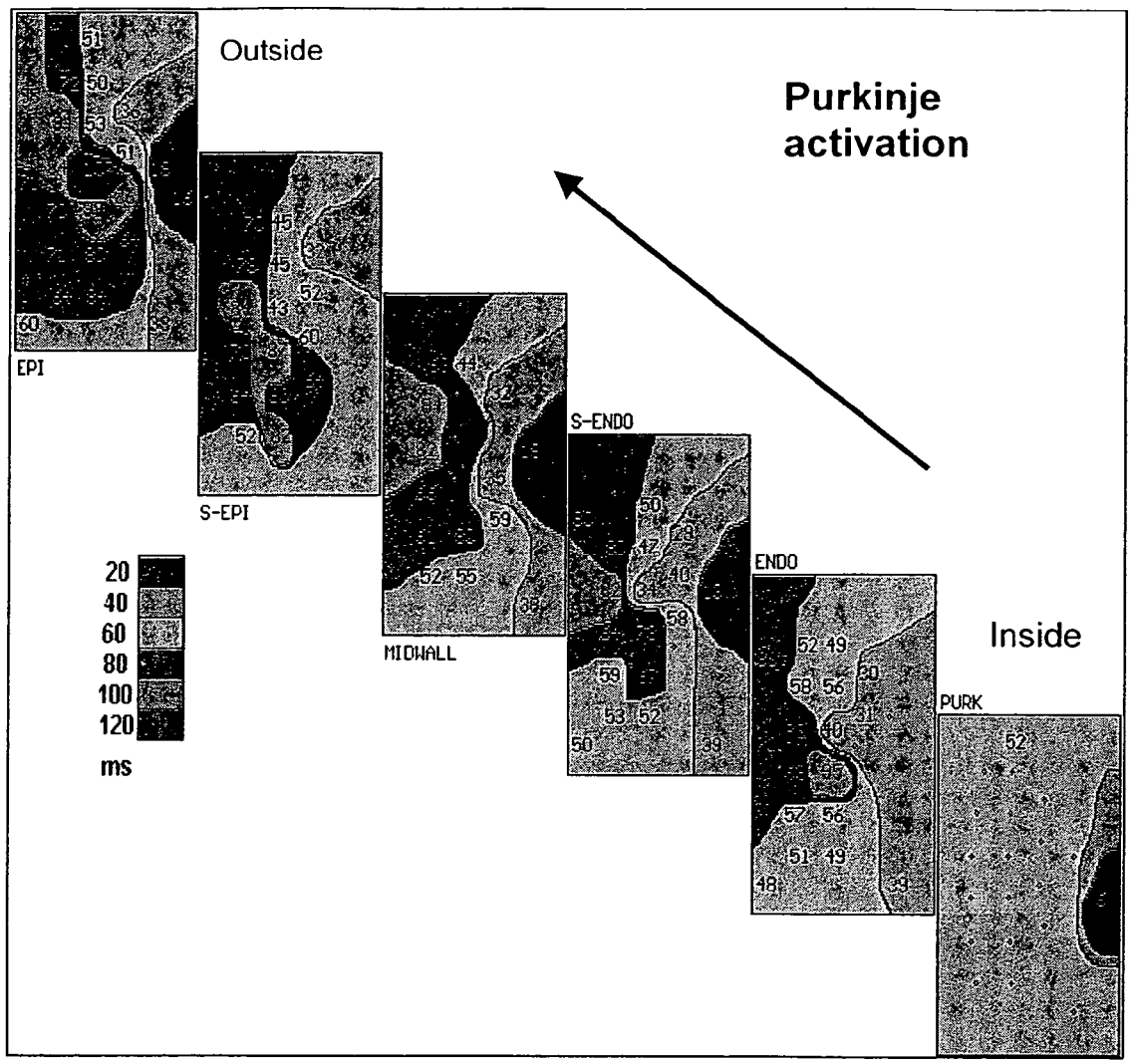
FIG. 6 is an activation map of a dog heart where the purkinje layer is stimulated about two hours after coronary artery occlusion with epicardial (EPI) activation plane on the upper left and subepicardial (S-EPI), MIDWALL, subendocardial (S-ENDO), endocardial (ENDO) and Purkinje (PURK) planes depicted down to the right of the last premature stimulus.

The first animal, from which FIGS. 6-9 are enclosed, was studied after induction of sustained monomorphic VT was induced only from the lateral ventricular pacing site twice in succession occurring at 2 hours and 10 minutes and repeated at 2 hours and 20 minutes following CAO. In FIG. 6, an activation map after septal stimulation is presented which failed to elicit VT. This shows the normal orthograde activation pattern with early activation of the PURK pacing site activated at 6 msec after the stimulus and the late activation of the epicardial site activated latest at 107 msec. Note that the adjacent activation time at 86 msec immediately east and south of the latest activation on the epicardium is E-S on FIG. 7. Epicardial activation of the first complex of the VT, which starts at −44 msec prior to the onset of the surface QRS and which corresponds to the electrogram recorded at E-C in FIG. 7.

Figure 7:
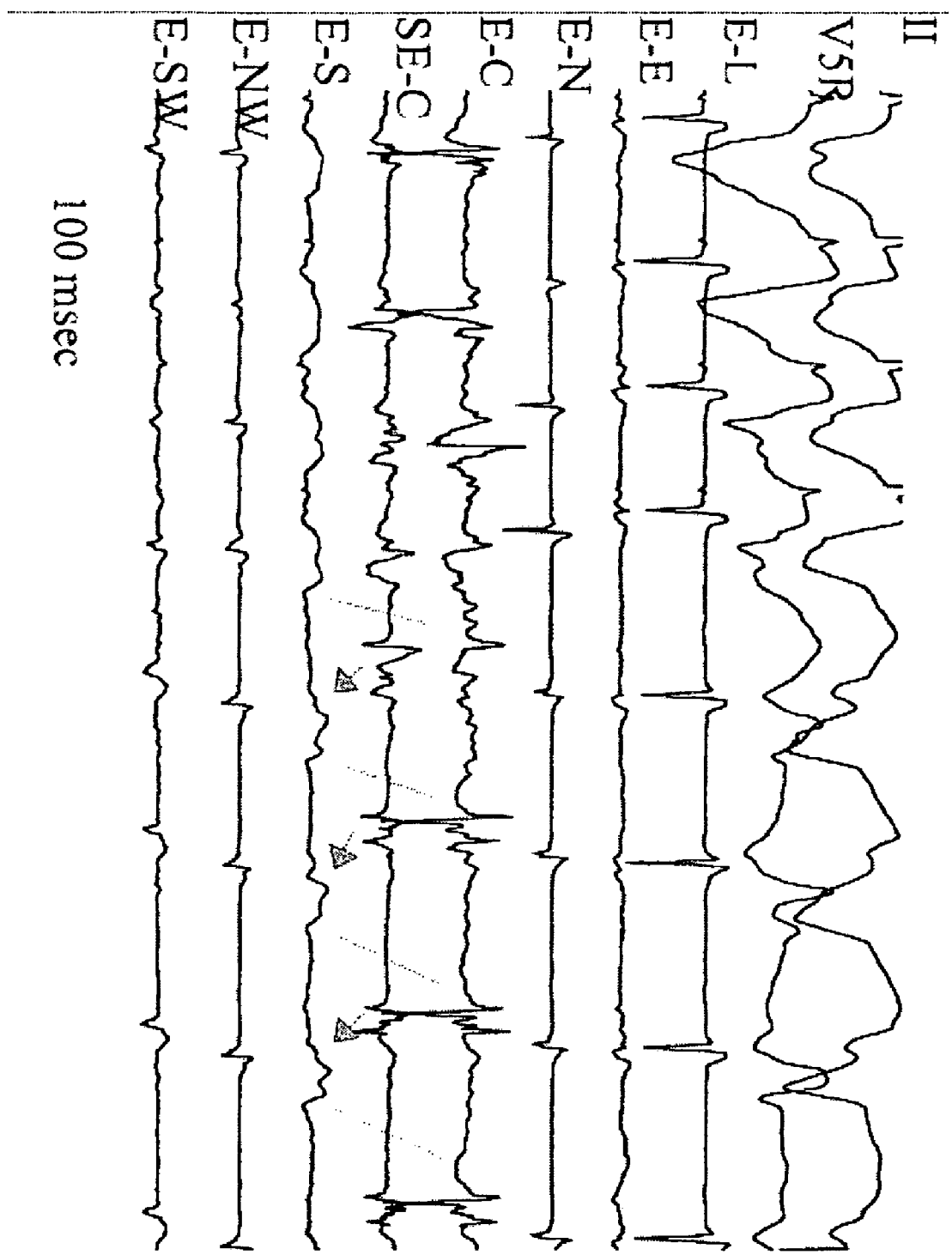
FIG. 7 illustrates epicardial (E-) electrograms in the same dog from which examples are presented in FIGS. 6, 7, 8 and 9 recorded with surface lead ECG II and V5R during the second through fifth premature extra-stimuli (seen best on E-L) with ensuring 4 complexes of VT. The electrograms are recorded from the lateral, border zone (L) pacing site and east (E), north (N), centrally (C), subepicardially (SE), below E-C, as well as south (S), and northwest (NW), and southwest (SW) of E-C.

In FIG. 7, the sustained monomorphic ventricular tachycardia (VT) induced by stimulation at the lateral epicardial ventricular pacing site causing a reentry circuit is shown. Activation proceeds in a double loop reentry activating first at −17 msec and then proceeding to 57 msec on the northwest loop. The southeast loop activating first to 2 msec, 31 msec and then to 57 msec. The protocol which induced VT was S1-S2=150, S1-S3=280, S1-S4=390, S1-S5=490 msec. The figure illustrates epicardial (E-) electrograms recorded with surface lead ECG II and V5R during the second through fifth premature extra-stimuli (seen best on E-L) with ensuring 4 complexes of VT. The electrograms are recorded from the lateral, border zone (L) pacing site and east (E), north (N), centrally (C), subepicardially (SE), below E-C, as well as south (S), and northwest (NW), and southwest (SW) of E-C. E-C show gradually dissociated electrograms with the last premature showing a block of the second component (perpendicular lines). Adjacent conduction delay on ES allowed for conduction to proceed around and back to the central site (EC) with the reentrant excitation continuing between EC and ES (straight line and line with arrow).

Figure 8:
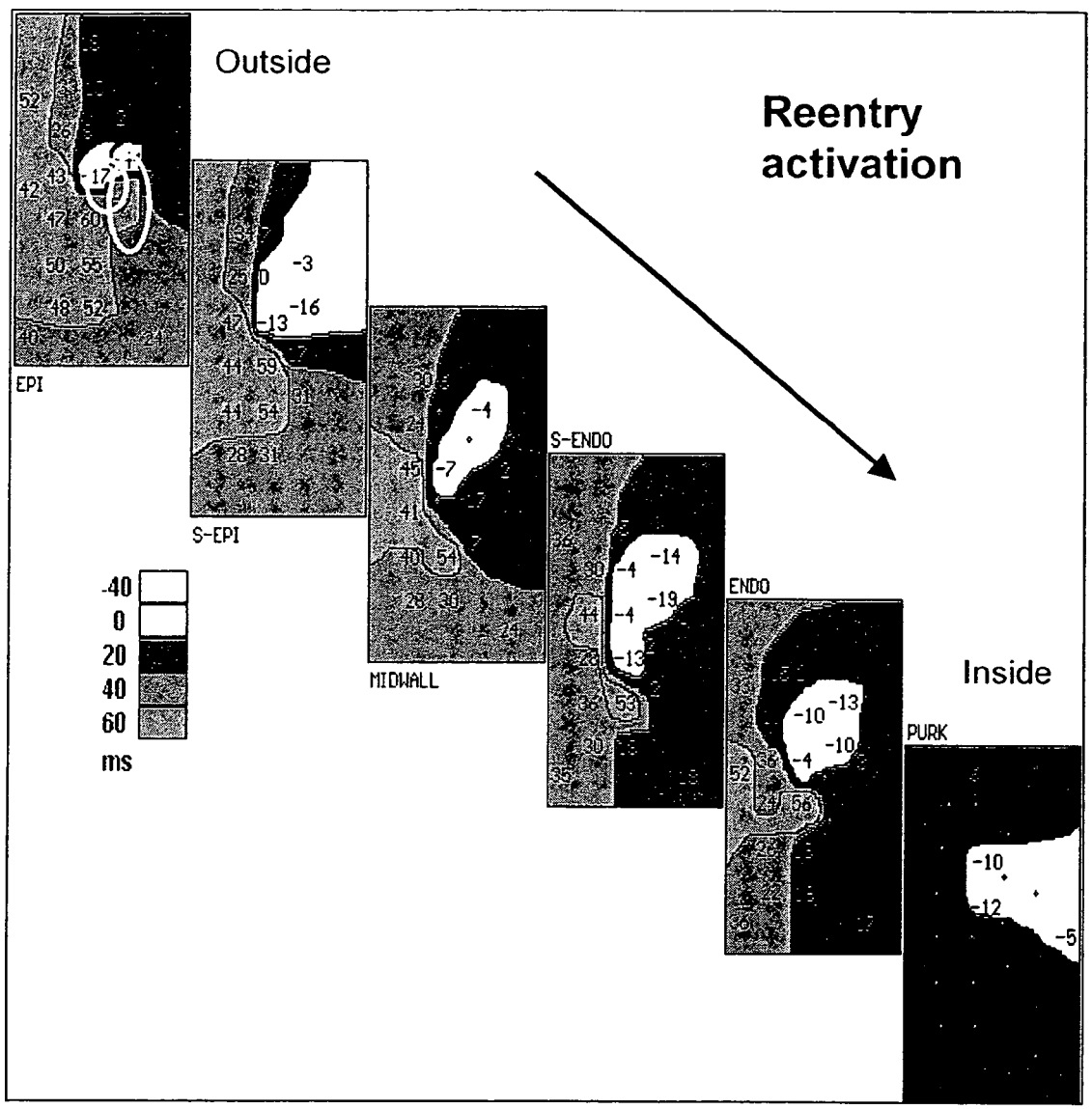
FIG. 8 illustrates epicardial activation of the first complex of the ventricular tachycardia which starts at −44 msec prior to the onset of the surface QRS and which corresponds to the electrogram recorded at E-C in FIG. 7. Activation proceeds in a double loop reentry activating first at −17 msec and then proceeding to 57 msec on the northwest loop. The southeast loop activating first to 2 msec, 31 msec and then to 57 msec.

FIG. 8 illustrates the activation map during epicardial activation of the first complex of the ventricular tachycardia, which starts at −44 msec prior to the onset of the surface QRS and which corresponds to the electrogram recorded at E-C in FIG. 7. Activation proceeds in a double loop reentry activating first at −17 msec and then proceeding to 57 msec on the northwest loop. The southeast loop activating first to 2 msec, 31 msec and then to 57 msec. This activation map also illustrates the retrograde activation of the ventricular wall during the reentry arrhythmia.

Figure 9:
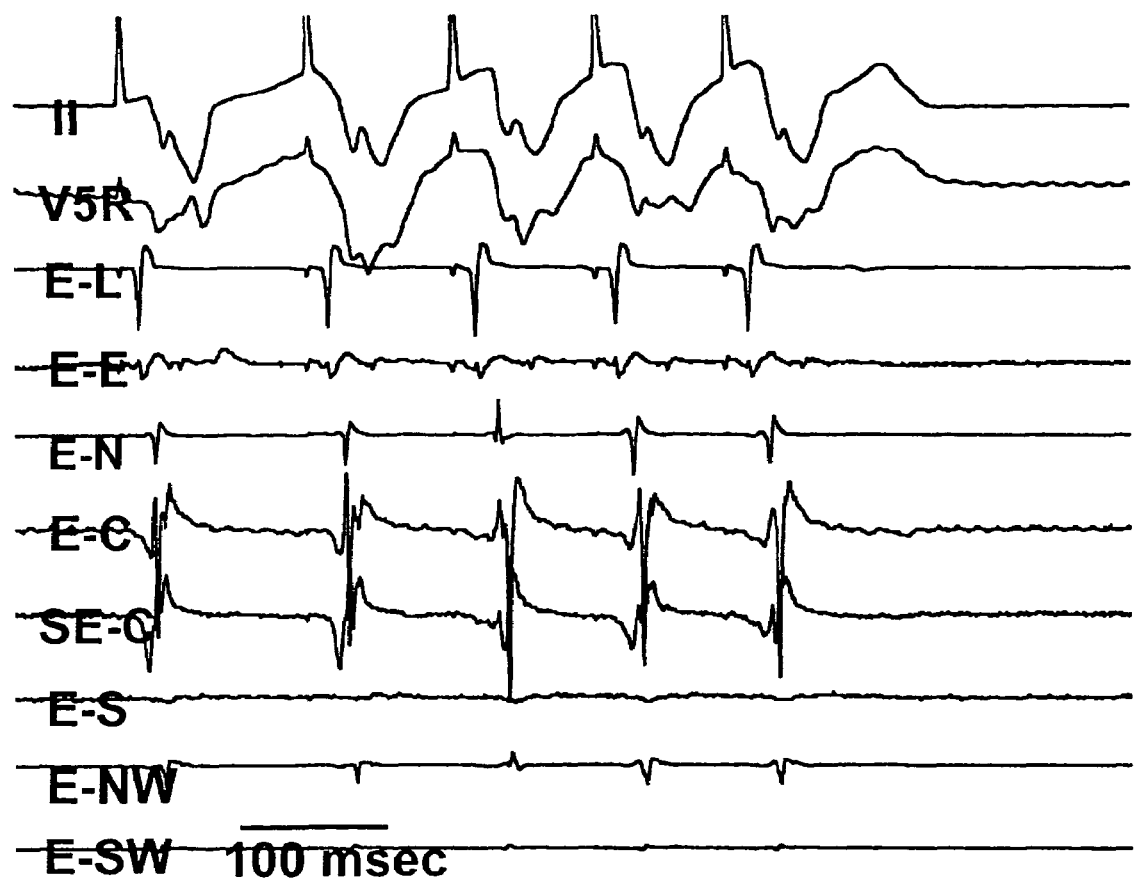
FIG. 9 shows the same leads from the same dog(s?) as presented in FIG. 7. This figure illustrates the epicardial (E-) electrograms recorded during stimulation of the same site as used in FIG. 7, but after i.v. after administration of Compound 2. After 30 minutes a second dose of Compound 2 was given, and after an additional 30 min a third dose was given. No VT was inducible after administration of either of these doses for up to an hour and a half after antiarrhythmic peptide was administered.

Compound 2 was administered in three incremental IV doses, which did not alter mean arterial pressure (MAP=80 mmHg). Effective refractory period in control was 150 msec, 154 msec after the lowest dose and was 148 msec at the highest and last dose. The VT that was inducible was typical epicardial reentry shown in FIGS. 7 and 8. After the first dose of Compound 2 (bolus: 0.1 µg/kg; infusion: 2 ng/kg/min), VT was no longer inducible despite the fact that the induction protocols induced VT prior to administration of Compound 2 were reproducibly achieved; the protocol which induced VT prior to drug administration was S1-S2=150, S1-S3=280, S1-S4=390, S1-S5=490 msec and during infusion of Compound 2 the intervals were 150, 270, 370 and 470 msec, respectively. No VT was inducible up to an hour and a half after infusion of the lowest dose of Compound 2 was started. Electrocardiographic recordings after i.v. administration of the lowest dose of Compound 2 are shown in FIG. 9. These results demonstrate that Compound 2 effectively blocked reentry VT in this dog.

A second dog was studied with inducible VT, this time from two border-zone, pacing sites located laterally and septally. Again Compound 2 produced no change in MAP, which started out 90 mmHg and ended at 90 mmHg. Effective refractory period in the two sites of induction remained at 163 and 144 msec respectively throughout the testing period of Compound 2, which started 85 minutes after CAO and continued for 2 further hours. After the lowest dose of Compound 2, the VT induced from the lateral wall was no longer inducible; mechanism of this VT was epicardial reentry, very similar to that shown in FIGS. 7-9. The VT induced from the septal site was also epicardial reentry prior to administration of Compound 2, but following i.v. administration of Compound 2 the epicardial reentry was completely blocked. Thus in these two experiments epicardial reentrant VT was inducible prior to induction of the lowest dose of Compound 2 and following administration of the substance no reentry was reinducible at any dose. Finally one additional animal underwent electrophysiologic testing during the time frame used in the two experiments described above without introduction of Compound 2 but with saline. Epicardial reentry was induced one hour after CAO and the same VT morphology and reentrant mechanism was induced 1½-2½ hours of CAO. Thus the reproduceability of reentrant VT in this time controlled experiment is consistent with Compound 2 being an effective antiarrhythmic compound during conditions with reentry arrhythmias.

These experiments demonstrate that Compound 2 is efficacious in the prevention and/or treatment of lethal reentry arrhythmias. Thus, it is a purpose of the present invention to provide compounds for the preparation of medicaments useful in prevention and/or treatment of cardiac reentry arrhythmias of either supraventricular or ventricular origin. This purpose is achieved with the present peptide compounds, such as the compounds of formulae I, XII, XIII, XIIIa, XIV, XV and XVI and formulae 2-12 herein, more specifically the compounds of Synthesis Examples 1-47 herein.

Experimental Example 8

Effect of Gap Junction Openers on Bone Cells

Background

Osteoblasts, which are the bone-forming cells, and osteocytes are well connected. Osteoblast-osteoblast, osteoblast-osteocyte, and osteocyte-osteocyte connections have been found in bone slices, examined by electron microscopy[42]. The most interesting connexin in relation to bone is Cx43, like in the heart. In bone cells, the expression of these proteins is linked to the expression of some osteoblast specific proteins. Calciotropic hormones can also regulate the expression of the gap junction proteins.

Human osteoblasts (HOB) and bone marrow derived stromal cells (BMSC) are both shown to express Cx43 and Cx45. They are functionally coupled as demonstrated with the Lucifer Yellow (LY) dye transfer technique[43]. The rat osteoblastic cell lines differ from the human primary cultures; the ROS 17/2.8 cells express only Cx43 and are well coupled, whereas UMR 106-01 predominantly express Cx45 and are poorly dye coupled[44]. Both rat osteoblastic cell lines are electrically coupled. Transfection of Cx43 into the UMR cells resulted in cells highly dye coupled. Thus, Cx43 permits transfer of LY and other larger molecules, whereas Cx45 does not permit this passage. In contrast, introduction of Cx45 to Cx43 expressing cells decreases the dye coupling. In osteoblast differentiation, Cx43 expression changes; thus, the more mature the osteoblasts is, the higher is Cx43 expression[45].

The effect of different stimuli on bone cells and the relation to changes in gap junction communication has been investigated. It is well known that moderate mechanical stress on bone, increases the bone density. To imitate this situation, ROS 17/2.8 cells were exposed to cyclic stress, which resulted in an increase in dye coupling of the cells. Cyclic stress applied to the poorly coupled UMR 106-01 cells resulted in an increase in dye coupling as well, but less dramatically compared to the ROS cells. No increase in mRNA for Cx43 was found, but more phosphorylated forms of Cx43 were found, indicating that cyclic stress on osteoblastic cells increases gap junctional communication between the cells by modulating intracellular localization of the gap junction protein Cx43. The same group has shown that transfection of Cx43 into the poorly coupled UMR 106-01 cells not only increases the dye coupling[46], but also increases the expression of the products of mature osteoblasts, osteocalcin and bone sialoprotein (BSP). Decreasing the coupling between osteoblastic cells (ROS) by transfecting Cx45 into the cells decreases the expression of osteocalcin and BSP, genes pivotal to bone matrix formation and calcification. A recent study showed that Cx43 knock-out mice have deficient bone formation and development compared to wild type mice[47]. Thus, a communicating intercellular network is required for the full elaboration of a differentiated osteoblastic phenotype as well as normal bone formation and turnover. Deficient gap junctional communication may therefore result in increased bone loss.

Gap junctions have also been shown to be partly responsible for the propagation of intercellular calcium signals in bone cells. Mechanical stimulation of one human osteoblast in a cell monolayer in vitro induces a calcium pulse, which is propagated to a number of surrounding cells. The propagation of this signal involves the passage of a messenger molecule through gap junctions, with subsequent activation of neighbouring cells[48;49]. These signals are probably propagated throughout the cellular network in bone in vivo in response to mechanical stimuli, and might be responsible for the increased bone formation in response to mechanical loading on bone.

Gap junctional communication and the effect of calciotropic hormones are linked. 1.25 (OH)$_2$ vit.D$_3$ stimulation of human skin fibroblasts has been shown to enhance communication via gap junctions as well as increase the levels of Cx43 protein and mRNA[50], but only in the presence of functional vitamin D receptors (VDR). Loss of Cx43 expression is shown to decrease the responsiveness of cells to PTH, without any change in the PTH receptor number or cAMP response[51]. The other way round, PTH and PGE2 enhance gap junctional communication in osteoblastic cell cultures via two mechanisms; an initial rapid redistribution of Cx43 to the cell membrane, and a later stimulation of Cx43 gene expression[52]. Thus, modulation of intercellular communication represents a mechanism by which osteotropic factors regulate the activity of bone forming cells.

Gap junctional intercellular communication may very well prove to be one of the most important mechanisms by which bone cells coordinate their activities and responses to mechanical and hormonal stimuli. Thus, if gap junctional communication between bone cells could be increased pharmacologically, osteoblast activity could be increased, enhancing bone formation in vivo.

Cardiac myocytes are also connected by gap junctions, and like in osteoblasts, the predominant connexin is Cx43. Certain compounds have been found to increase gap junctional communication between cardiac myocytes of which the artificially synthesized AAP10 (CE2) is the best investigated. Cardiac myocytes respond to ischaemia with a decrease in cellular coupling. In in vitro experiments, adding AAP10 (CE2) to cardiac myocytes exposed to ischaemia, some of the lost cellular coupling was restored. If cardiac myocytes can respond to this group of compounds with an increased gap junctional coupling, osteoblasts might do the same. In this case, it is evident that the increase in cellular coupling very well could be accompanied by an increase in osteoblast maturation and activity, and subsequent increase in bone formation. To investigate this hypothesis, we have examined the effect of Compound 2 on GJIC in human osteoblasts and rat osteosarcoma cells. Moreover, we have studied the effect of Compound 2 on a marker (i.e., alkaline phosphatase) for human osteoblast activity and bone formation.

Methods

Cell Culture

Human osteblast cells (hOB): Cells were isolated from human bone marrow obtained by puncture of the posterior iliac spine of healthy volunteers (aged 20-36): 10-15 ml marrow material was collected in 15 ml PBS+Ca,Mg (Life Technologies, Cat. No. 14040) with 100 U/ml Heparin (Sigma, Cat. No. H-3149). The mononuclear fraction of the marrow was isolated on a Lymphoprep gradient (Nycomed Pharma, Cat. No. 1001967), by centrifugation at 2200 rpm for 30 min. After harvesting, the mononuclear fraction was washed once with culture medium and centrifuged at 1800 rpm for 10 min. Subsequently cells were counted and plated in culture medium at 8×10$^6$ cells/100 mm dish. hOB medium (all reagents obtained from Life Technologies): MEM w/o Phenol Red w/Glutamax (Cat. No. 041-93013) supplemented with 10% heat inactivated fetal calf serum (Cat. No. 10106) and 0.1% Penicillin/Streptomycin (Cat. No. 15140). Medium was changed the following day and the cells were cultured at 37° C. in 5% $CO_2$ with medium change every 7 days. After 3-4 weeks of culture the cells had reached 70% confluence. The medium was then supplemented with 100 nM Dexamethasone (Sigma, Cat. No. D-4902) for 7 days. Cells were then plated for video imaging experiments: a 25 mm #1 glass coverslip was placed in a 35 mm dish (or each well of a 6-well multidish), cells were plated at 2.5×10$^5$ cells/coverslip and cultured for 2-3 days before use.

ROS 17/2.8 cells: Cells were cultured in 100 mm dishes at 37° C. with 5% $CO_2$ and medium change every 2-3 days. ROS medium (all reagents obtained from Life Technologies): MEM (Cat. No. 31095) supplemented with 10% heat-inactivated calf serum (Cat. No. 16170), 1% NEAA (Cat. No. 11140), 1% Sodium Pyruvate (Cat. No. 11360), 1% L-Glutamine (Cat. No. 25030) and 0.1% Penicillin/Streptomycin (Cat. No. 15140). For video imaging experiments, cells were plated on coverslips at 2-3×10$^5$ cells/coverslip and cultured for 2-3 days before use.

Measurement of Calcium Waves

The cells cultured on coverslips were loaded with 5 μM fura-2-AM (Molecular Probes, Cat. No. F-1221), for 30 minutes at 37° C., and incubated in fresh medium for 20 minutes. Coverslips were then affixed to a PDMI-2 culture chamber (Medical Systems Corp.), maintained at 37° C. with superfused $CO_2$, on a Zeiss Axiovert microscope. Intercellular calcium waves were induced by mechanical stimulation of a single cell using a borosilicate glass micro pipette affixed to an Eppendorf 5171 micromanipulator. Imaging was performed using a MetaMorph imaging system (Universal Imaging). The excitation light (340 and 380 nm) was provided by a monochromator (T.I.L.L. Photonics GmbH). Images were acquired with an intensified CCD camera (Dage MTI) and digitized with a Matrox MVP image processing board.

Microinjection

The cells cultured on coverslips were placed in the microscope as described above. Microinjections were performed using the Eppendorf 5171 micromanipulator and the Eppendorf Transjector 5346 system. A micropipette was loaded with a 10 mM Lucifer Yellow (LY) solution (Sigma, Cat. No. L-0259). A cell in the monolayer was carefully injected with LY for 30 seconds, the micropipette was removed from the cell and after 30 seconds the number of cells that showed dye transfer were counted. The excitation light for LY was 430 nm, and images were acquired as described above.

Alkaline Phosphatase Assay

Day 1: Cells were plated in 96-well plates at a conc. of 8000 cells/well (hOB) or 3000 cells/well (ROS) in 200 μl normal culture medium.

Day 2: Medium was changed on the cells.

Day 4: (Day 3 for ROS): Cells were washed with 200 μl MEM, 0.1% BSA (Sigma, Cat. No. A-9418). 200 μl MEM, 0.10/% BSA containing various concentrations of Compound 2 was added to the cells, and culture was continued for 4 days (2 days for ROS cells).

Day 8: (Day 5 for ROS): Alkaline Phosphatase (ALP) assay is a colorimetric endpoint method for measuring enzyme activity, and was done using Alkaline Phosphatase Kit (Sigma, Cat. No. 104-LL): Cells were washed once with 200 μl PBS+Ca,Mg. 100 μl Alkaline Buffer Solution was added to each well and plate was placed at 37° C. for 10 min. 100 μl Substrate Solution was added to each well and plate was incubated at 37° C. for 30 min. 100 μl 2.0 N NaOH was added to each well to stop the reaction. Absorbance was measured using a plate reader at 405 nm.

Effects of Compound 2 on GJIC

Figure 10:
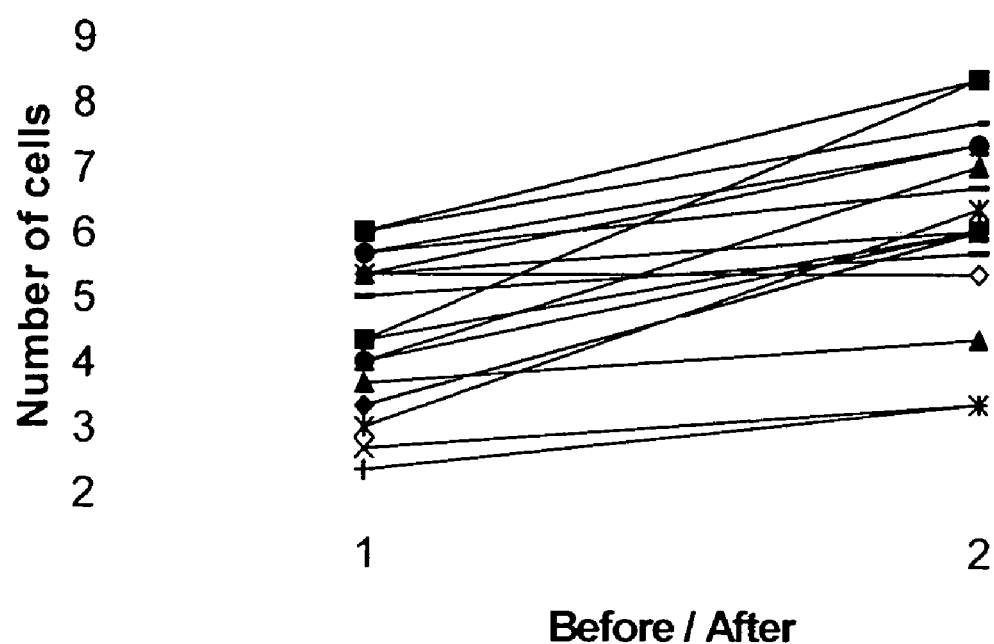
FIG. 10 shows the short-term effect of $1 \times 10^{-8}$ M of Compound 2 on intercellular calcium wave propagation in human osteoblasts. Number of cells in wave before (1) and 10 minutes after adding Compound 2 (2) to the bathing solution is plotted.

In order to assess the ability of gap junction modifiers to increase communication via gap junction mediated intercellular calcium signals, monolayers of human osteoblastic cells on glass coverslips were loaded with fura-2. During real-time imaging, a mechanical stimulation with a glass micropipette was performed. An increase in the intracellular calcium appeared, with a subsequent spread of the signal to surrounding cells. The average number of cells in the wave was 6.5 cells. Next, 100 µM adenosine tri-phosphate (ATP) was added in order to desensitize purinergic receptors. After desensitization, the calcium wave propagation depends exclusively on GJIC. Upon ATP stimulation an increase in intracellular calcium was seen in most cells in the field of view. Again, one single cell was stimulated mechanically. Now, the wave propagation was limited to an average of only 4.5 cells in the wave. Compound 2 was added in a concentration of $10^{-8}$ mol/l to the bathing solution. An increase in intracellular calcium concentrations was seen in most cells in the field of view. After 10 minutes of incubation with Compound 2, one single cell was stimulated mechanically. Again, the stimulated cell increased in intracellular calcium concentration, with a subsequent propagation of the wave. Now the wave extended to an average of 6.2 cells (FIG. 10), which is a significant increase compared to before adding Compound 2.

Figure 11:
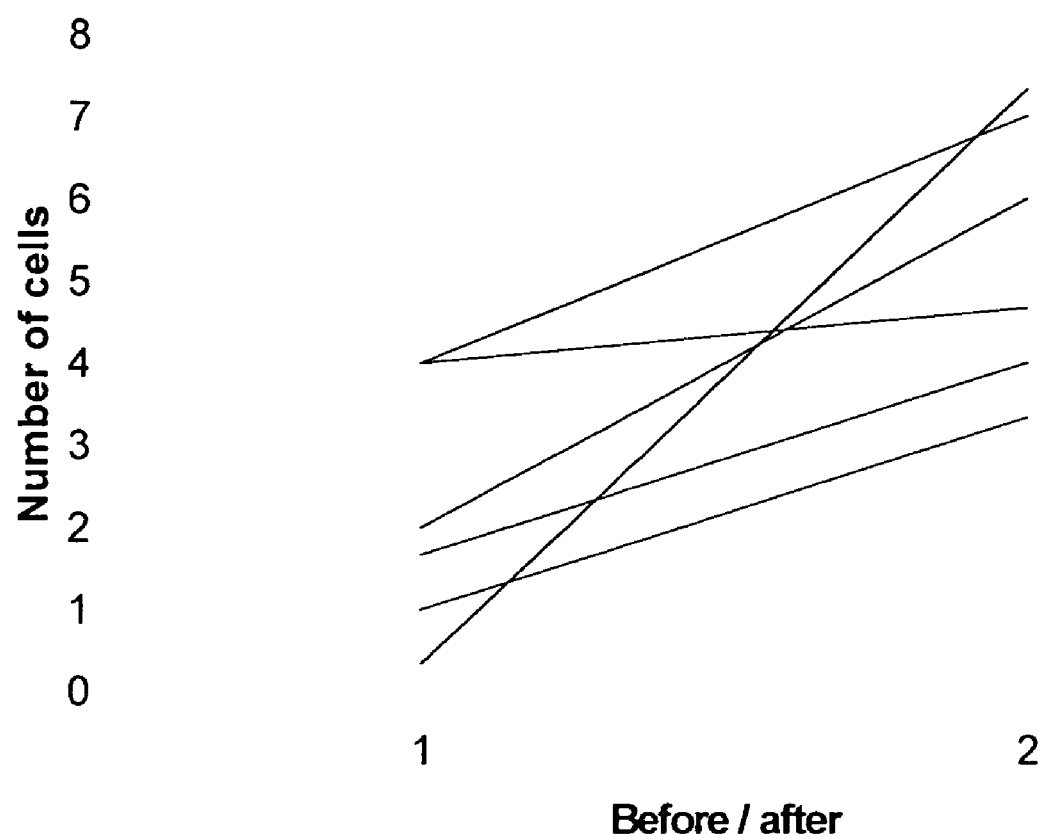
FIG. 11 shows the number of cells in the calcium wave plotted before (1) and 10 minutes after addition of $1 \times 10^{-8}$ M of Compound 2 (2) to ROS 17/2.8 cells, cultured under hypoxic conditions (5% $O_2$).

In order to test the compound's ability to restore suppressed gap junctional coupling, similar experiments were performed on the osteoblastic cell line ROS 17/2.8 (ROS), but after incubation of the cells for 48 hours under hypoxic conditions, with only 3-6% $O_2$, conditions known to decrease cellular coupling. ROS cells in monolayers were loaded with fura-2, and under the same conditions as above, a mechanical stimulation was performed. As ROS cells do not express purinergic receptors, pre-treatment with ATP was not done. Upon stimulation, the intracellular calcium concentration increased in the stimulated cell, and a wave was initiated, spreading to a total average of 2.2 cells (n=18). Then Compound 2 was added to the bathing solution in a final concentration of $10^{-8}$ M. After 10 minutes, the mechanical stimulation was repeated. Now, the wave propagated to an average of 5.4 cells (n=18) (FIG. 11), which is a significant increase compared to before the compound was added. Thus, Compound 2 efficiently increases gap junctional mediated intercellular calcium waves.

To assess the effect of the compound on direct cellular coupling, microinjection experiments were performed according to the method described above. The dye Lucifer Yellow (LY) was injected into one single human osteoblast in a monolayer. After 30 seconds, the number of cells containing dye was assessed. Under physiological conditions, the dye spread to an average of 14 cells (n=19). To suppress cellular coupling, cells were now incubated during hypoxia (3-6% $O_2$) for 48 hours. Then cellular coupling was re-assessed by microinjecting LY, and at this point the dye was only passed to an average of 7 cells (n=10). Compound 2 was added to the medium, and after 10 minutes, dye coupling was assessed again. Already after 10 minutes of incubation with Compound 2, the cellular coupling was increased with dye transfer to 9 cells (n=11).

Figure 12:
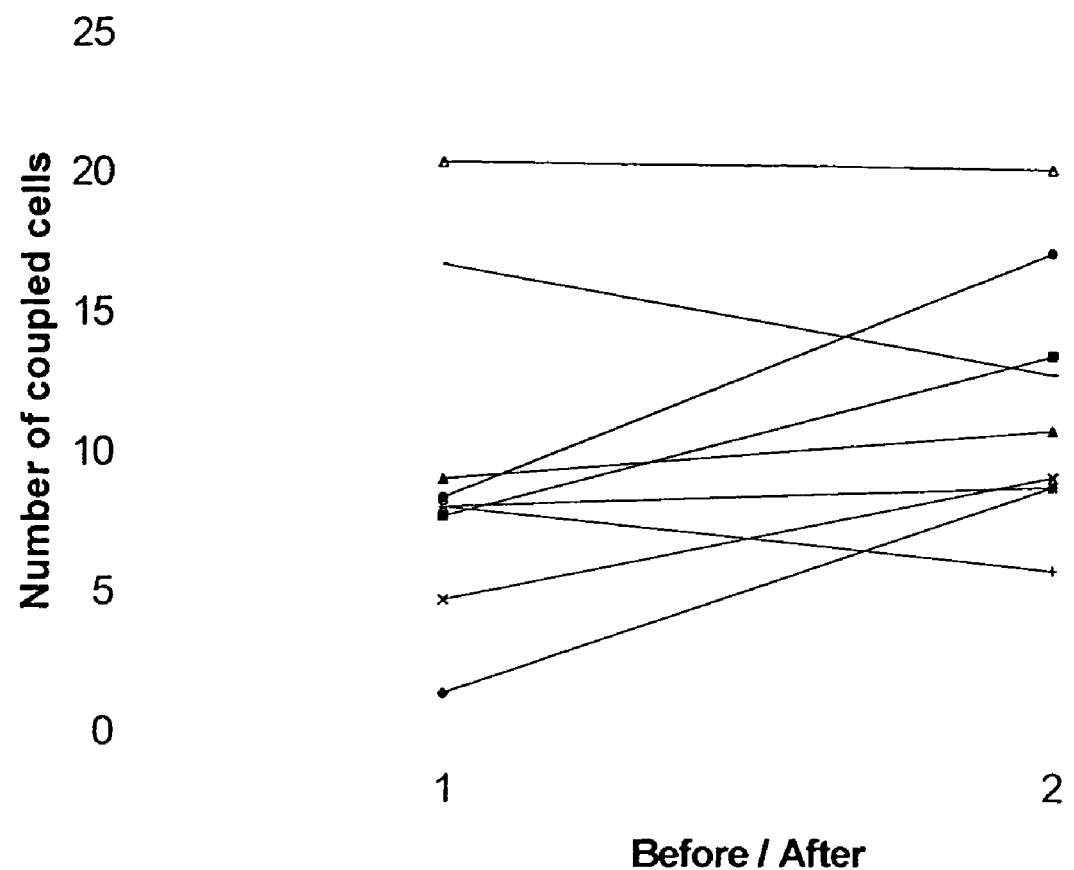
FIG. 12 illustrates dye transfer in ROS 17/2.8 cells, cultured under hypoxic conditions (3-6% $O_2$). Number of coupled cells is plotted before (1) and 10 minutes after adding $1 \times 10^{-8}$ M of Compound 2 to the bathing solution (2).

Similar experiments were performed with ROS cells. Basic coupling under physiological conditions in ROS cells was 12 cells (n=19). After 48 hours incubation in 3-6% $O_2$, a reduction in dye transfer was seen to 9 cells (n=27). Again, Compound 2 was added to the bathing solution, and the cellular coupling was actually restored to pre-hypoxic levels, with an average dye transfer to 12 cells (n=27), (FIG. 12). Thus, Compound 2 is able to increase gap junctional communication and restore hypoxia-induced reductions in cellular coupling.

Figure 13:
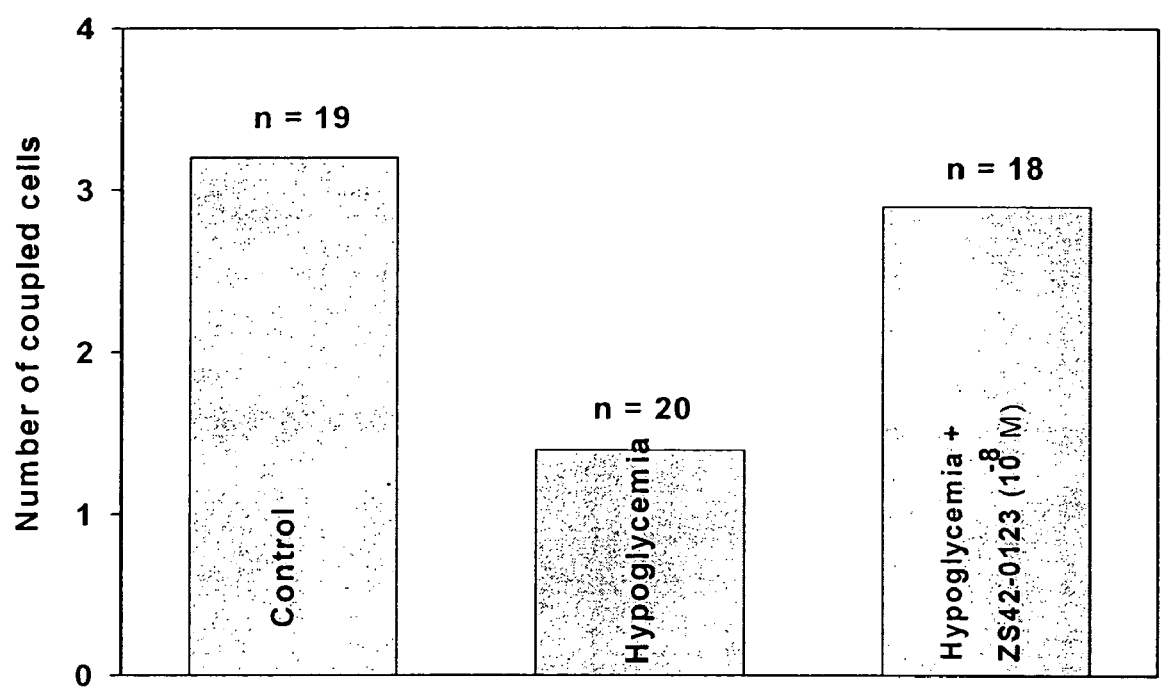
FIG. 13 illustrates the short-term effect of $1 \times 10^{-8}$ M of Compound 2 on intercellular calcium wave propagation in human osteoblasts under hypoglycemic conditions. The figure shows the number of cells in the wave during hypoglycemia (1) and 10 minutes after adding Compound 2 to the hypoglycemic bathing solution (2).

Metabolic stress induced by hypoglycemia is also known to decrease gap junctional communication. Therefore, we wanted to assess whether Compound 2 could reverse the hypoglycemia-induced reduction in cellular coupling. Human osteoblastic cells were cultured in monolayers on glass coverslips and loaded with fura-2. After ATP desensitization as described above, one single cell was stimulated mechanically, and the number of cells in the wave was recorded. In this set of experiments, the wave extended to an average of 3.2 cells (n=19). Medium was changed to medium without glucose, and after 8 minutes another mechanical stimulation was performed. Now, the wave was almost blocked, with a wave propagation of only 1.4 cells (n=20). Compound 2 was added to the medium in a final concentration of $10^{-8}$ M. A final stimulation was performed, and now the wave was almost restored, with an average extension to 2.9 cells (n=18), (FIG. 13). Thus, Compound 2 is able to restore hypoglycemia-induced uncoupling of cells.

Figure 14:
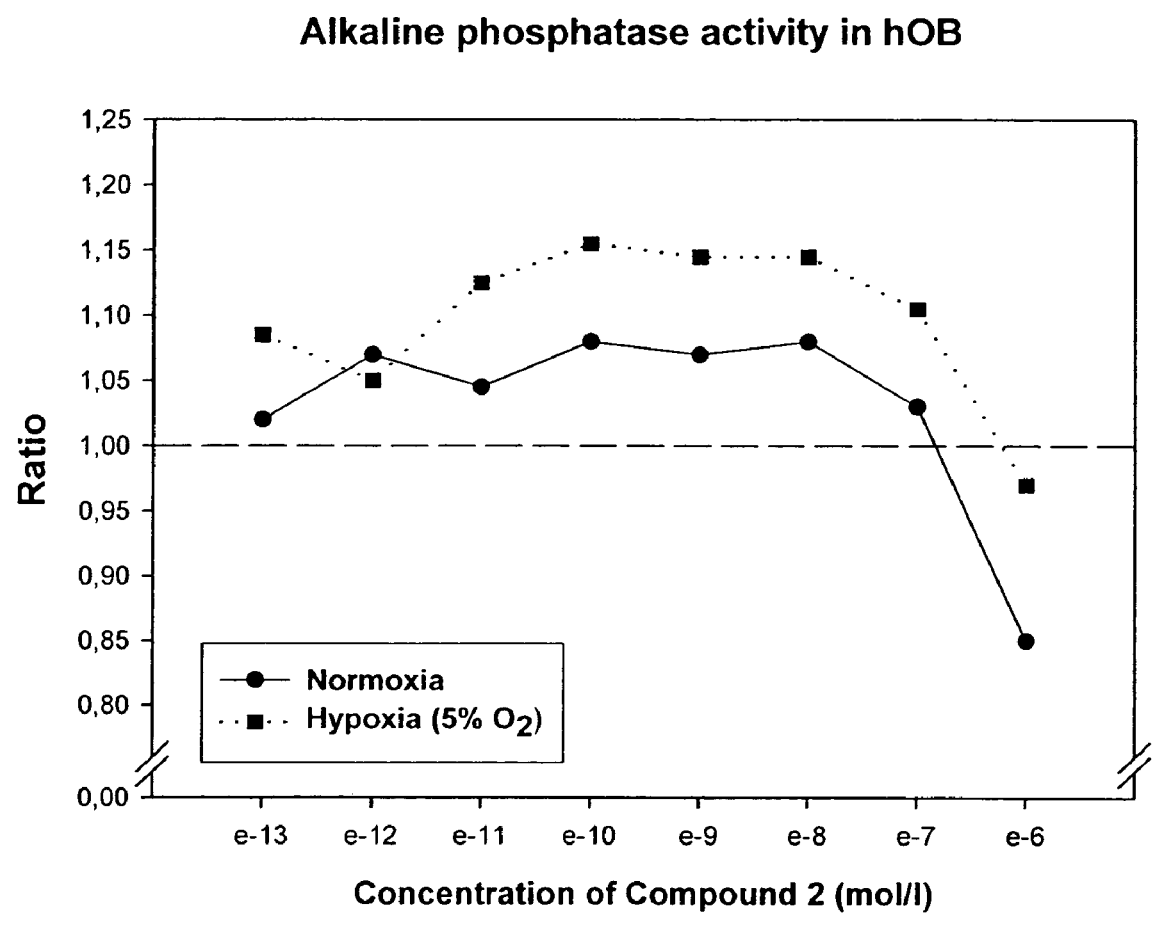
FIG. 14 shows alkaline phosphatase (ALP) activity in cultures of human osteoblastic cells. The ALP activity is a measure of osteoblastic activity. ALP activity was measured over four days stimulation with $10^{-13}$-$10^{-6}$ M of Compound 2 in each culture, and compared to untreated controls. The ratio between the ALP activity in the treated and untreated cultures are plotted for each concentration of the compound. Compound 2 stimulated ALP activity and thus osteoblastic activity at all concentrations in the concentration range $10^{-13}$-$10^{-7}$ M.
Figure 15:
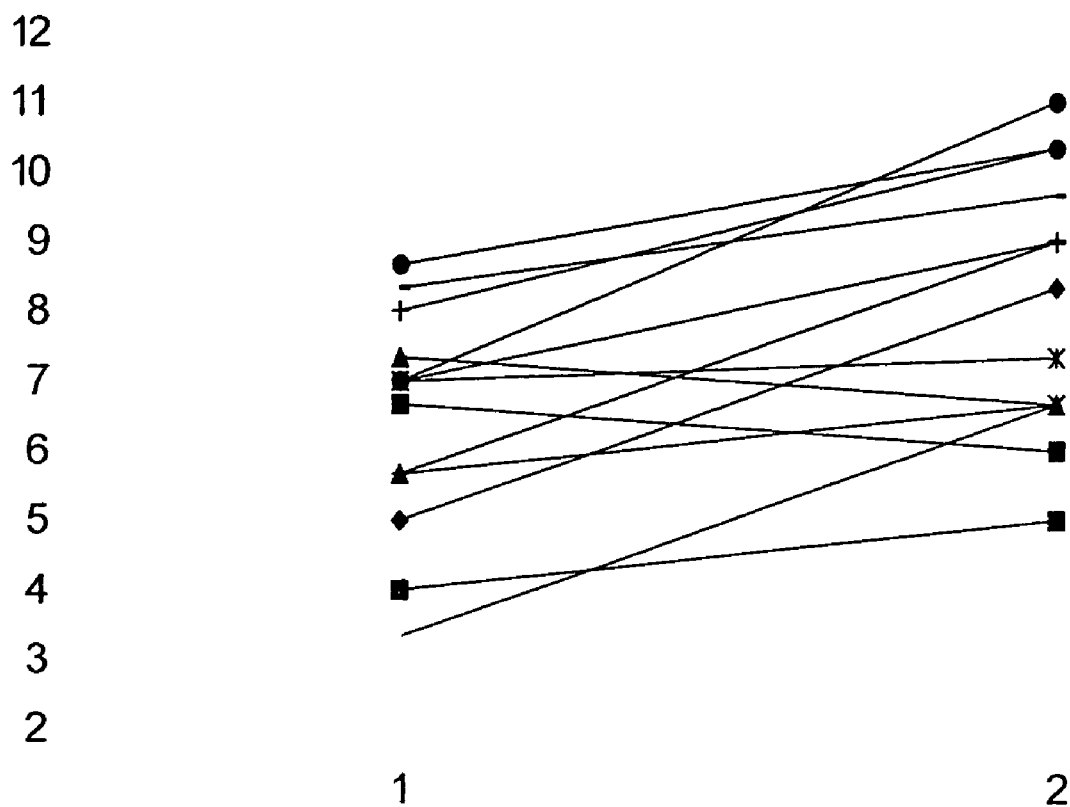
FIG. 15 shows the effect of Compound 2 on Lucifer Yellow (LY) dye transfer in human osteoblast cells treated with 13 μM DDT, the compound 1,1-bis(p-chlorophenyl)-2,2,2-trichlorethane. 10 minutes incubation with $10^{-8}$ M of Compound 2 produced an increase in the number of dye-coupled coupled cells in all experiments (1 indicated before and 2 indicated after addition of Compound 2 to the bath).

Finally, to assess the effect of Compound 2 on bone formation and osteoblast activity, we measured the effect of the compound on the alkaline phosphatase (ALP) activity of the cells. Human osteoblasts were stimulated with different concentrations of Compound 2 from $1\times10^{-13}$ to $1\times10^{-6}$, and compared to untreated controls. Under normal culture conditions, Compound 2 increased ALP activity at most of the concentrations tested, except for the highest concentration ($10^{-6}$ mol/l), which may be toxic (FIG. 14). Moreover, the effect of the compound on ALP activity was also tested during hypoxic conditions. Human osteoblasts were cultured for four days in 5% $O_2$. The medium was enriched with Compound 2 in different concentrations, and compared to the responses during normoxic conditions. During hypoxia, the Compound 2-induced stimulation of ALP activity was about 15% greater than during normoxia at all concentrations in the range $10^{-11}$ to $10^{-8}$ mol/l, (FIG. 15).

In summary, these results demonstrate that Compound 2 is able to normalize the attenuated GJIC between human osteoblast during hypoxia. Moreover, Compound 2 stimulates the production of alkaline phosphatase suggesting that Compound 2 is able to stimulate the activity of osteoblats, and therefore bone formation. Thus, Compound 2 may be useful in the treatment of bone diseases with impaired bone formation relative to bone resorption. The effect of Compound 2 on cell-to-cell coupling during hypoxia suggests that substances of the present invention may be useful in the treatment and/or prevention of bone diseases associated with poor vascularization, hypoxia and ischemia in bone tissue.

From these experiments it can be concluded that substances of this invention that increase GJIC may be useful for the preparation of medicaments for prevention and/or treatment of osteoporosis. In some instances, osteoporosis is a manifestation of another disease, such as Cushing's syndrome or osteogenesis imperfecta. In most cases of osteoporosis, however, no other disease is apparent. One form occurs in children or young adults of both sexes and with normal gonadal function and is frequently termed idiopathic osteoporosis, although most of the other forms are also of unknown pathogenesis. Type I osteoporosis occurs in a subset of postmenopausal women who are between 51 and 75 years of age and is characterized by an accelerated and disproportionate loss of trabecular bone. Fractures of vertebral bodies, and the distal forearm are common complications. Decreased parathyroid gland function may be compensatory to increased bone resorption. Type II osteoporosis occurs in women and men over the age of 70 and is associated with fractures of the femoral neck, proximal humerus, proximal tibia, and pelvis, sites that contain both cortical and trabecular bone. In addition to osteoporosis, substances that increase GJIC may also increase bone formation in metabolic bone diseases such as rickets and osteomalacia and in osteoporosis due to chronic glucocorticoid administration or chronic renal failure. Thus, it is a purpose of the present invention to provide compounds for the preparation of medicaments useful in prevention and/or treatment of osteoporosis. This purpose is achieved with the present peptide compounds, such as the compounds of formulae I, XII, XIII, XIIIa, XIV, and XV and formulae 2-12 herein, more specifically the compounds of Synthesis Examples 1-47 herein.

Effects of Gap Junction Openers on Cartilage

Articular cartilage is a tissue designed to withstand compression during joint movement and, in vivo, is subjected to a wide range of mechanical loading forces. Mechanosensitivity has been demonstrated to influence chondrocyte metabolism and cartilage homeostasis. In many cell types mechanical stimulation induces increases of the cytosolic $Ca^{2+}$ concentration that propagates from cell to cell as an intercellular $Ca^{2+}$ wave. Cell-to-cell communication through gap junctions underlies tissue co-ordination of metabolism and sensitivity to extracellular stimuli: gap junctional permeability to intracellular second messengers allows signal transduction pathways to be shared among several cells, ultimately resulting in co-ordinated tissue responses. Mechanically-induced $Ca^{2+}$ signalling has been investigated in chondrocytes and it has been demonstrated that gap junctional communication is essential for mechanically-induced $Ca^{2+}$ signaling in chondrocytes[53]. Moreover, mechanical stimulation activates phospholipase C, thus leading to an increase of intracellular inositol 1,4,5-trisphosphate. The second messenger, by permeating gap junctions, stimulates intracellular $Ca^{2+}$ release in neighbouring cells and this system is considered very important for the coordinated signaling in chondrocytes during mechanical strain and it may provide a mechanism for co-ordinating metabolic activity during metabolic stress in chondrocytes[53;54]. The predominant connexin in cartilage is Cx43 and it in addition to its role in the cell-to-cell regulation of metabolism and signalling, Cx43 is essential for normal chondrogenesis[47;55].

Thus, it appears that substances of this invention that increase GJIC may be used for the prevention and/or treatment of joint diseases that involves impaired cell-to-cell coupling. Like we have demonstrated in human osteoblastic cells, we suggest that substances that increase GJIC may be used for the prevention and/or treatment of joint diseases that involves metabolic stress. These would include any form of arthritis associated with decreased vascularization or healing of fractured cartilage tissue. Thus, it is a purpose of the present invention to provide compounds for the preparation of medicaments useful in prevention and/or treatment of joint diseases including arthritis. This purpose is achieved with the present peptide compounds, such as the compounds of formulae I, XII, XIII, XIIIa, XIV, and XV and formulae 2-12 herein, more specifically the compounds of Synthesis Examples 1-47 herein.

Effects of Gap Junction Openers on Cancer

The gap junction permeability and the regulation of GJIC happen on different levels in the cell. Decrease or absence of GJIC may be the result of changes in the Cx expression during transcription and translation, alteration of post translational processing and alteration of connexon assembly and insertion into the plasma membrane. An unusual feature of Cx is their short half-life in comparison with other membrane proteins. The rapid turn over of connexins has been found to be between 1.5 and 2 h. The degradation of Cx has been shown to dependent on phosphorylation, which leads to destabilization of some connexin subtypes. The fast turnover rate provides an additional mechanism by which GJIC can be rapidly regulated by substances affecting Cx mRNA half-life, translation, intracellular transport and assembly of Cx into gap junctions. Another way to regulate gap junctional permeability is complete or partial closure of gap junction channels under certain circumstances by mechanically twisting of the six subunits of connexon. The gating of gap junctions is known to be effected by tumour promoters which decrease GJIC. Tumor promoters are agents, which enhance or accelerate carcinogenesis when given repeatedly after tumor initiation. The mechanisms by which tumor promoters modulate GJIC are not fully understood, but there is evidence to support that tumor promoters may affect GJIC by alteration of phosphorylation of Cx and/or inhibition of Cx expression and assembly. Recent results have shown that retrovirus-mediated in vivo gene transfer of connexin 43 in malignancies with low GJIC capacity significantly reduced the tumorigenecity[56]. In further support of an essential role of normal GJIC in the prevention of cancer, it has been shown that Cx32 deficient mice have a very high incidence of spontaneous liver tumors and an increase susceptibility to develop chemically-induced liver tumors[57]. Furthermore, the tumor promoting action of Phenobarbital requires functional Cx32 for tumor progression[58]. This suggest that uncoupling of GJIC is important for the oncogenic actions of phenobarbital[58].

Carcinogenesis is characterized by the progressive impairment of growth control mechanisms in which growth factors, oncogenes and tumor suppressor genes are involved. Since the alteration of GJIC might result in the alteration of growth control, the effect of growth factors and oncogenes on GJIC might be crucial for tumorigenesis. Several oncogens have been shown to mediate a down regulation of GJIC[59]. It is shown that $pp60^{v\text{-}src}$ mediate Cx43 gap junction closure via a ball and chain mechanism which involves a C-terminal serine residue phoshorylation by the MAP kinase[59]. Interestingly, in some cases oncogene transfected cells could communicate with each other, but lack the heterologous communication with the adjacent normal cells.

Permeability of gap junctions in tumor cells using the dye-transfer assay was lower than GJIC in surrounding liver tissue. Interestingly, many tumors are encapsulated in an extracellular matrix-like structure and physically separated from the normal tissue.

Neoplastic transformation in the normal human tissues occurs as a result of an accumulation of genetic alterations. However, a general theme in carcinogenesis and tumorigenesis is the down regulation of the GJIC. The various connexins are expressed in a tissue specific manner. Cx43, Cx26, Cx32 has been detected in normal breast tissue. A panel of human breast cancers was analysed for the expression level of Cx43. Cx43 gap junctions were not observed in ductal carcinomas in situ, infiltrating ductal carcinomas, and infiltrating lobular carcinomas, and they seem to be independent of estrogen, progesterone, and erbB2 receptor status. In contrast, human breast cancer cell lines and rodent mammary carcinoma tissues showed a down regulation of Cx43 and It turned out to be at the mRNA level, suggesting a transcriptional mechanism for the decrease of Cx43 protein in breast cancer[60]. Another example on the connection between cancer and GJIC is hepatocellular carcinoma were the connexin 32 knock out have shown to be prone for this specific cancer type[57]. Studies with oval cells have indicated that they can differentiate into hepatocytes and that neoplastic derivatives of oval cells can produce both hepatocellular and biliary neoplasms. The specific connexin expressed by the differentiating oval cell determines whether it communicates with hepatocytes or biliary epithelial cells. This communication may be necessary for the further differentiation and regulated growth of the differentiating oval cells and impairment of GJIC may contribute to the formation of hepatocellular and cholangiocellular neoplasms. Thus, GJIC may be the key factor in the differentiation of oval cells and blocked GJIC may promote their neoplastic transformation. Furthermore, in vitro analysis of tumor invation in rat lung endothelial cells treated with malotilate showed that malotilate promoted the development of cell-to cell adhesion by gap junctions which resulted in inhibition of invation of tumor cells[61]. Taken together, these findings strongly support the hypothesis that alteration of GJIC is a critical event in carcinogenesis and that substances of this invention which increase GJIC might be beneficial in cancer therapy. Therefore, it is a further purpose of the invention to provide novel compounds that increase GJIC. We suggest that the peptide compounds of formulae I, XII, XIII, XIIIa, XIV, XV and XVI and formulae 2-12 herein may be particularly advantageous as medicaments for the treatment of cancer due to their low effective concentration and consequently low toxicity.

Experimental Example 9

The Effect of Compound 2 on Decrease in Gap Junctional Communication Induced by DDT in Human Osteoblastic Cells Protocol and Results The compound 1,1-bis(p-chlorophenyl)-2,2,2-trichlorethane, also known as the insecticide DDT, is an inhibitor of gap junctional communication, and has tumor promoting abilities. It inhibits cell-to-cell communication by reducing the gap junction number and size, as well as decreased cellular levels of phosphorylated (active) forms of the gap junction protein Cx43 and these actions are considered pivotal for the compounds oncogenic properties[62-64]. Thus, compounds with the capability of preventing tumor promoter-induced decrease of GJIC may be potential candidates for use in protection against tumor promotion and cancer treatment[65]. To examine if the substances of this invention prevents the tumor promoter-induced decrease in GJIC, we examined the effects of Compound 2 on DDT-induced uncoupling in human osteoblast cells.

Methods

Cell Culture

Human osteoblast cells: Cells were isolated from human bone marrow obtained by puncture of the posterior iliac spine of healthy volunteers (aged 20-36): 10-15 ml marrow material was collected in 15 ml PBS+Ca, Mg (Life Technologies, Cat. No. 14040) with 100 U/ml Heparin (Sigma, Cat. No. H-3149). The mononuclear fraction of the marrow was isolated on a Lymphoprep gradient (Nycomed Pharma, Cat. No. 1001967), by centrifugation at 2200 rpm for 30 min. After harvesting, the mononuclear fraction was washed once with culture medium and centrifuged at 1800 rpm for 10 min. Subsequently cells were counted and plated in culture medium at $8 \times 10^6$ cells/100 mm dish. hOB medium (all reagents obtained from Life Technologies): MEM w/o Phenol Red w/Glutamax (Cat. No. 041-93013) supplemented with 10% heat inactivated fetal calf serum (Cat. No. 10106) and 0.1% Penicillin/Streptomycin (Cat. No. 15140). Medium was changed the following day and the cells were cultured at 37° C. in 5% $CO_2$ with medium change every 7 days. After 3-4 weeks of culture the cells had reached 70% confluence. The medium was then supplemented with 100 nM Dexamethasone (Sigma, Cat. No. D-4902) for 7 days. Cells were then plated for video imaging experiments: a 25 mm #1 glass coverslip was placed in a 35 mm dish (or each well of a 6-well multidish), cells were plated at $2.5 \times 10^5$ cells/coverslip and cultured for 2-3 days before use.

Microinjection

Cells were cultured on coverslips, and were affixed to a PDMI-2 culture chamber (Medical Systems Corp.), maintained at 37° C. with superfused $CO_2$, on a Zeiss Axiovert microscope. Microinjections were performed using the Eppendorf 5171 micromanipulator and the Eppendorf Transjector 5346 system. A micropipette was loaded with a 10 mM Lucifer Yellow solution (Sigma, Cat. No. L-0259). A cell in the monolayer was carefully injected with LY for 30 seconds, the micropipette was removed from the cell and after 30 seconds the number of cells that showed dye transfer were counted. The excitation light (430 nm) was provided by a monochromator (T.I.L.L. Photonics GmbH). Images were acquired with an intensified CCD camera (Dage MTI) and digitized with a Matrox MVP image processing board, using the MetaMorph imaging software (Universal Imaging)

Results

In order to assess the ability of gap junction modifiers to prevent tumor promotion, we wanted to test whether gap junction modifiers could reverse the decrease in gap junctional communication, induced by a well known tumor promoting agent, DDT. Therefore, monolayers of human osteoblastic cells on glass coverslips were incubated at 37° C. in a humidified atmosphere containing 5% $CO_2$. DDT was added to the medium in a final concentration of 13 μM, and was left on for 60 minutes.

To assess the effect of Compound 2 on direct cellular coupling after DDT treatment, microinjection experiments were performed according to the method described above. The dye Lucifer Yellow (LY) was injected into one single human osteoblast in a monolayer. After 30 seconds, the number of cells containing dye was assessed. Under control conditions (no DDT treatment), the dye spread to a median of 14.5 cells (n=12). The same experiment was performed with the DDT-exposed cells. These cells showed a decreased cellular coupling with a median of 7 (n=13). Compound 2 was added to the bathing solution in a final concentration of $10^{-8}$ mol/l, and after 10 minutes, another microinjection was performed. Compound 2 produce an increase in cell-to-cell dye transfer in all preparations with a median of 8.3 cells (FIG. 15). This increase is highly significant with p<0.01, using the Wilcoxon non-parametric statistical test. Thus, gap junction openers are capable of reversing the decreased intercellular coupling related to tumor promotion, which suggest that the substances of this invention may be useful in the chemoprevention and/or treatment of cancer. The compounds of the present invention are useful for the preparation of medicaments for chemoprevention and/or treatment of cancer. The compounds of the present invention may also be used in a combination therapy with other anti-cancer agents. Thus, it is a purpose of the present invention to provide compounds for the preparation of medicaments useful in prevention and/or treatment of cancer. This purpose is achieved with the present peptide compounds, such as the compounds of formulae I, XII, XIII, XIIIa, XIV, and XV and formulae 2-12 herein, more specifically the compounds of Synthesis Examples 1-47 herein;

Effects of Gap Junction Openers in Wound Healing

A wound is a discontinuation of the normal anatomy involving the skin and can be a surgical or traumatic wound, or it can be secondary to several diseases such as diabetes, arterosclerosis, malnutrition etc. Normal wound healing is a systemic process, which occur stepwise and include hemostasis and inflammation. Remodelling follows these processes, which might last for years and is responsible for formation of scar tissue. The hemostasis with fibrin provides a surface beneath which migrations and movements of the wound edge occur. Epithelialization, fibroplasia and capillary proliferation into the healing wound begins immediately. The angiogenic capillary sprouts invade the fibrin wound clot and within few days organise into a microvascular net throughout the granulation tissue also consistent of leukocytes and phagocytic mononuclear cells. A very dynamic interaction takes place between the various tissue components involved in the wound healing process. The angiogenetic process is essential for a successful wound healing. Intercellular communication, gap junctions are essential for creation the synsythium of fibroblasts and proliferation of the capillary network. Normal distribution of connexin 43 is necessary for this growth of the different tissue component.

Several local factors often seen during pathological conditions as oedema, ischemia, low oxygen tension and infection may delay the wound healing process. Wound healing involves the interactions of many cell types, and intercellular communication mediated by gap junctions is considered to play an important role in the coordination of cellular metabolism during the growth and development of tissues and organs.[66-68].

We suggest that substances of this invention that increase GJIC may be used for the treatment of wounds, and in particular, to accelerate wound healing. Considering that experiments on cardiac and bone tissue suggest that these substances have an enhanced efficacy during metabolic stress (e.g., hypoglycemia, hypoxia, ischemia), it may be inferred that these substances may be particularly useful is the treatment of ischemic ulcers. Thus, it is a purpose of the present invention to provide compounds for the preparation of medicaments useful in treatment of wounds and in particular ischemic ulcers. This purpose is achieved with the present peptide compounds, such as the compounds of formulae I, XII, XIII, XIIIa, XIV, and XV and formulae 2-12 herein, more specifically the compounds of Synthesis Examples 1-47 herein.

Effects of Gap Junction Openers in Healing of Gastric and Duodenal Ulcers

Mine et al. have demonstrated that normal human gastric mucosa contains both connexin 32 and connexin 43[69;70]. In contrast, gastric mucosa surrounding a chronic gastric ulcer lesion contains a smaller amount of connexin 32 and connexin 43. In the studies by Mine et al. the relationship between the appearance of connexins and ulcer healing was investigated. When ulcer healing was observed, connexins 32 and 43, which decreased at the active ulcer stage, had returned almost to levels observed in normal gastric mucosa. These data indicate that disappearance of both connexin 32 and connexin 43 is closely related to the stage of chronic gastric ulcer lesions. Moreover, using a rat model of acetic acid-induced chronic gastric ulcer, the same group of investigators demonstrated that the clinical effect of the antiulcer drug cimetidine was closely related to the reappearance of connexin 32[69].

Therefore, the substances of this invention that increase GJIC may promote the healing of gastric and duodenal ulcers. Thus, it is a purpose of the present invention to provide compounds for the preparation of medicaments useful in treatment of gastric and duodenal ulcers. This purpose is achieved with the present peptide compounds, such as the compounds of formulae I, XII, XIII, XIIIa, XIV, and XV and formulae 2-12 herein, more specifically the compounds of Synthesis Examples 1-47 herein.

Role of Gap Junctions in Vascular Biology

Coordination of cellular responses at the endothelial interface between the blood and underlying tissues is mediated by multiple signaling mechanisms, including direct intercellular communication via gap junctions. Among the functions in which endothelial gap-junctional intercellular communication has been implicated are the migratory behavior of endothelial cells after injury, angiogenesis, endothelial growth and senescence, and the coordination of vasomotor responses[71].

The regulation of blood flow in a wide dynamic range requires coordinated responses of resistance and feeding arteries. Such a coordination between vessels can be achieved by the vascular effects of shear stress exerted by the streaming blood or by conduction of vasomotor signals along cells of the vascular wall. Indeed, local application of certain vasoactive compounds, such as acetylcholine (ACh) or norepinephrine (NE) induced not only local dilation or constriction but also vasomotor responses several millimeters upstream and downstream.[71]. Vasomotor responses can also be conducted from capillaries to arterioles and may contribute to the matching of tissue demands and blood supply. This has been demonstrated in the following way: When single muscle fibers were stimulated to contract, arterioles upstream of capillaries supplying these fibers were observed to dilate[72].

The high conduction velocity is consistent with electrotonic transmission of a signal along the vascular wall. In fact, locally induced hyperpolarizations and depolarizations have been demonstrated to be conducted several millimeters upstream in endothelial and vascular smooth muscle cells. The conduction of the electrical signal requires coupling of vascular cells by gap junctions that provide conduits of low electrical resistance between the cells. In vascular tissue, at least three different connexin (Cx) proteins (Cx37, Cx40, and Cx43) are expressed that form gap junctions. Cx40 seems to be the predominant connexin isoform in aortic endothelial cells, whereas in smooth muscle, Cx43 expression is abundant.

Studies in Cx40 deficient mice (Cx40−/−) have demonstrated spreading of the vasodilation induced by local application of acetylcholine or bradykinin is severely attenuated in Cx40$^{-/-}$ animals compared to normal wildtype (Cx+/+) animals[73]. Moreover, arterial blood pressure is significantly elevated in Cx40$^{-/-}$ animals compared to normal wildtype (Cx+/+) mice. These results support a significant role for Cx40 in vascular intercellular communication and they indicate that impaired gap junctional communication in the vascular wall is associated with decreased transmission of endothelium-dependent vasodilator responses, which is turn increases vascular resistance and causes hypertension. Recent in vivo studies suggest that normal pressure oscillations in the kidney are extremely important for the regulation of blood pressure[74]. Thus, impaired vasomotor responses due to poor cell-to-cell coupling may contribute to the development of hypertension in Cx40 deficient animals.

The down-regulation of cx43 mRNA and protein levels in senescent endothelial cells suggests that impaired gap junctional intercellular communication might play a role in the vascular aging process[75].

Based on available information on the role of gap junctions in vascular responses it is likely that a pharmacological compound that increases gap junctional coupling in the vascular wall could facilitate conducted vascular responses and improve blood supply during conditions with increased metabolic demand (e.g., physical exercise, tachycardia), and during ischemia. In addition, such a substance is likely to prevent and/or treat hypertension. It is therefore a further purpose of the invention to provide compounds that increase gap junctional coupling and/or GJIC in the vascular wall and, thus, are useful for the prevention or treatment of hypertension. This purpose is achieved with the present peptide compounds, such as the compounds of formulae I, XII, XIII, XIIIa, XIV, and XV and formulae 2-12 herein, more specifically the compounds of Synthesis Examples 1-47 herein.

Effects of Gap Junction Openers in Nervous Tissue

Eight different connexins are expressed in the CNS (Cx 26, 30, 32, 37, 40, 43, 45, 46). Furthermore, Cx36 seems to be preferentially expressed in neurones. The different connexins allow communication between diverse cell populations or segregate cells into isolated compartments according to their pattern of connexin expression. Compartmental interfaces where heterotypic coupling might have functional relevance are between oligodendrocytes (Cx32, Cx45) and astrocytes (Cx43, Cx45, Cx40, Cx30) or neurons (Cx26, Cx32, Cx43)[76].

It is feasible that a specific sets of connexins provide functional advantage in particular brain compartments; i.e. a higher of lower unitary conductance might be functionally facilitating or limiting in synchronising neural inputs or rapidity of conduction.

In immature neuroblasts and postnatal neurons extensive gap junction mediated intercellular coupling has been documented[76;77]. The postnatal increase of neuronal gap junctions and their cortical organization is suggestive for an essential role of these junctions in morphogenetic events underlying the critical phase of corticogenesis. The involvement of gap junction in neuronal trafficking is strengthened by the fact that neurotransmitters are able to modify gap junctional coupling.

Therefore, we suggest that the substances of this invention, which are known to increase GJIC may accelerate repair after nerve injury or during grafting of immature cells (progenitor cells) into brain tissue. Among the technologies that are currently undergoing experimental evaluation for the cellular repair in the central nervous system are grafting with progenitor cells, fetal tissue, and viral vectors to be used for treatment of diseases such as parkinsons disease, huntington's disease, and other neurodegenerative brain diseases.

Axon injury rapidly activates microglial and astroglial cells close to the axotomized neurons. Following motor axon injury, astrocytes upregulate within hour(s) the gap junction protein connexin-43, and within one day glial fibrillary acidic protein (GFAP). Concomitantly, microglial cells proliferate and migrate towards the axotomized neuron perikarya. A hypothetical scheme for glial cell activation following axon injury implies that injured neurons initially interact with adjacent astrocytes through GJIC. Subsequently, neighbouring resting microglia cells are activated. These glial reactions are amplified by paracrine and autocrine mechanisms, in which cytokines appear to be important mediators. The specific functional properties of the activated glial cells will determine their influence on neuronal survival, axon regeneration, and synaptic plasticity. The control of the induction and progression of these responses are therefore likely to be critical for the outcome of, for example, neurotrauma, brain ischemia and chronic neurodegenerative diseases[78].

Gap junctions are believed to provide the molecular link for co-ordinated long-range signalling among individual members of the glial compartment. Likewise, astrocytes are ideally suited for metabolic support of neurones since they are functionally polarized with one extremity touching the vascular bed and the other pole approximates neuronal parenchyma[76]. Thus, malfunctioning of such supportive mechanisms may be instrumental for the malfunctioning of integrated neuronal pathways and thereby the offspring of diseases in the central nervous system. Therefore, we suggest that the substances of this invention, which have been shown to increase GJIC may prevent ischemic damage in the brain by increasing the metabolic support between glia cells and neurons. Furthermore, the substances of the invention may be of great significance in patients with organic psychoses which may present with signs such as depression, anxiety, learning and memory deficit, fobias, and hallucinations. Thus, it is a purpose of the present invention to provide compounds for the preparation of medicaments useful in preventing ischemic damage in the brain and for the treatment of organic psychoses including depression, anxiety, learning and memory deficit, fobias, and hallucinations. This purpose is achieved with the peptide compounds of the invention when these are selected or formulated so as to be available to the central nervous system.

Effects of Gap Junction Openers on Cataract

The vertebrate eye lens is a solid cyst of cells, which grows throughout life by addition of new cells at the surface. The older cells, buried by the newer generations, differentiate into long, prismatic fibers, losing their cellular organelles and filling their cytoplasms with high concentrations of soluble proteins, the crystallins. The long-lived lens fibers are interconnected by gap junctions, both with themselves and with an anterior layer of simple cuboidal epithelial cells at the lens surface. This network of gap junctions joins the lens cells into a syncytium with respect to small molecules, permitting metabolic co-operation: intercellular diffusion of ions, metabolites, and water. In contact with nutrients at the lens surface, the epithelial cells retain their cellular organelles, and are able to provide the metabolic energy to maintain correct ion and metabolite concentrations within the lens fiber cytoplasms, such that the crystallins remain in solution and do not aggregate (cataract). Three kinds of connexins are present in the lens: Cx43, Cx46 and Cx50 and mutations in each of these gap junction proteins have been linked to cataract[79-81]. These findings demonstrate that GJIC is essential for normal metabolism and function of the lens. Therefore, we suggest that substances of this invention, which are known to increase GJIC may be used in the prevention and/or treatment of cataract. Thus, it is a purpose of the present invention to provide compounds for the preparation of medicaments useful in preyention and/or treatment of cataract. This purpose is achieved with the present peptide compounds, such as the compounds of formulae I, XII, XIII, XIIIa, XIV, and XV and formulae 2-12 herein, more specifically the compounds of Synthesis Examples 1-47 herein.

Effects of Gap Junction Openers in Ear Diseases

Many different mutations of Cx32 have been found in the hereditary peripheral neuropathy-deafness X-linked Charcot-Marie-Tooth syndrome and several mutations of Cx26 and Cx31 have been detected in deafness[80]. Thus, we suggest that substances of this invention, which are known to increase GJIC may be used in the prevention and/or treatment of certain kinds of deafness that are associated with impaired GJIC in the ear. Thus, it is a purpose of the present invention to provide compounds for the preparation of medicaments useful in prevention and/or treatment of deafness associated with impaired GJIC. This purpose is achieved with the present peptide compounds, such as the compounds of formulae I, XII, XIII, XIIIa, XIV, and XV and formulae 2-12 herein, more specifically the compounds of Synthesis Examples 1-47 herein.

Role of Gap Junction Openers in the Intestines

Both Cx43 and Cx45 are expressed in the wall of the small intestine[82]. It is believed that Cx45-expressing cells along the deep muscular plexus of the small intestine are likely to act as a constituent of a pacemaker system, which may include a conductive system, by forming a cellular network operating via specific types of gap junctions. In the intestine and in the colon, the interstitial cells of Cajal (ICC) are pacemaker cells located between intestinal smooth muscles; they generate spontaneous slow waves of the smooth muscle layers and mediate neurotransmission. The three-dimensional cellular network of ICC is connected by Cx43 gap junctions both between ICC and between ICC and smooth muscle cells[83]. In patients with Hirschsprung's disease, the lack of expression of Cx43 in the aganglionic bowel suggests that the impaired intercellular communication between ICCs and smooth muscle cells may partly be responsible for the motility dysfunction in this disorder[83]. Patients with Chagas's disease (due to an infection with the protozoa *Trypanosoma cruzii*) exert marked reduction of Cx expression which is considered responsible for both the cardiomyopathy as well as the severely dilated megacolon seen in these patients[7]. Thus, normal gap junction communication between ICC and between ICC and smooth muscle cells is considered essential for normal motility in the small intestine and in the colon. It is therefore a further purpose of the invention to provide a substance that increases gap junction conductance in the intestine and therefore may be useful in the treatment of gastrointestinal motility disorders.

Reproductive Organs and Gap Junctions

Ovaries

Gap junctions between granulosa cells, and between the oocyte and the surrounding granulosa cells play an important role during ovarian follicle development. At birth, the ovary contains primordial follicles consisting of meiotically arrested oocytes surrounded by a single layer of supporting (granulosa) cells. Periodically, subsets of primordial follicles undergo further development during which the oocyte increases in size and the granulosa cells proliferate, stratify and develop a fluid-filled antrum. After ovulation, oocytes resume meiosis and granulosa cells retained in the follicle differentiate into steroidogenic cells, forming the corpus luteum.

Gap junctions directly connect adjacent cells allowing the diffusional movement of ions, metabolites, and other potential signalling molecules of importance for the regulation of the ovarian cycle and female fertility. In support for an essential role of gap junctions for normal ovary function, it has been demonstrated that Cx37-deficient mice lack mature (Graafian) follicles, fail to ovulate and develop numerous inappropriate corpora lutea. In addition, oocyte development arrests before meiotic competence is achieved. Thus, cell-cell signalling through intercellular channels critically regulates the highly coordinated set of cellular interactions required for successful oogenesis and ovulation[84].

Follicle-stimulating hormone (FSH) is the major regulator of growth and development of the ovarian follicle. Along its many actions on follicular maturation, FSH improves cell-to-cell coupling between the granulosa cells and it enhances Cx43 gene expression, and possibly, formation of new gap junctions.[85]. Conversely, luteinizing hormone (LH) interrupts cell-to-cell communication within the ovarian follicle, leading to a decrease in intra-oocyte concentrations of cAMP followed by resumption of meiosis[86].

These data illustrate that the presence of normal gap junction communication through Cx37 and Cx43 are essential for normal follicular growth and ovulation. Thus, it is likely that certain forms of female infertility is due to poor cell-to-cell coupling in the ovaries. Therefore, a substance that increases cell-to-cell coupling may be used for the treatment of female infertility in women with impaired expression and/or regulation of ovarian gap junction function. The compounds of the present invention having the ability to increase GJIC are useful for the treatment of female infertility that is due to poor cell-to-cell coupling in the ovaries.

Uterus

The powerful synchronous contractions of the uterus in labour depend on electrical coupling of myometrial smooth muscle cells by gap junctions. In humans and other mammals, gap junctions are scarce in the myometrium of the non-pregnant uterus, but become abundant at term and/or with the onset of labor. The predominant gap-junctional protein expressed by human myometrial smooth muscle cells is Cx43, but also Cx26, Cx40 and Cx45 have been identified in the human myometrium[87;88].

Due to the great significance of coordinated muscle contractions during labour, it is a further purpose of the invention to provide a substance that increases cell-to-cell coupling in the myometrium which is expected to have a positive influence on the synchronization of muscle contractions and said substance may be used along with oxytocin for the induction and facilitation of labour. Said purpose is achieved with the present peptide compounds, such as the compounds of formulae I, XII, XIII, XIIIa, XIV, and XV and formulae 2-12 herein, more specifically the compounds of Synthesis Examples 1-47 herein, and the invention further relates to the use of the peptide compounds of the invention for the preparation of a medicament for the induction and facilitation of labour.

Male Reproductive Organs

Cx43 is the most abundant connexin in the testis, and interestingly, rat strains with decreased Cx43 expression have impaired spermatogenesis (ebo/ebo, jun-d-/-, Cx43+/- mice),[89]. Moreover, early work suggested that hypo- or aspermic patients have decreased gap junctions in the testes [90]. These data support the suggestion that decreased cell-to-cell coupling in the testes may lead to male infertility, and it is therefore a further purpose of the invention to provide a substance that increases cell-to-cell coupling and, thus, may be a useful therapeutic in the treatment of male infertility associated with impaired cell-to-cell coupling.

Role of Gap Junctions in the Pancreas

Gap junction channels made of Cx43 functionally couples the glucose-sensitive cells of pancreatic islets and of a rat insulinoma cell line[91]. In contrast, cells of several cell lines secreting insulin abnormally do not express Cx43, have few gap junctions, and are poorly coupled. After correction of these defects by stable transfection of Cx43 cDNA, cells expressing modest levels of Cx43 and coupling, as observed in native beta-cells, show an expression of the insulin gene and an insulin content that is markedly elevated, compared with those observed in both wild-type (uncoupled) cells and in transfected cells overexpressing Cx43. These findings indicate that adequate coupling of Cx43 are required for proper insulin production and storage[91] Moreover, in vivo stimulation of insulin release by glibenclamide is associated with increased expression of Cx43 and increased cell-to-cell coupling between neighbouring β-cells within the pancreatic islet[92].

These observations indicate an important role of gap junction coupling between pancreatic islet β-cells for the production and release of insulin. Thus, a still further purpose of the present invention is to provide a substance that increases the electrical conductance of gap junctions and, thus, improves glucose tolerance in subjects with non-insulin dependent diabetes mellitus. Said purpose is achieved with the peptide compounds of the invention, such as the compounds of formulae I, XII, XIII, XIIIa, XIV, and XV and formulae 2-12 herein, more specifically the compounds of Synthesis Examples 1-47 herein.

Effects of Gap Junction Openers (Antiarrhythmic Peptides) in Thrombosis

An antithrombotic activity of two peptides closely related to substances of the present invention have previously been shown to have antithrombotic activity. Thus, Dikshit et al.[15] found that the peptides (SEQ ID NO: 295) Gly-Pro-Prp-Gly-Ala-Gly and (SEQ ID NO: 296) Gly-Pro-Gly-Gly-Ala-Gly prevented the development of a pulmonary embolism in mice given an i.v. dose of collagen and adrenaline. U.S. Pat. No. 4,775,743 discloses HP5, a peptide derivative of AAP having the sequence (SEQ ID NO: 297) N-3-(4-hydroxyphenyl)propionyl-Pro-4Hyp-Gly-Ala-Gly-OH and being active against platelet agglutination. The compounds of the present invention have a striking similarity and it is likely that they may show similar effects on thrombosis. Thus, the substances of this invention may be used in the prevention of thrombosis.

Compositions

The invention also concerns a composition comprising a pharmacologically active antiarrhythmic peptide as defined herein in combination with a pharmaceutically acceptable carrier and/or diluent. Such compositions may be in a form adapted to oral, subcutaneous, parenteral (intravenous, intraperitoneal), intramuscular, rectal, epidural, intratracheal, intranasal, dermal, vaginal, buccal, ocularly, direct brain or pulmonary administration, preferably in a form adapted to subcutaneous, intravenous or oral administration, and such compositions may be prepared in a manner well-known to the person skilled in the art, e.g., as generally described in "Remington's Pharmaceutical Sciences", 17. Ed. Alfonso R. Gennaro (Ed.), Mark Publishing Company, Easton, Pa., U.S.A., 1985 and more recent editions and in the monographs in the "Drugs and the Pharmaceutical Sciences", series, Marcel Dekker. The compositions may appear in conventional forms, for example, solutions and suspensions for injection including i.v. infusion concentrates, capsules and tablets, preferably in the form of enteric formulations, e.g. as disclosed in U.S. Pat. No. 5,350,741, for oral administration.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene and water.

Similarly, the carrier or diluent may include any sustained release material known in the art, such as glyceryl monostearate or glyceryl distearate, alone or mixed with a wax.

If a solid carrier issued for oral administration, the preparation may be tabletted, placed in a hard gelatin capsule in powder or pellet form or it can be in the form of a troche or lozenge. The amount of solid carrier will vary widely but will usually be from about 25 mg to about 1 g.

A typical tablet which may be prepared by conventional tabletting techniques may contain:
Core: active compound (as free compound or salt thereof) 100 mg; colloidal silicon dioxide (Aerosil) 1.5 mg; cellulose, microcryst. (Avicel) 70 mg; modified cellulose gum (Ac-Di-Sol) 7.5 mg; magnesium stearate.
Coating: HPMC approx. 9 mg; *Mywacett 9-40T approx. 0.9 mg; *acylated monoglyceride used as plasticizer for film coating.

If a liquid carrier is used, the preparation may be in the form of a syrup, emulsion, soft gelatin capsule or sterile injectable liquid such as an aqueous or non-aqueous liquid suspension or solution.

The composition may also be in a form suited for local or systemic injection or infusion and may, as such, be formulated with sterile water or an isotonic saline or glucose solution. The compositions may be sterilized by conventional sterilization techniques which are well known in the art. The resulting aqueous solutions may be packaged for use or filtered under aseptic conditions and lyophilized, the lyophilized preparation being combined with the sterile aqueous solution prior to administration. The composition may contain pharmaceutically acceptable auxiliary substances as required to approximate physiological conditions, such as buffering agents, tonicity adjusting agents and the like, for instance sodium acetate, sodium lactate, sodium chloride, potassium chloride, calcium chloride, etc.

Formulation of Peptide for Intravenous Injection

Multi-dose formulations may be prepared as a solution of a compound of the invention in sterile, isotonic saline, stored in capped vials, and if necessary a preservative is added (e.g. benzoates). Fixed dose formulations may be prepared as a solution of the compound in sterile, isotonic saline, stored in glass ampoules, and if necessary filled with an inert gas. Each dose of the compound is stored dry in ampoules or capped vials, if necessary filled with inert gas. The multi-dose formulation demands the highest degree of stability of the compound. When the stability of the compound is low fixed dose formulations can be used. The peptide may also be formulated as an i.v. infusion concentrate.

For nasal administration, the preparation may contain a compound of the present invention dissolved or suspended in a liquid carrier, in particular, an aqueous carrier, for aerosol application. The carrier may contain additives such as solubilizing agents, e.g., propylene glycol, surfactants such as bile acid salts or polyoxyethylene higher alcohol ethers, absorption enhancers such as lecithin (phosphatidylcholine) or cyclodextrin, or preservatives such as parabines.

Moreover, the small size of the peptide compounds of the invention may be an advantage for oral and nasal administration, since the relatively fast absorption via mucosal membranes compared to larger peptides minimises enzymatic degradation, especially in the duodenum and the ileum.

Preparation of Enteric Tablets Containing Compound 2

400 mg L-tartaric acid and 40 mg polyethylene glycol-hydrogenated castor oil is dissolved in 5 ml methanol. The solution is placed in a mortar previously warmed to 30° C. To the solution is added 1.5 mg of Compound 2. Immediately after the addition of Compound 2 the mixture is stirred with a pestle under a hot air current of 40° C. and then placed in a dessicator under vacuum overnight to remove the solvent. The resulting solid mass is pulverised with the pestle and kneaded with 30 mg of sodium bicarbonate and a small amount of 70% ethanol. the mixture is then divided and shaped into tablets and dried. The dried tablets are given a coating of hydroxypropylmethylcellulose phthalat to obtain an enteric tablet.

The invention also concerns a pharmacologically active antiarrhythmic peptide or peptide derivative or a functional analogue thereof as disclosed herein for use in therapy, and the use thereof as defined herein for the manufacture of a pharmaceutical composition for use in therapy, e.g., in the treatment of arrhythmias and thrombotic complication during cardiovascular disorders, such as acute ischemic heart disease (e.g., stable angina pectoris, unstable angina pectoris, acute myocardial infaction), congestive heart failure (e.g., systolic, diastolic, high-output, low-output, right or left sided heart failure), congenital heart diseases, cor pulmonale, cardiomyopathies, myocarditides, hypertensive heart disease, and during coronary revascularization.

In specific embodiments, an antiarrhythmic peptide according to the present invention may be used to treat and/or prevent bradyarrhythmias (e.g., due to disease in sinus node, AV node, bundle of His, right or left bundle branch), and tachyarrhythmias associated with reentry (e.g., atrial premature complexes, AV junctional complexes, ventricular premature complexes, atrial fibrillation, atrial flutter, paroxymal supraventricular tachycardia, sinus node reentrant tachycardia, AV nodal reentrant tachycardia, and non-sustained ventricular tachycardia) either alone or in combination with other antiarrhythmic compounds, such as class I agents (e.g., lidocaine), class II agents (e.g., metoprolol or propranolol), class III agents (e.g., amiodarone or sotalol) or class IV agents (e.g., verapamil).

In specific embodiments, an antiarrhythmic peptide according to the present invention may be used to prevent thrombotic events in patients with diseases in the vessel wall (e.g., atherosclerosis), increased platelet production (universal polycytemia), and/or decreased flow (heart disease, vascular disease) either alone or in combination with either alone or in combination with GP IIb/IIIa inhibitors (e.g., c7E3 Fab; abciximab), cyclooxygenaseinhibitors (e.g., aspirin), thromboxane A2 antagonists, coumadine derivatives (e.g., warfarin), or the synthetic peptide, integrilin.

In specific embodiments, an antiarrhythmic peptide according to the present invention may, due to the effect on the intercellular gap junction channels, be used to treat and/or prevent bone loss and increase the healing of bone fractures [93]; treat and/or prevent disease in poorly vascularized cartilage and joints[94]; treat and/or prevent cataract[81]; treat and/or prevent vascularization of the cornea in disease states with poor nutrition of the cornea and increase the healing of corneal lesions[95]; treat and/or prevent growth and spreading of cancer cells, such as cancer cells derived from epithelial cell lines[96]; treat and/or prevent hypertension by increasing vasomotion[74]; prevent ejection of implantates, such as cell and organs, in an organism.

Peptide Synthesis

A preferred general procedure is described below. However, more detailed descriptions of solid phase peptide syntheses are found in WO98/11125 hereby incorporated in its entirety.

Apparatus and Synthetic Strategy

Peptides were synthesized batchwise in a polyethylene vessel equipped with a polypropylene filter for filtration using 9-fluorenylmethyloxycarbonyl (Fmoc) as N-α-amino protecting group and suitable common protection groups for side-chain functionalities.

Solvents

Solvent DMF (N,N-dimethylformamide, Riedel de-Häen, Germany) was purified by passing through a column packed with a strong cation exchange resin (Lewatit S 100 MB/H strong acid, Bayer AG Leverkusen, Germany) and analyzed for free amines prior to use by addition of 3,4-dihydro-3-hydroxy-4-oxo-1,2,3-benzotriazine (Dhbt-OH) giving rise to a yellow color (Dhbt-O$^-$ anion) if free amines are present. Solvent DCM (dichloromethane, analytical grade, Riedel de-Häen, Germany) was used directly without purification. Acetonitril (HPLC-grade, Lab-Scan, Dublin Ireland) was used directly without purification.

Amino Acids

Fmoc-protected amino acids were purchased from Advanced ChemTech (ACT) in suitabel side-chain protected forms. Otherwise protected amino acids (Fmoc-Glu(OH)—OAllyl; Fmoc-Asp(OH)—OAllyl from NovaBiochem (Switzerland), Fmoc-4-Hyp(OtBu)-OH; from Bachem (Switzerland).

Coupling Reagents

Coupling reagent diisopropylcarbodiimide (DIC) was purchased from (Riedel de-Häen, Germany), PyBop from Advanced ChemTech.

Linkers (4-hydroxymethylphenoxy)acetic acid (HMPA), was purchased from Novabiochem, Switzerland; and was coupled to the resin as a preformed 1-hydroxybenzotriazole (HOBt) ester generated by means of DIC.

Solid Supports

Peptides synthesized according to the Fmoc-strategy on TentaGel S resins 0.22-0.31 mmol/g (TentaGel-S—NH$_2$; TentaGel S-Ram, TentaGel S RAM-Lys(Boc)Fmoc; Rapp polymere, Germany);

Catalysts and Other Reagents

Diisopropylethylamine (DIEA) was purchased from Aldrich, Germany, and ethylenediamine from Fluka, piperidine and pyridine from Riedel-de Häen, Frankfurt, Germany. 4-(N,N-dimethylamino)pyridine (DMAP) was purchased from Fluka, Switzerland and used as a catalyst in coupling reactions involving symmetrical anhydrides. Ethandithiol was purchased from Riedel-de Häen, Frankfurt, Germany. 3,4-dihydro-3-hydroxy-4-oxo-1,2,3-benzotriazine (Dhbt-OH), 1-hydroxybenzotriazole (HOBt) (HOAt) were obtained from Fluka, Switzerland.

Coupling Procedures

The first amino acid was coupled as a symmetrical anhydride in DMF generated from the appropriate N-α-protected amino acid and DIC. The following amino acids were coupled as in situ generated HOBt or HOAt esters made from appropriate N-α-protected amino acids and HOBt or HOAt by means of DIC in DMF. Acylations were checked by the ninhydrin test performed at 80° C. in order to prevent Fmoc deprotection during the test[97].

Deprotection of the N-α-Amino Protecting Group (Fmoc).

Deprotection of the Fmoc group was performed by treatment with 20% piperidine in DMF (1×5 and 1×10 min.), followed by wash with DMF (5×15 ml, 5 min. each) until no yellow color could be detected after addition of Dhbt-OH to the drained DMF.

Deprotection of Allyl

A solution of 3 eq. Pd(PPh$_3$)$_4$ dissolved in 15-20 ml CHCl$_3$, AcOH, NMM (37:2:1) was added to the peptid resin. The treatment was continued for three hours at room temperature accompanied by bubbling a stream of N$_2$ through the mixture.

Coupling of HOBt-Esters 3 eq. N-α-amino protected amino acid was dissolved in DMF together with 3 eq. HOBt and 3 eq. DIC and then added to the resin.

Preformed Symmetrical Anhydride 6 eq. N-α-amino protected amino acid was dissolved in DCM and cooled to 0° C. DIC (3 eq.) was added and the reaction continued for 10 min. The solvent was removed in vacuo and the remanence dissolved in DMF. The solution was immediately added to the resin followed by 0.1 eq. of DMAP.

Cyclization of the Peptide on the Resin 1.5 eq. PyBop was dissolved in DMF together with 1.5 eq. HOBt and 3 eq. NMM was added to the peptide resin. The reaction was continued over night.

Cleavage of Peptide From Resin With Acid

Peptides were cleaved from the resins by treatment with 95% triflouroacetic acid (TFA, Riedel-de Häen, Frankfurt, Germany)-water v/v or with 95% TFA and 5% ethandithiol v/v at r.t. for 2 h. The filtered resins were washed with 95% TFA-water and filtrates and washings evaporated under reduced pressure. The residue was washed with ether and freeze dried from acetic acid-water. The crude freeze dried product was analyzed by high-performance liquid chromatography (HPLC) and identified by electrospray ionisation mass spectrometry (ESMS).

Batchwise Peptide Synthesis on TentaGel Resin (PEG-PS)

TentaGel resin (1 g, 0.22-0.31 mmol/g) was placed in a polyethylene vessel equipped with a polypropylene filter for filtration. The resin was swelled in DMF (15 ml), and treated with 20% piperidine in DMF to secure the presence of non-protonated amino groups on the resin. The resin was drained and washed with DMF until no yellow color could be detected after addition of Dhbt-OH to the drained DMF. HMPA (3 eq.) was coupled as a preformed HOBt-ester as described above and the coupling was continued for 24 h. The resin was drained and washed with DMF (5×5 ml, 5 min each) and the acylation checked by the ninhydrin test. The first amino acid was coupled as a preformed symmetrical anhydride as described above. The following amino acids according to the sequence were coupled as preformed Fmoc-protected HOBt esters (3 eq.) as described above. The couplings were continued for 2 h, unless otherwise specified. The resin was drained and washed with DMF (5×15 ml, 5 min each) in order to remove excess reagent. All acylations were checked by the ninhydrin test performed at 80° C. After completed synthesis the peptide-resin was washed with DMF (3×15 ml, 5 min each), DCM (3×15 ml, 1 min each) and finally diethyl ether (3×15 ml, 1 min each) and dried in vacuo.

HPLC Conditions

Gradient HPLC analysis was done using a Hewlett Packard HP 1100 HPLC system consisting of a HP 1100 Quaternary Pump, a HP 1100 Autosampler a HP 1100 Column Thermostat and HP 1100 Multiple Wavelength Detector. Hewlett Packard Chemstation for LC software (rev. A.06.01) was used for instrument control and data acquisition.

The following columns and HPLC buffer system was used:

Column

Kromasil, Phenomenex 00F-3033-E0, 329889 (new); 5 μm C-18, 100 Å 150×4.6 mm; Batch nr. 5243-10.

Buffer system: A: 0.1% TFA in MQV; B: 0.085% TFA, 10% MQV, 90% MeCN.

Gradient:
1-1.5 min. 25% B
1.5-13.5 min 25-50% B
13.5-14.5 min 50-100,% B
14.5-15.5 min 100% B
15.5-17.5 min 100-25% B
17.5-20 min 25% B Flow 1.5 ml/min Oven temperature 40° C.

UV detection: λ=215 nm

Mass spectra were obtained on a Micro-mass LCT instrument.

The invention is further illustrated by the following specific synthesis examples.

Peptide Synthesis of Individual Peptides

Synthesis Example 1

Peptide Synthesis of (SEQ ID NO; 70) Ac-Tyr-Pro-4Hyp-Gly-Ala-Gly-OH (Compound 1) on TentaGel-S—NH-2; Rapp Polymere, Germany First batch: Dry TentaGel-S—NH$_2$ (0.27 mmol/g, 1 g) was placed in a polyethylene vessel equipped with a polypropylene filter for filtration and treated as described under "batchwise peptide synthesis on TentaGel resin" until finishing the coupling of the N-terminal Tyrosine. All couplings were continued over night. After deprotection of the Fmoc group the N-terminal amino group was acetylated with acetic acid anhydride (1 ml, 10.5 mmol) together with 100 μl pyridine dissolved in 2 ml DMF. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. The crude freeze dried product was analyzed by HPLC and the purity was found to be better than 70% and the identity of the peptide was confirmed by ES-MS (found MH$^+$ 619.24, calculated MH$^+$ 619.26). Yield of crude material 137.7 mg. After purification using preparative HPLC as described above, 58 mg peptide product was collected with a purity better than 95%. Total yield of purified peptide product was 35%.

Second batch: Dry TentaGel-S—NH-2 (0.27 mmol/g, 1 g) was placed in a polyethylene vessel equipped with a polypropylene filter for filtration and treated as described under "batchwise peptide synthesis on TentaGel resin" until finishing the coupling of the N-terminal Tyrosine. All couplings were continued over night. After deprotection of the Fmoc group the N-terminal amino group was acetylated with acetic acid anhydride (1 ml, 10.5 mmol) together with 100 μl pyridine dissolved in 2 ml DMF. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. The crude freeze dried product was analyzed by HPLC and the purity was found to be better than 70% and the identity of the peptide was confirmed by ES-MS (found $MH^+$ 619.25, calculated $MH^+$ 619.26). Yield of crude material 137.3 mg. After purification using preparative HPLC as described above, 27.9 mg peptide product was collected with a purity better than 91%. Total yield of purified peptide product was 15.5%.

Synth. Ex. 2

Peptide Synthesis of (SEQ ID NO; 298) Ac-D-Tyr-D-Pro-D-4Hyp-Gly-D-Ala-Gly-$NH_2$ (Compound 2) on TentaGel-S-Ram; Rapp Polymere, Germany First batch: Dry TentaGel-S-Ram (0.23 mmol/g, 1 g) was placed in a polyethylene vessel equipped with a polypropylene filter for filtration and treated as described under "batchwise peptide synthesis on TentaGel resin" until finishing the coupling of the N-terminal D-Tyrosine. All couplings were continued over night. After deprotection of the Fmoc group the N-terminal amino group was acetylated with acetic acid anhydride (1 ml, 10.5 mmol) together with 100 µl pyridine dissolved in 2 ml DMF. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above freeze and dried from acetic acid. The yield of crude freeze dried product was 119.7 mg. The identity of the peptide was confirmed by ES-MS (found $MH^+$ 618.25, calculated $MH^+$ 618.28). After purification using preparative HPLC as described above, 42 mg peptide product was collected with a purity better than 95%. Total yield of purified peptide product was 30%.

Second batch: Dry TentaGel-S-Ram (0.23 mmol/g, 1 g) was placed in a polyethylene vessel equipped with a polypropylene filter for filtration and treated as described under "batchwise peptide synthesis on TentaGel resin" until finishing the coupling of the N-terminal D-Tyrosine. All couplings were continued over night. After deprotection of the Fmoc group the N-terminal amino group was acetylated with acetic acid anhydride (1 ml, 10.5 mmol) together with 100 µl pyridine dissolved in 2 ml DMF. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above freeze and dried from acetic acid. The yield of crude freeze dried product was 119.7 mg. The identity of the peptide was confirmed by ES-MS (found $MH^+$ 618.29, calculated $MH^+$ 618.28). After purification using preparative HPLC as described above, 100 mg peptide product was collected with a purity better than 99%. Total yield of purified peptide product was 71%.

Synth. Ex. 3

Peptide Synthesis of (SEQ ID NO: 298) Cyclo(Tyr-Pro-4Hyp-Gly-Ala-Gly-Asn) (Compound 3) on TentaGel-S-Ram; Rapp Polymere, Germany First batch: Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp(OH)—OAll was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid, yield 57 mg crude product. After purification using preparative HPLC as described above, 2.7 mg cyclic peptide product was collected with a purity better than 95%. Total yield of purified peptide product was 1.3%. The identity of the peptide was confirmed by ES-MS (found $MH^+$ 673.32, calculated $MH^+$ 673.28).

Second batch: Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp(OH)—OAll was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid, yield 57 mg crude product. After purification using preparative HPLC as described above, 10 mg cyclic peptide product was collected with a purity better than 99%. Total yield of purified peptide product was 7%. The identity of the peptide was confirmed by ES-MS (found $MH^+$ 673.30, calculated $MH^+$ 673.29).

Synth. Ex. 4

Peptide Synthesis of (SEQ ID NO: 299) Cyclo(Tyr-Pro-4Hyp-Gly-Ala-Asn) (Compound 4) on TentaGel-S-Ram; Rapp Polymere, Germany First batch: Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp(OH)—OAll was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid to yield the crude product. After purification using preparative HPLC as described above, a cyclic peptide product was collected.

Second batch: Dry TentaGel-S-Ram (0.23 mmol/g, 1 g) was placed in a polyethylene vessel equipped with a polypropylene filter for filtration. and treated as described under "batchwise peptide synthesis on TentaGel resin". The first amino acid Fmoc-Asp(OH)—OAll was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid to yield the crude product 58.6 mg.

After purification using preparative HPLC as described above, 5.7 mg cyclic peptide product was collected with a purity better than 98%. Total yield of purified peptide product was 4.4%. The identity of the peptide was confirmed by ES-MS (found MH$^+$ 616.25, calculated MH$^+$ 616.27).

Synth. Ex. 5

Peptide Synthesis of H-Gly-Ala-Gly-D-Hyp-Pro-Tyr-NH$_2$ (Compound 5) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. After purification using preparative HPLC as described above, 46.6 mg peptide product was collected with a purity better than 99%. Total yield of purified peptide product was 28.6%.

The identity of the peptide was confirmed by ES-MS (found MH$^+$ 576.27, calculated MH$^+$ 576.26).

Synth. Ex. 6

Peptide Synthesis of H-Gly-Ala-Gly-D-Pro-Pro-Tyr-NH$_2$ (Compound 6) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. After purification using preparative HPLC as described above, 26 mg peptide product was collected with a purity better than 98%. Total yield of purified peptide product was 16.3%.

The identity of the peptide was confirmed by ES-MS (found MH$^+$ 560.25, calculated MH$^+$ 560.28).

Synth. Ex. 7

Peptide Synthesis of H-Gly-Ala-Gly-D-Pro-Ala-Tyr-NH$_2$ (Compound 7) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. After purification using preparative HPLC as described above, 18.9 mg peptide product was collected with a purity better than 98%. Total yield of purified peptide product was 12.2%.

The identity of the peptide was confirmed by ES-MS (found MH$^+$ 534.25, calculated MH$^+$ 534.26).

Synth. Ex. 8

Peptide Synthesis of H-Gly-Ala-Gly-Gly-D-Pro-Tyr-NH$_2$ (Compound 8) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 130 mg. After purification using preparative HPLC as described above, 70.1 mg peptide product was collected with a purity better than 94%. Total yield of purified peptide product was 48.2%.

The identity of the peptide was confirmed by ES-MS (found MH$^+$ 520.25, calculated MH$^+$ 520.56).

Synth. Ex. 9

Peptide Synthesis of H-Gly-Ala-Gly-D-Hyp-Ala-Tyr-NH$_2$ (Compound 9) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 131 mg. After purification using preparative HPLC as described above, 72.4 mg peptide product was collected with a purity better than 92%. Total yield of purified peptide product was 49%.

The identity of the peptide was confirmed by ES-MS (found MH$^+$ 550.28, calculated MH$^+$ 550.59).

Synth. Ex. 10

Peptide Synthesis of H-Gly-Ala-Gly-D-Hyp-D-Pro-Tyr-NH$_2$ (Compound 10) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each)>DCM (3×15 ml, 1 min each), diethyl ether (3×15 ml, 1 min each) and dried in vacuo. The peptide was cleaved from the resin as described above and freeze dried from acetic acid. Yield of crude material 150.8 mg. After purification using preparative HPLC as described above, 93.1 mg peptide product was collected with a purity better than 99%. Total yield of purified peptide product was 58%.

The identity of the peptide was confirmed by ES-MS (found MH$^+$ 576.63, calculated MH$^+$ 576.63).

Synth. Ex. 11

Peptide Synthesis of (SEQ ID NO; 64) H-Gly-Ala-Gly-NCG-Pro-Tyr-NH$_2$ (Compound 11) on Tenta-Gel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 24.3 mg. After purification using preparative HPLC as described above, 10.2 mg peptide product was collected with a purity better than 91%. Total yield of purified peptide product was 4%.

The identity of the peptide was confirmed by ES-MS (found MH$^+$ 602.23, calculated MH$^+$ 602.32).

Synth. Ex. 12

Peptide Synthesis of (SEQ ID NO; 65) H-Gly-Ala-Gly-T4C-Pro-Tyr-NH$_2$ (Compound 12) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 29.9 mg. After purification using preparative HPLC as described above, 19 mg peptide product was collected with a purity better than 97%. Total yield of purified peptide product was 50%.

The identity of the peptide was confirmed by ES-MS (found MH$^+$ 578.18, calculated MH$^+$ 578.23).

Synth. Ex. 13

Peptide Synthesis of (SEQ ID NO; 66) H-Gly-Ala-Gly-A2C-Pro-Tyr-NH$_2$ (Compound 13) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 27.3 mg. After purification using preparative HPLC as described above, 12.7 mg peptide product was collected with a purity better than 97%. Total yield of purified peptide product was 34%.

The identity of the peptide was confirmed by ES-MS (found MH$^+$ 546.28, calculated MH$^+$ 546.55).

Synth. Ex. 14

Peptide Synthesis of (SEQ ID NO; 67) H-Gly-Ala-Gly-PC-Pro-Tyr-NH$_2$ (Compound 14) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 23.4 mg. After purification using preparative HPLC as described above, 13.5 mg peptide product was collected with a purity better than 97%. Total yield of purified peptide product was 34.6%.

The identity of the peptide was confirmed by ES-MS (found MH$^+$ 574.32, calculated MH$^+$ 574.29).

Synth. Ex. 15

Peptide Synthesis of (SEQ ID NO; 274) Ac-Tyr-Pro-Hyp-Gly-Ala-Gly-NH$_2$ (Compound 15) on Tenta-Gel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Tyrosine. All couplings were continued over night. After deprotection of the Fmoc group the N-terminal amino group was acetylated with acetic acid anhydride (1 ml, 10.5 mmol) together with 100 µl pyridine dissolved in 2 ml DMF. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 89.9 mg. After purification using preparative HPLC as described above, 80.1 mg peptide product was collected with a purity better than 99%. Total yield of purified peptide product was 58.9%.

The identity of the peptide was confirmed by ES-MS (found MH$^+$ 618.30, calculated MH$^+$ 618.28).

Synth. Ex. 16

Peptide Synthesis of (SEQ ID NO; 275) H-Cys(Acm)-Gly-Ala-Gly-Hyp-Pro-Tyr-Cys(Acm)-NH$_2$ (Compound 16) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Cystine(Acm). All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 47.3 mg. After purification using preparative HPLC as described above, 29.1 mg peptide product was collected with a purity better than 97%. Total yield of purified peptide product was 12.9%.

The identity of the peptide was confirmed by ES-MS (found MH$^+$ 924.50, calculated MH$^+$ 924.36).

Synth. Ex. 17

Peptide Synthesis of (SEQ ID NO; 276) H-Cys(Acm)-Gly-Hyp-Pro-Tyr-Cys(Acm)-NH$_2$ (Compound 17) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Cystine(Acm). All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 45.67 mg. After purification using preparative HPLC as described above, 29.15 mg peptide product was collected with a purity better than 94%. Total yield of purified peptide product was 14.9%.

The identity of the peptide was confirmed by ES-MS (found MH$^+$ 796.25, calculated MH$^+$ 796.30).

Synth. Ex. 18

Peptide Synthesis of (SEQ ID NO; 277) H-Cys(Acm)-Tyr-Pro-Hyp-Gly-Ala-Gly-Cys(Acm)-NH$_2$ (Compound 18) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Cystine(Acm). All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. The crude freeze dried product was analyzed by HPLC and purified and characterized in a similar manner as compound 17 Synth. Ex. 19. Peptide synthesis of (SEQ ID NO; 278) H-Cys(Acm)-Tyr-Pro-Hyp-Gly-Cys(Acm)-NH$_2$ (Compound 19) on TentaGel-S-Ram; Rapp polymere, Germany.

Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Cystine(Acm). All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. After purification using preparative HPLC as described above, 2.76 mg peptide product was collected with a purity better than 94%. Total yield of purified peptide product was 17.9%.

The identity of the peptide was confirmed by ES-MS (found MH$^+$ 796.25, calculated MH$^+$ 796.30).

filtration. and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. After purification using preparative HPLC as described above, 47 mg peptide product was collected with a purity better than 94%. Total yield of purified peptide product was 30%.

(SEQ ID; 222) Synth. Ex. 20. Synthesis of H-Cys-Tyr-Pro-Hyp-Gly-Cys-NH$_2$    (Compound 20)

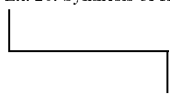

19 mg of the peptide (SEQ ID NO; 222) H-Cys-Tyr-Pro-Hyp-Gly-Cys-NH$_2$ is oxidised by dissolving the peptide in 1.5 ml (5% acetic acid in water and DMSO 4:1 v/v pH ~6). The mixture is placed in the freezer for 6 days.

After purification using preparative HPLC as described above, 91 mg peptide product was collected with a purity better than 97%. Total yield of purified peptide product was 47%. The identity of the peptide was confirmed by ES-MS (found MH$^+$ 652.29, calculated MH$^+$ 652.21

The identity of the peptide was confirmed by ES-MS (found MH$^+$ 576.26, calculated MH$^+$ 576.26).

Synth. Ex. 23

Peptide Synthesis of H-Gly-D-Ala-Gly-D-Hyp-D-Pro-D-Tyr-D-Asn-OH (Compound 23) on TentaGel-S-Ram; Rapp Polymere, Germany Dry TentaGel-S-Ram (0.23 mmol/g, 1 g) was placed in a polyethylene vessel equipped with a polypropylene filter for (SEQ ID NO; 219) Synth. Ex. 21. Synthesis of H-Cys-Gly-Hyp Pro-Tyr-Cys-NH$_2$    (Compound 21)

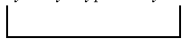

32 mg of the peptide (SEQ ID NO; 219) H-Cys-Gly-4Hyp-Pro-Tyr-Cys-NH$_2$ is oxidised by dissolving the peptide in 1.5 ml (5% acetic acid in water and DMSO 4:1 v/v pH ~6). The mixture is placed in the freezer for 6 days.

After purification using preparative HPLC as described above, 6.13 mg peptide product was collected with a purity better than 99%. Total yield of purified peptide product was 3%.

The identity of the peptide was confirmed by ES-MS (found MH$^+$ 652.23, calculated MH$^+$ 652.21

Synth. Ex. 22

Peptide Synthesis of H-Gly-D-Ala-Gly-D-Hyp-D-Pro-D-Tyr-NH$_2$ (Compound 22) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 93.7 mg. After purification using preparative HPLC as described above, 60.7 mg peptide product was collected with a purity better than 93%. Total yield of purified peptide product was 47.5%.

The identity of the peptide was confirmed by ES-MS (found MH$^+$ 690.32, calculated MH$^+$ 690.30).

Synth. Ex. 24

Synthesis of Ac-D-Tyr(3,5-di-I)-D-Pro-D-Hyp-Gly-D-Ala-Gly-NH$_2$ (Compound 24)

40.6 mg (64 µmol) of the peptide (compound 2) is dissolved in 10 ml 0.1M phosphate buffer pH 6.5 (solution A).

75.6 mg KI (400 µmol) is dissolved in 10 ml phosphate buffer pH 6.5 and 120 Iodobeads (IODO-BEADS, N-chlorobenzensulfonamide, Oxidative capacity 0.55 µmol/bead; PIERCE, 28665ZZ) are added and the solution is left at r.t. for 10 min (solution B).

Solution A and B are combined and gently agitated for 15 min. The Iodinated peptide was isolated and purified using preparative HPLC as described above, 39.5 mg peptide product was collected with a purity better than 90%. The identity of the peptide was confirmed by ES-MS (found MH$^+$ 870.09, calculated MH$^+$ 870.08).

Synth. Ex. 25

Synthesis of Ac-D-Tyr(mono-Iodo)-D-Pro-D-Hyp-Gly-D-Ala-Gly-NH$_2$ (Compound 25)

40.6 mg (64 µmol) of the peptide (compound 2) is dissolved in 10 ml 0.1M phosphate buffer pH 6.5 (solution A).

75.6 mg KI (400 µmol) is dissolved in 10 ml phosphate buffer pH 6.5 and 120 Iodobeads (IODO-BEADS, N-chlorobenzensulfonamide, Oxidative capacity 0.55 µmol/bead; PIERCE, 28665ZZ) are added and the solution is left at r.t. for 10 min (solution B).

Solution A and B are combined and gently agitated for 15 min. The iodinated peptide was isolated and purified using preparative HPLC as described above, 3.3 mg peptide product was collected with a purity better than 90%. The identity of the peptide was confirmed by ES-MS (found MH$^+$ 744.19, calculated MH$^+$ 744.18).

Synth. Ex. 26

Peptide Synthesis of Ac-D-Tyr-D-Pro-D-4Hyp-(1,2$^{13}$C,$^{15}$N-Gly)-D-Ala-(1,2$^{13}$C,$^{15}$N-Gly)-NH$_2$ (Compound 26) on TentaGel-S-Ram; Rapp Polymere, Germany Dry TentaGel-S-Ram (0.23 mmol/g, 1 g) was placed in a polyethylene vessel equipped with a polypropylene filter for filtration and treated as described under "batchwise peptide synthesis on TentaGel resin" until finishing the coupling of the N-terminal D-Tyrosine. All couplings were continued over night. After deprotection of the Fmoc group the N-terminal amino group was acetylated with acetic acid anhydride (1 ml, 10.5 mmol) together with 100 µl pyridine dissolved in 2 ml DMF. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 142.4 mg. After purification using preparative HPLC as described above, 79.7 mg peptide product was collected with a purity better than 99%. Total yield of purified peptide product was 50%.

The identity of the peptide was confirmed by ES-MS (found MH$^+$ 624.25, calculated MH$^+$ 624.26).

Synth. Ex. 27

Peptide Synthesis of (SEQ ID NO; 279) H-Pro-Tyr-Asn-Gly-Ala-Gly-Hyp-NH$_2$ (Compound 27) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Proline. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. After purification using preparative HPLC as described above, 135.7 mg peptide product was collected with a purity better than 98%. Total yield of purified peptide product was 82.7%.

The identity of the peptide was confirmed by ES-MS (found MH$^+$ 690.38, calculated MH$^+$ 690.31).

Synth. Ex. 28

Peptide Synthesis of (SEQ ID NO; 280) H-Hyp-Pro-Tyr-Asn-Gly-Ala-Gly-NH$_2$ (Compound 28) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal 4-hydroxy-Proline. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. After purification using preparative HPLC as described above, 127 mg peptide product was collected with a purity better than 98%. Total yield of purified peptide product was 69.8%.

The identity of the peptide was confirmed by ES-MS (found MH$^+$ 690.25, calculated MH$^+$ 690.31).

Synth. Ex. 29

Peptide Synthesis of H-Sar-Ala-Sar-Hyp-Pro-Tyr-NH$_2$ (Compound 29) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Sarcosine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 150 mg. After purification using preparative HPLC as described above, 85.5 mg peptide product was collected with a purity better than 93%. Total yield of purified peptide product was 57%.

The identity of the peptide was confirmed by ES-MS (found MH$^+$ 604.33, calculated MH$^+$ 604.30).

Synth. Ex. 30

Peptide Synthesis of (SEQ ID NO; 281) H-Gly-Ala-Sar-Hyp-Pro-Tyr-NH$_2$ (Compound 30) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 124 mg. After purification using preparative HPLC as described above, 64.8 mg peptide product was collected with a purity better than 96%. Total yield of purified peptide product was 41.6%.

The identity of the peptide was confirmed by ES-MS (found MH$^+$ 590.19, calculated MH$^+$ 590.29).

Synth. Ex. 31

Peptide Synthesis of (SEQ ID NO; 282) ASAL-Pro-Hyp-Gly-Ala-Gly-NH$_2$ (Compound 31) on Tenta-Gel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Proline. All couplings were continued over night. After deprotection of the Fmoc group the N-terminal amino group was acetylated with Azido salicylic acid using standard coupling procedure as described above. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. After purification using preparative HPLC as described above, 15.9 mg peptide product was collected with a purity better than 94%.

The identity of the peptide was confirmed by ES-MS (found MH$^+$ 575.23, calculated MH$^+$ 575.56).

Synth. Ex. 32

Peptide Synthesis of (SEQ ID NO; 283) ASAL (mono-iodo)-Pro-Hyp-Gly-Ala-Gly-NH$_2$ (Compound 32)

10.3 mg of the peptide (compound 31) is dissolved in 2.5 ml 0.1M phosphate buffer pH 6.5 (solution A).

18.9 mg KI (100 µmol) is dissolved in 2.5 ml phosphate buffer pH 6.5 and 30 Iodobeads (IODO-BEADS, N-chlorobenzensulfonamide, Oxidative capacity 0.55 µmol/bead; PIERCE, 28665ZZ) are added and the solution is left at r.t. for 10 min (solution B). Solution A and B are combined and gently agitated for 1 hours. The Iodinated peptide was isolated and purified using preparative HPLC as described above, 4.4 mg peptide product was collected with a purity better than 99%. The identity of the peptide was confirmed by ES-MS(found MH$^+$ 701.13, calculated MH$^+$ 701.46).

Synth. Ex. 33

Peptide Synthesis of (SEQ ID NO; 281) AB-Tyr-Pro-Hyp-Gly-Ala-Gly-NH$_2$ (Compound 33) on Tenta-Gel-S-Ram; Rapp Polymere, Germany Dry TentaGel-S-Ram (0.23 mmol/g, 1 g) was placed in a polyethylene vessel equipped with a polypropylene filter for filtration and treated as described under "batchwise peptide synthesis on TentaGel resin" until finishing the coupling of the N-terminal Tyrosine. All couplings were continued over night. After deprotection of the Fmoc group the N-terminal amino group was acetylated with Azido Benzoicic acid using standard coupling procedure as described above. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. After purification using preparative HPLC as described above, 20.5 mg peptide product was collected with a purity better than 90%.

The identity of the peptide was confirmed by ES-MS (found MH$^+$ 721.28, calculated MH$^+$ 721.26).

Synth. Ex. 34

Peptide Synthesis of (SEQ ID NO; 285) AB-Tyr(3,5-di-iodo)-Pro-Hyp-Gly-Ala-Gly-NH$_2$ (Compound 34) 10.3 mg of the Peptide (Compound 33) is Dissolved in 2.5 ml 0.1M Phosphate Buffer pH 6.5 (Solution A)

18.9 mg KI (100 µmol) is dissolved in 2.5 ml phosphate buffer pH 6.5 and 30 Iodobeads (IODO-BEADS, N-chlorobenzensulfonamide, Oxidative capacity 0.55 µmol/bead; PIERCE, 28665ZZ) are added and the solution is left at r.t. for 10 min (solution B).

Solution A and B are combined and gently agitated for 1 hours. The Iodinated peptide was isolated and purified using preparative HPLC as described above, 1.2 mg peptide product was collected with a purity better than 90%. The identity of the peptide was confirmed by ES-MS (found MH$^+$ 973.08, calculated MH$^+$ 973.46).

Synth. Ex. 35

Peptide Synthesis (SEQ ID NO; 286) cyclo(-Gly-Ala-Gly-Hyp-Pro-Tyr-Gln-) (Compound 35) on TentaGel-S-Ram; Rapp Polymere, Germany Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Glu (OH)—OAII was connected to the TentaGel-S-Ram resin via the side-chain carboxylic acid, which finally after cleavage will end up amidated (Gln). The procedure described under "batchwise peptide synthesis on TentaGel resin" was followed until finishing the coupling of the N-terminal Glycine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 135.3 mg. After purification using preparative HPLC as described above, 19.1 mg peptide product was collected with a purity better than 98%. Total yield of purified peptide product was 6.6%.

The identity of the peptide was confirmed by ES-MS (found MH$^+$ 687.38, calculated MH$^+$ 687.32).

Synth. Ex. 36

Peptide Synthesis (SEQ ID NO; 287) Cyclo(-Gly-Ala-Gly-Hyp-Pro-Tyr-Asn-) (Compound 36) on TentaGel-S-Ram; Rapp Polymere, Germany Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp (OH)—OAII was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Glycine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 63.4 mg. After purification using preparative HPLC as described above, 13.2 mg peptide product was collected with a purity better than 97%. Total yield of purified peptide product was 6.2%.

The identity of the peptide was confirmed by ES-MS (found MH$^+$ 673.38, calculated MH$^+$ 673.30).

Synth. Ex. 37

Peptide Synthesis (SEQ ID NO; 288) Cyclo(-Gly-Ala-Gly-Pro-Pro-Tyr-Asn-) (Compound 37) on TentaGel-S-Ram; Rapp Polymere, Germany Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp (OH)—OAII was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Glycine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 85.1 mg. After purification using preparative HPLC as described above, 9.8 mg peptide product was collected with a purity better than 98%. Total yield of purified peptide product was 3.5%.

The identity of the peptide was confirmed by ES-MS (found MH$^+$ 657.38, calculated MH$^+$ 657.31).

Synth. Ex. 38

Synthesis of (SEQ ID NO; 291) Cyclo(Tyr(3,5-di-iodo)-Pro-4Hyp-Gly-Ala-Gly-Asn) (Compound 38)

10.8 mg of the peptide (compound 3) is dissolved in 2.5 ml 0.1M phosphate buffer pH 6.5 (solution A).

18.9 mg KI (400 μmol) is dissolved in 2.5 ml phosphate buffer pH 6.5 and 30 Iodobeads (IODO-BEADS, N-chlorobenzensulfonamide, Oxidative capacity 0.55 μmol/bead; PIERCE, 28665ZZ) are added and the solution is left at r.t. for 10 min (solution B).

Solution A and B are combined and gently agitated for 2 hours. The Iodinated peptide was isolated and purified using preparative HPLC as described above, 9.8 mg peptide product was collected with a purity better than 95%. The identity of the peptide was confirmed by ES-MS (found MH$^+$ 925.10, calculated MH$^+$ 925.30).

Synth. Ex. 39

Peptide Synthesis of (SEQ ID NO; 292) H-Gly-Ala-Gly-Asn-Tyr-NH$_2$ (Compound 39) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 124 mg. After purification using preparative HPLC as described above, 26.5 mg peptide product was collected with a purity better than 96%. Total yield of purified peptide product was 20.5%.

The identity of the peptide was confirmed by ES-MS (found MH$^+$ 480.24, calculated MH$^+$ 480.50).

Synth. Ex. 40

Peptide Synthesis of Ac-Gly-Asn-Tyr-NH$_2$ (Compound 40) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Glycine. After deprotection of the Fmoc group the N-terminal amino group was acetylated with acetic acid anhydride (1 ml, 10.5 mmol) together with 100 µl pyridine dissolved in 2 ml DMF. The coupling was continued over night. The acylations were checked by the ninhydrin test performed at 80° C. as earlier described. After acylation of the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 90.4 mg. After purification using preparative HPLC as described above, 63.4 mg peptide product was collected with a purity better than 99%. Total yield of purified peptide product was 65.1%.

The identity of the peptide was confirmed by ES-MS (found MH$^+$ 394.16, calculated MH$^+$ 394.20).

Synth. Ex. 41

Peptide Synthesis of H-Gly-Asn-Tyr-NH$_2$ (Compound 41) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 91.4 mg. After purification using preparative HPLC as described above, 62.1 mg peptide product was collected with a purity better than 95%. Total yield of purified peptide product was 54.5%.

The identity of the peptide was confirmed by ES-MS (found MH$^+$ 352.16, calculated MH$^+$ 352.18).

Synth. Ex. 42

Peptide Synthesis of (SEQ ID NO; 293) Ac-Ala-Gly-Asn-Tyr-NH$_2$ (Compound 42) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Alanine. After deprotection of the Fmoc group the N-terminal amino group was acetylated with acetic acid anhydride (1 ml, 10.5 mmol) together with 100 µl pyridine dissolved in 2 ml DMF. The coupling was continued over night. The acylations were checked by the ninhydrin test performed at 80° C. as earlier described. After acylation of the N-terminal amino group the peptide-resin was washed with DMF (3×15 ml, 1 ml each), DCM (3×15 ml, 1 min each), diethyl ether (3×15 ml, 1 min each) and dried in vacuo.

The peptide was cleaved from the resin as described above and freeze dried from acetic acid. Yield of crude material 105 mg. After purification using preparative HPLC as described above, 52 mg peptide product was collected with a purity better than 98%. Total yield of purified peptide product was 45%.

The identity of the peptide was confirmed by ES-MS (found MH$^+$ 465.22, calculated MH$^+$ 465.30).

Synth. Ex. 43

Peptide Synthesis of (SEQ ID NO; 249) H-Ala-Gly-Asn-Tyr-NH$_2$ (Compound 43) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Alanine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 104.5 mg. After purification using preparative HPLC as described above, 77.8 mg peptide product was collected with a purity better than 96%. Total yield of purified peptide product was 58.8%.

The identity of the peptide was confirmed by ES-MS (found MH$^+$ 423.19, calculated MH$^+$ 423.28).

Synth. Ex. 44

Peptide Synthesis (SEQ ID NO; 180) Cyclo(-Tyr-Ala-Ser-Ala-Gly-Asn-) (Compound 44) on Tenta-Gel-S-Ram; Rapp Polymere, Germany Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp (OH)—OAII was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 60.2 mg. After purification using preparative HPLC as described above, 5.0 mg peptide product was collected with a purity better than 87%. Total yield of purified peptide product was 4.3%.

The identity of the peptide was confirmed by ES-MS (found MH$^+$ 564.25, calculated MH$^+$ 564.57).

Synth. Ex. 45

Peptide Synthesis (SEQ ID NO; 181) Cyclo(-Tyr-Gly-Asn-Tyr-Gly-Asn-) (Compound 45) on Tenta-Gel-S-Ram; Rapp Polymere, Germany Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp (OH)—OAll was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 79.1 mg. After purification using preparative HPLC as described above, 20 mg peptide product was collected with a purity better than 90%. Total yield of purified peptide product was 14.0%.

The identity of the peptide was confirmed by ES-MS (found MH$^+$ 569.25, calculated MH$^+$ 569.67).

Synth. Ex. 46

Peptide Synthesis (SEQ ID NO; 182) Cyclo(-Tyr-Gly-Asn-Tyr-Ala-Gly-Asn-) (Compound 46) on TentaGel-S-Ram; Rapp Polymere, Germany Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp (OH)—OAll was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 58.9 mg. After purification using preparative HPLC as described above, 15.9 mg peptide product was collected with a purity better than 98%. Total yield of purified peptide product was 11%.

The identity of the peptide was confirmed by ES-MS (found MH$^+$ 740.31, calculated MH$^+$ 740.75).

Synth. Ex. 47

Peptide Synthesis (SEQ ID NO; 183) Cyclo(-Tyr-Val-Ser-Gly-Ala-Gly-Asn-) (Compound 47) on TentaGel-S-Ram; Rapp Polymere, Germany Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp (OH)—OAll was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 54.1 mg. After purification using preparative HPLC as described above, 19.6 mg peptide product was collected with a purity better than 95%. Total yield of purified peptide product was 15%.

The identity of the peptide was confirmed by ES-MS (found MH$^+$ 649.10, calculated MH$^+$ 649.68).

Synth. Ex. 48

Peptide Synthesis of (SEQ ID NO; 266) H-Gly-Pro-Hyp-Gly-Ala-Gly-OH (Compound CE-1) on Tenta-Gel-S—NH-2; Rapp Polymere, Germany Dry TentaGel-S—NH-2 (0.27 mmol/g, 1 g) was placed in a polyethylene vessel equipped with a polypropylene filter for filtration and treated as described under "batchwise peptide synthesis on TentaGel resin" until finishing the coupling of the N-terminal Glycine. All couplings were continued over night. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. After purification using preparative HPLC as described above, 16.9 mg peptide product was collected with a purity better than 92%. Total yield of purified peptide product was 10.1%.

The identity of the peptide was confirmed by ES-MS (found MH$^+$ 471.22, calculated MH$^+$ 471.21).

Synth. Ex. 49

Peptide Synthesis of (SEQ ID NO; 267) H-Gly-Ala-Gly-Hyp-Pro-Tyr-NH$_2$ (Compound CE-2) on Tenta-Gel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 159 mg. After purification using preparative HPLC as described above, 101 mg peptide product was collected with a purity better than 98%. Total yield of purified peptide product was 60%.

The identity of the peptide was confirmed by ES-MS (found MH$^+$ 576.26, calculated MH$^+$ 576.26).

Synth. Ex. 50

Peptide Synthesis of (SEQ ID NO; 268) 3-(4-hydroxyphenyl)propionyl-Pro-Hyp-Gly-Ala-Gly-NH2 (Compound CE-3) on TentaGel-S-Ram; Rapp Polymere, Germany Dry TentaGel-S-Ram (0.23 mmol/g, 1 g) was placed in a polyethylene vessel equipped with a polypropylene filter for filtration. and treated as described under "batchwise peptide synthesis on TentaGel resin" until finishing the coupling of the N-terminal Proline. All couplings were continued over night. After deprotection of the Fmoc group the N-terminal amino group was acetylated with 3-(4-hydroxyphenyl)propionic acid using standard coupling procedure as described above. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo. The peptide was cleaved from the resin as described above and freeze dried from acetic acid. Yield of crude material 143 mg. After purification using preparative HPLC as described above, 73.7 mg peptide product was collected with a purity better than 95%. Total yield of purified peptide product was 50%. The identity of the peptide was confirmed by ES-MS (found MH$^+$ 561.30, calculated MH$^+$ 561.24).

REFERENCE LIST

[1.] A. L. Waldo, A. J. Camm, H. deRuyter, P. L. Friedman, D. J. MacNeil, J. F. Pauls, B. Pitt, C. M. Pratt, P. J. Schwartz, E. P. Veltri, Lancet 1996, 348 7-12.
[2.] P. A. Guerrero, R. B. Schuessler, L. M. Davis, E. C. Beyer, C. M. Johnson, K. A. Yamada, J. E. Saffitz, J Clin Invest 1997, 99 1991-1998.
[3.] D. L. Lerner, K. A. Yamada, R. B. Schuessler, J. E. Saffitz, Circulation 2000, 101 547-552.
[4.] A. Hagendorff, B. Schumacher, S. Kirchhoff, B. Luderitz, K. Willecke, Circulation 1999, 99 1508-1515.
[5.] S. Kirchhoff, E. Nelles, A. Hagendorff, O. Kruger, O. Traub, K. Willecke, Curr Biol 1998, 8 299-302.
[6.] A. M. Simon, D. A. Goodenough, D. L. Paul, Curr Biol 1998, 8 295-298.
[7.] A. C. de Carvalho, M. O. Masuda, H. B. Tanowitz, M. Wittner, R. C. Goldenberg, D. C. Spray, J Cardiovasc Electrophysiol 1994, 5 686-698.
[8.] R. R. Kaprielian, M. Gunning, E. Dupont, M. N. Sheppard, S. M. Rothery, R. Underwood, D. J. Pennell, K. Fox, J. Pepper, P. A. Poole-Wilson, N. J. Severs, Circulation 1998, 97 651-660.
[9.] N. S. Peters, C. R. Green, P. A. Poole-Wilson, N. J. Severs, Circulation 1993, 88 864-875.
[10.] J. E. Saffitz, R. B. Schuessler, K. A. Yamada, Cardiovasc Res 1999, 42 309-317.
[11.] S. Aonuma, Y. Kohama, K. Akai, Y. Komiyama, S. Nakajima, M. Wakabayashi, T. Makino, Chem Pharm Bull (Tokyo) 1980, 28 3332-3339.
[12.] S. Aonuma, Y. Kohama, K. Akai, S. Iwasaki, Chem Pharm Bull (Tokyo) 1980, 28 3340-3346.
[13.] S. Aonuma, Y. Kohama, T. Makino, Y. Fujisawa, J Pharmacobiodyn 1982, 5 40-48.
[14.] M. A. Ronsberg, T. K. Saunders, P. S. Chan, P. Cervoni, Med Sci 86 A. D., 14 350-351.
[15.] M. Dikshit, R. Srivastava, B. Kundu, K. B. Mathur, K. Kar, Indian J Exp Biol 1988, 26 874-876.
[16.] Y. Kohama, N. Okimoto, T. Mimura, C. Fukaya, M. Watanabe, K. Yokoyama, Chem Pharm Bull (Tokyo) 1987, 35 3928-3930.
[17.] Y. Kohama, S. Kuwahara, K. Yamamoto, M. Okabe, T. Mimura, C. Fukaya, M. Watanabe, K. Yokoyama, Chem Pharm Bull (Tokyo) 1988, 36 4597-4599.
[18.] S. Dhein, N. Manicone, A. Muller, R. Gerwin, U. Ziskoven, A. Irankhahi, C. Minke, W. Klaus, Naunyn Schmiedebergs Arch Pharmacol 1994, 350 174-184.
[19.] T. Argentieri, E. Cantor, J. R. Wiggins, Experientia 1989, 45 737-738.
[20.] A. Muller, M. Gottwald, T. Tudyka, W. Linke, W. Klaus, S. Dhein, Eur J Pharmacol 1997, 327 65-72.
[21.] R. Grover, S. Dhein, Peptides 1998, 19 1725-1729.
[22.] S. Dhein, T. Tudyka, Drugs 1995, 49 851-855.
[23.] C. S. Kuo, K. Munakata, C. P. Reddy, B. Surawicz, Circulation 1983, 67 1356-1367.
[24.] S. Dhein, K. Krusemann, T. Schaefer, Br J Pharmacol 1999, 128 1375-1384.
[25.] N. S. Peters, J. Coromilas, N. J. Severs, A. L. Wit, Circulation 1997, 95 988-996.
[26.] D. W. Liu, C. Antzelevitch, Circ Res 1995, 76 351-365.
[27.] Kanagaratnam, P., Severs, N. J., and Peters, N. S. The Relationship between Conduction, Activation pattern and Quantity of Immunoreactive Connexin in Chronic Human Atrial Fibrillation. Circulation 102[18], II-485. 2000. Ref Type: Abstract
[28.] J. M. Pastore, D. S. Rosenbaum, Circulation Research 2000, 87 1157-1163.
[29.] R. D. Berger, Circulation Research 2000, 87 1083-1084.
[30.] J. E. Saffitz, K. A. Yamada, Circulation 1998, 97 630-632.
[31.] Gutstein, D. E., Morley, G. E., Tamaddon, Houman S., Vaidya, D., Schneider, M. D., Chen, J., Chien, K. R., Stuhlmann, H., and Fishman, G. I. Genetic Manipulation of Connexin43 Expression in the Heart: Establishing a Role for Gap Junction Remodeling in Arrhythmogenesis and Ventricular Dysfunction. Circulation 102[18], II-15. 2001. Ref Type: Abstract

[32.] A. Muller, T. Schaefer, W. Linke, T. Tudyka, M. Gottwald, W. Klaus, S. Dhein, *Naunyn Schmiedebergs Arch. Pharmacol.* 1997, 356 76-82.

[33.] S. Dhein, R. Grover, A. Müller, M. Lauven, P. Poeppel, T. Schaefer, *Circulation* 1999, 100 I-426.

[34.] Koenig, J. I. Radioligand binding in intact cells. Keen, M. [106], 89-98. 1999. Totowa, N.J., Humana Press Inc. Methods in Molecular Biology. Ref Type: Serial (Book, Monograph)

[35.] K. Wassermann, K. Mølgaard, E. Steiness, *Cancer Chemother. Pharmacol.* 1985, 15 244-252.

[36.] E. Meier, K. Frederiksen, M. Nielsen, H. L. Lembøl, H. Pedersen, J. Hyttel, *Drug Development Research* 1997, 40 1-16.

[37.] J. J. Lynch, R. G. Rahwan, D. T. Witiak, *J Cardiovasc. Pharmacol.* 1981, 3 49-60.

[38.] M. Zabel, S. H. Hohnloser, S. Behrens, R. L. Woosley, M. R. Franz, *J Cardiovasc Electrophysiol* 1997, 8 1239-1245.

[39.] S. Dhein, N. Manicone, A. Muller, R. Gerwin, U. Ziskoven, A. Irankhahi, C. Minke, W. Klaus, *Naunyn Schmiedebergs Arch Pharmacol* 1994, 350 174-184.

[40.] X. D. Huang, G. E. Sandusky, D. P. Zipes, *J Cardiovasc. Electrophysiol.* 1999, 10 79-91.

[41.] D. Xing, J. B. Martins, *Am J Physiol Heart Circ. Physiol* 2001, 280H684-H692.

[42.] F. Shapiro, *Calcif Tissue Int* 1997, 61 285-293.

[43.] R. Civitelli, E. C. Beyer, P. M. Warlow, A. J. Robertson, S. T. Geist, T. H. Steinberg, *J. Clin. Invest.* 1993, 91 1888-1896.

[44.] T. H. Steinberg, R. Civitelli, S. T. Geist, A. J. Robertson, E. Hick, R. D. Veenstra, H. Z. Wang, P. M. Warlow, E. M. Westphale, J. G. Laing, a. et, *EMBO J.* 1994, 13 744-750.

[45.] H. Chiba, N. Sawada, M. Oyamada, T. Kojima, S. Nomura, S. Ishii, M. Mori, *Cell Struct. Funct.* 1993, 18 419-426.

[46.] F. Lecanda, D. A. Towler, K. Ziambaras, S. L. Cheng, M. Koval, T. H. Steinberg, R. Civitelli, *Mol Biol Cell* 1998, 9 2249-2258.

[47.] F. Lecanda, P. M. Warlow, S. Sheikh, F. Furlan, T. H. Steinberg, R. Civitelli, *J. Cell Biol.* 2000, 151 931-943.

[48.] N. R. Jorgensen, S. T. Geist, R. Civitelli, T. H. Steinberg, *J. Cell Biol.* 1997, 139 497-506.

[49.] N. R. Jorgensen, Z. Henriksen, C. Brot, E. F. Eriksen, O. H. Sorensen, R. Civitelli, T. H. Steinberg, *J Bone Miner. Res.* 2000, 15 1024-1032.

[50.] A. Clairmont, D. Tessman, A. Stock, S. Nicolai, W. Stahl, H. Sies, *Carcinogenesis* 1996, 17 1389-1391.

[51.] M. A. Van der Molen, C. T. Rubin, K. J. McLeod, L. K. McCauley, H. J. Donahue, *J. Biol. Chem.* 1996, 271 12165-12171.

[52.] R. Civitelli, K. Ziambaras, P. M. Warlow, F. Lecanda, T. Nelson, J. Harley, N. Atal, E. C. Beyer, T. H. Steinberg, *J. Cell Biochem.* 1998, 68 8-21.

[53.] P. D'Andrea, A. Calabrese, I. Capozzi, M. Grandolfo, R. Tonon, F. Vittur, *Biorheology* 2000, 37 75-83.

[54.] P. D'Andrea, F. Vittur, *Cell Calcium* 1996, 20 389-397.

[55.] S. Loty, C. Foll, N. Forest, J. Sautier, *Arch. Oral Biol.* 2000, 45 843-856.

[56.] N. Cirenei, B. M. Colombo, M. Mesnil, S. Benedetti, H. Yamasaki, G. Finocchiaro, *Gene Ther.* 1998, 5 1221-1226.

[57.] O. Moennikes, A. Buchmann, K. Willecke, O. Traub, M. Schwarz, *Hepatology* 2000, 32 501-506.

[58.] O. Moennikes, A. Buchmann, A. Romualdi, T. Ott, J. Werringloer, K. Willecke, M. Schwarz, *Cancer Res.* 2000, 60 5087-5091.

[59.] L. Zhou, E. M. Kasperek, B. J. Nicholson, *J. Cell Biol.* 1999, 144 1033-1045.

[60.] D. W. Laird, P. Fistouris, G. Batist, L. Alpert, H. T. Huynh, G. D. Carystinos, M. A. Alaoui-Jamali, *Cancer Res.* 1999, 59 4104-4110.

[61.] T. Shibata, H. Nagayasu, J. Hamada, S. Konaka, M. Hosokawa, T. Kawano, H. Kitajo, M. Arisue, *Tumour. Biol.* 2000, 21 299-308.

[62.] X. Guan, R. J. Ruch, *Carcinogenesis* 1996, 17 1791-1798.

[63.] R. J. Ruch, W. J. Bonney, K. Sigler, X. Guan, D. Matesic, L. D. Schafer, E. Dupont, J. E. Trosko, *Carcinogenesis* 1994, 15 301-306.

[64.] B. V. Madhukar, H. L. Feijter-Rupp, J. E. Trosko, *Cancer Lett.* 1996, 106 117-123.

[65.] W. K. Hong, M. B. Sporn, *Science* 1997, 278 1073-1077.

[66.] K. M. Abdullah, G. Luthra, J. J. Bilski, S. A. Abdullah, L. P. Reynolds, D. A. Redmer, A. T. Grazul-Bilska, *Endocrine.* 1999, 10 35-41.

[67.] M. Saitoh, M. Oyamada, Y. Oyamada, T. Kaku, M. Mori, *Carcinogenesis* 1997, 18 1319-1328.

[68.] J. A. Goliger, D. L. Paul, *Mol. Biol. Cell* 1995, 6 1491-1501.

[69.] T. Mine, R. Kushima, T. Fujita, *J. Clin. Gastroenterol.* 1997, 25 *Suppl* 1 S111-S115.

[70.] T. Mine, H. Yusuda, A. Kataoka, A. Tajima, J. Nagasawa, T. Takano, *J. Clin. Gastroenterol.* 1995, 21 *Suppl* 1 S104-S107.

[71.] G. J. Christ, P. R. Brink, *Braz. J Med Biol. Res.* 2000, 33 423-429.

[72.] B. R. Berg, K. D. Cohen, I. H. Sarelius, *Am J Physiol* 1997, 272H2693-H2700.

[73.] C. de Wit, F. Roos, S. S. Bolz, S. Kirchhoff, O. Kruger, K. Willecke, U. Pohl, *Circulation Research* 2000, 86 649-655.

[74.] B. Nafz, J. Stegemann, M. H. Bestle, N. Richter, E. Seeliger, I. Schimke, H. W. Reinhardt, P. B. Persson, *Circulation* 2000, 101 553-557.

[75.] H. Q. Xie, V. W. Hu, *Exp. Cell Res.* 1994, 214 172-176.

[76.] R. Dermietzel, *Brain Res Brain Res Rev* 1998, 26 176-183.

[77.] R. Rozental, M. Srinivas, S. Gokhan, M. Urban, R. Dermietzel, J. A. Kessler, D. C. Spray, M. F. Mehler, *Brain Res. Brain Res. Rev.* 2000, 32 57-71.

[78.] H. Aldskogius, E. N. Koziova, *Prog. Neurobiol.* 1998, 55 1-26.

[79.] J. D. Pal, X. Liu, D. Mackay, A. Shiels, V. M. Berthoud, E. C. Beyer, L. Ebihara, *Am J Physiol Cell Physiol* 2000, 279 C596-C602.

[80.] V. Krutovskikh, H. Yamasaki, *Mutat. Res.* 2000, 462 197-207.

[81.] D. Mackay, A. Ionides, Z. Kibar, G. Rouleau, V. Berry, A. Moore, A. Shiels, S. Bhattacharya, *Am J Hum. Genet.* 1999, 64 1357-1364.

[82.] K. Nakamura, Y. Shibata, *Cells Tissues. Organs* 1999, 165 16-21.

[83.] L. Nemeth, S. Maddur, P. Puri, *J Pediatr. Surg.* 2000, 35 823-828.

[84.] A. M. Simon, D. A. Goodenough, E. Li, D. L. Paul, *Nature* 1997, 385 525-529.

[85.] B. Sommersberg, A. Bulling, U. Salzer, U. Frohlich, R. E. Garfield, A. Amsterdam, A. Mayerhofer, *Biol. Reprod.* 2000, 63 1661-1668.

[86.] I. Granot, N. Dekel, *Hum. Reprod.* 1998, 13 *Suppl* 4 85-97.

[87.] W. M. Kilarski, E. Dupont, S. Coppen, H. I. Yeh, C. Vozzi, R. G. Gourdie, M. Rezapour, U. Ulmsten, G. M. Roomans, N. J. Severs, *Eur. J Cell Biol.* 1998, 75 1-8.

[88.] H. N. Ciray, X. Fu, M. Olovsson, G. Ahisen, C. Shuman, B. Lindblom, U. Ulmsten, *Am J Obstet. Gynecol.* 2000, 182 926-930.

[89.] C. Batias, N. Defamie, A. Lablack, D. Thepot, P. Fenichel, D. Segretain, G. Pointis, *Cell Tissue Res.* 1999, 298 113-121.

[90.] E. Schleiermacher, *Hum. Genet.* 1980, 54 391-404.

[91.] C. Vozzi, S. Ullrich, A. Charollais, J. Philippe, L. Orci, P. Meda, *J. Cell Biol.* 1995, 131 1561-1572.

[92.] P. Meda, M. Chanson, M. Pepper, E. Giordano, D. Bosco, O. Traub, K. Willecke, A. el Aoumari, D. Gros, E. C. Beyer, *Exp. Cell Res.* 1991, 192 469-480.

[93.] K. Ziambaras, F. Lecanda, T. H. Steinberg, R. Civitelli, *J. Bone Miner. Res.* 1998, 13 218-228.

[94.] I. Capozzi, R. Tonon, P. D'Andrea, *Biochem J* 1999, 344 Pt 2 545-553.

[95.] S. G. Spanakis, S. Petridou, S. K. Masur, *Invest Ophthalmol. Vis. Sci.* 1998, 39 1320-1328.

[96.] H. Yamasaki, V. Krutovskikh, M. Mesnil, T. Tanaka, D. M. Zaidan, Y. Omori, *C. R. Acad. Sci. III.* 1999, 322 151-159.

[97.] B. D. Larsen, A. Holm, *Int. J Pept. Protein Res.* 1994, 43 1-9.

All references disclosed herein are incorporated by reference.

The invention has been described with reference to preferred embodiments thereof. However, it will be appreciated that those skilled in the art, upon consideration of this disclosure, may make modifications and improvements within the spirit and scope of the invention.

---

The invention claimed is:

1. A compound having the formula:

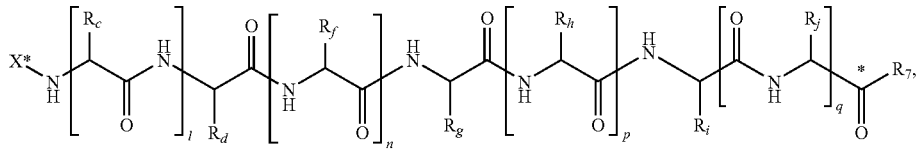

or a retro form, an all D form, or a retro all D form thereof, said compound optionally being cyclic through a covalent bond between N* and C*;

wherein:

X is H, Ac, TFa, DBF, ASAL optionally iodinated, or HP;

l and n are 1;

p and q are independently 0 or 1;

$R_c$ is the side chain of Gly;

$R_d$ is the side chain of Ala;

$R_f$ is the acid side chain of Gly;

$R_g$ is the side chain of L-Hyp, D-Hyp, Pro, D-Pro, Ncg, A2C, Gly, Asn, T4c, or Pc, if the compound is a cyclic compound, or $R_g$ is the side chain of D-Hyp, Pro, D-Pro, Ncg, A2C, Gly, Asn, T4c, or Pc, if the compound is a linear peptide, wherein said side chain of L-Hyp, D-Hyp, Pro, D-Pro, or Thio-Pro is cyclized by attachment to the N atom bonded to the C atom to which $R_g$ is attached;

$R_h$ is the side chain of Pro, D-Pro, or Ala, wherein said side chain of Pro or D-Pro is cyclized by attachment to the N atom bonded to the C atom to which $R_h$ is attached;

$R_i$ is the side chain of Tyr or D-Tyr, wherein the aromatic ring of said side chain is optionally substituted with one or more halogen groups;

$R_j$ is the side chain of Gln or Asn;

$R_7$ is OH or $NH_2$, or is absent if the compound is cyclized between N* and C*, or a pharmaceutically acceptable salt thereof.

2. The compound according to claim 1, or a pharmaceutically acceptable salt thereof, wherein $R_7$ is $NH_2$.

3. The compound according to claim 1, or a pharmaceutically acceptable salt thereof, wherein $R_g$ is the amino acid side chain of Asn, D-4Hyp, or L-/D-Pro when said compound is a linear peptide, wherein, when $R_g$ is the amino acid side chain of D-4Hyp or L-/D-Pro, the side chain is cyclized by attachment to the N atom bonded to the C atom to which $R_g$ is attached.

4. The compound according to claim 1, or a pharmaceutically acceptable salt thereof, wherein $R_h$ is the amino acid side chain of Pro or D-Pro, wherein the side chain is cyclized by attachment to the N atom bonded to the C atom to which $R_h$ is attached.

5. The compound according to claim 1, or a pharmaceutically acceptable salt thereof, wherein $R_i$ is the amino acid side chain of Tyr.

6. The compound according to claim 1, or a pharmaceutically acceptable salt thereof, wherein $R_j$ is the amino acid side chain of Asn.

7. The compound of claim 1, wherein said compound is cyclo(-Gly-Ala-Gly-Hyp-Pro-Tyr-Asn-) (SEQ ID NO:287), or a pharmaceutically acceptable salt thereof.

8. The compound of claim 1, wherein said compound is cyclo(-Tyr-Pro-4Hyp-Gly-Ala-Gly-Asn-) (SEQ ID NO: 174), or a pharmaceutically acceptable salt thereof.

9. The compound of claim 1, wherein said compound is cyclo(-Gly-Ala-Gly-Pro-Pro-Tyr-Asn-) (SEQ ID NO:288), or a pharmaceutically acceptable salt thereof.

10. The compound of claim 1, wherein said compound is cyclo(-Gly-Ala-Gly-Pro-Pro-Tyr-Gln-) (SEQ ID NO: 300), or a pharmaceutically acceptable salt thereof.

11. The compound of claim 1, wherein said compound is Gly-Ala-Gly-Pro-Pro-Tyr-$NH_2$ (SEQ ID NO: 301), or a pharmaceutically acceptable salt thereof.

12. The compound of claim 1, wherein said compound is Ac-D-Tyr-D-Pro-D-Pro-Gly-D-Ala-Gly-$NH_2$, or a pharmaceutically acceptable salt thereof.

13. The compound of claim 1, wherein said compound is Ac-D-Tyr-D-Hyp-D-Hyp-Gly-D-Ala-Gly-$NH_2$, or a pharmaceutically acceptable salt thereof.

14. The compound of claim 1, wherein said compound is Gly-Ala-Gly-Asn-Tyr-$NH_2$ (SEQ ID NO:254), or a pharmaceutically acceptable salt thereof.

15. The compound of claim 1, or a pharmaceutically acceptable salt thereof, wherein X is Ac or H and $R_g$ is selected from the group consisting of Pro, D-Pro, Hyp, D-Hyp, Gly, or Asn.

* * * * *

UNITED STATES PATENT AND TRADEMARK OFFICE
CERTIFICATE OF CORRECTION

PATENT NO. : 7,737,113 B2
APPLICATION NO. : 10/772774
DATED : June 15, 2010
INVENTOR(S) : Larsen et al.

It is certified that error appears in the above-identified patent and that said Letters Patent is hereby corrected as shown below:

Title page, under OTHER PUBLICATIONS, in Grover et al., replace "spectrospcopy"
        with --spectroscopy--.

Column 18, Line 8, replace "Ac-Tyr-4Hyp-Sar-Sar-Ata-Sar-OH/$NH_2$" with
        --Ac-Tyr-4Hyp-Sar-Sar-Ala-Sar-OH/$NH_2$--.

Column 57, Line 57, replace
        "H—Thr(O)—Thr-Pro—4Hyp—Gly—Ala—Gly" with
        --H—Thr(O)—Tyr—Pro—4Hyp—Gly—Ala—Gly--;

Line 64, replace "AC—Thr(O)-Thr—Pro—4Hyp—Gly—Ala—Gly" with
        --AC—Thr(O)-Tyr—Pro—4Hyp—Gly—Ala—Gly--.

Column 58, Line 17, replace "Compound 21 os ex. 21" with
        --Compound 21 of ex. 21--;

Line 18, replace "SEQ ID NO: 220)" with --(SEQ ID NO: 220)--.

Column 59, Line 37, insert --(XI)--.

Column 61, Line 49, replace "Asn, Gin, Orn" with --Asn, Gln, Orn--.

Column 62, Line 49, replace "i.a." with --i.e.--.

Column 67, Line 1, replace "N-hydroxysuccinimid" with --N-hydroxysuccinimide--;

Column 67, Line 14, replace "(1-125)" with --(I-125)--;

Line 15, replace "tyrosine og" with --tyrosine or--.

Signed and Sealed this
Third Day of April, 2012

David J. Kappos
*Director of the United States Patent and Trademark Office*

CERTIFICATE OF CORRECTION (continued)
U.S. Pat. No. 7,737,113 B2

Column 71, Line 35, replace "autosamler" with --autosampler--.

Column 72, Line 34, replace "Compound 48180" with --Compound 48 180--.

Column 73, Line 36, replace "i.a.," with --i.e.,--.

Column 74, Line 48, insert "Homeostasis. GJIC permits the" on a new line.

Column 75, Line 24, replace "arrhythmiac" with --arrhythmias--.

Column 77, Line 62, replace "perusion" with --perfusion--.

Column 80, Line 9, replace "152 $\mu g_{prot}$/cell" with --152 $pg_{prot}$/cell--.

Column 88, Lines 44-46, replace
"(SEQ ID NO: 285)" with
--(SEQ ID NO: 285)
34   AB-Tyr(3,5-di-I)-Pro-Hyp-Gly-Ala-Gly-NH$_2$   nd--.

Column 89, Lines 5-7, remove
"34   AB-Tyr(3,5-di-I)-Pro-Hyp-Gly-Ala-Gly-NH$_2$
nd" ;

Lines 23-26, replace
"Group 12
Formula X-Zd-G(N/Q)Y-NH$_2$:Zd is a sequence of 0, 1, or 2 amino
12 acid residues selected from G or A; X is H, Ac"

with

| --Group 12 | Formula X-Zd-G(N/Q)Y-NH$_2$:Zd is a sequence of |
|---|---|
| Formula | 0, 1, or 2 amino acid residues selected from G |
| 12 | or A; X is H, Ac--. |

Column 98, Line 57, replace "0.10/%" with --0.1%--.

Column 100, Line 45, replace "osteoblats" with --osteoblasts--.

Column 102, Line 37, replace "oncogens" with --oncogenes--.

Column 103, Line 14, replace "invation" with --invasion--.

Column 106, Line 61, replace "which is turn" with --which in turn--.

Column 113, Line 8, replace "phthalat" with --phthalate--;

CERTIFICATE OF CORRECTION (continued)
U.S. Pat. No. 7,737,113 B2

Column 113, Line 19, replace "infaction" with --infarction--;

Lines 44-45, replace "either alone or in combination with either alone or in combination with" with --either alone or in combination with--.

Column 114, Line 22, replace "suitabel" with --suitable--;

Line 50, replace "Ethandithiol" with --Ethanedithiol--.

Column 115, Line 7, replace "peptid" with --peptide--;

Line 29, replace "ethandithiol" with --ethanedithiol--.

Column 121, Line 46, replace "each)>DCM" with --each), DCM--.

Column 124, Line 2, replace "Cystine" with --Cysteine--.

Column 130, Line 25, replace "Azido Benzoicic acid" with --Azido Benzoic acid--.

Column 139, under [41.], replace "280H684-H692" with --280 H684-H692--;

Line 64, insert --Synth. Ex. 19-- on a new line.

Column 140, under [72.], replace "272H2693-H2700" with --272 H2693-H2700--;

Column 140, under [78.], replace "Koziova" with --Kozlova--.

SEQUENCE LISTING

```
<160> NUMBER OF SEQ ID NOS: 299

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 1

Gly Pro Xaa Gly Ala Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 2

Gly Ala Gly Xaa Pro Tyr
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 3
```

```
Gly Ala Gly Xaa Pro Tyr
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 4

Gly Ala Gly Xaa Pro Tyr
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 5

Pro Xaa Gly Ala Gly
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 6

Gly Pro Xaa Gly Ala Gly
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 7

Gly Pro Leu Gly Pro
 1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
```

```
<220> FEATURE:
<221> NAME/KEY: MOD_RES
<222> LOCATION: (2)
<223> OTHER INFORMATION: 4Hyp

<400> SEQUENCE: 8

Pro Xaa Gly Ala Gly
 1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 9

Pro Xaa Gly Ala Gly
 1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 10

Pro Xaa Gly Ala Gly
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 11

Pro Xaa Gly Ala Gly
 1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 12

Pro Pro Gly Ala Gly
 1               5
```

-continued

```
<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 13

Gly Ala Gly Xaa Pro Tyr
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 14

Gly Ala Gly Xaa Pro Tyr
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 15

Ala Gly Xaa Pro Tyr
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar

<400> SEQUENCE: 16

Gly Xaa Pro Gly Ala Gly
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
```

```
<220> FEATURE:
<221> NAME/KEY: MOD_RES
<222> LOCATION: (3)
<223> OTHER INFORMATION: Sar

<400> SEQUENCE: 17

Gly Pro Xaa Gly Ala Gly
  1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)..(3)
<223> OTHER INFORMATION: Sar

<400> SEQUENCE: 18

Gly Xaa Xaa Gly Ala Gly
  1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp
<220> FEATURE:
<221> NAME/KEY: MOD_RES
<222> LOCATION: (6)
<223> OTHER INFORMATION: Tyr(3-I)

<400> SEQUENCE: 19

Gly Ala Gly Xaa Pro Tyr
  1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp
<220> FEATURE:
<221> NAME/KEY: MOD_RES
<222> LOCATION: (6)
<223> OTHER INFORMATION: Tyr(3-F)

<400> SEQUENCE: 20

Gly Ala Gly Xaa Pro Tyr
  1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
      antiarrythmic peptide
<220> FEATURE:
<221> NAME/KEY: MOD_RES
<222> LOCATION: (4)
<223> OTHER INFORMATION: Hyp
<220> FEATURE:
<221> NAME/KEY: MOD_RES
<222> LOCATION: (6)
<223> OTHER INFORMATION: Tyr(3-Cl)

<400> SEQUENCE: 21

Gly Ala Gly Xaa Pro Tyr
 1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp
<220> FEATURE:
<221> NAME/KEY: MOD_RES
<222> LOCATION: (6)
<223> OTHER INFORMATION: Tyr(3-Br)

<400> SEQUENCE: 22

Gly Ala Gly Xaa Pro Tyr
 1               5

<210> SEQ ID NO 23
<211> LENGTH: 6
<212> TYPE: PRT
<213> ORGANISM: Artificial Sequence
<220> FEATURE:
<221> NAME/KEY: MOD_RES
<222> LOCATION: (4)
<223> OTHER INFORMATION: Hyp
<220> FEATURE:
<223> OTHER INFORMATION: Description of Artificial Sequence: Synthetic
      antiarrythmic peptide

<400> SEQUENCE: 23

Arg Ala Gly Xaa Pro Tyr
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp

<400> SEQUENCE: 24

Val Ala Gly Xaa Pro Tyr
 1               5

<210> SEQ ID NO 25
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp

<400> SEQUENCE: 25

Ala Ala Gly Xaa Pro Tyr
 1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp

<400> SEQUENCE: 26

Gly Ala Gly Xaa His Tyr
 1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp

<400> SEQUENCE: 27

Gly Ala Gly Xaa Pro Phe
 1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 28

Gly Ala Gly Xaa Pro Tyr
 1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp
```

```
<400> SEQUENCE: 29

Gly Ala Gly Xaa Pro Tyr
 1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 30

Gly Pro Xaa Gly Ala Gly
 1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 31

Gly Pro Xaa Gly Ala Gly
 1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 32

Gly Ala Gly Xaa Pro Tyr
 1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 33

Gly Ala Gly Xaa Pro Tyr
 1               5

<210> SEQ ID NO 34
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp
<220> FEATURE:
<221> NAME/KEY: MOD_RES
<222> LOCATION: (6)
<223> OTHER INFORMATION: Tyr(3-I)

<400> SEQUENCE: 34

Gly Ala Gly Xaa Pro Tyr
 1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar

<400> SEQUENCE: 35

Gly Pro Xaa Gly Ala Gly
 1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 36

Pro Xaa Gly Ala Gly
 1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 37

Pro Xaa Gly Ala Gly
 1               5

<210> SEQ ID NO 38
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      antiarrythmic peptide

<400> SEQUENCE: 38

Pro Pro Gly Ala Gly
  1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 39

Gly Ala Gly Xaa Pro Tyr
  1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 40

Gly Ala Gly Xaa Pro Tyr
  1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 41

Gly Pro Leu Gly Pro
  1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 42

Pro Xaa Gly Ala Gly
  1               5

<210> SEQ ID NO 43
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 43

Pro Xaa Gly Ala Gly
 1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 44

Pro Xaa Gly Ala Gly
 1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 45

Pro Xaa Gly Ala Gly
 1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 46

Pro Pro Gly Ala Gly
 1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp
```

```
<400> SEQUENCE: 47

Gly Ala Gly Xaa Pro Tyr
 1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 48

Gly Ala Gly Xaa Pro Tyr
 1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 49

Ala Gly Xaa Pro Tyr
 1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar

<400> SEQUENCE: 50

Gly Xaa Pro Gly Ala Gly
 1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar

<400> SEQUENCE: 51

Gly Pro Xaa Gly Ala Gly
 1               5

<210> SEQ ID NO 52
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)..(3)
<223> OTHER INFORMATION: Sar

<400> SEQUENCE: 52

Gly Xaa Xaa Gly Ala Gly
 1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp
<220> FEATURE:
<221> NAME/KEY: MOD_RES
<222> LOCATION: (6)
<223> OTHER INFORMATION: Tyr(3-I)

<400> SEQUENCE: 53

Gly Ala Gly Xaa Pro Tyr
 1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp
<220> FEATURE:
<221> NAME/KEY: MOD_RES
<222> LOCATION: (6)
<223> OTHER INFORMATION: Tyr(3-F)

<400> SEQUENCE: 54

Gly Ala Gly Xaa Pro Tyr
 1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp
<220> FEATURE:
<221> NAME/KEY: MOD_RES
<222> LOCATION: (6)
<223> OTHER INFORMATION: Tyr(3-Cl)

<400> SEQUENCE: 55
```

```
Gly Ala Gly Xaa Pro Tyr
 1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp
<220> FEATURE:
<221> NAME/KEY: MOD_RES
<222> LOCATION: (6)
<223> OTHER INFORMATION: Tyr(3-Br)

<400> SEQUENCE: 56

Gly Ala Gly Xaa Pro Tyr
 1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp

<400> SEQUENCE: 57

Arg Ala Gly Xaa Pro Tyr
 1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp

<400> SEQUENCE: 58

Val Ala Gly Xaa Pro Tyr
 1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp

<400> SEQUENCE: 59

Ala Ala Gly Xaa Pro Tyr
 1               5
```

```
<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp

<400> SEQUENCE: 60

Gly Ala Gly Xaa His Tyr
 1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp

<400> SEQUENCE: 61

Gly Ala Gly Xaa Pro Phe
 1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 62

Gly Ala Gly Xaa Pro Tyr
 1               5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 63

Gly Ala Gly Xaa Pro Tyr
 1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
``` antiarrythmic peptide
<220> FEATURE:
<223> OTHER INFORMATION: NCG between positions 3 and 4

<400> SEQUENCE: 64

Gly Ala Gly Pro Tyr
1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<223> OTHER INFORMATION: T4C between positions 3 and 4

<400> SEQUENCE: 65

Gly Ala Gly Pro Tyr
1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<223> OTHER INFORMATION: A2C between positions 3 and 4

<400> SEQUENCE: 66

Gly Ala Gly Pro Tyr
1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<223> OTHER INFORMATION: PC between positions 3 and 4

<400> SEQUENCE: 67

Gly Ala Gly Pro Tyr
1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 68

Gly Ala Gly Gly Pro Tyr
1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide

```
<220> FEATURE:
<221> NAME/KEY: MOD_RES
<222> LOCATION: (3)
<223> OTHER INFORMATION: 4Hyp

<400> SEQUENCE: 69

Tyr Pro Xaa Gly Ala Gly
 1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 70

Tyr Pro Xaa Gly Ala Gly
 1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 71

Tyr Pro Xaa Gly Ala Gly
 1               5

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 72

Tyr Pro Pro Gly Ala Gly
 1               5

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 73

Tyr Xaa Pro Gly Ala Gly
 1               5
```

```
<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)..(3)
<223> OTHER INFORMATION: 4Hyp

<400> SEQUENCE: 74

Tyr Xaa Xaa Gly Ala Gly
 1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar
<220> FEATURE:
<221> NAME/KEY: MOD_RES
<222> LOCATION: (3)
<223> OTHER INFORMATION: 4Hyp

<400> SEQUENCE: 75

Tyr Xaa Xaa Gly Ala Gly
 1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp
<220> FEATURE:
<221> NAME/KEY: MOD_RES
<222> LOCATION: (3)
<223> OTHER INFORMATION: Sar

<400> SEQUENCE: 76

Tyr Xaa Xaa Gly Ala Gly
 1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar

<400> SEQUENCE: 77

Tyr Pro Xaa Gly Ala Gly
 1               5
```

```
<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar

<400> SEQUENCE: 78

Tyr Xaa Pro Gly Ala Gly
 1               5

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)..(3)
<223> OTHER INFORMATION: Sar

<400> SEQUENCE: 79

Tyr Xaa Xaa Gly Ala Gly
 1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 80

Tyr Pro Xaa Gly Ala Gly
 1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 81

Tyr Pro Xaa Gly Ala Gly
 1               5

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
``` antiarrythmic peptide
<220> FEATURE:
<221> NAME/KEY: MOD_RES
<222> LOCATION: (3)
<223> OTHER INFORMATION: 4Hyp

<400> SEQUENCE: 82

Tyr Pro Xaa Gly Ala Gly
 1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 83

Tyr Pro Pro Gly Ala Gly
 1               5

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 84

Tyr Xaa Pro Gly Ala Gly
 1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)..(3)
<223> OTHER INFORMATION: 4Hyp

<400> SEQUENCE: 85

Tyr Xaa Xaa Gly Ala Gly
 1               5

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar
<220> FEATURE:
<221> NAME/KEY: MOD_RES
<222> LOCATION: (3)
<223> OTHER INFORMATION: 4Hyp

<400> SEQUENCE: 86

Tyr Xaa Xaa Gly Ala Gly
  1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp
<220> FEATURE:
<221> NAME/KEY: MOD_RES
<222> LOCATION: (3)
<223> OTHER INFORMATION: Sar

<400> SEQUENCE: 87

Tyr Xaa Xaa Gly Ala Gly
  1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar

<400> SEQUENCE: 88

Tyr Pro Xaa Gly Ala Gly
  1               5

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar

<400> SEQUENCE: 89

Tyr Xaa Pro Gly Ala Gly
  1               5

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)..(3)
<223> OTHER INFORMATION: Sar

<400> SEQUENCE: 90

Tyr Xaa Xaa Gly Ala Gly
  1               5

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 91

Pro Xaa Gly Ala Gly
 1               5

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 92

Pro Xaa Gly Ala Gly
 1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 93

Pro Xaa Gly Ala Gly
 1               5

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: 4HBG
<220> FEATURE:
<221> NAME/KEY: MOD_RES
<222> LOCATION: (3)
<223> OTHER INFORMATION: 4Hyp

<400> SEQUENCE: 94

Xaa Pro Xaa Gly Ala Gly
 1               5

<210> SEQ ID NO 95

-continued

```
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 95

Pro Pro Gly Ala Gly
  1               5

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 96

Pro Pro Gly Ala Gly
  1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 97

Pro Pro Gly Ala Gly
  1               5

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 98

Pro Pro Gly Ala Gly
  1               5

<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: 4HBG

<400> SEQUENCE: 99

Xaa Pro Pro Gly Ala Gly
  1               5

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
```

-continued

```
      antiarrythmic peptide
<220> FEATURE:
<221> NAME/KEY: MOD_RES
<222> LOCATION: (1)
<223> OTHER INFORMATION: 4Hyp

<400> SEQUENCE: 100

Xaa Pro Gly Ala Gly
  1               5

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: 4Hyp

<400> SEQUENCE: 101

Xaa Pro Gly Ala Gly
  1               5

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: 4Hyp

<400> SEQUENCE: 102

Xaa Pro Gly Ala Gly
  1               5

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: 4Hyp

<400> SEQUENCE: 103

Xaa Pro Gly Ala Gly
  1               5

<210> SEQ ID NO 104
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: 4HBG
<220> FEATURE:
<221> NAME/KEY: MOD_RES
```

```
<222> LOCATION: (2)
<223> OTHER INFORMATION: 4Hyp

<400> SEQUENCE: 104

Xaa Xaa Pro Gly Ala Gly
 1               5

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: Sar

<400> SEQUENCE: 105

Xaa Pro Gly Ala Gly
 1               5

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: Sar

<400> SEQUENCE: 106

Xaa Pro Gly Ala Gly
 1               5

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: Sar

<400> SEQUENCE: 107

Xaa Pro Gly Ala Gly
 1               5

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: Sar

<400> SEQUENCE: 108

Xaa Pro Gly Ala Gly
 1               5
```

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: 4HBG
<220> FEATURE:
<221> NAME/KEY: MOD_RES
<222> LOCATION: (1)
<223> OTHER INFORMATION: Sar

<400> SEQUENCE: 109

Xaa Xaa Pro Gly Ala Gly
 1               5

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar

<400> SEQUENCE: 110

Pro Xaa Gly Ala Gly
 1               5

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar

<400> SEQUENCE: 111

Pro Xaa Gly Ala Gly
 1               5

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar

<400> SEQUENCE: 112

Pro Xaa Gly Ala Gly
 1               5

<210> SEQ ID NO 113

```
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar

<400> SEQUENCE: 113

Pro Xaa Gly Ala Gly
 1               5

<210> SEQ ID NO 114
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: 4HBG
<220> FEATURE:
<221> NAME/KEY: MOD_RES
<222> LOCATION: (3)
<223> OTHER INFORMATION: Sar

<400> SEQUENCE: 114

Xaa Pro Xaa Gly Ala Gly
 1               5

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Sar
<220> FEATURE:
<221> NAME/KEY: MOD_RES
<222> LOCATION: (6)
<223> OTHER INFORMATION: Sar

<400> SEQUENCE: 115

Tyr Pro Pro Xaa Ala Xaa
 1               5

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Sar
<220> FEATURE:
<221> NAME/KEY: MOD_RES
<222> LOCATION: (6)
<223> OTHER INFORMATION: Sar

<400> SEQUENCE: 116
```

Tyr Pro Pro Xaa Ala Xaa
 1               5

<210> SEQ ID NO 117
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp
<220> FEATURE:
<221> NAME/KEY: MOD_RES
<222> LOCATION: (4)
<223> OTHER INFORMATION: Sar

<400> SEQUENCE: 117

Tyr Pro Xaa Xaa Ala Gly
 1               5

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Sar

<400> SEQUENCE: 118

Tyr Pro Pro Xaa Ala Gly
 1               5

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp
<220> FEATURE:
<221> NAME/KEY: MOD_RES
<222> LOCATION: (4)
<223> OTHER INFORMATION: Sar

<400> SEQUENCE: 119

Tyr Xaa Pro Xaa Ala Gly
 1               5

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)..(4)
<223> OTHER INFORMATION: Sar

<400> SEQUENCE: 120

```
Tyr Pro Xaa Xaa Ala Gly
 1               5
```

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar
<220> FEATURE:
<221> NAME/KEY: MOD_RES
<222> LOCATION: (4)
<223> OTHER INFORMATION: Sar

<400> SEQUENCE: 121

```
Tyr Xaa Pro Xaa Ala Gly
 1               5
```

<210> SEQ ID NO 122
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp
<220> FEATURE:
<221> NAME/KEY: MOD_RES
<222> LOCATION: (4)
<223> OTHER INFORMATION: Sar

<400> SEQUENCE: 122

```
Tyr Pro Xaa Xaa Ala Gly
 1               5
```

<210> SEQ ID NO 123
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Sar

<400> SEQUENCE: 123

```
Tyr Pro Pro Xaa Ala Gly
 1               5
```

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp
<220> FEATURE:

```
<221> NAME/KEY: MOD_RES
<222> LOCATION: (4)
<223> OTHER INFORMATION: Sar

<400> SEQUENCE: 124

Tyr Xaa Pro Xaa Ala Gly
 1               5

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)..(4)
<223> OTHER INFORMATION: Sar

<400> SEQUENCE: 125

Tyr Pro Xaa Xaa Ala Gly
 1               5

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar
<220> FEATURE:
<221> NAME/KEY: MOD_RES
<222> LOCATION: (4)
<223> OTHER INFORMATION: Sar

<400> SEQUENCE: 126

Tyr Xaa Pro Xaa Ala Gly
 1               5

<210> SEQ ID NO 127
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar

<400> SEQUENCE: 127

Pro Pro Xaa Ala Gly
 1               5

<210> SEQ ID NO 128
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar
```

```
<400> SEQUENCE: 128

Pro Pro Xaa Ala Gly
 1               5

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar

<400> SEQUENCE: 129

Pro Pro Xaa Ala Gly
 1               5

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar

<400> SEQUENCE: 130

Pro Pro Xaa Ala Gly
 1               5

<210> SEQ ID NO 131
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: 4HBG
<220> FEATURE:
<221> NAME/KEY: MOD_RES
<222> LOCATION: (4)
<223> OTHER INFORMATION: Sar

<400> SEQUENCE: 131

Xaa Pro Pro Xaa Ala Gly
 1               5

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp
<220> FEATURE:
<221> NAME/KEY: MOD_RES
<222> LOCATION: (6)
```

```
<223> OTHER INFORMATION: Sar

<400> SEQUENCE: 132

Tyr Pro Xaa Gly Ala Xaa
 1               5

<210> SEQ ID NO 133
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (6)
<223> OTHER INFORMATION: Sar

<400> SEQUENCE: 133

Tyr Pro Pro Gly Ala Xaa
 1               5

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp
<220> FEATURE:
<221> NAME/KEY: MOD_RES
<222> LOCATION: (6)
<223> OTHER INFORMATION: Sar

<400> SEQUENCE: 134

Tyr Xaa Pro Gly Ala Xaa
 1               5

<210> SEQ ID NO 135
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar
<220> FEATURE:
<221> NAME/KEY: MOD_RES
<222> LOCATION: (6)
<223> OTHER INFORMATION: Sar

<400> SEQUENCE: 135

Tyr Pro Xaa Gly Ala Xaa
 1               5

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
```

```
<222> LOCATION: (2)
<223> OTHER INFORMATION: Sar
<220> FEATURE:
<221> NAME/KEY: MOD_RES
<222> LOCATION: (6)
<223> OTHER INFORMATION: Sar

<400> SEQUENCE: 136

Tyr Xaa Pro Gly Ala Xaa
 1               5

<210> SEQ ID NO 137
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp
<220> FEATURE:
<221> NAME/KEY: MOD_RES
<222> LOCATION: (6)
<223> OTHER INFORMATION: Sar

<400> SEQUENCE: 137

Tyr Pro Xaa Gly Ala Xaa
 1               5

<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (6)
<223> OTHER INFORMATION: Sar

<400> SEQUENCE: 138

Tyr Pro Pro Gly Ala Xaa
 1               5

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp
<220> FEATURE:
<221> NAME/KEY: MOD_RES
<222> LOCATION: (6)
<223> OTHER INFORMATION: Sar

<400> SEQUENCE: 139

Tyr Xaa Pro Gly Ala Xaa
 1               5

<210> SEQ ID NO 140
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar
<220> FEATURE:
<221> NAME/KEY: MOD_RES
<222> LOCATION: (6)
<223> OTHER INFORMATION: Sar

<400> SEQUENCE: 140

Tyr Pro Xaa Gly Ala Xaa
 1               5

<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar
<220> FEATURE:
<221> NAME/KEY: MOD_RES
<222> LOCATION: (6)
<223> OTHER INFORMATION: Sar

<400> SEQUENCE: 141

Tyr Xaa Pro Gly Ala Xaa
 1               5

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (5)
<223> OTHER INFORMATION: Sar

<400> SEQUENCE: 142

Pro Pro Gly Ala Xaa
 1               5

<210> SEQ ID NO 143
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (5)
<223> OTHER INFORMATION: Sar

<400> SEQUENCE: 143

Pro Pro Gly Ala Xaa
 1               5

<210> SEQ ID NO 144
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (5)
<223> OTHER INFORMATION: Sar

<400> SEQUENCE: 144

Pro Pro Gly Ala Xaa
 1               5

<210> SEQ ID NO 145
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (5)
<223> OTHER INFORMATION: Sar

<400> SEQUENCE: 145

Pro Pro Gly Ala Xaa
 1               5

<210> SEQ ID NO 146
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: 4HBG
<220> FEATURE:
<221> NAME/KEY: MOD_RES
<222> LOCATION: (6)
<223> OTHER INFORMATION: Sar

<400> SEQUENCE: 146

Xaa Pro Pro Gly Ala Xaa
 1               5

<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp
<220> FEATURE:
<221> NAME/KEY: MOD_RES
<222> LOCATION: (5)
<223> OTHER INFORMATION: Aib

<400> SEQUENCE: 147

Tyr Pro Xaa Gly Xaa Gly
 1               5

<210> SEQ ID NO 148
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (5)
<223> OTHER INFORMATION: Aib

<400> SEQUENCE: 148

Tyr Pro Pro Gly Xaa Gly
  1               5

<210> SEQ ID NO 149
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp
<220> FEATURE:
<221> NAME/KEY: MOD_RES
<222> LOCATION: (5)
<223> OTHER INFORMATION: Aib

<400> SEQUENCE: 149

Tyr Xaa Pro Gly Xaa Gly
  1               5

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar
<220> FEATURE:
<221> NAME/KEY: MOD_RES
<222> LOCATION: (5)
<223> OTHER INFORMATION: Aib

<400> SEQUENCE: 150

Tyr Pro Xaa Gly Xaa Gly
  1               5

<210> SEQ ID NO 151
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar
<220> FEATURE:
<221> NAME/KEY: MOD_RES
<222> LOCATION: (5)
<223> OTHER INFORMATION: Aib

<400> SEQUENCE: 151

Tyr Xaa Pro Gly Xaa Gly
```

-continued

```
<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp
<220> FEATURE:
<221> NAME/KEY: MOD_RES
<222> LOCATION: (5)
<223> OTHER INFORMATION: Aib

<400> SEQUENCE: 152

Tyr Pro Xaa Gly Xaa Gly
 1               5

<210> SEQ ID NO 153
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (5)
<223> OTHER INFORMATION: Aib

<400> SEQUENCE: 153

Tyr Pro Pro Gly Xaa Gly
 1               5

<210> SEQ ID NO 154
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp
<220> FEATURE:
<221> NAME/KEY: MOD_RES
<222> LOCATION: (5)
<223> OTHER INFORMATION: Aib

<400> SEQUENCE: 154

Tyr Xaa Pro Gly Xaa Gly
 1               5

<210> SEQ ID NO 155
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar
<220> FEATURE:
<221> NAME/KEY: MOD_RES
<222> LOCATION: (5)
```

<223> OTHER INFORMATION: Aib

<400> SEQUENCE: 155

Tyr Pro Xaa Gly Xaa Gly
 1               5

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar
<220> FEATURE:
<221> NAME/KEY: MOD_RES
<222> LOCATION: (5)
<223> OTHER INFORMATION: Aib

<400> SEQUENCE: 156

Tyr Xaa Pro Gly Xaa Gly
 1               5

<210> SEQ ID NO 157
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Aib

<400> SEQUENCE: 157

Pro Pro Gly Xaa Gly
 1               5

<210> SEQ ID NO 158
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Aib

<400> SEQUENCE: 158

Pro Pro Gly Xaa Gly
 1               5

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Aib

<400> SEQUENCE: 159

```
Pro Pro Gly Xaa Gly
  1               5

<210> SEQ ID NO 160
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Aib

<400> SEQUENCE: 160

Pro Pro Gly Xaa Gly
  1               5

<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: 4HBG
<220> FEATURE:
<221> NAME/KEY: MOD_RES
<222> LOCATION: (5)
<223> OTHER INFORMATION: Aib

<400> SEQUENCE: 161

Xaa Pro Pro Gly Xaa Gly
  1               5

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Sar
<220> FEATURE:
<221> NAME/KEY: MOD_RES
<222> LOCATION: (5)
<223> OTHER INFORMATION: Aib

<400> SEQUENCE: 162

Tyr Pro Pro Xaa Xaa Gly
  1               5

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Sar
<220> FEATURE:
```

```
<221> NAME/KEY: MOD_RES
<222> LOCATION: (4)
<223> OTHER INFORMATION: Aib

<400> SEQUENCE: 163

Tyr Pro Pro Xaa Xaa Gly
  1               5

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (5)
<223> OTHER INFORMATION: Aib
<220> FEATURE:
<221> NAME/KEY: MOD_RES
<222> LOCATION: (6)
<223> OTHER INFORMATION: Sar

<400> SEQUENCE: 164

Tyr Pro Pro Gly Xaa Xaa
  1               5

<210> SEQ ID NO 165
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (5)
<223> OTHER INFORMATION: Aib
<220> FEATURE:
<221> NAME/KEY: MOD_RES
<222> LOCATION: (6)
<223> OTHER INFORMATION: Sar

<400> SEQUENCE: 165

Tyr Pro Pro Gly Xaa Xaa
  1               5

<210> SEQ ID NO 166
<211> LENGTH: 4
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 166

Gly Ala Gly Asn
  1

<210> SEQ ID NO 167
<211> LENGTH: 4
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 167

Gly Ala Gly Gln
```

```
<210> SEQ ID NO 168
<211> LENGTH: 4
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 168

Gly Ala Gly Asp
 1

<210> SEQ ID NO 169
<211> LENGTH: 4
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 169

Gly Ala Gly Glu
 1

<210> SEQ ID NO 170
<211> LENGTH: 4
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 170

Gly Ala Gly Asp
 1

<210> SEQ ID NO 171
<211> LENGTH: 4
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 171

Gly Ala Gly Glu
 1

<210> SEQ ID NO 172
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 172

Tyr Pro Xaa Gly Ala Asn
 1               5

<210> SEQ ID NO 173
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 173

Tyr Pro Xaa Gly Ala Asp
  1               5

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 174

Tyr Pro Xaa Gly Ala Gly Asn
  1               5

<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 175

Tyr Pro Xaa Gly Ala Gly Asp
  1               5

<210> SEQ ID NO 176
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 176

Tyr Pro Xaa Gly Ala Gln
  1               5

<210> SEQ ID NO 177
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
```

```
<222> LOCATION: (3)
<223> OTHER INFORMATION: 4Hyp

<400> SEQUENCE: 177

Tyr Pro Xaa Gly Ala Glu
  1               5

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 178

Tyr Pro Xaa Gly Ala Gly Gln
  1               5

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 179

Tyr Pro Xaa Gly Ala Gly Glu
  1               5

<210> SEQ ID NO 180
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 180

Tyr Ala Ser Ala Gly Asn
  1               5

<210> SEQ ID NO 181
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 181

Tyr Gly Asn Tyr Gly Asn
  1               5

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
``` antiarrythmic peptide

<400> SEQUENCE: 182

Tyr Gly Asn Tyr Ala Gly Asn
 1               5

<210> SEQ ID NO 183
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 183

Tyr Val Ser Gly Ala Gly Asn
 1               5

<210> SEQ ID NO 184
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 184

Tyr Pro Xaa Gly Ala Gly
 1               5

<210> SEQ ID NO 185
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 185

Tyr Xaa Pro Gly Ala Gly
 1               5

<210> SEQ ID NO 186
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)..(3)
<223> OTHER INFORMATION: 4Hyp

<400> SEQUENCE: 186

Tyr Xaa Xaa Gly Ala Gly
 1               5

<210> SEQ ID NO 187
<211> LENGTH: 6
<212> TYPE: PRT

```
<213> ORGANISM: Artificial Sequence
<220> FEATURE:
<223> OTHER INFORMATION: Description of Artificial Sequence: Synthetic
      antiarrythmic peptide

<400> SEQUENCE: 187

Tyr Pro Pro Gly Ala Gly
  1               5

<210> SEQ ID NO 188
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)..(3)
<223> OTHER INFORMATION: Sar

<400> SEQUENCE: 188

Tyr Xaa Xaa Gly Ala Gly
  1               5

<210> SEQ ID NO 189
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar

<400> SEQUENCE: 189

Tyr Xaa Pro Gly Ala Gly
  1               5

<210> SEQ ID NO 190
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp
<220> FEATURE:
<221> NAME/KEY: MOD_RES
<222> LOCATION: (3)
<223> OTHER INFORMATION: Sar

<400> SEQUENCE: 190

Tyr Xaa Xaa Gly Ala Gly
  1               5

<210> SEQ ID NO 191
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
```

<223> OTHER INFORMATION: Sar

<400> SEQUENCE: 191

Tyr Pro Xaa Gly Ala Gly
 1               5

<210> SEQ ID NO 192
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar
<220> FEATURE:
<221> NAME/KEY: MOD_RES
<222> LOCATION: (4)
<223> OTHER INFORMATION: 4Hyp

<400> SEQUENCE: 192

Tyr Xaa Xaa Gly Ala Gly
 1               5

<210> SEQ ID NO 193
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 193

Tyr Pro Xaa Gly Ala Gly
 1               5

<210> SEQ ID NO 194
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 194

Tyr Xaa Pro Gly Ala Gly
 1               5

<210> SEQ ID NO 195
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)..(3)
<223> OTHER INFORMATION: 4Hyp

<400> SEQUENCE: 195

Tyr Xaa Xaa Gly Ala Gly
1               5

<210> SEQ ID NO 196
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 196

Tyr Pro Pro Gly Ala Gly
1               5

<210> SEQ ID NO 197
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)..(3)
<223> OTHER INFORMATION: Sar

<400> SEQUENCE: 197

Tyr Xaa Xaa Gly Ala Gly
1               5

<210> SEQ ID NO 198
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar

<400> SEQUENCE: 198

Tyr Xaa Pro Gly Ala Gly
1               5

<210> SEQ ID NO 199
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp
<220> FEATURE:
<221> NAME/KEY: MOD_RES
<222> LOCATION: (3)
<223> OTHER INFORMATION: Sar

<400> SEQUENCE: 199

Tyr Xaa Xaa Gly Ala Gly
1               5

<210> SEQ ID NO 200
<211> LENGTH: 6

```
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar

<400> SEQUENCE: 200

Tyr Pro Xaa Gly Ala Gly
 1               5

<210> SEQ ID NO 201
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar
<220> FEATURE:
<221> NAME/KEY: MOD_RES
<222> LOCATION: (3)
<223> OTHER INFORMATION: 4Hyp

<400> SEQUENCE: 201

Tyr Xaa Xaa Gly Ala Gly
 1               5

<210> SEQ ID NO 202
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 202

Tyr Pro Xaa Gly Ala Gly
 1               5

<210> SEQ ID NO 203
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 203

Tyr Xaa Pro Gly Ala Gly
 1               5

<210> SEQ ID NO 204
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      antiarrythmic peptide
<220> FEATURE:
<221> NAME/KEY: MOD_RES
<222> LOCATION: (2)..(3)
<223> OTHER INFORMATION: 4Hyp

<400> SEQUENCE: 204

Tyr Xaa Xaa Gly Ala Gly
 1               5

<210> SEQ ID NO 205
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 205

Tyr Pro Pro Gly Ala Gly
 1               5

<210> SEQ ID NO 206
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)..(3)
<223> OTHER INFORMATION: Sar

<400> SEQUENCE: 206

Tyr Xaa Xaa Gly Ala Gly
 1               5

<210> SEQ ID NO 207
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar

<400> SEQUENCE: 207

Tyr Xaa Pro Gly Ala Gly
 1               5

<210> SEQ ID NO 208
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp
<220> FEATURE:
<221> NAME/KEY: MOD_RES
<222> LOCATION: (4)
<223> OTHER INFORMATION: Sar
```

```
<400> SEQUENCE: 208

Tyr Xaa Xaa Gly Ala Gly
 1               5

<210> SEQ ID NO 209
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar

<400> SEQUENCE: 209

Tyr Pro Xaa Gly Ala Gly
 1               5

<210> SEQ ID NO 210
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar
<220> FEATURE:
<221> NAME/KEY: MOD_RES
<222> LOCATION: (3)
<223> OTHER INFORMATION: 4Hyp

<400> SEQUENCE: 210

Tyr Xaa Xaa Gly Ala Gly
 1               5

<210> SEQ ID NO 211
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 211

Tyr Pro Xaa Gly Ala Gly
 1               5

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 212

Tyr Xaa Pro Gly Ala Gly
```

-continued

```
    1               5

<210> SEQ ID NO 213
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 213

Tyr Pro Xaa Gly Ala Gly
 1               5

<210> SEQ ID NO 214
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 214

Tyr Xaa Pro Gly Ala Gly
 1               5

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: Ser(O)
<220> FEATURE:
<221> NAME/KEY: MOD_RES
<222> LOCATION: (4)
<223> OTHER INFORMATION: 4Hyp

<400> SEQUENCE: 215

Ser Tyr Pro Xaa Gly Ala Gly
 1               5

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: Ser(O)
<220> FEATURE:
<221> NAME/KEY: MOD_RES
<222> LOCATION: (4)
<223> OTHER INFORMATION: 4Hyp

<400> SEQUENCE: 216
```

```
Ser Tyr Pro Xaa Gly Ala Gly
  1               5
```

<210> SEQ ID NO 217
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: Thr(O)
<220> FEATURE:
<221> NAME/KEY: MOD_RES
<222> LOCATION: (4)
<223> OTHER INFORMATION: 4Hyp

<400> SEQUENCE: 217

```
Thr Tyr Pro Xaa Gly Ala Gly
  1               5
```

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: Thr(O)
<220> FEATURE:
<221> NAME/KEY: MOD_RES
<222> LOCATION: (4)
<223> OTHER INFORMATION: 4Hyp

<400> SEQUENCE: 218

```
Thr Tyr Pro Xaa Gly Ala Gly
  1               5
```

<210> SEQ ID NO 219
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Hyp

<400> SEQUENCE: 219

```
Cys Gly Xaa Pro Tyr Cys
  1               5
```

<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 220

```
Cys Tyr Pro Xaa Gly Ala Gly Cys
 1               5
```

<210> SEQ ID NO 221
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 221

```
Cys Tyr Pro Xaa Gly Ala Cys
 1               5
```

<210> SEQ ID NO 222
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 222

```
Cys Tyr Pro Xaa Gly Cys
 1               5
```

<210> SEQ ID NO 223
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 223

```
Cys Tyr Pro Xaa Cys
 1               5
```

<210> SEQ ID NO 224
<211> LENGTH: 8
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 224

```
Cys Tyr Pro Xaa Gly Ala Gly Cys
 1               5
```

<210> SEQ ID NO 225
<211> LENGTH: 7

<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 225

Cys Tyr Pro Xaa Gly Ala Cys
  1               5

<210> SEQ ID NO 226
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 226

Cys Tyr Pro Xaa Gly Cys
  1               5

<210> SEQ ID NO 227
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: 4Hyp

<400> SEQUENCE: 227

Cys Tyr Pro Xaa Cys
  1               5

<210> SEQ ID NO 228
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 228

Tyr Pro Xaa Gly Ala Gly
  1               5

<210> SEQ ID NO 229
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES

```
<222> LOCATION: (2)
<223> OTHER INFORMATION: 4Hyp

<400> SEQUENCE: 229

Tyr Xaa Pro Gly Ala Gly
 1               5

<210> SEQ ID NO 230
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)..(3)
<223> OTHER INFORMATION: 4Hyp

<400> SEQUENCE: 230

Tyr Xaa Xaa Gly Ala Gly
 1               5

<210> SEQ ID NO 231
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 231

Tyr Pro Pro Gly Ala Gly
 1               5

<210> SEQ ID NO 232
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)..(3)
<223> OTHER INFORMATION: Sar

<400> SEQUENCE: 232

Tyr Xaa Xaa Gly Ala Gly
 1               5

<210> SEQ ID NO 233
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar

<400> SEQUENCE: 233

Tyr Xaa Pro Gly Ala Gly
 1               5

<210> SEQ ID NO 234
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp
<220> FEATURE:
<221> NAME/KEY: MOD_RES
<222> LOCATION: (3)
<223> OTHER INFORMATION: Sar

<400> SEQUENCE: 234

Tyr Xaa Xaa Gly Ala Gly
 1               5

<210> SEQ ID NO 235
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar

<400> SEQUENCE: 235

Tyr Pro Xaa Gly Ala Gly
 1               5

<210> SEQ ID NO 236
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar
<220> FEATURE:
<221> NAME/KEY: MOD_RES
<222> LOCATION: (3)
<223> OTHER INFORMATION: 4Hyp

<400> SEQUENCE: 236

Tyr Xaa Xaa Gly Ala Gly
 1               5

<210> SEQ ID NO 237
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 237

Tyr Pro Xaa Gly Ala Gly
 1               5

<210> SEQ ID NO 238
```

-continued

```
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 238

Tyr Xaa Pro Gly Ala Gly
  1               5

<210> SEQ ID NO 239
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)..(3)
<223> OTHER INFORMATION: 4Hyp

<400> SEQUENCE: 239

Tyr Xaa Xaa Gly Ala Gly
  1               5

<210> SEQ ID NO 240
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 240

Tyr Pro Pro Gly Ala Gly
  1               5

<210> SEQ ID NO 241
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)..(3)
<223> OTHER INFORMATION: Sar

<400> SEQUENCE: 241

Tyr Xaa Xaa Gly Ala Gly
  1               5

<210> SEQ ID NO 242
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar
```

<400> SEQUENCE: 242

Tyr Xaa Pro Gly Ala Gly
 1               5

<210> SEQ ID NO 243
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp
<220> FEATURE:
<221> NAME/KEY: MOD_RES
<222> LOCATION: (3)
<223> OTHER INFORMATION: Sar

<400> SEQUENCE: 243

Tyr Xaa Xaa Gly Ala Gly
 1               5

<210> SEQ ID NO 244
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar

<400> SEQUENCE: 244

Tyr Pro Xaa Gly Ala Gly
 1               5

<210> SEQ ID NO 245
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Sar
<220> FEATURE:
<221> NAME/KEY: MOD_RES
<222> LOCATION: (3)
<223> OTHER INFORMATION: 4Hyp

<400> SEQUENCE: 245

Tyr Xaa Xaa Gly Ala Gly
 1               5

<210> SEQ ID NO 246
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Dapa

```
<220> FEATURE:
<221> NAME/KEY: MOD_RES
<222> LOCATION: (4)
<223> OTHER INFORMATION: Hyp

<400> SEQUENCE: 246

Gly Xaa Gly Xaa Pro Tyr
 1               5

<210> SEQ ID NO 247
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Dab
<220> FEATURE:
<221> NAME/KEY: MOD_RES
<222> LOCATION: (4)
<223> OTHER INFORMATION: Hyp

<400> SEQUENCE: 247

Gly Xaa Gly Xaa Pro Tyr
 1               5

<210> SEQ ID NO 248
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Dab
<220> FEATURE:
<221> NAME/KEY: MOD_RES
<222> LOCATION: (5)
<223> OTHER INFORMATION: Hyp

<400> SEQUENCE: 248

Gly Xaa Ala Gly Xaa Pro Tyr
 1               5

<210> SEQ ID NO 249
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Dapa
<220> FEATURE:
<221> NAME/KEY: MOD_RES
<222> LOCATION: (5)
<223> OTHER INFORMATION: Hyp

<400> SEQUENCE: 249

Gly Xaa Ala Gly Xaa Pro Tyr
 1               5

<210> SEQ ID NO 250
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Hyp

<400> SEQUENCE: 250

Tyr Pro Xaa Gly Glu Gly
  1               5

<210> SEQ ID NO 251
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Hyp

<400> SEQUENCE: 251

Tyr Pro Xaa Gly Asp Gly
  1               5

<210> SEQ ID NO 252
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Hyp

<400> SEQUENCE: 252

Tyr Pro Xaa Gly Ala Asp Gly
  1               5

<210> SEQ ID NO 253
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Hyp

<400> SEQUENCE: 253

Tyr Pro Xaa Gly Ala Glu Gly
  1               5

<210> SEQ ID NO 254
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 254
```

-continued

```
Gly Ala Gly Asn Tyr
 1               5

<210> SEQ ID NO 255
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 255

Tyr Ala Ser Ala Gly Asn
 1               5

<210> SEQ ID NO 256
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 256

Tyr Ala Ser Ala Gly Asn
 1               5

<210> SEQ ID NO 257
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 257

Tyr Gly Asn Tyr Ala Gly Asn
 1               5

<210> SEQ ID NO 258
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 258

Tyr Val Ser Gly Ala Gly Asn
 1               5

<210> SEQ ID NO 259
<211> LENGTH: 4
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 259

Ala Gly Asn Tyr
 1

<210> SEQ ID NO 260
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      antiarrythmic peptide

<400> SEQUENCE: 260

Ala Gly Asn Tyr
 1

<210> SEQ ID NO 261
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Hyp

<400> SEQUENCE: 261

Pro Xaa Gly Ala Gly
 1               5

<210> SEQ ID NO 262
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Hyp

<400> SEQUENCE: 262

Pro Xaa Gly Ala Gly
 1               5

<210> SEQ ID NO 263
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Hyp

<400> SEQUENCE: 263

Pro Xaa Gly Ala Gly
 1               5

<210> SEQ ID NO 264
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Hyp

<400> SEQUENCE: 264

Tyr Pro Xaa Gly Ala Gly
```

```
<210> SEQ ID NO 265
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: Tyr(3,5-di-I)
<220> FEATURE:
<221> NAME/KEY: MOD_RES
<222> LOCATION: (3)
<223> OTHER INFORMATION: Hyp

<400> SEQUENCE: 265

Tyr Pro Xaa Gly Ala Gly
 1               5

<210> SEQ ID NO 266
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Hyp

<400> SEQUENCE: 266

Gly Pro Xaa Gly Ala Gly
 1               5

<210> SEQ ID NO 267
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp

<400> SEQUENCE: 267

Gly Ala Gly Xaa Pro Tyr
 1               5

<210> SEQ ID NO 268
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Hyp

<400> SEQUENCE: 268

Pro Xaa Gly Ala Gly
 1               5
```

<210> SEQ ID NO 269
<211> LENGTH: 5
<212> TYPE: PRT
<213> ORGANISM: Artificial Sequence
<220> FEATURE:
<223> OTHER INFORMATION: Description of Artificial Sequence: Synthetic antiarrythmic peptide
<220> FEATURE:
<223> OTHER INFORMATION: NCG between positions 3 and 4

<400> SEQUENCE: 269

Gly Ala Gly Pro Tyr
1               5

<210> SEQ ID NO 270
<211> LENGTH: 5
<212> TYPE: PRT
<213> ORGANISM: Artificial Sequence
<220> FEATURE:
<223> OTHER INFORMATION: Description of Artificial Sequence: Synthetic antiarrythmic peptide
<220> FEATURE:
<223> OTHER INFORMATION: T4C between positions 3 and 4

<400> SEQUENCE: 270

Gly Ala Gly Pro Tyr
1               5

<210> SEQ ID NO 271
<211> LENGTH: 5
<212> TYPE: PRT
<213> ORGANISM: Artificial Sequence
<220> FEATURE:
<223> OTHER INFORMATION: Description of Artificial Sequence: Synthetic antiarrythmic peptide
<220> FEATURE:
<223> OTHER INFORMATION: A2C between positions 3 and 4

<400> SEQUENCE: 271

Gly Ala Gly Pro Tyr
1               5

<210> SEQ ID NO 272
<211> LENGTH: 5
<212> TYPE: PRT
<213> ORGANISM: Artificial Sequence
<220> FEATURE:
<223> OTHER INFORMATION: Description of Artificial Sequence: Synthetic antiarrythmic peptide
<220> FEATURE:
<223> OTHER INFORMATION: PC between positions 3 and 4

<400> SEQUENCE: 272

Gly Ala Gly Pro Tyr
1               5

<210> SEQ ID NO 273
<211> LENGTH: 6
<212> TYPE: PRT
<213> ORGANISM: Artificial Sequence
<220> FEATURE:
<223> OTHER INFORMATION: Description of Artificial Sequence: Synthetic antiarrythmic peptide
<220> FEATURE:
<221> NAME/KEY: MOD_RES
<222> LOCATION: (3)
<223> OTHER INFORMATION: Hyp

<400> SEQUENCE: 273

Tyr Pro Xaa Gly Ala Gly

```
                    1               5

<210> SEQ ID NO 274
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Hyp

<400> SEQUENCE: 274

Tyr Pro Xaa Gly Ala Gly
  1               5

<210> SEQ ID NO 275
<211> LENGTH: 8
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: Cys(Acm)
<220> FEATURE:
<221> NAME/KEY: MOD_RES
<222> LOCATION: (5)
<223> OTHER INFORMATION: Hyp
<220> FEATURE:
<221> NAME/KEY: MOD_RES
<222> LOCATION: (6)
<223> OTHER INFORMATION: Cys(Acm)

<400> SEQUENCE: 275

Cys Gly Ala Gly Xaa Pro Tyr Cys
  1               5

<210> SEQ ID NO 276
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: Cys(Acm)
<220> FEATURE:
<221> NAME/KEY: MOD_RES
<222> LOCATION: (3)
<223> OTHER INFORMATION: Hyp
<220> FEATURE:
<221> NAME/KEY: MOD_RES
<222> LOCATION: (6)
<223> OTHER INFORMATION: Cys(Acm)

<400> SEQUENCE: 276

Cys Gly Xaa Pro Tyr Cys
  1               5

<210> SEQ ID NO 277
<211> LENGTH: 8
<212> TYPE: PRT
<213> ORGANISM: Artificial Sequence
<220> FEATURE:
<223> OTHER INFORMATION: Description of Artificial Sequence: Synthetic
``` antiarrythmic peptide
<220> FEATURE:
<221> NAME/KEY: MOD_RES
<222> LOCATION: (1)
<223> OTHER INFORMATION: Cys(Acm)
<220> FEATURE:
<221> NAME/KEY: MOD_RES
<222> LOCATION: (4)
<223> OTHER INFORMATION: Hyp
<220> FEATURE:
<221> NAME/KEY: MOD_RES
<222> LOCATION: (8)
<223> OTHER INFORMATION: Cys(Acm)

<400> SEQUENCE: 277

Cys Tyr Pro Xaa Gly Ala Gly Cys
 1               5

<210> SEQ ID NO 278
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: Cys(Acm)
<220> FEATURE:
<221> NAME/KEY: MOD_RES
<222> LOCATION: (4)
<223> OTHER INFORMATION: Hyp
<220> FEATURE:
<221> NAME/KEY: MOD_RES
<222> LOCATION: (6)
<223> OTHER INFORMATION: Cys(Acm)

<400> SEQUENCE: 278

Cys Tyr Pro Xaa Gly Cys
 1               5

<210> SEQ ID NO 279
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (7)
<223> OTHER INFORMATION: Hyp

<400> SEQUENCE: 279

Pro Tyr Asn Gly Ala Gly Xaa
 1               5

<210> SEQ ID NO 280
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: Hyp

<400> SEQUENCE: 280

Xaa Pro Tyr Asn Gly Ala Gly

```
<210> SEQ ID NO 281
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Sar
<220> FEATURE:
<221> NAME/KEY: MOD_RES
<222> LOCATION: (4)
<223> OTHER INFORMATION: Hyp

<400> SEQUENCE: 281

Gly Ala Xaa Xaa Pro Tyr
 1               5

<210> SEQ ID NO 282
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Hyp

<400> SEQUENCE: 282

Pro Xaa Gly Ala Gly
 1               5

<210> SEQ ID NO 283
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: Hyp

<400> SEQUENCE: 283

Pro Xaa Gly Ala Gly
 1               5

<210> SEQ ID NO 284
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Hyp

<400> SEQUENCE: 284

Tyr Pro Xaa Gly Ala Gly
 1               5
```

```
<210> SEQ ID NO 285
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: Tyr(3,5-di-I)
<220> FEATURE:
<221> NAME/KEY: MOD_RES
<222> LOCATION: (3)
<223> OTHER INFORMATION: Hyp

<400> SEQUENCE: 285

Tyr Pro Xaa Gly Ala Gly
  1               5

<210> SEQ ID NO 286
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp

<400> SEQUENCE: 286

Gly Ala Gly Xaa Pro Tyr Gln
  1               5

<210> SEQ ID NO 287
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (4)
<223> OTHER INFORMATION: Hyp

<400> SEQUENCE: 287

Gly Ala Gly Xaa Pro Tyr Asn
  1               5

<210> SEQ ID NO 288
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 288

Gly Ala Gly Pro Pro Tyr Asn
  1               5

<210> SEQ ID NO 289
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
```

```
<220> FEATURE:
<221> NAME/KEY: MOD_RES
<222> LOCATION: (3)
<223> OTHER INFORMATION: Hyp

<400> SEQUENCE: 289

Tyr Pro Xaa Gly Ala Gly Asn
 1               5

<210> SEQ ID NO 290
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: Hyp

<400> SEQUENCE: 290

Tyr Pro Xaa Gly Ala Asn
 1               5

<210> SEQ ID NO 291
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (1)
<223> OTHER INFORMATION: Tyr(3-I,5-I)
<220> FEATURE:
<221> NAME/KEY: MOD_RES
<222> LOCATION: (3)
<223> OTHER INFORMATION: 4Hyp

<400> SEQUENCE: 291

Tyr Pro Xaa Gly Ala Gly Asn
 1               5

<210> SEQ ID NO 292
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 292

Gly Ala Gly Asn Tyr
 1               5

<210> SEQ ID NO 293
<211> LENGTH: 4
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 293

Ala Gly Asn Tyr
 1
```

```
<210> SEQ ID NO 294
<211> LENGTH: 4
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 294

Ala Gly Asn Tyr
 1

<210> SEQ ID NO 295
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 295

Gly Pro Pro Gly Ala Gly
 1               5

<210> SEQ ID NO 296
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide

<400> SEQUENCE: 296

Gly Pro Gly Gly Ala Gly
 1               5

<210> SEQ ID NO 297
<211> LENGTH: 5
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (2)
<223> OTHER INFORMATION: 4Hyp

<400> SEQUENCE: 297

Pro Xaa Gly Ala Gly
 1               5

<210> SEQ ID NO 298
<211> LENGTH: 7
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 298

Tyr Pro Xaa Gly Ala Gly Asn
 1               5

<210> SEQ ID NO 299
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      antiarrythmic peptide
<220> FEATURE:
<221> NAME/KEY: MOD_RES
<222> LOCATION: (3)
<223> OTHER INFORMATION: 4Hyp

<400> SEQUENCE: 299

Tyr Pro Xaa Gly Ala Asn
 1               5
```